US010227362B2

(12) United States Patent
Luo et al.

(10) Patent No.: US 10,227,362 B2
(45) Date of Patent: Mar. 12, 2019

(54) ANTI-PULMONARY TUBERCULOSIS NITROIMIDAZOLE DERIVATIVE

(71) Applicant: MEDSHINE DISCOVERY INC., Nanjing, Jiangsu (CN)

(72) Inventors: Wei Luo, Shanghai (CN); Charles Z. Ding, Shanghai (CN); Zhigang Huang, Shanghai (CN); Shuhui Chen, Shanghai (CN)

(73) Assignee: MEDSHINE DISCOVERY INC., Nanjing (CN)

( * ) Notice: Subject to any disclaimer, the term of this patent is extended or adjusted under 35 U.S.C. 154(b) by 0 days.

(21) Appl. No.: 15/546,841

(22) PCT Filed: Jan. 28, 2016

(86) PCT No.: PCT/CN2016/072447
§ 371 (c)(1),
(2) Date: Dec. 15, 2017

(87) PCT Pub. No.: WO2016/119706
PCT Pub. Date: Aug. 4, 2016

(65) Prior Publication Data
US 2018/0162878 A1 Jun. 14, 2018

(30) Foreign Application Priority Data

Jan. 29, 2015 (CN) .......................... 2015 1 0048040
Jan. 6, 2016 (CN) .......................... 2016 1 0006632

(51) Int. Cl.
*A61P 31/04* (2006.01)
*A61P 31/06* (2006.01)
*A61K 31/437* (2006.01)
*A61K 31/519* (2006.01)
*C07D 519/00* (2006.01)
*A61K 31/4375* (2006.01)
*A61K 31/4545* (2006.01)
*A61K 31/4985* (2006.01)
*A61K 31/5377* (2006.01)

(52) U.S. Cl.
CPC .......... *C07D 519/00* (2013.01); *A61K 31/437* (2013.01); *A61K 31/4375* (2013.01); *A61K 31/4545* (2013.01); *A61K 31/4985* (2013.01); *A61K 31/519* (2013.01); *A61K 31/5377* (2013.01); *A61P 31/04* (2018.01); *A61P 31/06* (2018.01)

(58) Field of Classification Search
None
See application file for complete search history.

(56) References Cited

U.S. PATENT DOCUMENTS

| 5,668,127 | A | 9/1997 | Baker et al. |
| 6,087,358 | A | 7/2000 | Baker et al. |
| 7,262,212 | B2 | 8/2007 | Tsubouchi et al. |
| 8,163,753 | B2 | 4/2012 | Tsubouchi et al. |

FOREIGN PATENT DOCUMENTS

| CN | 1705670 | A | 12/2005 | |
| CN | 1878777 | A | 12/2006 | |
| JP | 2005320316 | A | 11/2005 | |
| JP | 2005-330266 | A | 12/2005 | |
| JP | 4787529 | B2 | 10/2011 | |
| WO | WO-2005042542 | A1 * | 5/2005 | .......... C07D 498/04 |
| WO | 2007/075872 | A2 | 7/2007 | |
| WO | 2008/008480 | A3 | 3/2008 | |
| WO | 2008/140090 | A1 | 11/2008 | |
| WO | 2009/120789 | A1 | 10/2009 | |
| WO | 2011/014774 | A1 | 2/2011 | |
| WO | 2011/014776 | A1 | 2/2011 | |
| WO | 2011/093529 | A1 | 8/2011 | |
| WO | 2011/151320 | A1 | 12/2011 | |
| WO | 2011/087995 | A3 | 3/2013 | |
| WO | 2013/072903 | A1 | 5/2013 | |

OTHER PUBLICATIONS

English Translation of the Written Opinion of the International Searching Authority issued in International Patent Application No. PCT/CN2016/072447, ISA/CN, Haidian District, Beijing, dated May 6, 2016.

Kmentova et al., "Synthesis and Structure-Activity Relationship of Aza- and Diazabiphenyl Analogues of the Antitubercular Drug (6S)-2-Nitro-6-{[4-(trifluoromethoxy)benzyl]oxy}-6,7-dihydro-5H-imidazo[2,1-b][1,3]oxazine (PA-824)", J. Med. Chem., 2010, 53 (23), pp. 8421-8439.

Singh et al., "PA-824 Kills Nonreplicating *Mycobacterium tuberculosis* by Intracellular No Release", Science. Nov. 28, 2008; 322(5906): 1392-1395.

Stover et al. "A small-molecule nitroimidazopyran drug candidate for the treatment of tuberculosis", Nature. Jun. 22, 2000;405(6789):962-6.

Berge et al., Pharmaceutical Salts, Journal of Pharmaceutical Sciences 66: 1-19 (1977).

Hubert Maehr et al., A Proposed New Convention for Graphic Presentation of Molecular Geometry and Topography, Journal of Chemical Education, vol. 62, No. 2, Feb. 1985.

Remington: The Science and Practice of Pharmacy, 21st Edition., Lippincott, Williams & Wilkins (2005).

Protective Groups in Organic Synthesis, Wiley and Sons, 1991.

Still et al. "Rapid chromatographic technique for preparative separations with moderate resolution", J. Org. Chem., 1978, 43 (14), pp. 2923-2925.

(Continued)

*Primary Examiner* — Zinna Northington Davis
(74) *Attorney, Agent, or Firm* — Harness, Dickey & Pierce, P.L.C.

(57) ABSTRACT

Disclosed is a substituted nitroimidazole derivative, which is mainly used for treating related diseases caused by mycobacterial infections, such as Mycobacterium tuberculosis, especially being suitable for diseases caused by resistant Mycobacterium tuberculosis.

11 Claims, No Drawings

(56) References Cited

OTHER PUBLICATIONS

The first office action dated May 29, 2018 issued on counterpart Japanese patent application 2017-540142.
EESR dated Jun. 11, 2018 issued on counterpart European patent application 16742768.1.
The first office action dated Jun. 21, 2018 issued on Russian patent application 2017130546.
The First Office Action of related CN201680006991.1 dated Aug. 24, 2018.
The Search Report of CN201680006991.1, (2016).

* cited by examiner

ANTI-PULMONARY TUBERCULOSIS NITROIMIDAZOLE DERIVATIVE

CROSS-REFERENCE TO RELATED APPLICATIONS

This application is a 371 U.S. National Stage of International Application No. PCT/CN2016/072447, filed Jan. 28, 2016, which claims the benefit of and priority to Chinese Patent Applications Nos. 201510048040.8, filed Jan. 29, 2015 and 201610006632.8, filed Jan. 6, 2016. The entire disclosures of the above applications are incorporated herein by reference.

REFERENCES

The contents of the following documents are incorporated herein by reference.
U.S. Pat. No. 5,668,127
U.S. Pat. No. 6,087,358
JP 2005330266
WO 2004/033463
WO 2007/075872
WO 2008/140090
WO 2008/008480
WO2009/120789
WO 2011/151320
WO 2011/093529
WO 2011/087995
WO 2011/014774
WO 2011/014776
WO 2013072903

FIELD OF INVENTION

The present invention relates to a substituted nitroimidazole derivative, which is mainly used for treating related diseases caused by mycobacterial infections, such as Mycobacterium tuberculosis, especially being suitable for diseases caused by resistant Mycobacterium tuberculosis.

PRIOR ARTS

Mycobacterium tuberculosis is the pathogen of tuberculosis. As a widely distributed and lethal infectious disease, according to the World Health Organization statistics, about more than 800 million people are infected with tuberculosis, and 200 million people die of tuberculosis each year. In the past decade, tuberculosis cases have grown at a rate of 20% worldwide, especially in poverty-stricken areas. If the trend continues this way, tuberculosis cases are likely to continue to grow with a 41% increase in the next two decades. Tuberculosis has always been a main infectious disease that causes death to an adult after AIDS in the fifty years after the initial application of chemotherapy. Complications of tuberculosis have led to the emergence of many drug-resistant strains, and reached a symbiotic relationship with AIDS. Compared with people with negative HIV testing result, people with positive HIV testing result and at the same time infected with tuberculosis have 30 times the chance to develop into active tuberculosis. On average, every three patients died of AIDS, there is one person is caused by tuberculosis.

The existing treatment of tuberculosis uses a combination of a variety of pharmaceutical formulations recommended by the US Department of Public Health, which includes the use of the combination of isoniazid, rifampicin, pyrazinamide and ethambutol for two months at first, and then the use of the combination of isoniazid and rifampicin alone for four months. For patients infected with AIDS, the use of this combination of drugs needs to extended to seven months. For patients infected with multidrug-resistant tuberculosis (MDR-TB), this combination of drugs also needs to add other second-line pharmaceuticals, such as streptomycin, kanamycin, amikacin, capreomycin, ethionamide, cycloserine, ciprofloxacin and ofloxacin. This combination of therapeutic drugs for patients infected with MDR-TB (usually over 2 years course) generally has lower activity and higher side effects compared to currently first-line drugs on the market.

Therefore, there is an urgent need for such novel nitroimidazo oxazole derivatives that are highly active in both aerobic (active) and anaerobic (latency or stubborn) environments as anti-tuberculosis drugs. Obviously, drugs that both shorten the duration of treatment and reduce the frequency of surveillance can bring the greatest benefit.

Currently, Deltyba (delamanid), a new product of Otsuka, has been marketed as a combined drug for multidrug-resistant tuberculosis treatment, which has been approved for adult treatment in view of drug resistance and tolerance considerations. Similarly, nitroimidazo oxazine compounds PA-824 and TBA-354 (J. Org. Chem. 53; 8421-8439 (2010)) show better in vitro and in vivo activity in inhibiting Mycobacterium tuberculosis. The mechanism of action of PA-824 relates to the release of nitric oxide gas (Singh et al., Science 322; 1392-1395 (2008)), and the reduction step bacterial glucose 6-phosphate dehydrogenase (FGD1) and cofactor (F420) involved (Stover et al., Nature 405; 962-966 (2000)). Studies on wild-type mutagenic strains, FGD1 and F420 by gene chip technology have found that an unknown function protein consisting of 151 amino acids (17.37 kDa), (Rv3547) seems to play a leading role in this series of reduction steps. This hypothesis is also confirmed by studying the reduction of FA-824. TBA-354 is a nitroimidazo oxazine derivative derived from PA-824. The mechanism of action of Delamanid is to inhibit the synthesis of methoxy and keto mycolic acids, thereby killing bacteria, which are important components of the Mycobacterium tuberculosis cell wall. Nitroimidazole derivatives and treatments for Mycobacterium tuberculosis have previously been extensively reported (U.S. Pat. Nos. 5,668,127 and 6,087,358; Jiricek et al., WO2007075872A2; Tsubochi et al., WO2005042542A1 and WO2004033463A1; JP 2005330266A; THOMPSON et al., WO2011014776; MUSONDA et al., WO2013072903).

In clinical research and development of all anti-Mycobacterium tuberculosis drugs, nitroimidazole derivatives are becoming more advanced and more attractive. It can be seen from the above patent applications, the general formulas of the main patents for the treatment of tuberculosis, particularly for the treatment of multidrug-resistant tuberculosis, are as follows (1 and 2):

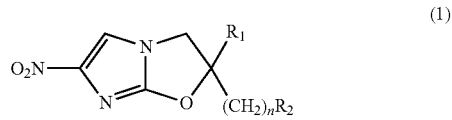

(1)

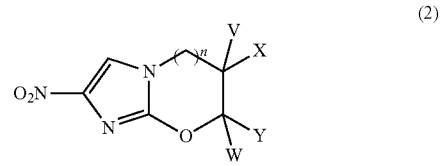

(2)

From research, two new active molecules, OPC-67683 (delamanid) and TBA-354, have been developed for the treatment of tuberculosis, the structures are as follows (3 and 4):

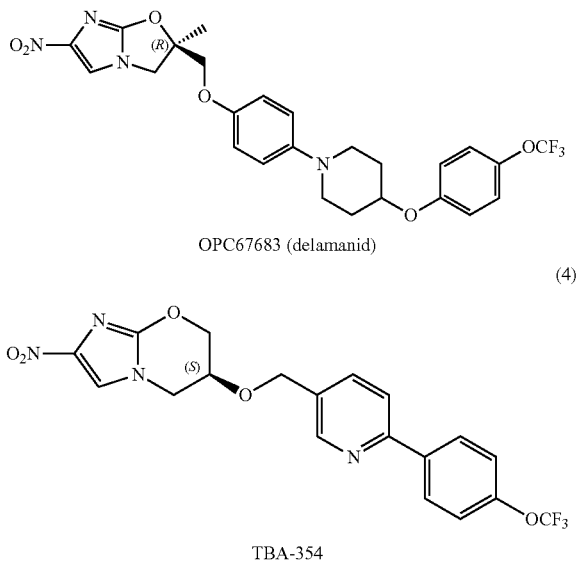

Delamanid is a nitro-2H-imidazooxazole derivative, which acts mainly by inhibiting the biosynthesis of mycolic acid and exhibits a high activity against Mycobacterium tuberculosis both in vitro and in vivo. On Nov. 21, 2013, Deltyba (Delamanid) was conditionally approved by the Committee for Medicinal Products for Human Use (CHMP), and 50 mg of film-coated tablets were used for the treatment of Mycobacterium tuberculosis. It was officially launched in Europe on Apr. 28, 2014. Deltyba was identified as an orphan drug on Feb. 1, 2008. The present invention is directed to the development of a novel nitroimidazole compound for the treatment of tuberculosis and multidrug-resistant tuberculosis.

Although OPC-67683 has been shown to have a clinical effect on the treatment of multidrug-resistant tuberculosis, it has a further optimized space in the course of treatment and cure rate, and meanwhile there is also this need. The nitroimidazole derivatives of the present invention have been shown to have better water solubility and pharmacokinetic properties. It is expected that this improvement will lead to better clinical performance.

CONTENT OF THE PRESENT INVENTION

The present invention provides a compound having a structure of formula (I), a pharmaceutically acceptable salt thereof or an optical isomer thereof,

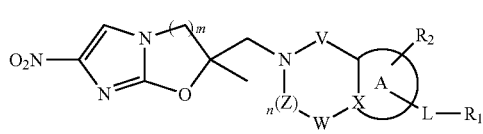

wherein, ring A is a 5- to 6-membered aryl or heteroaryl;

X is N, C(R) or C;

R is H, a halogen, OH, CN, $NO_2$, or selected from the group consisting of an amino, a $C_{1-6}$ alkylamino, a N,N-di($C_{1-6}$ alkyl)amino, a $C_{1-6}$ alkyl, a $C_{1-6}$ heteroalkyl, a $C_{2-6}$ alkenyl, a $C_{2-6}$ alkynyl, a $C_{3-7}$ cycloalkyl, a $C_{3-7}$ heterocycloalkyl, a 5- to 7-membered aryl, and a 5- to 7-membered heteroaryl, each of which is optionally substituted by any substituent;

each of V and W is independently selected from the group consisting of a methylene, —$CH_2CH_2$—, C(=O), —S(=O)— and —S(=O)$_2$—, wherein, the methylene and the —$CH_2CH_2$— are optionally substituted by 1 or 2 R(s);

Z is a methylene which is optionally substituted by 1 or 2 R(s);

L is a single bond, —O—, —S—, N(R), C(R)(R), —C(=O)—, —C(=S)—, —S(=O)—, or —S(=O)$_2$—;

each of $R_1$ and $R_2$ is independently selected from H, a halogen, OH, CN, $NO_2$, or each of $R_1$ and $R_2$ is independently selected from the group consisting of an amino, a $C_{1-6}$ alkyl, a $C_{1-6}$ heteroalkyl, a $C_{2-6}$ alkenyl, a $C_{2-6}$ alkynyl, a $C_{3-7}$ cycloalkyl, a $C_{3-7}$ cycloalkyl-$C_{1-6}$ alkyl, a $C_{3-7}$ heterocycloalkyl and a 5- to 7-membered aryl or heteroaryl, each of which is optionally substituted by any substituent;

optionally, the substituent R on Z and the substituent R on V are attached to the same atom or atomic group to form a 5- to 7-membered ring;

optionally, the moiety

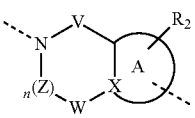

may be replaced with

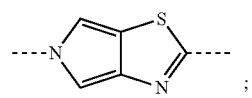

$R_2$ may also be absence;

m is 1, 2 or 3;

n is 0, 1, 2 or 3;

the "hetero" represents a heteroatom or a hetero-atomic group, which is selected from the group consisting of —C(=O)NH—, —NH—, —C(=NH)—, —S(=O)$_2$NH—, —S(=O)NH—, —O—, —S—, N, =O, =S, —C(=O)O—, —C(=O)—, —C(=S)—, —S(=O)—, —S(=O)$_2$—, and —NHC(=O)NH—;

the number of the heteroatom or the hetero-atomic group is independently 0, 1, 2 or 3.

In some embodiments of the present invention, each of the above mentioned substituent and the R is independently selected from the group consisting of H, F, Cl, Br, I, OH, CN, $NH_2$, a $C_{1-4}$ alkyl and a $C_{1-4}$ heteroalkyl, wherein the $C_{1-4}$ alkyl or the $C_{1-4}$ heteroalkyl may optionally be further substituted by 0 to 3 substituents that are selected from a halogen, OH and/or $NH_2$.

In some embodiments of the present invention, each of the above mentioned substituent is selected from the group consisting of F, Cl, Br, I, CN, —$CF_3$, —$OCF_3$, —$CH_2CF_3$, $OCH_3$, and $(CH_3)_3COC(=O)$—.

In some embodiments of the present invention, each of the above mentioned $R_1$ and $R_2$ is independently selected from the group consisting of H, halogen, CN, or selected from the group consisting of

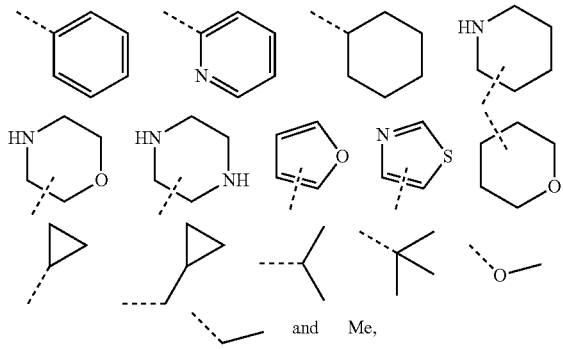

and Me, each of which is optionally substituted.

In some embodiments of the present invention, each of the above mentioned $R_1$ and $R_2$ is independently selected from the group consisting of H, halogen, CN, or selected from the group consisting of

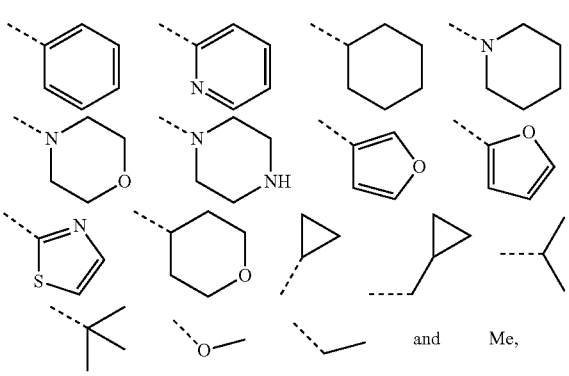

and Me, each of which is optionally substituted.

In some embodiments of the present invention, each of the above mentioned $R_1$ and $R_2$ is independently selected from the group consisting of

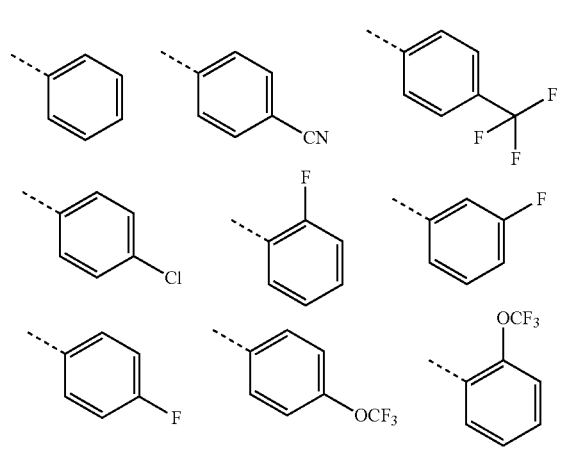

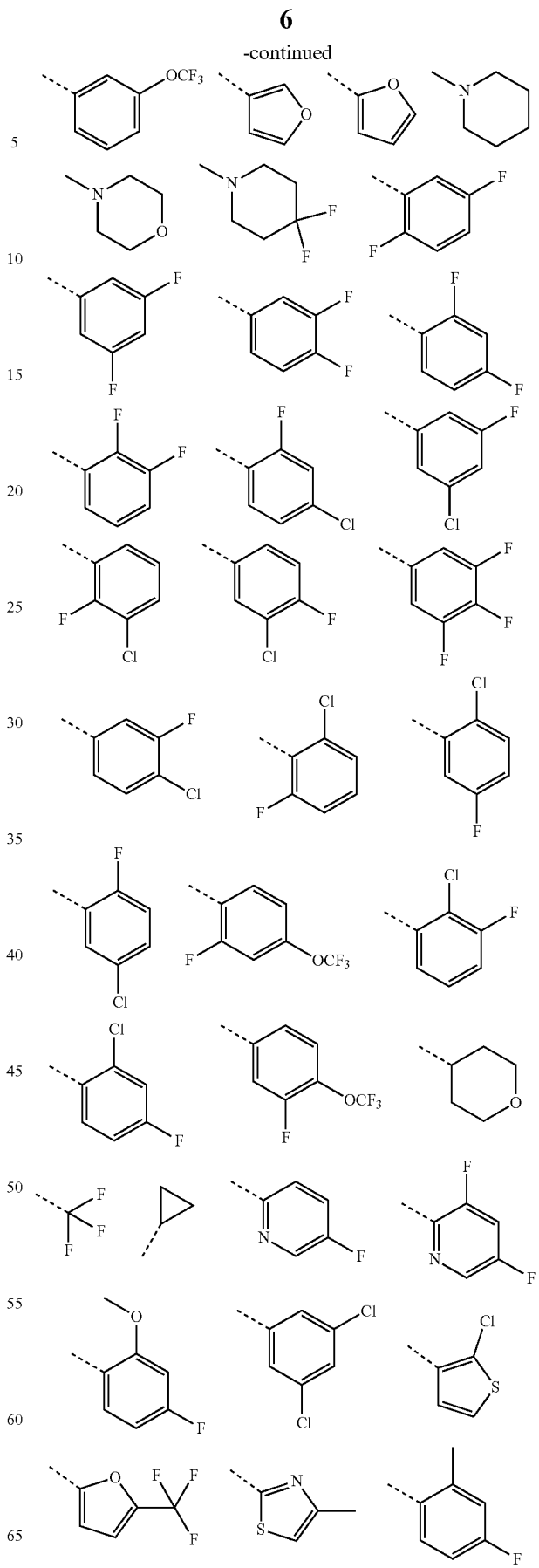

-continued

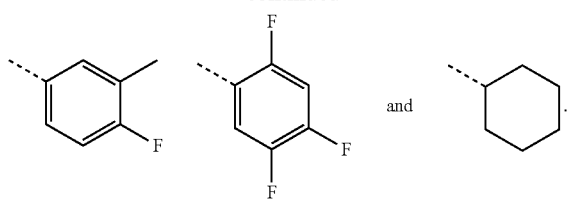

and

In some embodiments of the present invention, the above mentioned R is selected from the group consisting of H, Cl, Br, I, OH, CN, NH$_2$, Me and Et.

In some embodiments of the present invention, the above mentioned ring A is selected from the group consisting of a pyridyl, a thiazolyl, an oxazolyl, an imidazolyl and a pyrimidinyl.

In some embodiments of the present invention, the above mentioned ring A is selected from the group consisting of

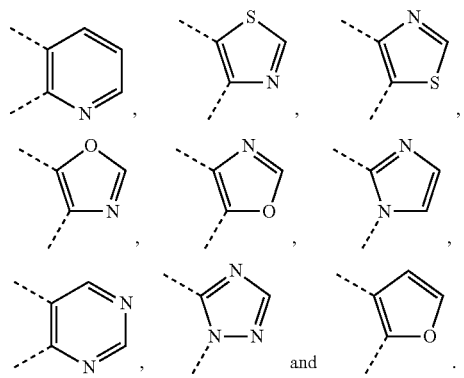

and

In some embodiments of the present invention, the above mentioned moiety

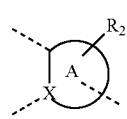

is selected from the group consisting of

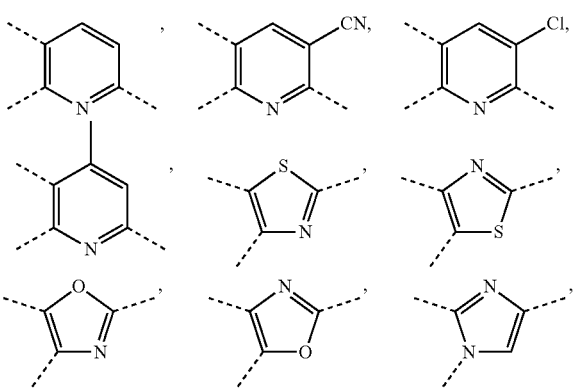

-continued

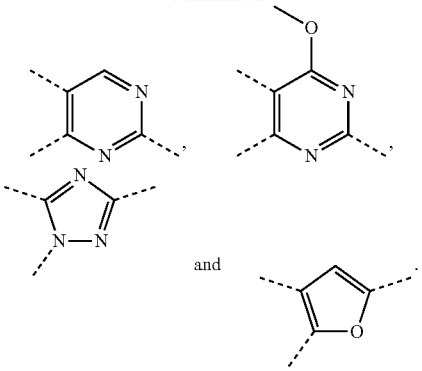

and

In some embodiments of the present invention, the above mentioned moiety

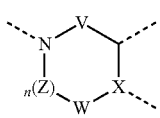

is selected from the group consisting of

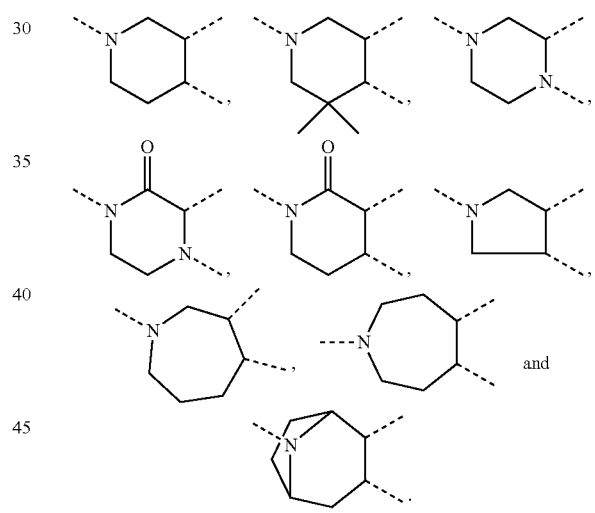

and

In some embodiments of the present invention, the above mentioned moiety

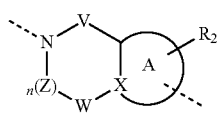

is selected from the group consisting of

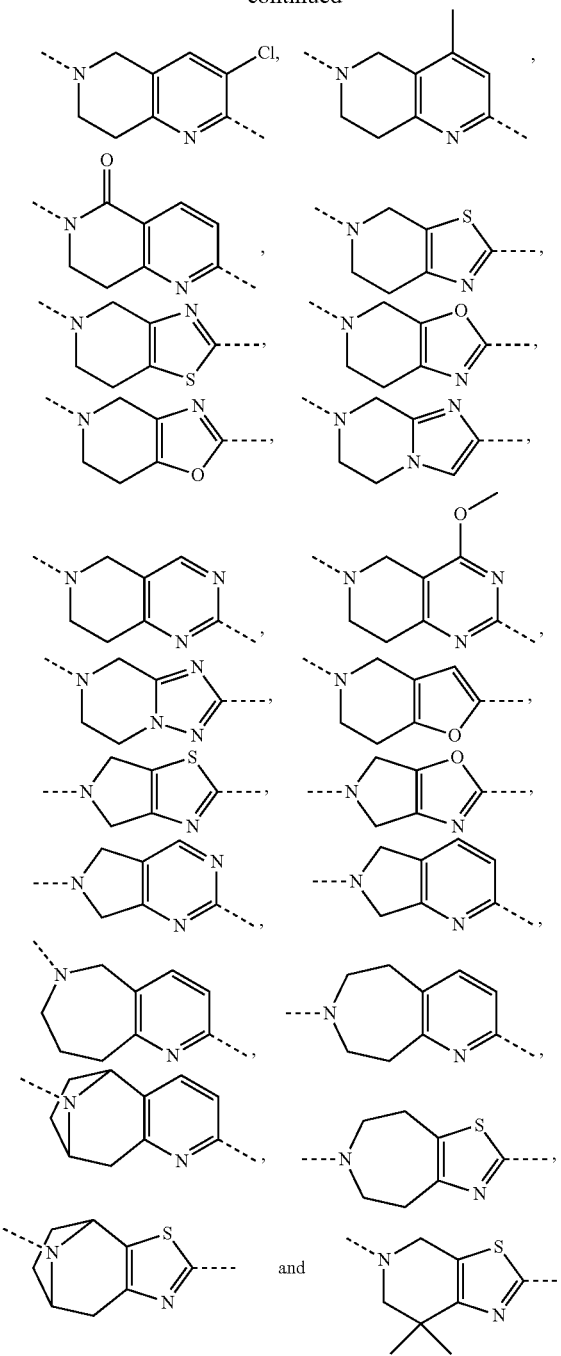
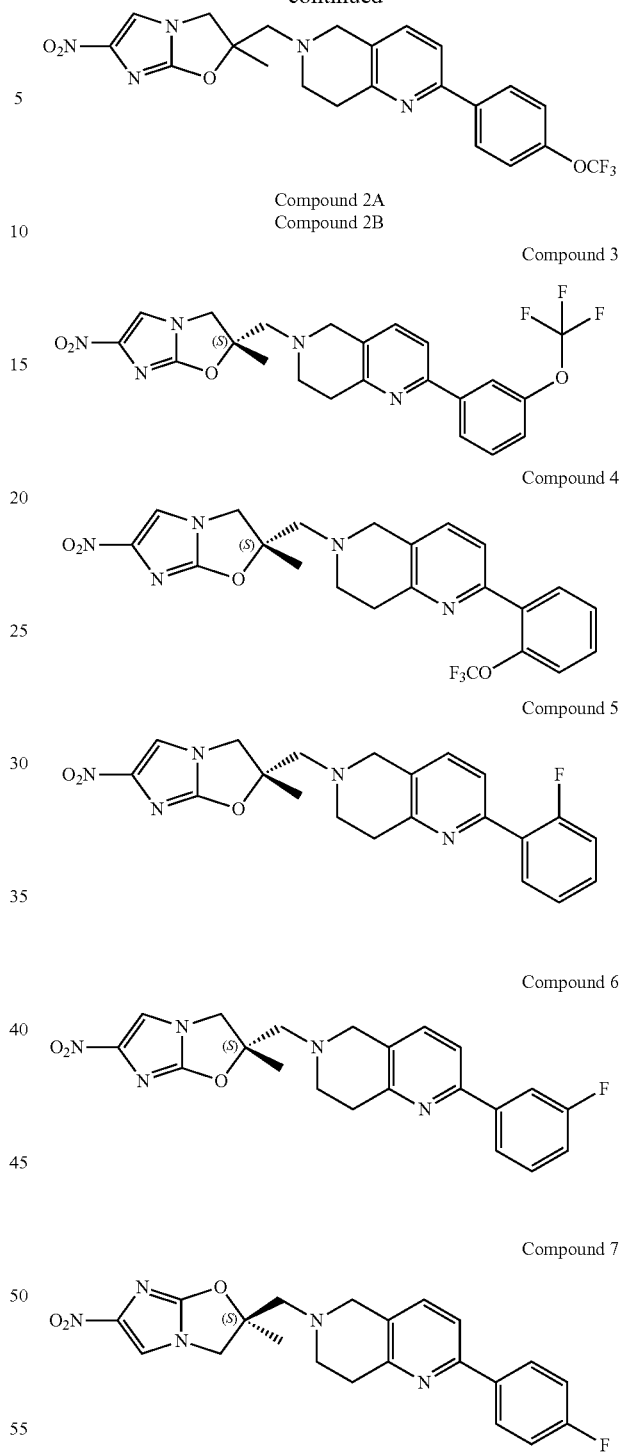
Specifically, the compounds of the present invention are selected from the group consisting of
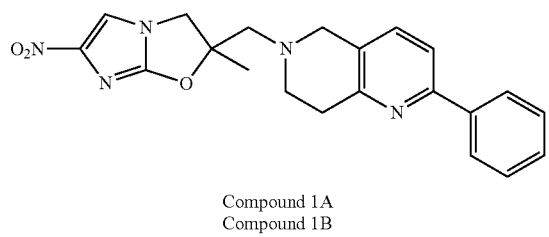
Compound 1A
Compound 1B
Compound 2A
Compound 2B
Compound 3
Compound 4
Compound 5
Compound 6
Compound 7
Compound 8
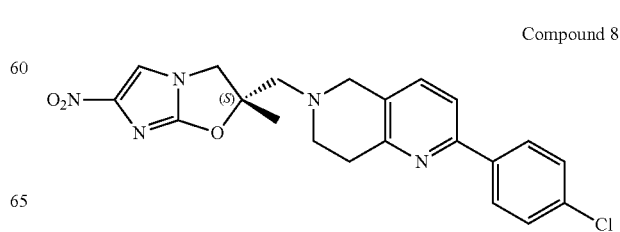

Compound 9
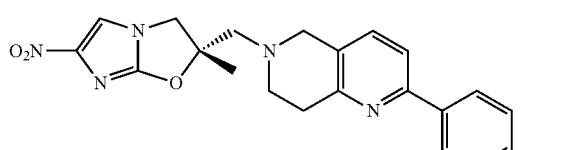
Compound 10
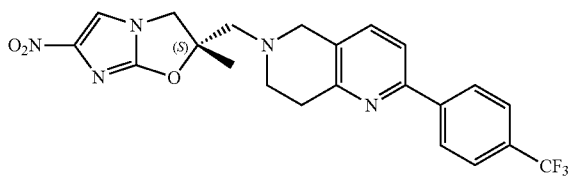
Compound 11
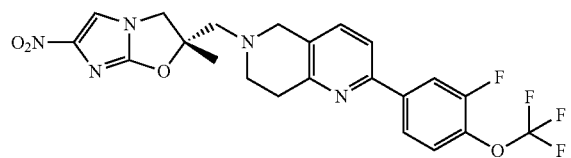
Compound 12
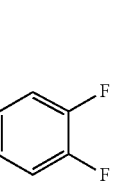
Compound 13

Compound 14
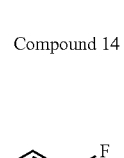
Compound 15
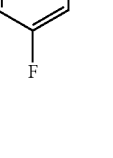
Compound 16
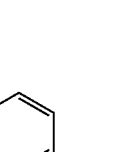
Compound 17
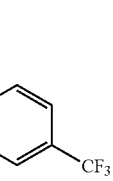
Compound 18
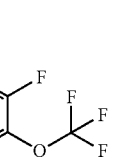
Compound 19
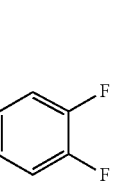
Compound 20
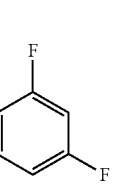
Compound 21
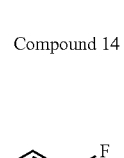
Compound 22
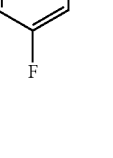

Compound 23
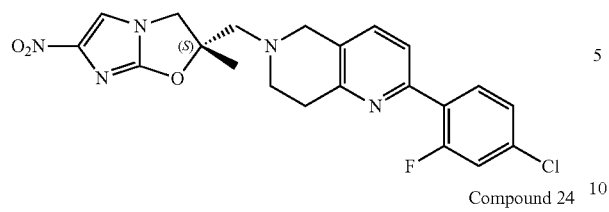
Compound 24
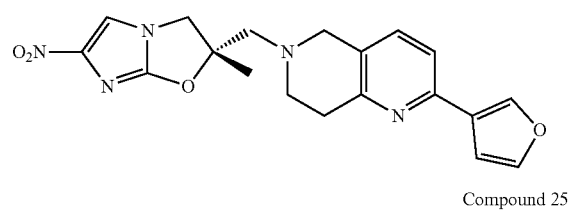
Compound 25
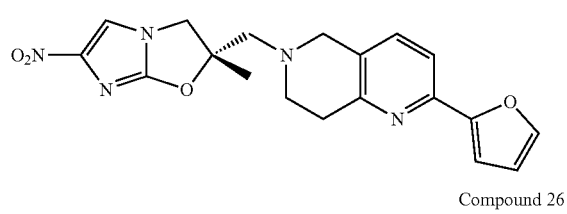
Compound 26
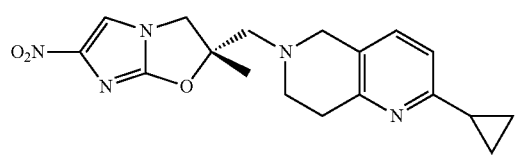
Compound 27
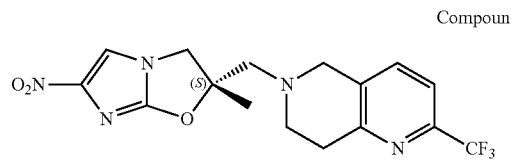
Compound 28
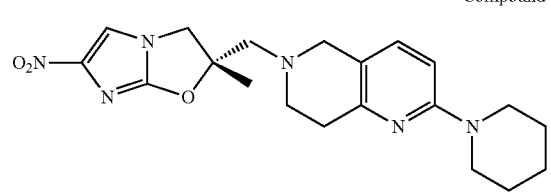
Compound 29
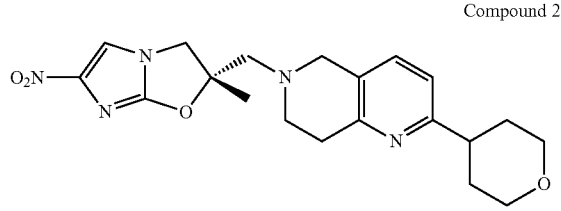
Compound 30
Compound 31
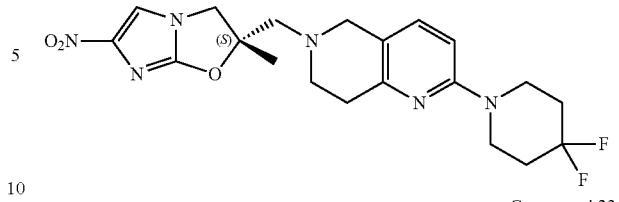
Compound 32
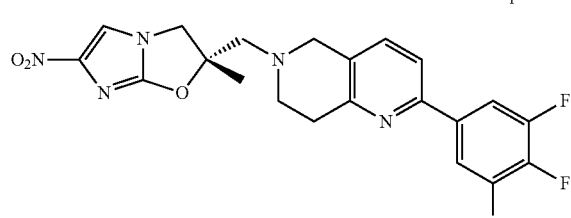
Compound 33
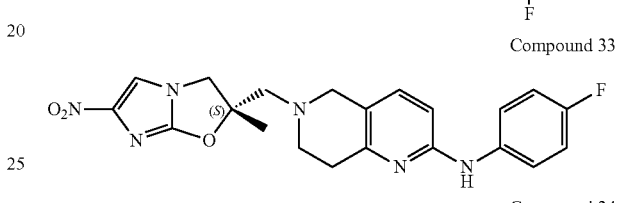
Compound 34
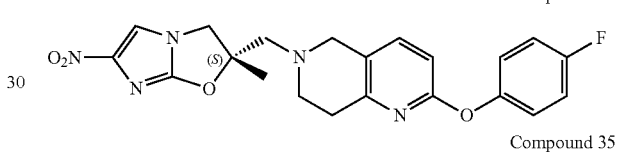
Compound 35
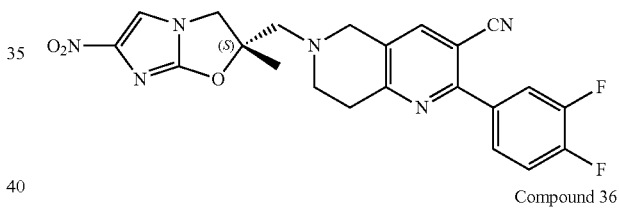
Compound 36
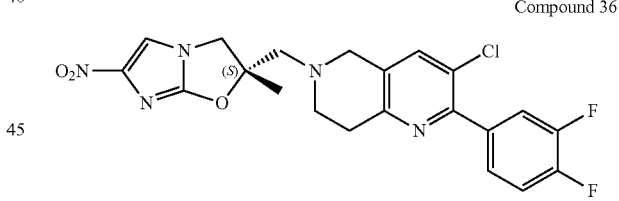
Compound 37
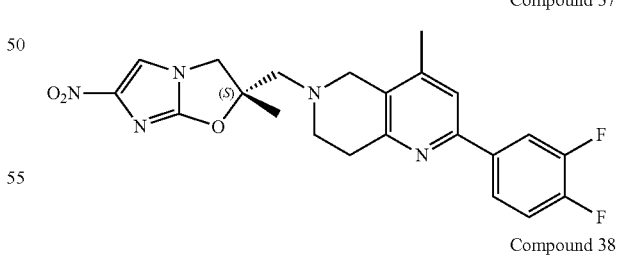
Compound 38
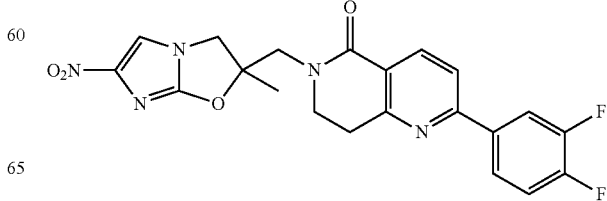

-continued
Compound 39
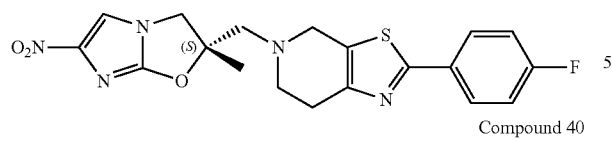
Compound 40
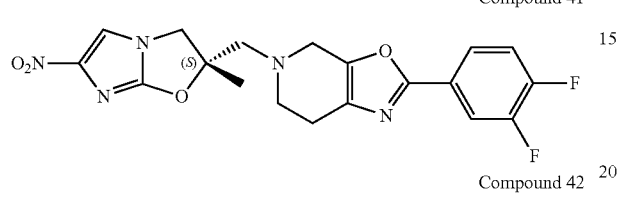
Compound 41
Compound 42
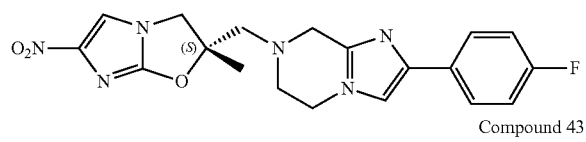
Compound 43
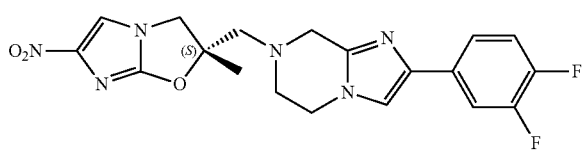
Compound 44
Compound 45
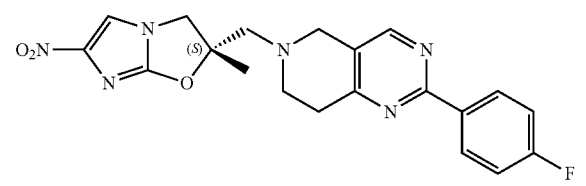
Compound 46
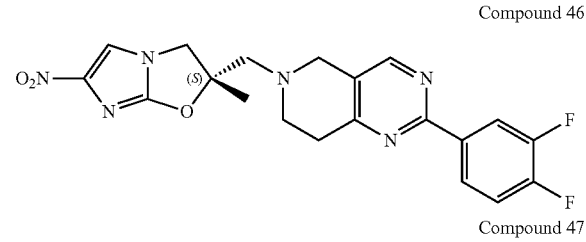
Compound 47
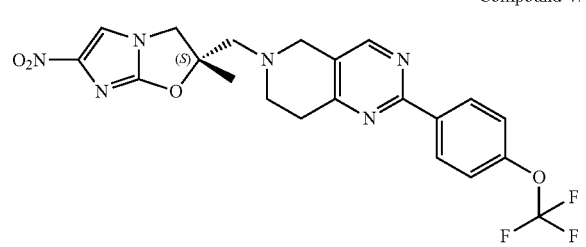
-continued
Compound 48
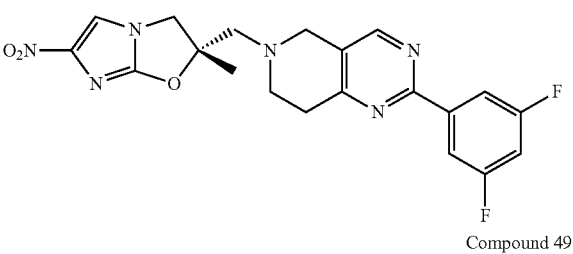
Compound 49
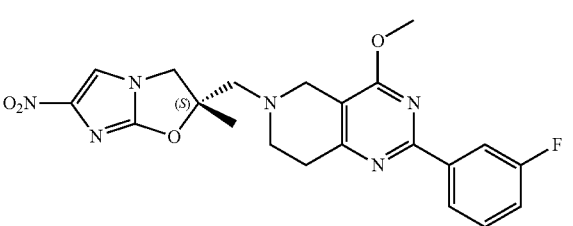
Compound 50
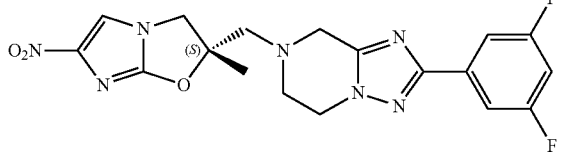
Compound 51
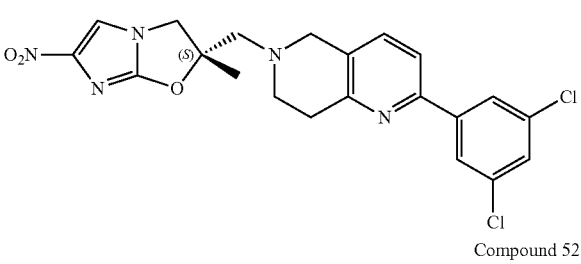
Compound 52
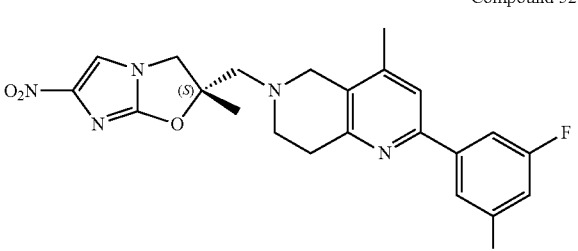
Compound 53
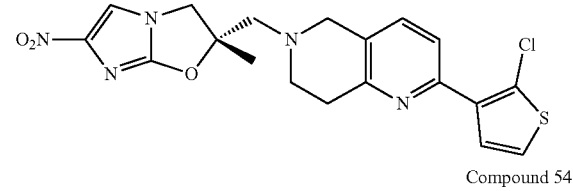
Compound 54
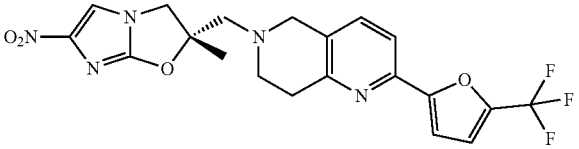

Compound 55
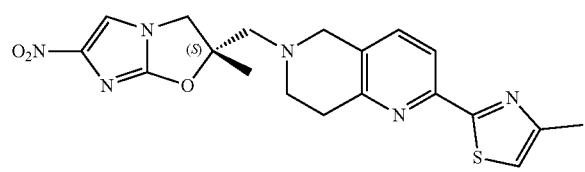
Compound 56
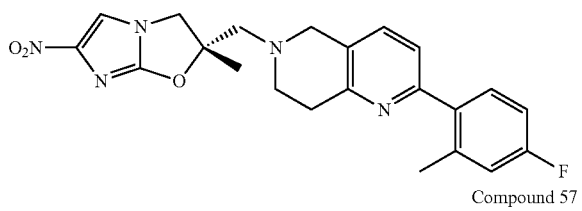
Compound 57
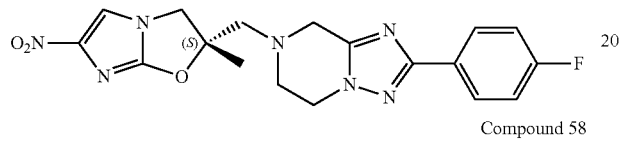
Compound 58
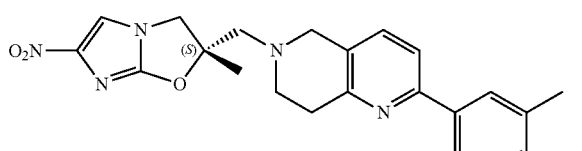
Compound 59
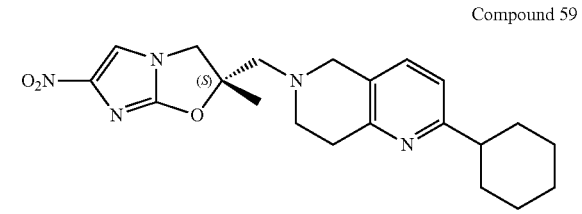
Compound 60
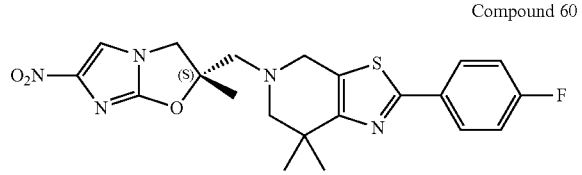
Compound 61
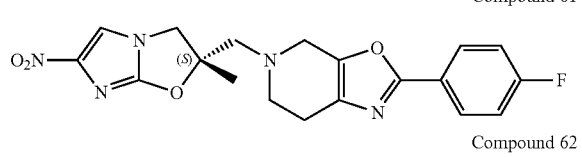
Compound 62
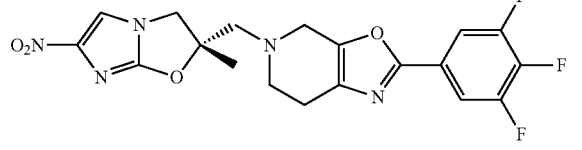
Compound 63
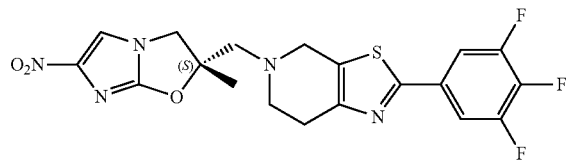
Compound 64
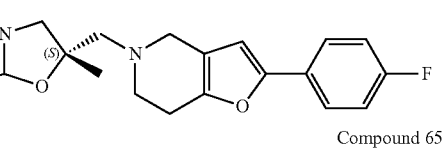
Compound 65
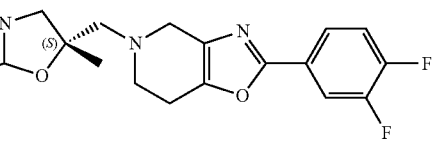
Compound 66
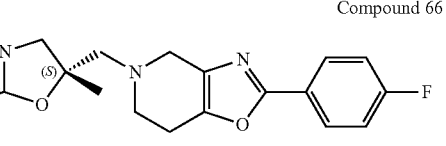
Compound 67
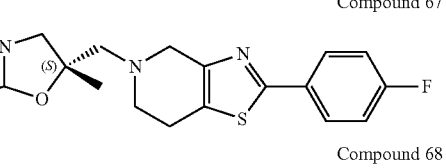
Compound 68
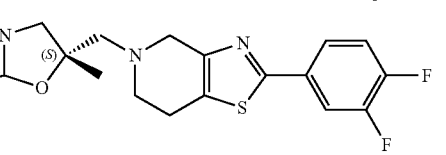
Compound 69
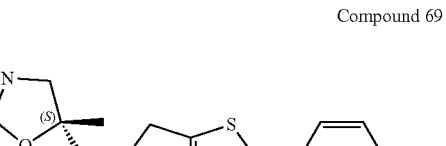
Compound 70
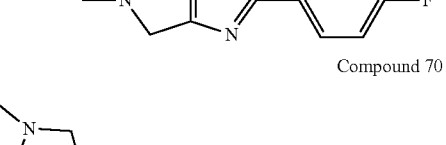
Compound 71
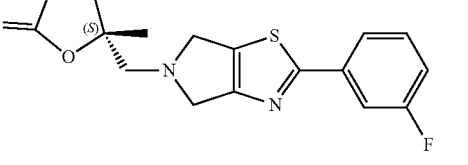
Compound 72

Compound 73
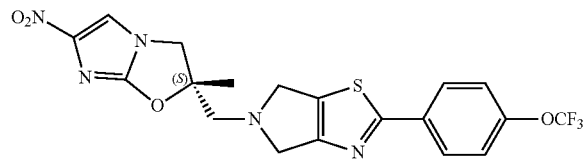
Compound 74
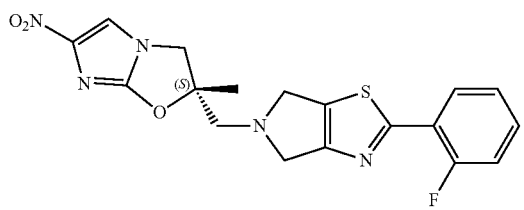
Compound 75
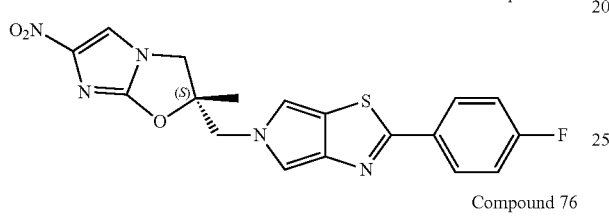
Compound 76
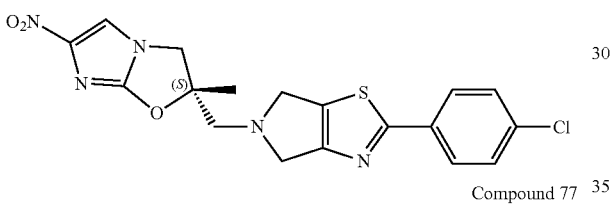
Compound 77
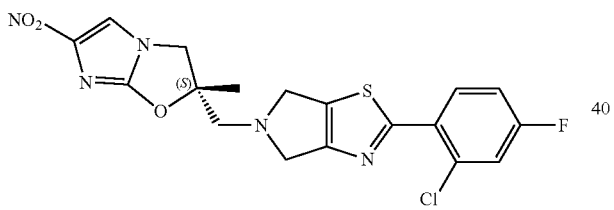
Compound 78
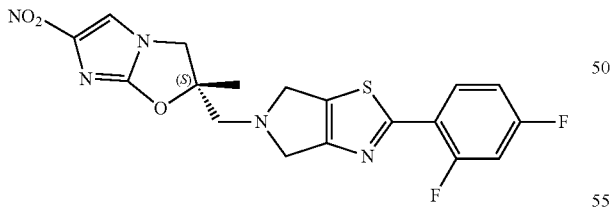
Compound 79
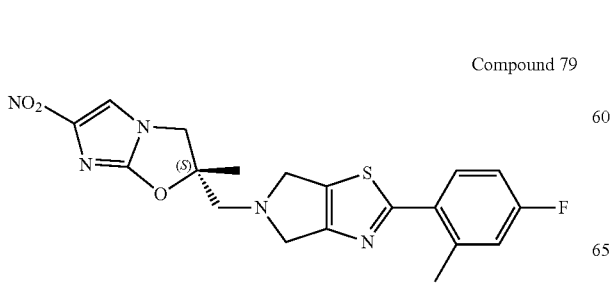
Compound 80
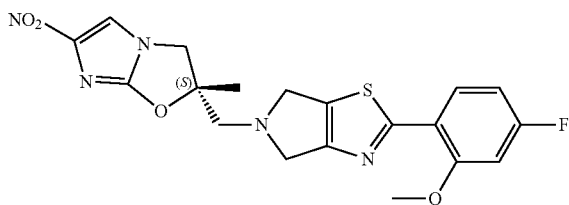
Compound 81
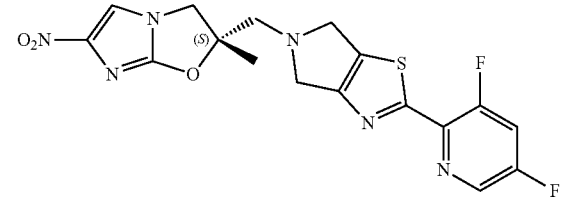
Compound 82
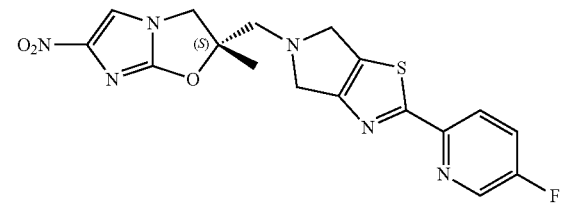
Compound 83
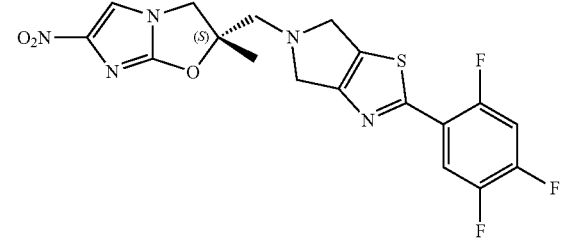
Compound 84
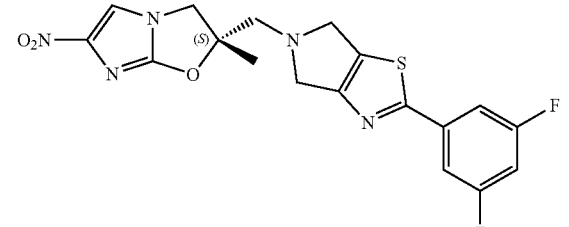
Compound 85
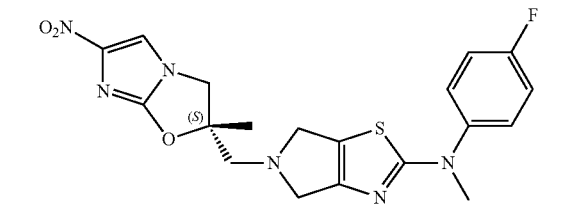

Compound 86
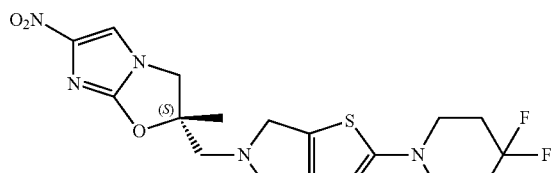
Compound 87
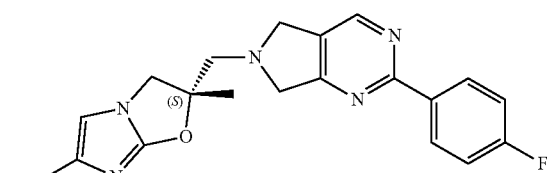
Compound 88
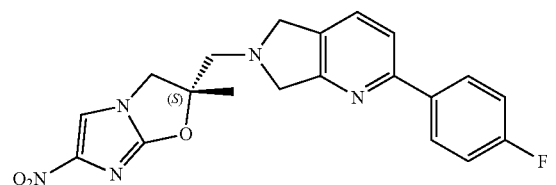
Compound 89
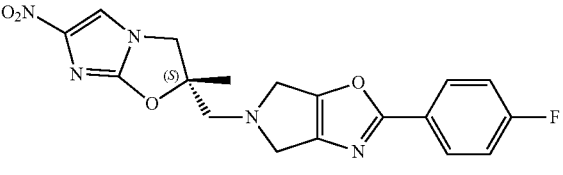
Compound 90
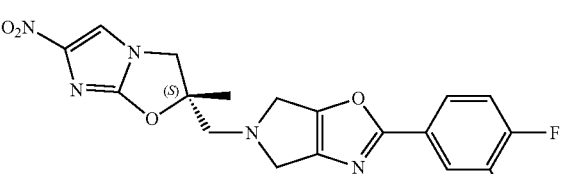
Compound 91
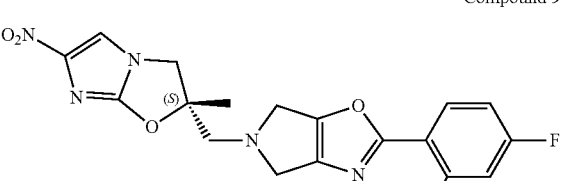
Compound 92
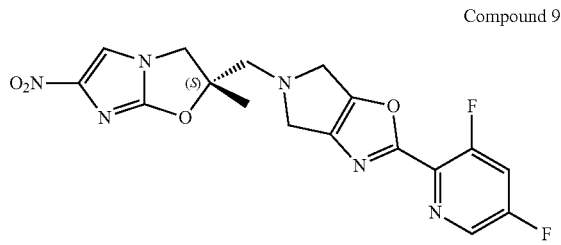
Compound 93
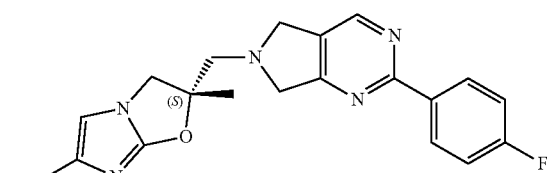
Compound 94
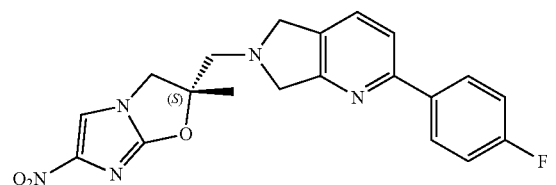
Compound 95
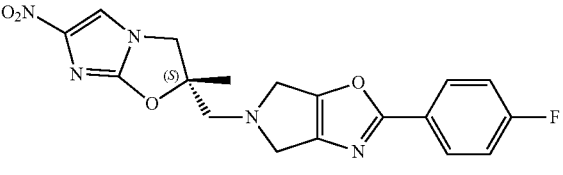
Compound 96
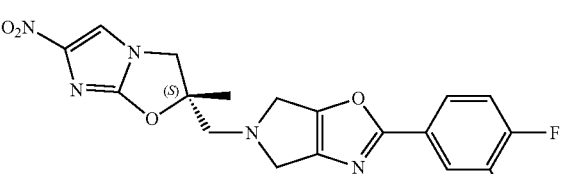
Compound 97
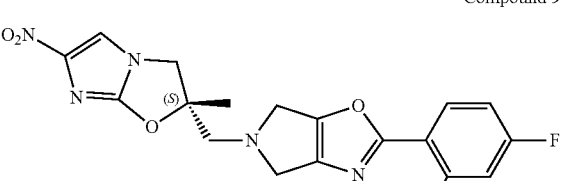
Compound 98A
Compound 98B
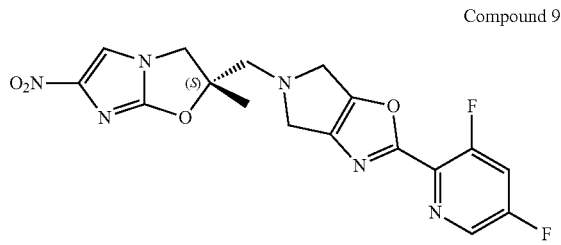

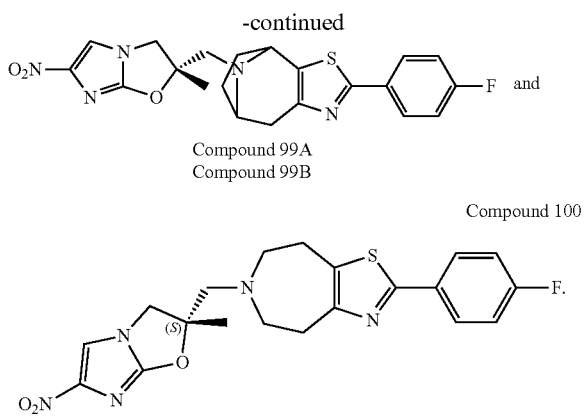

Compound 99A
Compound 99B

Compound 100

The present invention also provides a pharmaceutical composition comprising an effective amount of the compound of formula (I), the pharmaceutically acceptable salt thereof, the optical isomer thereof mentioned above, or a pharmaceutically acceptable carrier.

The present invention also provides a use of the compound of formula (I), the pharmaceutically acceptable salt thereof, the optical isomer thereof mentioned above, or the composition mentioned above in manufacturing a medicament for the treatment and prevention of Mycobacterium tuberculosis or other microbial infections.

The present invention also provides a process for preparing the compound of formula (I), comprising:

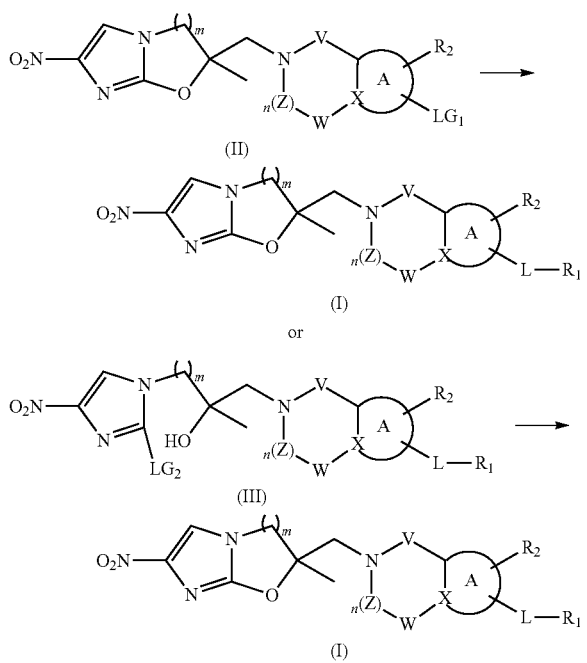

wherein $LG_2$ represents a suitable leaving group, and the other variables are defined as above.

In some embodiments of the present invention, the above mentioned $LG_2$ represents a halogen.

The present invention also provides an intermediate for the preparation of the compound of formula (I),

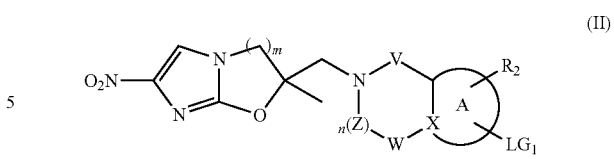

wherein $LG_1$ represents a suitable leaving group, and the other variables are defined as above.

In some embodiments of the present invention, the above mentioned $LG_1$ represents a halogen.

The present invention also provides intermediates for the preparation of a compound of formula (I) according to claim 1, comprising:

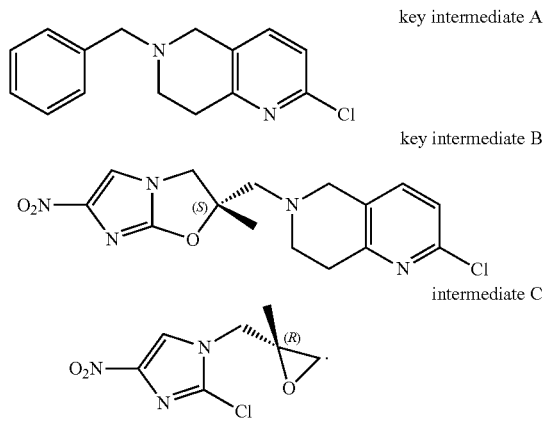

key intermediate A key intermediate B intermediate C

Relevant Definitions

Unless otherwise specified, the following terms and phrases used herein are intended to have the following meanings. A particular term or phrase should not be considered uncertain or unclear in the absence of a specific definition while should be understood according to the ordinary meaning. When a trade name appears herein, it refers to the corresponding commodity or its active ingredient.

$C_{1-12}$ is selected from the group consisting of $C_1$, $C_2$, $C_3$, $C_4$, $C_5$, $C_6$, $C_7$, $C_8$, $C_9$, $C_{10}$, $C_{11}$ and $C_{12}$, $C_{3-12}$ is selected from the group consisting of $C_3$, $C_4$, $C_5$, $C_6$, $C_7$, $C_8$, $C_9$, $C_{10}$, $C_{11}$ and $C_{12}$.

$C_{1-12}$ alkyl or heteroalkyl, $C_{3-12}$ cyclohydrocarbonyl or heterocyclohydrocarbonyl, $C_{1-12}$ alkyl or heteroalkyl substituted by $C_{3-12}$ cyclohydrocarbonyl or heterocyclohydrocarbonyl include but are not limited to:

$C_{1-12}$ alkyl, $C_{1-12}$ alkylamino, N, N-di($C_{1-12}$ alkyl)amino, $C_{1-12}$ alkoxy, $C_{1-12}$ alkylacyl, $C_{1-12}$ alkoxycarbonyl, $C_{1-12}$ alkylsulfonyl, $C_{1-12}$ alkylsulfinyl, $C_{3-12}$ cycloalkyl, $C_{3-12}$ cycloalkylamino, $C_{3-12}$ heterocycloalkylamino, $C_{3-12}$ cycloalkoxy, $C_{3-12}$ cycloalkylacyl, $C_{3-12}$ cycloalkyloxycarbonyl, $C_{3-12}$ cycloalkylsulfonyl, $C_{3-12}$ cycloalkylsulfinyl, 5- to 12-membered aryl or heteroaryl, 5- to 12-membered arylalkyl or heteroarylalkyl, methyl, ethyl, n-propyl, isopropyl, —CH$_2$C(CH$_3$)(CH$_3$)(OH), cyclopropyl, cyclobutyl, propylmethylene, cyclopropionyl, benzyloxy, trifluoromethyl, aminomethyl, hydroxymethyl, methoxyl, formyl, methoxycarbonyl, methanesulfonyl, methylsulfinyl, ethoxy, acetyl, ethanesulfonyl, ethoxycarbonyl, dimethylamino, diethylamino, dimethylaminocarbonyl, diethylaminocarbonyl, $N(CH_3)_2$, $NH(CH_3)$, $—CH_2CF_3$, $—CH_2CH_2CF_3$, $—CH_2CH_2F$, $—CH_2CH_2S(=O)_2CH_3$, $—CH_2CH_2CN$, $—CH_2CH(OH)(CH_3)_2$, $—CH_2CH(F)(CH_3)_2$, $—CH_2CH_2F$, $—CH_2CF_3$, $—CH_2CH_2CF_3$, $—CH_2CH_2NH_2$, $—CH_2CH_2OH$, $—CH_2CH_2OCH_3$, $—CH_2CH_2CH_2OCH_3$, $—CH_2CH_2N(CH_3)_2$, $—S(=O)_2CH_3$, $—CH_2CH_2S(=O)_2CH_3$, and phenyl, thiazolyl, biphenyl, naphthyl, cyclopentyl, furyl, 3-pyrrolinyl, pyrrolidinyl, 1,3-dioxolanyl, pyrazolyl, 2-pyrazolinyl, pyrazolidinyl, imidazolyl, oxazolyl, thiazolyl, 1,2,3-oxazolyl, 1,2,3-triazolyl, 1,2,4-triazolyl, 1,3,4-thiadiazolyl, 4H-pyranyl, pyridyl, piperidinyl, 1,4-dioxanyl, morpholinyl, pyridazinyl, pyrimidinyl, pyrazinyl, piperazinyl, 1,3,5-trithiyl, 1,3,5-triazinyl, benzofuranyl, benzothienyl, indolyl, benzimidazolyl, benzothiazolyl, purinyl, quinolinyl, isoquinolinyl, cinnolinyl or quinoxalinyl.

Herein, the term "pharmaceutically acceptable" is aimed at those compounds, materials, compositions and/or formulations, which are within the scope of reliable medical judgment and applicable for use in contact with human and animal tissues but without too much toxicity, irritation, allergic reactions or other problems or complications, also meet the reasonable benefit/risk ratio.

The term "pharmaceutically acceptable salt" refers to a salt of the compound of the present invention, which is prepared from the compound with specific substituent discovered by the present invention and relatively non-toxic acid or alkali. When the compound of the present invention contains a relatively acidic functional group, an alkali-addition salt can be obtained by contacting the compound in a neutral form with sufficient amount of alkali in a pure solution or suitable inert solvent. The pharmaceutically acceptable alkali-addition salt includes the salt of sodium, potassium, calcium, ammonium, organic ammonia or magnesium or the like. When the compound of the present invention contains a relatively alkaline functional group, an acid-addition salt can be obtained by contacting the compound in a neutral form with sufficient amount of acid in a pure solution or suitable inert solvent. Examples of the pharmaceutically acceptable acid-addition salt include a salt of inorganic acid, the inorganic acid includes such as hydrochloric acid, hydrobromic acid, nitric acid, carbonic acid, bicarbonate, phosphoric acid, hydrogen phosphate, dihydrogen phosphate, sulfuric acid, hydrogen sulfate, hydriodic acid, phosphorous acid etc; and salt of organic acid, the organic acid includes such as acetic acid, propionic acid, isobutyric acid, maleic acid, malonic acid, benzoic acid, succinic acid, suberic acid, fumaric acid, lactic acid, mandelic acid, phthalic acid, phenylsulfonic acid, p-toluene sulfonic acid, citric acid, tartaric acid, methylsulfonic acid and the like; and also includes salt of amino acid (e.g. arginine etc.), and salt of organic acid such as glucuronic acid and the like (see Berge et al., "Pharmaceutical Salts", Journal of Pharmaceutical Science 66: 1-19 (1977)). Some specific compound of the present invention contains both alkaline and acidic functional groups so as to be transformed to be any alkali-addition or acid-addition salt.

Preferably, the neutral form of a compound is regenerated by contacting a salt with a base or an acid in a conventional manner and then separating the parent compound. The difference between a parent form of a compound and the various salt forms lies in some physical properties, such as that the solubility in a polar solvent is different.

The "pharmaceutically acceptable salt" in the present invention is the derivatives of the compound of the present invention, wherein, the parent compound is modified by salifying with an acid or an alkali. Examples of the pharmaceutically acceptable salt include but not limited to: an inorganic acid or organic acid salt of an alkali such as amine, an alkali metal or organic salt of acid radical such as carboxylic acid and so on. The pharmaceutically acceptable salt includes conventionally non-toxic salts or quaternary ammonium salts of the parent compound, such as a salt formed by a non-toxic inorganic acid or organic acid. The conventionally non-toxic salt includes but not limited to those salts derived from inorganic acids and organic acids, the inorganic acids or organic acids are selected from 2-acetoxybenzoic acid, 2-isethionic acid, acetic acid, ascorbic acid, phenylsulfonic acid, benzoic acid, bicarbonate, carbonic acid, citric acid, edetic acid, ethanedisulfonic acid, ethanesulfonic acid, fumaric acid, glucoheptose, gluconic acid, glutamic acid, glycolic acid, hydrobromic acid, hydrochloric acid, hydriodate, hydroxyl, hydroxynaphthoic, isethionic acid, lactic acid, lactose, dodecanesulfonic acid, maleic acid, malic acid, mandelic acid, methanesulfonic acid, nitric acid, oxalic acid, pamoic acid, pantothenic acid, phenylacetic acid, phosphoric acid, polygalacturonan, propionic acid, salicylic acid, stearic acid, folinate acid, succinic acid, aminosulfonic acid, sulfanilic acid, sulphuric acid, tannic acid, tartaric acid and p-toluene sulfonic acid.

The pharmaceutically acceptable salt of the present invention can be prepared by a conventional method with a parent compound containing an acidic or alkaline group. Generally, the preparation method of the salt comprising: reacting these compounds in forms of free acids or alkalis with stoichiometric amount of proper alkalis or acids in water or an organic solvent or the mixture of water and organic solvent. In general, preferably choose non-aqueous media such as ether, ethyl acetate, ethanol, isopropanol or acetonitrile and so on.

Except for the form of salt, there is a form of prodrug for the compound in the present invention. The prodrug of the compound described in the present invention is easily transformed to be the compound of the present invention via chemical changes under physiological conditions. Besides, the prodrug can be transformed to be the compound of the present invention via chemical or biochemical method in vivo environment.

Some compounds of the present invention can exist in the form of non-solvate or solvate forms, including hydrate forms. In general, the solvate form is similar to the non-solvate form, both of which are included within the scope of the present invention.

Some compounds of the present invention can contain asymmetric carbon atoms (optical center) or double bonds. The racemic isomers, diastereomers, geometric isomers and single isomers are included within the scope of the present invention.

The diagrammatic representation of the racemic isomer, the ambiscalemic and scalemic or the enantiopure compound of the present invention is from Maehr, J. Chem. Ed. 1985, 62: 114-120. Unless otherwise indicated, the absolute configuration of a stereocenter is represented by the wedge and dashed lines. When the compound of the present invention contains a vinyl double bond or other geometric asymmetric center, unless otherwise specified, E, Z geometric isomers are included. Similarly, all tautomeric forms are included within the scope of the present invention.

The compound of the present invention may exist as a specific geometric or stereoisomeric isomer. The present invention envisages all of this class of compounds, including cis- and trans-isomers, (−)- and (+)-antimers, (R)- and (S)-antimers, diastereomers, (D)-isomer, (L)-isomer, as well as racemic mixtures and other mixtures, such as enantiomers- or diasteroisomers-enriched mixtures, all of these mixtures are within the scope of the present invention. Other asymmetric carbon atoms may exist in substituents such as in an alkyl. All of these isomers and their mixtures are included within the scope of the present invention.

Optically active (R)- and (S)-isomers, (D)- and (L)-isomers can be prepared by asymmetric synthesis or chiral reagents or other conventional techniques. If an enantiomer of a compound of the present invention is wanted, asymmetric synthesis or derivatization action of the chiral auxiliaries can be employed in preparation, in which the resulting diastereomer mixtures are isolated, and the auxiliary groups are cleaved to provide the pure desired enantiomer. Or, when a molecule contains an alkaline functional group (such as amino) or an acidic functional groups (such as carboxyl), a salt of diastereomer is formed with an appropriate optical active acid or alkali, and then the pure enantiomer can be recycled after resolution on the salt of diastereomer by methods which is known in the art. In addition, the separation of an enantiomer and a diastereomer is usually realized by the chromatographic method, the chromatography method employs a chiral stationary phase, and optionally combined with the chemical derivatization method (e.g. an amine generates a carbamate).

One or more atoms constituting the compound of the present invention may comprise an unnatural proportion of atomic isotopes. For example, the compound can be labeled by a radioactive isotope, such as tritium ($^3$H), iodine-125 ($^{125}$I) or C-14 ($^{14}$C). All the variations in the isotopic composition of the compound disclosed in the present invention, whether radioactive or not, are included within the scope of the present invention.

The term "a pharmaceutically acceptable carrier" refers to any formulation or carrier medium which is capable of delivering effective amount of the active substance disclosed in the present invention, does not interfere with the biological activity of the active substance, and is with no toxic side-effects on host or patient, representative carrier includes water, oil, vegetables and minerals, cream base, lotion matrix, ointment matrix etc. The matrix comprises a suspension, a viscosity increaser, transdermal enhancers etc. Their formulations are well known to the person in cosmetic or topical drug art. Other information about the carrier can refer to Remington: The Science and Practice of Pharmacy, 21st Ed., Lippincott, Williams & Wilkins (2005), the content of which is incorporated into this article as reference.

The term "excipient" usually refers to a carrier, diluent and/or medium required for the preparation of an effective pharmaceutical composition.

In terms of drug or pharmacological active agent, the term "effective amount" or "therapeutically effective amount" refers to enough quantity of the drug or formulation that can achieve desired effects but is with no toxicity. For the oral formulation of the present invention, "an effective amount" of one active substance in the composition is the amount required to achieve desired effects in combination with another active substance in the composition. The determination of the effective amount varies from person to person, which depends on the age and the general situation of the recipient, also on the specific active substance. In one case, an appropriate effective amount can be determined by the person skilled in the art according to conventional tests.

The term "active ingredient", "therapeutic agent", "active substance" or "active agent" refers to a chemical entity, which can effectively treat disorder, illness or disease of a target subject.

The term "substituted" refers to one or more hydrogen atoms in a specific atom optionally substituted by a substituent, including a deuterium and a variant of hydrogen, as long as the valence state of the specific atom is normal and the compound obtained after substitution is stable. When the substituent is a ketone group (i.e. =O), it means that two hydrogen atoms are substituted. A substitution of ketone group does not occur in an aryl. The term "optionally substituted" means that it may be substituted or not be substituted, unless otherwise specified, the type and number of substituents can be arbitrary under the premise of stability available in chemistry.

When any parameter (e.g. R) shows an occurrence for more than one time in the composition or structure of the compound, the definition of each occurrence is independent. Therefore, for example, if a group is substituted by 0 to 2 of R(s), the group may optionally be substituted by at most two R(s), and R has an independent option in each case. In addition, the combination of substituents and/or their variants is allowed only if such a combination will lead to a stable compound.

When the number of the connection group is 0, such as —(CRR)$_0$—, it indicates that the connection group is a single bond. When one of the parameters is selected from a single bond, it indicates that the two groups which it is attached are directly connected, for example, when the L in A-L-Z represents a single bond, it indicates that the structure actually is A-Z.

When a substituent is vacant, it indicates that the substituent is absent, for example, when X in A-X is vacant, it indicates that the structure is actually A.

When bonds of a substituent can be crossly connected to two atoms of a ring, the substituent can be bonded to arbitrary atoms in the ring. When the listed substituent does not specify through which atom it is connected to the general structure formula including the compound that is not specifically mentioned, the substituent can be bonded through any of its atoms. The combination of substituents and/or their variants is allowed only if such a combination will lead to a stable compound. For example, the structural unit

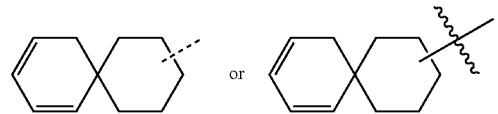

represents that the connection can occur on any atom in the cyclohexyl or cyclohexadiene.

The substituent in alkyl and heteroalkyl group is generally called "alkyl substituent", which can be selected from but not limited to the group consisting of —R', —OR', =O, =NR', =N—OR', —NR'R", —SR', halogen, —SiR'R"R'", OC(O)R', —C(O)R', —CO$_2$R', —C(=O)NR'R", —OC(O)NR'R", —NR"C(O)R', NR' C(O)NR"R'", —NR"C(O)$_2$R', —NR''''—C(NR'R"R''')=NR'''', NR'''' C(NR'R")=NR''', —S(O)R', —S(O)$_2$R', —S(O)$_2$NR'R", NR"SO$_2$R', —CN, —NO$_2$, —N$_3$, —CH(Ph)$_2$ and fluoro(C$_1$-C$_4$)alkyl, the number of the substituent is between 0 and (2m'+1), wherein m' is the total number of the carbon atoms in the group. R', R", R''', R'''' and R''''' are independently selected from H, substituted or unsubstituted heteroalkyl, substituted or unsubstituted aryl (e.g. aryl substituted by 1-3 of halogen), substituted or unsubstituted alkyl, alkoxy, thioalkoxy or aralkyl. When the compound of the present invention includes more than one R group, for example, each of the R group is independently selected, as each of R', R", R'", R"" and R""' group is when more than one of them are included. When R' and R" are attached to the same nitrogen atom, they can form 5-, 6-, or 7-membered ring together with the nitrogen atom. For example, —NR'R" includes but not limited to 1-pyrrolidinyl and 4-morpholinyl. According to the above discussion on substituent, the person skilled in the art can understand, the term "alkyl" is intended to include a group formed by bonding a carbon atom to a non-hydrogen group, such as a halogenated alkyl (e.g. —CF$_3$, —CH$_2$CF$_3$) and an acyl (e.g. —C(O)CH$_3$, —C(O)CF$_3$, C(O)CH$_2$OCH$_3$, etc.).

Similar to the substituent in the alkyl group, the substituent in aryl and heteroaryl group is generally called "aryl substituent", which can be selected from such as —R', —OR', —NR'R", —SR', -halogen, —SiR'R"R'", OC(O)R', —C(O)R', —CO$_2$R', —C(=O)NR'R", —OC(O)NR'R", —NR"C(O)R', NR' C(O)NR"R'", —NR"C(O)$_2$R', —NR""—C(NR'R"R'")=NR"", NR"" C(NR'R")=NR'", —S(O)R', —S(O)$_2$R', —S(O)$_2$NR'R", NR"SO$_2$R', —CN, —NO$_2$, —N$_3$, —CH(Ph)$_2$, fluoro(C$_1$-C$_4$) alkoxy and fluoro (C$_1$-C$_4$)alkyl, etc., a number of the substituent ranges from 0 to the total opening valence of the aromatic ring; wherein R', R", R'", R"" and R""' are independently and preferably selected from H, substituted or unsubstituted alkyl, substituted or unsubstituted heteroalkyl, substituted or unsubstituted aryl and substituted or unsubstituted heteroaryl. When the compound of the present invention includes more than one R group, for example, each of the R group is independently selected, as each of R', R", R'", R"" and R""' group is when more than one of them are included.

Two substituents attached to adjacent atoms in an aryl or a heteroaryl ring can optionally be substituted by a substituent with a general formula as -T-C(O)—(CRR')q-U—, wherein the T and U are independently selected from —NR—, —O—, CRR'— or a single bond, q is an integer from 0 to 3. As an alternative, two substituents attached to adjacent atoms in an aryl or a heteroaryl ring can optionally be substituted by a substituent with a general formula as -A(CH$_2$)r B—, wherein the A and B are independently selected from —CRR'—, —O—, —NR—, —S—, —S(O)—, S(O)$_2$—, —S(O)$_2$NR'— or a single bond, r is an integer from 1 to 4. Optionally, a single bond in the new ring thereby formed can be replaced by a double bond. As an alternative, two substituents attached to adjacent atoms in an aryl or a heteroaryl ring can optionally be substituted by a substituent with a general formula as -A(CH$_2$)$_s$X(CH$_2$)$_d$B—, wherein each of s and d is independently selected from an integer from 0 to 3, X is —O—, —NR', —S—, —S(O)—, —S(O)$_2$— or —S(O)$_2$NR'—. The substituent R, R', R" and R'" are respectively and preferably selected from hydrogen and substituted or unsubstituted (C$_1$-C$_6$) alkyl.

Unless otherwise specified, the term "halogenated" or "halogen" itself or as a part of another substituent refers to fluorine, chlorine, bromine or iodine atom. In addition, the term "halogenated alkyl" is intended to include monohalogenated alkyl and polyhalogenated alkyl. For example, the term "halogenated (C$_1$-C$_4$) alkyl" is intended to include but not limited to trifluoromethyl, 2,2,2-trifluoroethyl, 4-chlorobutyl and 3-bromopropyl, etc.

Examples of halogenated alkyl include but not limited to: trifluoromethyl, trichloromethyl, pentafluoroethyl, and pentachloroethyl. The "alkoxy" represents that the alkyl group with a specific number of carbon atoms is connected by an oxygen bridge. The C$_{1-6}$ alkoxy includes C$_1$, C$_2$, C$_3$, C$_4$, C$_5$ and C$_6$ alkoxy. Examples of alkoxy include but not limited to: methoxy, ethoxy, n-propoxy, iso-propoxy, n-butoxy, sec-butoxy, tert-butoxy, n-pentyloxy and S-pentyloxy. The "cycloalkyl" includes saturated cyclic group, such as cyclopropyl, cyclobutyl or cyclopentyl. The 3- to 7-membered cycloalkyl includes C$_3$, C$_4$, C$_5$, C$_6$ and C$_7$ cycloalkyl. The "alkenyl" includes linear or branched hydrocarbon chain, wherein any stable sites on the chain exist one or more C—C double bonds, such as vinyl and propenyl.

The term "halo" or "halogen" refers to fluorine, chlorine, bromine and iodine.

Unless otherwise specified, the term "hetero" refers to a heteroatom or a heteroatomic group (i.e. a group containing a heteroatom), including atoms except carbon (C) and hydrogen (H) and groups containing these heteroatoms, such as including oxygen (O), nitrogen (N), sulfur (S), silicon (Si), germanium (Ge), aluminum (Al), boron (B), —O—, —S—, =O, =S, —C(=O)O—, —C(=O)—, —C(=S)—, —S(=O), —S(=O)$_2$—, and optionally substituted —C(=O)N(H)—, —N(H)—, —C(=NH)—, —S(=O)$_2$N(H)— or —S(=O) N(H)—.

Unless otherwise specified, the "ring" refers to substituted or unsubstituted cycloalkyl, heterocycloalkyl, cycloalkenyl, heterocycloalkenyl, cycloalkynyl, heterocycloalkynyl, aryl or heteroaryl. The ring includes a single ring, a joint ring, a spiro ring, a fused ring or a bridged ring. A number of the atoms in the ring is usually defined as the member of the ring, for example, "5- to 7-membered ring" is a ring looped with 5 to 7 atoms. Unless otherwise specified, the ring optionally contains 1-3 of heteroatoms. Therefore, "5- to 7-membered ring" includes, for example, phenyl pyridine and piperidinyl; on the other hand, the term "5- to 7-membered heterocycloalkyl ring" includes pyridyl and piperidinyl, but does not include phenyl. The term "ring" also includes a ring system containing at least one ring, wherein each ring is of the above definition independently.

Unless otherwise specified, the term "heterocycle" or "heterocyclyl" refers to a stable monocyclic, bicyclic or tricyclic ring containing a heteroatom and a heteroatomic group, they can be saturated, partially unsaturated or unsaturated (aromatic), they contain carbon atoms and 1, 2, 3 or 4 of heteroatom in the ring which is independently selected from the group consisting of N, O and S, wherein any of the heterocycle can be fused to a benzene ring to form a bicyclic ring. Nitrogen and sulfur atoms can be optionally oxidized (i.e., NO and S(O)$_p$). The nitrogen atom can be substituted or unsubstituted (i.e. N or NR, wherein R is H or other substituent that has been defined herein). The heterocycle can be attached to the side group of any heteroatom or carbon atom to form a stable structure. If the formed compound is stable, the heterocycle described herein can be substituted on its carbon or nitrogen atom. The nitrogen atom in the heterocycle is optionally quaternized. As a preferred embodiment of the present invention, when the total number of S and O atoms contained in the heterocycle exceeds 1, these heteroatoms are not adjacent to each other. As another preferred embodiment of the present invention, the total number of S and O atoms in the heterocycle is no more than 1. As used herein, the term "aromatic heterocyclic group" or "heteroaryl" refers to a stable 5-, 6-, 7-membered monocycle or bicycle or 7-, 8-, 9- or 10-membered bicyclic heteroaromatic ring, which contains carbon atoms and 1, 2, 3 or 4 of heteroatom in the ring which independently selected from the group consisting of N, O and S. The nitrogen atom can be substituted or unsubstituted (i.e. N or NR, wherein R is H or other substituent that has been defined herein). Nitrogen and sulfur atoms can be optionally oxidized (i.e., NO and S(O)$_p$). It is worth noting that, the total number of S and O atoms in the heteroaromatic ring is no more than 1. Bridged rings are also included in the definition of the heterocycle. When one or more atoms (i.e. C, O, N, or S) are connected to two nonadjacent carbon atoms or nitrogen atoms, a bridged ring is formed. The preferred bridged ring includes but not limited to: one carbon atom, two carbon atoms, one nitrogen atom, two nitrogen atoms and one carbon-nitrogen group. It is worth noting that, a bridge always converts a monocyclic ring into a tricyclic ring. In the bridged ring, the substituent in the ring can also locate on the bridge.

Examples of heterocyclic compound include but not limited to: acridinyl, azocinyl, benzimidazolyl, benzofuranyl, benzomercaptofuranyl, benzomercaptophenyl, benzoxazolyl, benzoxazolinyl, benzothiazolyl, benzotriazolyl, benzotetrazolyl, benzoisoxazolyl, benzoisothiazolyl, benzoimidazolinyl, carbazolyl, 4aH-carbazolyl, carbolinyl, chromanyl, chromene, cinnolinyl decahydroquinolyl, 2H,6H-1,5,2-dithiazinyl, dihydrofuro[2,3-b]tetrahydrofuranyl, furanyl, furazanyl, imidazolidinyl, imidazolinyl, imidazolyl, 1H-indazolyl, indoalkenyl, indolinyl, indolizinyl, indolyl, 3H-indolyl, isatino group, isobenzofuranyl, pyranyl, isoindolyl, isoindolinyl, isoindolyl, indolyl, isoquinolyl, isothiazolyl, isoxazolyl, methylenedioxyphenyl, morpholinyl, naphthyridinyl, octahydroisoquinolyl, oxadiazolyl, 1,2,3-oxadiazolyl, 1,2,4-oxadiazolyl, 1,2,5-oxadiazolyl, 1,3,4-oxadiazolyl, oxazolidinyl, oxazolyl, isoxazolyl, hydroxyl indyl, pyrimidyl, phenanthridinyl, phenanthrolinyl, phenazine, phenothiazine, benzopurinyl, phenoxazinyl, phthalazinyl, piperazinyl, piperidyl, oxopiperidinyl, 4-oxopiperidinyl, piperonyl, pteridyl, purinyl, pyranyl, pyrazinyl, pyrazolidinyl, pyrazolinyl, pyrazolyl, pyridazinyl, oxazolopyridine, pyridinoimidazole, pyridinothiazole, pyridyl, pyrimidinyl, pyrrolidinyl, pyrrolinyl, 2H-pyrrolyl, pyrrolyl, pyrazolyl, quinazolinyl, quinolyl, 4H-quinolizinyl, quinoxalinyl, quinuclidinyl, tetrahydrofuryl, tetrahydroisoquinolinyl, tetrahydroquinolinyl, tetrazolyl, 6H-1,2,5-thiadiazinyl, 1,2,3-thiadiazolyl, 1,2,4-thiadiazolyl, 1,2,5-thiadiazolyl, 1,3,4-thiadiazolyl, thianthrenyl, thiazyl, isothiazolylthienyl, thienyl, thiophenoxazolyl, thiophenothiazolyl, thiophenoimidazolyl, thienyl, triazinyl, 1,2,3-triazolyl, 1,2,4-triazolyl, 1,2,5-triazolyl, 1,3,4-triazolyl and xanthenyl. Fused ring and spiro ring compound are also included.

Unless otherwise specified, the term "hydrocarbonyl" or its specific concept (such as alkyl, alkenyl, alkynyl, phenyl, etc.) itself or as a part of another substituent represents a linear, branched or cyclic hydrocarbonyl or a combination thereof, which can be fully saturated, monocyclic or polycyclic unsaturated, can be monosubstituted, disubstituted or polysubstituted, can be univalent (such as methyl), bivalent (such as methylene) or multivalent (such as methenyl), can include bivalent or multivalent atomic groups, with a specified number of carbon atoms (such as that $C_1$-$C_{10}$ refers to having 1-10 carbon atoms). The term "alkyl" includes but not limited to an aliphatic hydrocarbonyl and aromatic hydrocarbonyl, the aliphatic hydrocarbonyl includes linear and cyclic structures, specifically includes but not limited to alkyl, alkenyl and alkynyl, the aromatic hydrocarbonyl includes but not limited to 6- to 12-membered aromatic hydrocarbonyl such as benzene, naphthalene and the like. In some embodiments, the term "hydrocarbonyl" refers to linear or branched groups or their combination, which can be completely saturated, monocyclic or polycyclic unsaturated, can include divalent and polyvalent groups. Examples of saturated hydrocarbonyl include but not limited to homologues or isomers of methyl, ethyl, n-propyl, iso-propyl, n-butyl, tert-butyl, iso-butyl, sec-butyl, iso-butyl, cyclohexyl, (cyclohexyl) methyl, cyclopropyl methyl, and n-amyl, n-hexyl, n-heptyl, n-octyl and the like. Unsaturated alkyl has one or more double or triple bond, examples of which includes but not limited to vinyl, 2-propenyl, butenyl, crotyl, 2-isopentenyl, 2-butadienyl, 2,4-(pentadienyl), 3-(1,4-pentadienyl), acetenyl, 1- and 3-propinyl, 3-butynyl, and more advanced homologues and isomers.

Unless otherwise specified, the term "heterohydrocarbonyl" or its specific concepts (such as heteroalkyl, heteroalkenyl, heteroalkynyl, heteroaryl, etc.) itself or the term combining with another term refers to a stable linear, branched or cyclic hydrocarbonyl or their combinations, which consists of a certain number of carbon atoms and at least one heteroatom. In some embodiments, the term "heterohydrocarbonyl" itself or the term combining with another term refers to a stable linear, branched hydrocarbonyl or their combinations, which consists of a certain number of carbon atoms and at least one heteroatom. In a typical embodiment, the heteroatom is selected from the group consisting of B, O, N and S, in which the nitrogen and sulfur atoms are optionally oxidized, and the nitrogen atom is optionally quaternized. The heteroatom or the hetero-atomic group can be located in any internal position of the heterohydrocarbonyl (including the position where hydrocarbonyl is attached to the rest part of the molecule). Examples include but not limited to —$CH_2$—$CH_2$—O—$CH_3$, —$CH_2$—$CH_2$—NH—$CH_3$, —$CH_2$—$CH_2$—N($CH_3$)—$CH_3$, —$CH_2$—S—$CH_2$—$CH_3$, —$CH_2$—$CH_2$, —S(O)—$CH_3$, —$CH_2$—$CH_2$—S(O)$_2$—$CH_3$, —CH=CH—O—$CH_3$, —$CH_2$—CH=N—$OCH_3$ and —CH=CH—N($CH_3$)—$CH_3$. At most two heteroatoms are adjacent, such as —$CH_2$—NH—$OCH_3$.

The terms "alkoxy", "alkylamino" and "alkylthio" (or thioalkoxy) are the idiomatic expressions, which refers to the alkyl group is attached to the rest of molecule through an oxygen, an amino, or a sulfur atom, respectively.

Unless otherwise specified, the term "cyclohydrocarbonyl", "heterocyclohydrocarbonyl" or its specific concept (such as aryl, heteroaryl, cycloalkyl, heterocycloalkyl, cycloalkenyl, heterocyclovinyl, cycloalkynyl, heterocycloalkynyl, etc.) itself or the term combining with other terms respectively refers to a cyclic "hydrocarbonyl", "heterohydrocarbonyl". In addition, in terms of heterohydrocarbonyl or heterocyclohydrocarbonyl (such as heteroalkyl, heterocycloalkyl), heteroatoms can occupy the position where the heterocyclic ring is attached to the rest part of the molecule. Examples of the cycloalkyl include but not limited to cyclopentyl, cyclohexyl, 1-cyclohexenyl, 3-cyclohexenyl, cycloheptyl etc. Unrestricted examples of the heterocyclyl include 1-(1,2,5,6-tetrahydropyridinyl), 1-piperidyl, 2-piperidyl, 3-piperidyl, 4-morpholinyl, 3-morpholinyl, tetrahydrofuran-2-yl, tetrahydrofuranylindol-3-yl, tetrahydrothiophene-2-yl, tetrahydrothiophene-3-yl, 1-piperazinyl and 2-piperazinyl.

Unless otherwise specified, the term "aryl" refers to a polyunsaturated aromatic hydrocarbon substituent, which can be monosubstituted, disubstituted or multisubstituted, can be univalent, bivalent or multivalent. It can be monocyclic or polycyclic (such as 1 to 3 rings, at least one of which is aromatic). They fuse together or connect by a covalent linkage. The term "heteroaryl" refers to an aryl (or ring) containing 1 to 4 heteroatoms. In an exemplary embodiment, the heteroatom is selected from the group consisting of B, N, O, and S, in which the nitrogen and sulfur atoms are optionally oxidized, and the nitrogen atom is optionally quaternized. The heteroaryl group can be connected to the rest part of the molecule via a heteroatom. Unrestricted examples of an aryl or a heteroaryl include phenyl, 1-naphthyl, 2-naphthyl, 4-biphenyl, 1-pyrrolyl, 2-pyrrolyl, 3-pyrrolyl, 3-pyrazolyl, 2-imidazolyl, 4-imidazolyl, pyrazinyl, 2-oxazolyl, 4-oxazolyl, 2-phenyl-4-oxazolyl, 5-oxazolyl, 3-isoxazolyl, 4-isoxazolyl, 5-isoxazolyl, 2-thiazolyl, 4-thiazolyl, 5-thiazolyl, 2-furanyl, 3-furanyl, 2-thienyl, 3-thienyl, 2-pyridyl, 3-pyridyl, 4-pyridyl, 2-pyrimidinyl, 4-pyrimidinyl, 5-benzothiazolyl, purinyl, 2-benzoimidazolyl, 5-indolyl, 1-isoquinolyl, 5-isoquinolyl, 2-quinoxalyl, 5-quinoxalyl, 3-quinolyl and 6-quinolyl. Any one of the substituents in the aryl and heteroaryl ring system is selected from the acceptable substituents described below.

For the sake of briefness, when used in combination with other terms (e.g. aryloxy, arylthio, aralkyl), the aryl includes the definition of aryl and heteroaryl ring defined above. Therefore, the term "aralkyl" is intended to include the groups that aryl attached to alkyl (e.g. benzyl, phenyl ethyl, pyridyl methyl), including those alkyls wherein carbon atoms (such as methylene) has been replaced by such as oxygen atoms, such as phenoxy methyl, 2-pyridyloxymethyl-3-(1-naphthoxy) propyl, etc.

The term "leaving group" refers to a functional group or atom which can be replaced by another functional group or atom through a substitution reaction (e.g., nucleophilic substitution reaction). For example, representative leaving groups include triflate; chlorine, bromine, iodine; sulfonate, such as mesylate, tosylate, p-bromobenzene sulfonate, p-tosylate etc.; acyloxy, such as acetoxy, trifluoroacetoxy and so on.

The term "protecting group" includes but not limited to "the protecting group of an amino", "the protecting group of a hydroxyl", or "the protecting group of a mercapto". The term "the protecting group of an amino" refers to a protecting group that is suitable for preventing side reactions occur at the nitrogen atom of an amino group. A representative protecting group of an amino includes but not limited to: formyl; acyl, such as alkanoyl (such as acetyl, trichloroacetyl or trifluoroacetyl); alkoxycarbonyl, such as tert-butoxycarbonyl (Boc); aryl methoxycarbonyl, such as benzyloxycarbonyl (Cbz) and 9-fluorenylmethoxycarbonyl (Fmoc); aryl methyl, such as benzyl (Bn), triphenyl methyl (Tr), 1,1-bis-(4'-methoxyphenyl) methyl; silyl, such as trimethylsilyl (TMS) and tert-butyldimethylsilyl (TBS) and etc. The term "the protecting group of a hydroxyl" refers to a protecting group that is suitable for preventing side reactions of a hydroxyl group. A representative protecting group of a hydroxyl includes but not limited to: alkyl, such as methyl, ethyl, and tert-butyl; acyl, such as alkanoyl (such as acetyl); aryl methyl, such as benzyl (Bn), p-methoxybenzyl (PMB), 9-fluorenylmethyl (Fm) and diphenylmethyl (diphenylmethyl, DPM); silyl, such as trimethylsilyl (TMS) and tert-butyldimethylsilyl (TBS) and etc.

The compound of the present invention can be prepared through many synthetic methods which are well-known to the person skilled in the art, including the specific embodiments listed below and its combination with other chemical synthetic methods and the equivalent alternative methods which are known to the person skilled in the art, the preferred embodiments include but not limited to the embodiments of the present invention.

The solvents used in the present invention are commercially available. The present invention adopts the following abbreviations: aq. is water; eq. is equivalent, SEMCl is (2-(chloromethoxy)ethyl)trimethylsilane, i-PrOH is isopropanol; DCM is dichloromethane; PE is petroleum ether; DIPEA is N,N-diisopropylethylamine; DMF is N, N-dimethylformamide, EtOAc is ethyl acetate; EtOH is ethanol; MeOH is methanol, THF is tetrahydrofuran, DMSO is dimethyl sulfoxide; AcOH is acetic acid; BOC is tert-butoxycarbonyl, amino protecting group, Bn is benzyl; CuI is cuprous iodide; AcOCu is copper acetate; Pd(OH)$_2$ is palladium hydroxide; RT is room temperature; POCl$_3$ is phosphorus oxychloride, Boc$_2$O is Boc anhydride, Bn$_2$NH is dibenzylamine, (N-Bu)$_4$Sn is tetra-n-butyltin, DMAP is N,N-dimethylaminopyridine; (NH$_4$)$_2$CO$_3$ is ammonium carbonate; TFA is trifluoroacetate; TFAA is trifluoroacetic anhydride; TEA is triethylamine; DIBAl—H is diisobutylaluminum hydride; NIS is N-iodosuccinimide; Pd(PPh$_3$P)$_2$Cl$_2$ is bis(triphenylphosphine) palladium chloride; DAST is N,N-diethyl sulfide; N-BuSn is n-butyltin; Pd(PPh$_3$)$_4$ is tetraphenylphenylphosphine; LDA is lithium diisopropylamide; B(i-PrO)$_3$ is triisopropyl borate; CsF is cesium fluoride; NaH is sodium hydride; TMSCF$_3$ is trimethyl trifluoromethylsilane; MS is molecular sieve; Cbz is benzyloxycarbonyl; TBDMS is tert-butyldimethylsilyl.

Compounds are named by manual work or software ChemDraw®, or named in accordance with suppliers' catalogue on the current market.

Synthetic Methods

The compound of the present invention may be prepared by a series of synthetic steps in a variety of synthetic methods well known to those skilled in the art. The compounds of the present invention may be synthesized using synthetic methods described or alternative below.

Preferable methods include but not limited to the below description.

In particular, the compound of formula (I) may be prepared by reacting a reaction intermediate of formula (II) with a suitable aryl boric acid or borate when LG$_1$ represents a suitable leaving group halogen (e.g., chlorine, bromine, iodine) or the like, or with an aromatic halide when LG$_1$ represents a boric acid or a borate. The reaction is carried out in a suitable solvent (such as dioxane/water, toluene, etc.), which requires the use of a suitable base (such as cesium fluoride, sodium carbonate, sodium bicarbonate) and a suitable catalyst (such as Pd(dppf)Cl$_2$, Pd(PPh$_3$)$_4$, etc.). According to reaction scheme 1, the reaction is preferably carried out at 80° C. to 120° C.:

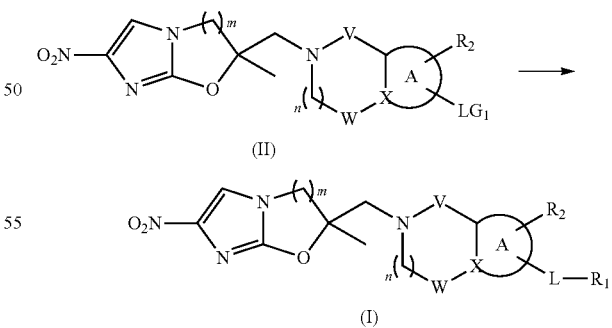

Reaction Scheme 1

All variables are defined as formula (I).

The intermediate of formula (II) may be prepared according to conventional reactions by a variety of synthetic methods well known to those skilled in the art. For example, the intermediate of formula (II) may be prepared according to reaction scheme 2:

Reaction Scheme 2

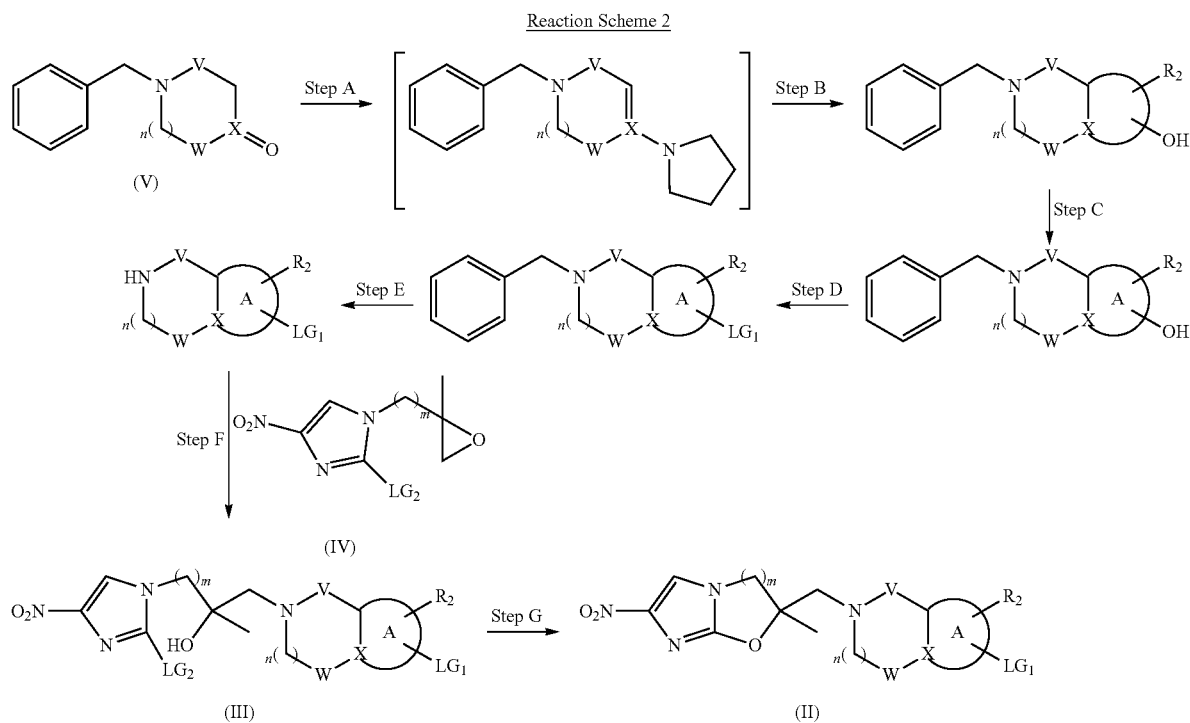

The variable LG$_1$ represents a suitable leaving group such as halogen, such as chlorine, bromine, iodine, boric acid or borate, etc. The variable LG$_2$ represents a suitable leaving group such as halogen (e.g., chlorine, bromine, iodine, etc.). All other variables are defined as formula (I). Step A and Step B of reaction scheme 2 are removing water of a benzyl-protected ketone and pyrrole in a suitable solvent such as toluene by azeotropic method at a suitable temperature and then cyclizing with acrylamide or propiolamide. Step C is aromatizing the cyclized product of the preceding step in the action of a suitable reagent such as liquid bromine, which usually need to be carried out under heating condition. The next step D is the reaction of a dehydrating reagent (e.g., phosphorus oxychloride, phosphorus oxybromide, etc.) with the product delivered from the preceding step at 110 to 130° C. In step E, the benzyl protecting group on the nitrogen atom is removed by hydrogenation or chemical means, the solvent is usually methanol or ethanol. In the next step F, the ring-opening reaction is usually carried out in a polar solvent (e.g., methanol, ethanol, isopropanol) in the presence of a base such as DIPEA. In step G, in the presence of a suitable base (such as sodium hydride, sodium acetate) and a suitable solvent (such as DMF or t-butyl acetate), a reaction is carried out at 0 to 120° C. to deliver the intermediate compound of formula (II).

It is clear that the reaction product may be separated from the reaction medium in the reaction mentioned before and after, and if necessary, further purified by methods of purification known to those skilled in the art, such as extraction, and chromatography. More specifically for the reaction product in which more than one enantiomer is present, the compound of formula (I) may be isolated to be isomers by methods of separation known to those skilled in the art, in particular preparative chromatography, such as preparative HPLC, SFC or the like.

The compound of formula (I) may also be prepared by cyclizing the compound of formula (III) directly under the action of a suitable base from reaction scheme 3:

Reaction Scheme 3

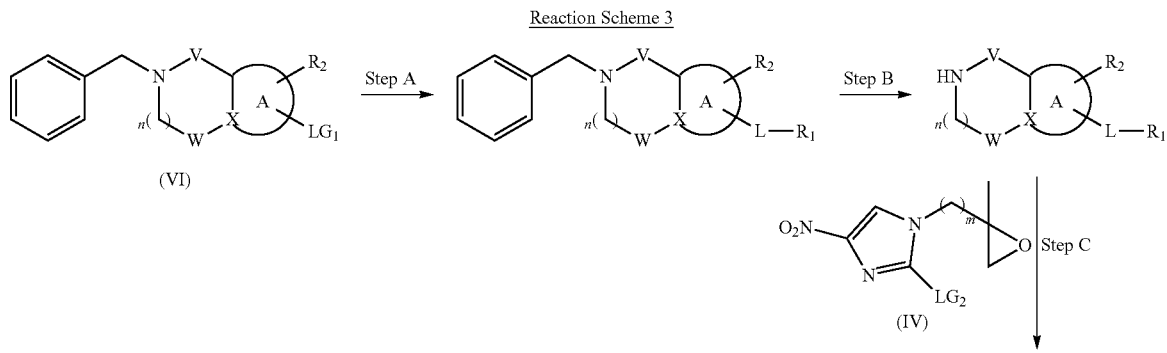

-continued

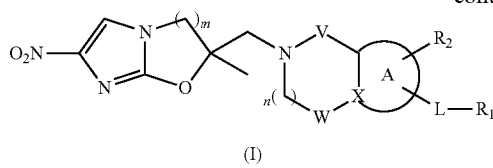

(I)

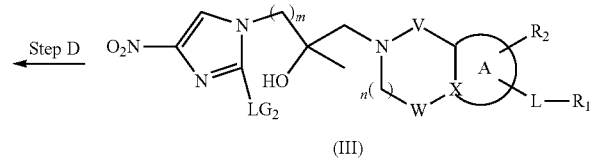

(III)

The variable LG₁ represents a suitable leaving group such as halogen, such as chlorine, bromine, iodine, boric acid or borate, etc. The variable LG₂ represents a suitable leaving group such as halogen such as chlorine, bromine, iodine, etc. All other variables are defined as formula (I) above.

C. The next step D is carried out in a suitable base (such as sodium hydride, sodium acetate) and a suitable solvent (such as DMF or t-butyl acetate) at 0 to 120° C.

In addition, the compound of formula (I) can also be prepared by reaction scheme 4:

Reaction Scheme 4:

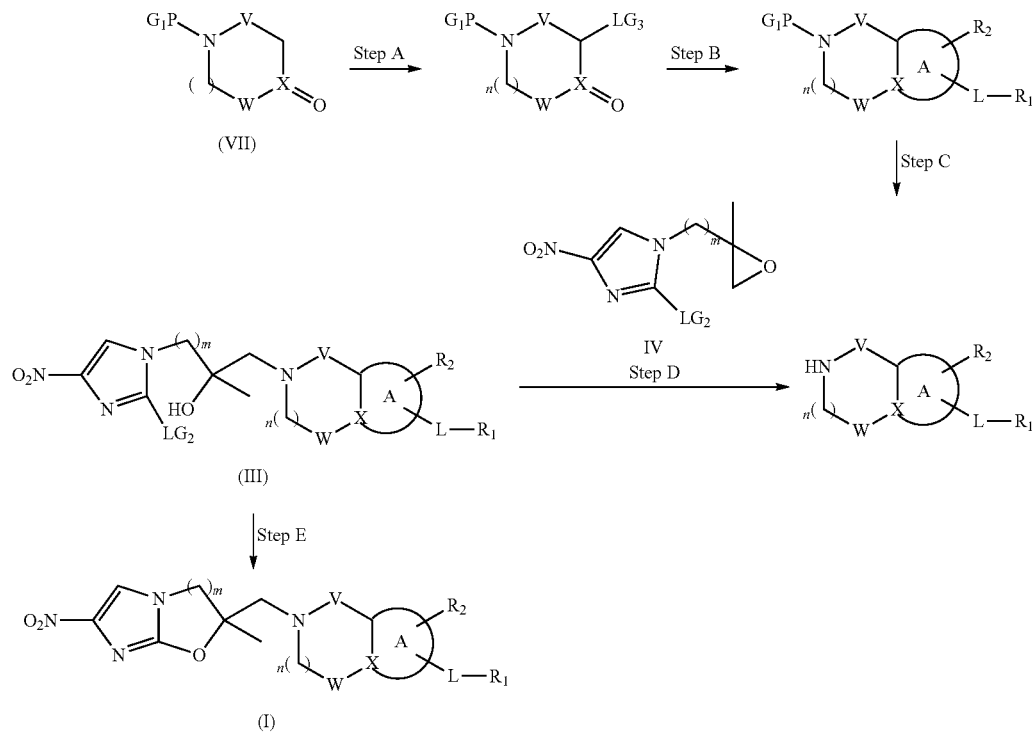

In step A, reacting the compound of formula (VI) with a suitable aryl boric acid or borate when $LG_1$ represents a suitable leaving group halogen (e.g., chlorine, bromine, iodine or the like), or with an aromatic halide when $LG_1$ represents a boric acid or borate. The reaction is necessary to use a suitable base (such as cesium fluoride, sodium carbonate, sodium bicarbonate), a suitable catalyst (such as Pd(dppf)Cl₂ etc.), in a suitable solvent (such as dioxane/water, toluene, etc.). According to the reaction scheme 1, the reaction is preferably carried out at 80° C. to 120° C. In step B, the benzyl protecting group on the nitrogen atom is removed by hydrogenation or chemical means such as chloroethylchloroformate and methanol, and the reaction is generally carried out at 60° C. to 80° C. In step C, the reaction of an epoxidized intermediate with a nucleophile usually requires a suitable base (such as DIPEA, sodium acetate, etc.), which is carried out in a suitable solvent (such as methanol, ethanol, isopropanol, t-butanol) at 80 to 100° C.

X is C, the variable $PG_1$ represents a suitable leaving group such as t-butoxycarbonyl, benzyl, benzyloxycarbonyl and the like, $LG_2$, $LG_3$ represents a suitable leaving group such as halogen, such as chlorine, bromine, iodine, N, N-dimethylaminomethylene and the like. All other variables are defined as formula (I).

The reaction scheme 4 comprises step A, which comprising reacting piperidone or pyrrolidone which has a suitable protecting group on the nitrogen with N, N-dimethylformamide dimethyl acetal or a suitable brominating reagent (liquid bromine, bromosuccinimide, copper bromide, phenyltrimethylamine tribromide) in a suitable solvent (such as toluene, xylene, DMF). The reaction usually requires a higher temperature of 50 to 140° C. In the next step B, the reaction of the resulting adduct with a nucleophile is carried out in the presence of a suitable solvent (such as methanol, ethanol, isopropanol, t-butanol, DMF) and a suitable base (such as triethylamine, DIPEA, or the like). In step C, the removal of the protecting group PG$_1$ is accomplished by hydrogenation or chemical means. In step D, the reaction of the epoxidized intermediate with a nucleophile generally requires a suitable base (such as DIPEA, sodium acetate, etc.), which is carried out in a suitable solvent (such as methanol, ethanol, isopropanol, t-butanol) at 80° C. to 100° C. The next step E is carried out in the presence of a suitable base (such as sodium hydride, sodium acetate) and a suitable solvent (such as DMF or t-butyl acetate) at 0 to 120° C. to deliver the compound of formula (I).

Intermediates in the preceding schemes may be obtained commercially available or may be prepared according to a general reaction scheme well known to those skilled in the art. For example, the intermediate compound of formula (IV) may be prepared according to reaction scheme 5:

Reaction Scheme 5:

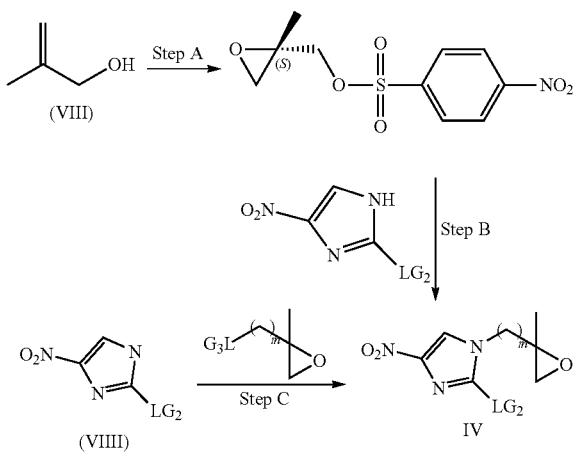

Each of the variable LG$_2$, LG$_3$ represents a suitable leaving group, such as halogen (e.g., chlorine, bromine, iodine, methanesulfonyl, etc.) respectively. All other variables are defined as formula (I).

The reaction scheme 5 comprises step A which comprising reacting an allyl alcohol with cumene peroxide by an oxidation reaction in the presence of the corresponding (+) diisopropyl tartrate or (−) diisopropyl tartrate and tetraisopropyl titanate. The reaction is usually carried out in a suitable solvent such as dichloromethane, toluene. The protection reaction of p-nitrobenzenesulfonyl chloride requires a suitable base (e.g., triethylamine, diisopropylethylamine, N,N-dimethylpyridine), and the reaction is usually carried out at a temperature range of −20° C. to 0° C. In the next step B, the transfer of epoxy to nitroimidazole is carried out by heating the above-obtained epoxy intermediate with the raw nitroimidazole. The reaction requires a suitable solvent (such as ethanol, isopropanol, t-butanol, tert-butyl acetate, etc.), a suitable base (e.g., diisopropylethylamine, potassium carbonate, etc.). The reaction is usually carried out at a temperature range of 40° C. to 100° C. In step C, by heating the epoxy with a leaving group and nitroimidazole, we could also directly obtain the non-optically active intermediate compound of formula (IV). The reaction requires a suitable solvent (such as ethanol, isopropanol, tert-butyl alcohol, t-butyl acetate, etc.), a suitable base (such as diisopropylethylamine, sodium acetate and the like). And the reaction is usually carried out at a temperature range of 40° C. to 100° C.

In order to obtain the compound of the present invention, it is sometimes desirable for those skilled in the art to modify or select the synthesis step or the reaction scheme on the basis of the existing embodiments.

The compound having the structure of formula (I) may also be delivered from a compound having the structure of formula (I) itself by a functional group conversion well known in the art.

The chemical reaction of a specific embodiment of the present invention is carried out in a suitable solvent, the solvent should be suitable for chemical changes and the reagents and materials required of the present invention. In order to obtain the compound of the present invention, it is sometimes desirable for those skilled in the art to modify or select the synthesis step or the reaction scheme on the basis of the existing embodiments.

An important consideration in any synthetic route planning in the art is the selection of a suitable protecting group for a reactive functional group (such as the amino group in the present invention). For trained practitioners, "Protective Groups in Organic Synthesis, Wiley and Sons, 1991" of Greene and Wuts is the authority of this area. All references cited herein are incorporated by reference in their entirety.

The compounds of the present invention may be prepared by a variety of synthetic methods well known to those skilled in the art including the specific embodiments listed below, embodiments thereof in combination with other chemical synthesis methods, and equivalent replacement methods known to those skilled in the art. Preferred embodiments include, but are not limited to, embodiments of the present invention.

The following examples further illustrate the present invention, but the present invention is not limited thereto.

All of the solvents used in the present invention are commercially available and can be used without further purification. The reaction is generally carried out under inert nitrogen in an anhydrous solvent. Proton nuclear magnetic resonance data are recorded on a Bruker Avance III 400 (400 MHz) spectrometer with a chemical shift represented by (ppm) at the low field of tetramethylsilane. The mass spectrum is measured on the Agilent 1200 Series plus 6110 (& 1956A). LC/MS or Shimadzu MS contains a DAD: SPD-M20A (LC) and Shimadzu Micromass 2020 Detector. The mass spectrometer is equipped with an electrospray ion source (ESI) operating in positive or negative mode.

Compounds are named by manual work or software ChemDraw®, commercially available compounds are named in accordance with suppliers' catalogue.

High performance liquid chromatography (HPLC) analyses are performed on a Shimadzu LC20AB system equipped with a Shimadzu SIL-20A autosampler and a Shimadzu DAD: SPD-M20A detector. Xtimate C18 column (the packing is 3 m, the specification is 2.1×300 mm) is used. Method of 0-60AB_6 min includes: applying a linear gradient, start eluting with 100% A (A is an aqueous solution of 0.0675% TFA in water) and end eluting with 60% B (B is a solution of 0.0625% TFA in MeCN) overall for 4.2 min and then eluting with 60% B for 1.0 min. The column is then re-equilibrated over 0.8 min to 100:0 with a total run time of 6 min. Method of 10-80AB_6 min includes: applying a linear gradient, start eluting with 90% A (A is an aqueous solution of 0.0675% TFA in water) and end eluting with 80% B (B is a solution of 0.0625% TFA in MeCN) overall for 4.2 min and then eluting with 80% B for 1.0 min. The column is then re-equilibrated over 0.8 min to 90:10 with a total run time of 6 min. The column temperature is at 50° C. with a flow rate of 0.8 mL/min. The Diode Array Detector has a scanning wavelength from 200 to 400 nm.

Thin layer chromatography (TLC) is performed on Silica gel GF254 in Sanpont-group and the spots are visualized by UV irradiation. Additional methods are also employed to visualize the spots in some cases. In these cases the TLC plate is developed with iodine (prepared by adding approximately 1 g of $I_2$ to 10 g silica gel and thoroughly mixing), vanillin (prepared by dissolving about 1 g vanillin in 100 mL 10% $H_2SO_4$), ninhydrin (available commercially from Aldrich), or Magic Stain (prepared by thoroughly mixing $(NH_4)_6Mo_7O_{24}.4H_2O$, 5 g $(NH_4)_2Ce(IV)(NO_3)_6$, 450 mL $H_2O$ and 50 mL concentrated $H_2SO_4$) to visualize the compound. Flash chromatography is performed using 40 to 63 μm (230 to 400 mesh) silica gel of Silicycle using analogous techniques as disclosed in Still, W. C.; Kahn, M.; and Mitra, M. Journal of Organic Chemistry, 1978, 43, 2923-2925. Typical solvents used for flash chromatography or thin layer chromatography are a mixture of dichloromethane/methanol, ethyl acetate/methanol and hexanes/ethyl acetate.

Preparative chromatography is performed on a Gilson-281 Prep LC 322 System using a Gilson UV/VIS-156 Detector. The column used is a Agella Venusil ASB Prep C18, 5 μm, 150×21.2 mm or Phenomenex Gemini C18, 5 μm, 150×30 mm; Boston Symmetrix C18, 5 μm, 150×30 mm or Phenomenex Synergi C18, 4 μm, 150×30 mm. Narrow gradients with acetonitrile/water, with the water containing 0.05% HCl or 0.25% HCOOH or 0.5% $NH_3.H_2O$, are used to elute the compounds at a flow rate of approximately 25 mL/min and a total run time of 8 to 15 min.

SFC analyses are performed on an Agilent 1260 Infinity SFC system with an Agilent 1260 Autosampler and an Agilent DAD: 1260 Detector. The column used is Chiralcel OD-H 250×4.6 mm I.D., 5 μm or Chiralpak AS-H 250×4.6 mm I.D., 5 μm or Chiralpak AD-H 250×4.6 mm I.D., 5 μm. Chromatographic conditions of OD-H_5_40_2.35ML: Chiralcel OD-H (the specification is 250×4.6 mm I.D., the packing is 5 μm); the mobile phase is 40% ethanol (0.05% DEA) in $CO_2$; the flow rate is 2.35 mL/min; the detection wavelength is 220 nm. Chromatographic conditions of AS-H_3_40_2.35ML: Chiralpak AS-H (the specification is 250×4.6 mm I.D., the packing is 5 μm); the mobile phase is 40% methanol (0.05% DEA) in $CO_2$; the flow rate is 2.35 mL/min; the detection wavelength is 220 nm. Chromatographic conditions of OD-H_3_40_2.35M: Chiralcel OD-H (the specification is 250×4.6 mm I.D., the packing is 5 μm); the mobile phase is 40% methanol (0.05% DEA) in $CO_2$; the flow rate is 2.35 mL/min; the detection wavelength is 220 nm. Chromatographic conditions of AD-H_2_50_2.35ML: Chiralpak AD-H (the specification is 250×4.6 mm I.D., the packing is 5 μm); the mobile phase is 50% methanol (0.1% MEA) in $CO_2$; the flow rate is 2.35 mL/min; the detection wavelength is 220 nm.

Preparative SFC analyses are performed on a Waters Thar 80 Pre-SFC System using a Gilson UV Detector. The column used is Chiralcel OD-H 250×4.6 mm I.D., 5 μm or Chiralpak AD-H 250×4.6 mm I.D., 5 μm. Narrow gradients with ethanol or methanol in $CO_2$, with the ethanol or methanol containing 0.05% $NH_3.H_2O$ or 0.05% DEA or 0.1% MEA, are used to elute the compound at a flow rate between 40 to 80 mL/min and a total run time between 20 to 30 min.

The following examples further illustrate the present invention, but the present invention is not limited thereto.

The absolute stereoscopic configurations of the chiral center carbon atoms of certain compounds or intermediates, or the configurations of double bonds, have not been tested experimentally. In this case, the isomers first isolated by chiral preparative chromatography are labeled "A" and the followed were labeled "B". Any one with ordinary skill in the art can distinguish the isomers A and B by certain means, such as NMR. This method is the most appropriate method of determining stereoscopic configuration.

The examples set forth below are prepared, separated and described by the methods described herein. The following examples are merely representative of the scope of the invention and are not intended to be exhaustive. The invention has been described in detail herein, in which the embodiments thereof are also disclosed, and various changes and modifications will be apparent to be obvious those skilled in the art without departing from the spirit and scope of the invention with respect to the specific embodiments of the invention.

Preparation of key intermediates A, B and C:
(S)-2-((2-Chloro-7,8-dihydro-1,6-naphthyridin-6(5H)-yl)methyl)-2-methyl-6-nitro-2,3-dihydroimidazo[2,1-b]oxazole

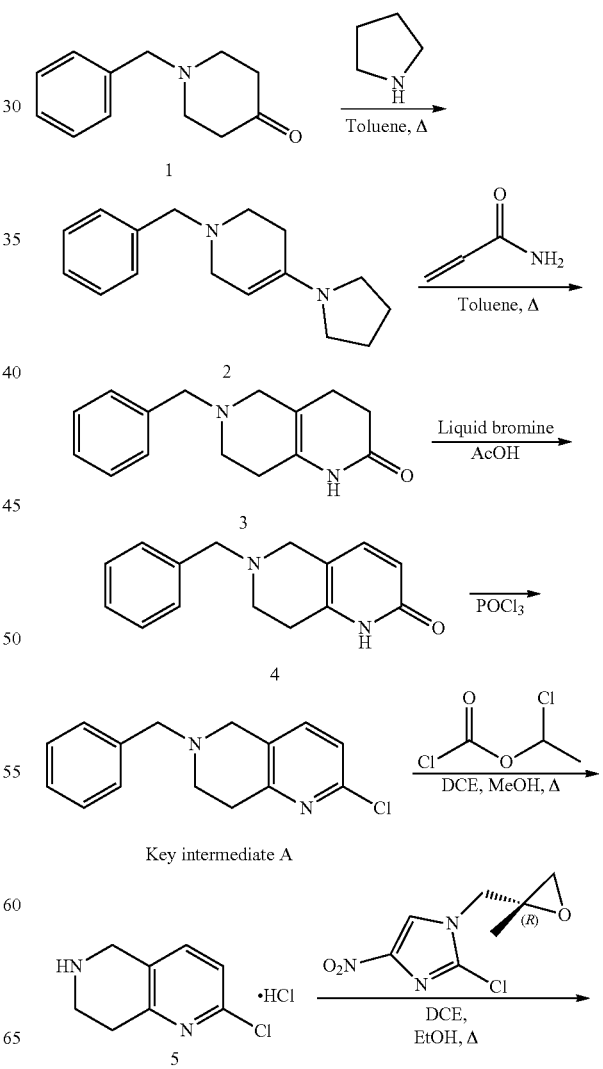

-continued

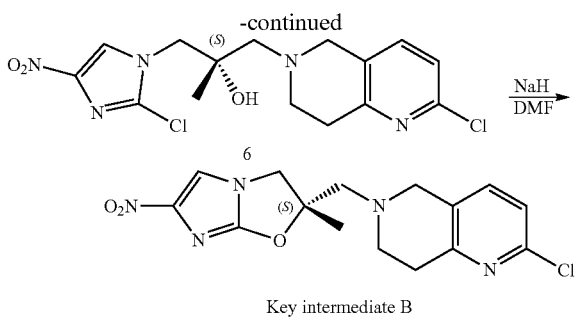

Key intermediate B

Step 1:

1-Benzyl-4-pyrrolidin-1-yl-3,6-dihydro-2H-pyridine

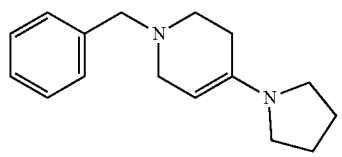 [SMILES: C1=C(N2CCCC2)CCN(Cc2ccccc2)C1]

Pyrrolidine (33.82 g, 475.56 mmol, 1.00 eq) was added to a solution of 1-benzyl-4-one (90.00 g, 475.56 mmol, 1.00 eq.) in toluene (70.00 mL) at 30° C. under the nitrogen gas atmosphere. The mixture was stirred at 130° C. for 12 hours. The mixture was then concentrated in vacuo at 45° C. to deliver 1-benzyl-4-pyrrolidin-1-yl-3,6-dihydro-2H-pyridine (110.00 g, crude) as a yellow solid which was used for the next step without further purification.

Step 2:

6-Benzyl-1,3,4,5,7,8-hexahydro-1,6-naphthyridin-2-one

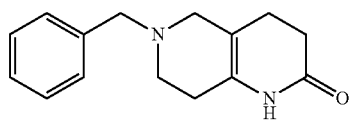 [SMILES: O=C1CCC2=C(CCN(Cc3ccccc3)C2)N1]

Propan-2-enamide (52.35 g, 736.51 mmol, 1.50 eq) was added to a solution of 1-benzyl-4-pyrrolidin-1-yl-3,6-dihydro-2H-pyridine (119.00 g, 491.01 mmol, 1.00 eq) in toluene (80.00 mL) at 30° C. The mixture was then stirred at 130° C. for 12 hours, the mixture was cooled to 30° C. and concentrated under reduced pressure at 45° C. The residue was washed with petroleum ether (100 mL), filtered and the cake was concentrated in vacuo to deliver 6-benzyl-1,3,4,5,7,8-hexahydro-1,6-naphthyridin-2-one (76.00 g, 313.63 mmol, 63.88% yield) as a yellow solid.

Step 3:

6-Benzyl 1,5,7,8-tetrahydro-1,6-naphthyridin-2-one

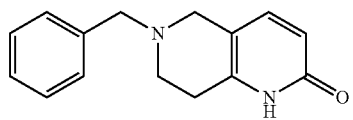 [SMILES: O=c1ccc2c([nH]1)CCN(Cc1ccccc1)C2]

6-Benzyl-1,3,4,5,7,8-hexahydro-1,6-naphthyridin-2-one (35.00 g, 144.44 mmol, 1.00 eq) was dissolved in acetic acid (200.00 mL). A mixture of liquid bromine (23.08 g, 144.44 mmol, 1.00 eq) and acetic acid (200.00 mL) was added to the solution at 0° C. under the nitrogen gas atmosphere. The mixture was stirred at 0° C. for 30 minutes and then heated to 110° C. and stirred for 12 hours. The mixture was cooled to 30° C. and concentrated under reduced pressure at 45° C. The residue was poured into an aqueous solution of sodium carbonate (70 mL) and stirred for 10 minutes. The solid was filtered and washed with petroleum ether (30 mL) and dried in vacuo to deliver 6-benzyl 1,5,7,8-tetrahydro-1,6-naphthyridin-2-one (35.00 g, crude) as a yellow solid. LCMS (ESI) m/z: 241 (M+1).

Step 4:

6-Benzyl-2-chloro-7,8-dihydro-5H-1,6-naphthyridine

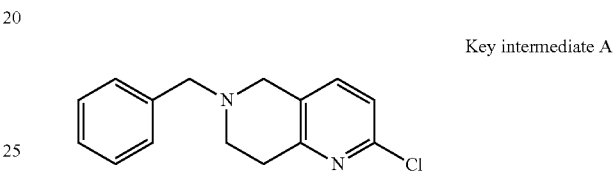

Key intermediate A

6-Benzyl-1,5,7,8-tetrahydro-1,6-naphthyridin-2-one (35.00 g, 145.65 mmol, 1.00 eq) was added to phosphorus oxychloride (178.62 g, 1.16 moles, 8.00 eq) in portions at 30° C., after the addition, the mixture was stirred for 10 minutes and then the mixture was heated to 130° C. for 12 hours. The mixture was cooled and the phosphorus oxychloride was distilled off at 50° C. under reduced pressure. The residue was diluted with dichloromethane and poured into water (500 mL) and the mixture was basified with a saturated sodium carbonate solution (500 mL). The aqueous phase was extracted with dichloromethane (500 mL×3). The combined organic phases were washed with saturated brine (30 mL×2), dried over anhydrous sodium sulfate, filtered and concentrated in vacuo. The residue was purified by silica gel chromatography (petroleum ether/ethyl acetate=15/1, 7/1) to deliver 6-benzyl-2-chloro-7,8-dihydro-5H-1,6-naphthyridine (the key intermediate A) (17.00 g, 65.70 mmol, 45.11% yield) as a yellow solid. $^1$H NMR (400 MHz, CDCl$_3$): δ 7.41-7.30 (m, 5H), 7.26 (d, J=8.0 Hz, 1H), 7.10 (d, J=8.0 Hz, 1H), 3.73 (s, 2H), 3.61 (s, 2H), 3.07-3.01 (m, 2H), 2.88-2.83 (m, 2H).

Step 5:

2-Chloro-5,6,7,8-tetrahydro-1,6-naphthyridine hydrochloride

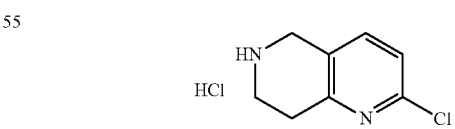

6-Benzyl-2-chloro-7,8-dihydro-5H-1,6-naphthyridine (15.00 g, 57.97 mmol, 1.00 eq) was dissolved in dichloroethane (80.00 mL), 1-chloroethyl carbonochloridate (12.43 g, 86.96 mmol, 1.50 eq) was added at 0° C. under the nitrogen gas atmosphere. The mixture was stirred at 0° C. for 0.5 h and then heated to 85° C. and stirred for 12 hours. The mixture was concentrated and then dissolved in methanol (30.00 mL) and the mixture was stirred at 80° C. for an additional hours. The mixture was cooled and filtered to deliver 2-chloro-5,6,7,8-tetrahydro-1,6-naphthyridine (6.30 g crude) as a white solid, which was used for the next step without further purification.

Step 6:

(S)-1-(2-Chloro-4-nitro-1H-imidazol-1-yl)-3-(2-chloro-7,8-dihydro-1,6-naphthyridin-6(5H)-yl)-2-methylpropan-2-ol

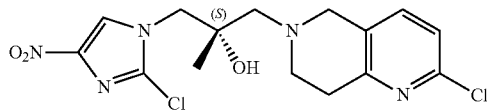

2-Chloro-5,6,7,8-tetrahydro-1,6-naphthyridine (11.00 g, 65.24 mmol, 1.00 eq) and 2-chloro-1-[[(2R)-2-methyloxiran-2-yl]methyl]-4-nitroimidazole (14.20 g, 65.24 mmol, 1.00 eq) were dissolved in ethanol (150.00 mL), N, N-diisopropylethylamine (21.08 g, 163.10 mmol, 2.50 eq) was added to the solution at 15° C. under the nitrogen gas atmosphere. The mixture was stirred at 85° C. for 12 hours. The mixture was then cooled to 15° C. and concentrated under reduced pressure at 60° C. Water (30 mL) was added to the residue. The mixture was extracted with ethyl acetate (200 mL×4) and the combined organic phases were washed with saturated brine (100 mL×2), dried over anhydrous sodium sulfate, filtered and concentrated in vacuo. The residue was purified by silica gel chromatography (petroleum ether/ethyl acetate=20/1, 1/2) to deliver (S)-1-(2-chloro-7,8-dihydro-5H-1,6-naphthyridin-6-yl)-3-(2-chloro-4-nitroimidazol-1-yl)-2-methyl-propan-2-ol (20.00 g, 51.78 mmol, 79.37% yield) as a yellow solid. LCMS (ESI) m/z: 386 (M+1).

Step 7:

(S)-2-((2-Chloro-7,8-dihydro-1,6-naphthyridin-6(5H)-yl)methyl)-2-methyl-6-nitro-2,3-dihydroimidazo[2,1-b]oxazole Key intermediate B

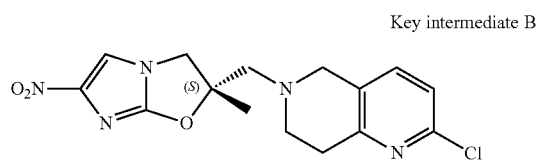

(S)-1-(2-Chloro-7,8-dihydro-5H-1,6-naphthyridin-6-yl)-3-(2-chloro-4-nitroimidazol-1-yl))-2-methyl-propan-2-ol (9.00 g, 23.30 mmol, 1.00 eq) was dissolved in DMF (80.00 mL) and NaH (1.12 g, 46.60 mmol, 2.00 eq) was added at −20° C. under the nitrogen gas atmosphere. The mixture was stirred at −20° C. for 10 minutes, and then warmed to −5° C. and stirred for 10 minutes. The mixture was then warmed to 15° C. and stirred for another 10 minutes. The mixture was cooled to 0° C., and then added dropwise to an aqueous hydrochloric acid solution (0.25 mol, 400 mL) and the mixture was basified with an aqueous sodium bicarbonate solution to the pH=7 to 8. The precipitate was filtered and dried to deliver (S)-2-((2-chloro-7,8-dihydro-1,6-naphthyridin-6(5H)-yl)methyl)-2-methyl-6-nitro-2,3-dihydroimidazo [2,1-b]oxazole (the key intermediate B) (6.70 g, 19.16 mmol, 82.22% yield) as a yellow solid. ¹H NMR (400 MHz, CDCl₃) δ: 7.52 (s, 1H), 7.27 (s, 1H), 7.12 (d, T=8.0 Hz, 1H), 4.39 (d, T=9.6 Hz, 1H), 3.96 (d, J=9.6 Hz, 1H), 3.82 (q, J=15.3 Hz, 2H), 3.14-3.03 (m, 2H), 3.02-2.85 (m, 3H), 2.80 (d, T=14.8 Hz, 1H), 1.68 (s, 3H). LCMS (ESI) m/z: 350 (M+1).

(R)-2-chloro-1-((2-methyloxiran-2-yl)methyl)-4-nitro-1H-imidazole

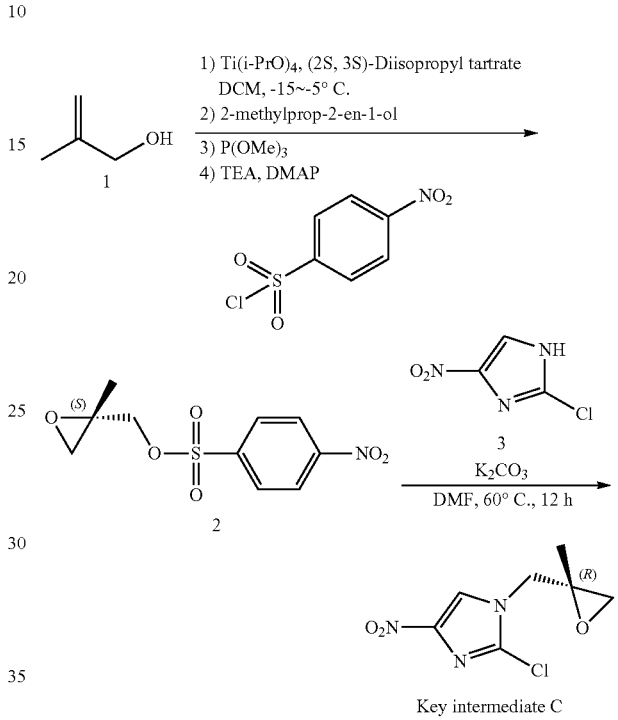

Key intermediate C

Step 1:

(S)-(2-Methyloxiran-2-yl)methyl-4-nitrobenzenesulfonate

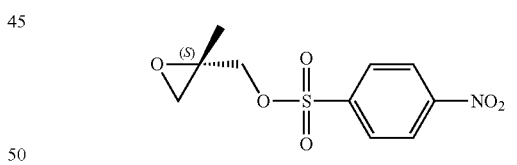

2-Methylprop-2-en-1-ol (15.00 g, 208.02 mmol, 1.00 eq) and (2S,3S)-diisopropyl tartrate (2.92 g, 12.48 mmol, 0.06 eq)) were added to a suspension of 4A molecular sieves (15.00 g) in DCM (300.00 mL) at 10 to 30° C. under the nitrogen gas atmosphere. The mixture was cooled to −10 to 0° C. and titanium tetraisopropoxide (3.55 g, 12.48 mmol, 0.06 eq) was added dropwise to the reaction mixture to maintain the reaction temperature at −15 to −5° C. and the mixture was stirred for 0.5 hour. (1-Hydroperoxy-1-methylethyl) benzene (63.32 g, 416.03 mmol, 2.00 eq) was added dropwise to the mixture, the temperature was maintained at −15 to −5° C. After 3 hours, trimethyl phosphite (25.83 g, 208.02 mmol, 1.0 eq) was added to the reaction mixture at −15 to −5° C. After 20 minutes, 4-nitrobenzenesulfonyl chloride (46.10 g, 208.02 mmol, 1.00 eq), DMAP (1.27 g, 10.40 mmol, 0.05 eq) were added to the reaction mixture.

And then triethylamine (25.81 g, 208.02 mmol, 1.0 eq) was added dropwise. After the addition, the mixture was gradually raised to a temperature of 20° C. After 1 hour, water (100 mL) was added to the reaction mixture and stirred for 20 minutes and filtered. The filtrate was extracted with dichloromethane (50 mL×3). The combined organic phases were washed with saturated brine (30 mL*1), dried over anhydrous sodium sulfate, filtered and concentrated in vacuo. The residue was purified by silica gel chromatography (column height: 250 mm, diameter: 100 mm, 100-200 mesh silica gel, petroleum ether/ethyl acetate=30/1, 5/1) to deliver (S)-(2-methyloxiran-2-yl)methyl-4-nitrobenzenesulfonate (24.00 g, 87.83 mmol, 42.22% yield) as a pale yellow solid. $^1$H NMR (400 MHz, CDCl$_3$): δ 8.47-8.37 (m, 2H), 8.17-8.11 (m, 2H), 4.28 (d, J=10.9 Hz, 1H), 4.04 (d, J=10.9 Hz, 1H), 2.77-2.65 (m, 2H), 1.43-1.35 (m, 3H).

Step 2:

(R)-2-Chloro-1-((2-methyloxiran-2-yl)methyl)-4-nitro-1H-imidazole

Key intermediate C

Potassium carbonate (56.21 g, 406.71 mmol, 3.00 eq) was added to a mixture of 2-chloro-4-nitro-1H-imidazole (20.00 g, 135.57 mmol, 1.00 eq) and (S)-(2-methyloxiran-2-yl)methyl-4-nitrobenzenesulfonate (37.05 g, 135.57 mmol, 1.00 eq) in DMF (300 mL), the reaction mixture was degassed and replaced 3 times with nitrogen, the mixture was then stirred at 60° C. for 12 hours. The reaction mixture was concentrated under reduced pressure to remove the solvent. The residue was diluted, neutralized with a saturated sodium carbonate solution (200 mL). And the resulting mixture was extracted with ethyl acetate (50 mL×3). The combined organic layers were washed with saturated brine (50 mL×2), dried over sodium sulfate, filtered and concentrated under reduced pressure to give a residue. The residue was purified by column chromatography (SiO$_2$, petroleum ether/ethyl acetate=5/1, 2/1) to deliver (the key intermediate C) (R)-2-chloro-1-((2-methyloxiran-2-yl)methyl)-4-nitro-1H-imidazole (17.86 g, 82.07 mmol, 60.54% yield) as a yellow oil. LCMS (ESI) m/z: 218 (M+1).

Embodiment 1

2-Methyl-6-nitro-2-((2-phenyl-7,8-dihydro-1,6-naphthyridin-6(5H)-yl)methyl)-2,3-dihydroimidazo[2,1-b]oxazole

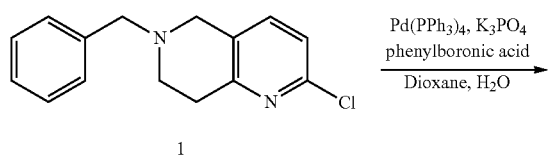

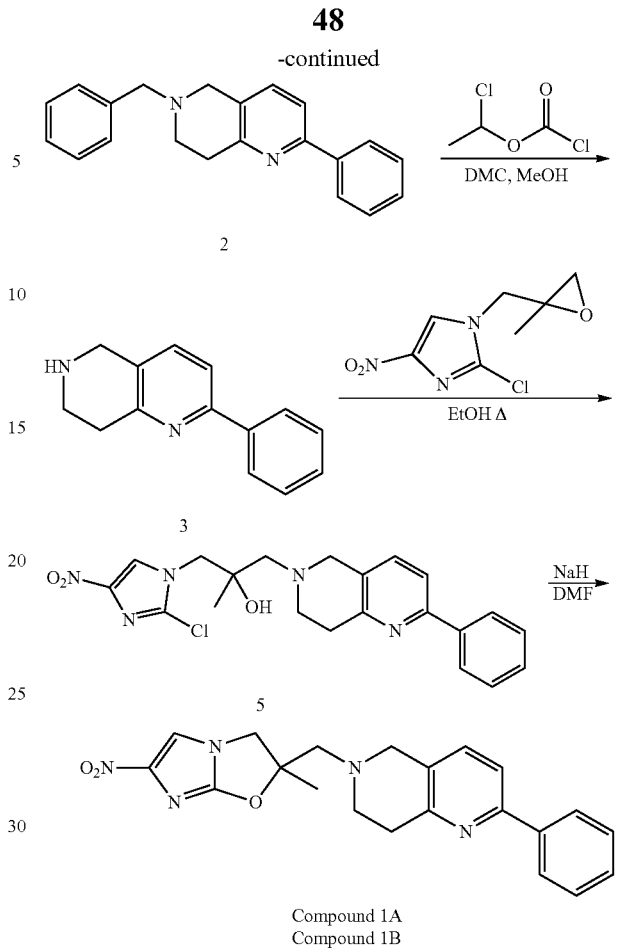

Compound 1A
Compound 1B

Step 1:

6-Benzyl-2-phenyl-5,6,7,8-tetrahydro-1,6-naphthyridine

Potassium phosphate (2.23 g, 10.51 mmol), phenylboronic acid (1.03 g, 8.45 mmol) and Pd(PPh$_3$)$_4$ (734.00 mg, 635.19 μmol) were added to a mixed solution of key intermediate A (1.10 g, 4.25 mmol) in dioxane/water (11 mL, 10/1). The mixture was stirred at 130° C. for 3 hours. The mixture was filtered and the filtrate was concentrated and the residue was purified by silica gel chromatography (petroleum ether/ethyl acetate=10/0, 10/1) to deliver 6-benzyl-2-phenyl-7,8-dihydro-5H-1,6-naphthyridine (750.00 mg, 58.75%) as a white solid. $^1$H NMR (400 MHz, CDCl$_3$): δ 7.96 (d, J=7.2 Hz, 2H), 7.53-7.36 (m, 10H), 3.76 (s, 2H), 3.69 (s, 2H), 3.16 (t, J=5.9 Hz, 2H), 2.93 (t, J=5.9 Hz, 2H). LCMS (ESI) m/z: 301 (M+1). LCMS (ESI) m/z: 301 (M+1).

Step 2:

2-Phenyl-5,6,7,8-tetrahydro-1,6-naphthyridine

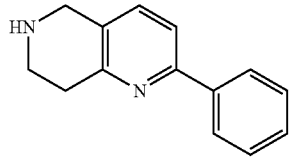 [SMILES: c1ccc(-c2ccc3c(n2)CCNC3)cc1]

1-Chloroethyl carbonochloridate (232.02 mg, 1.62 mmol) was added to a solution of 6-benzyl-2-phenyl-7,8-dihydro-5H-1,6-naphthyridine (375.00 mg, 1.25 mmol) in dichloroethane (15 mL) at 0° C. The mixture was stirred at 0° C. for 15 minutes and then heated to 85° C. and stirred for 12 hours. The mixture was concentrated under reduced pressure, and methanol (15 mL) was added to the residue, and then then mixture was stirred at 60° C. for 1 hour. The mixture was concentrated to deliver 2-phenyl-5,6,7,8-tetrahydro-1,6-naphthyridine hydrochloride (340.00 mg, crude) as a white solid. LCMS (ESI) m/z: 211 (M+1).

Step 3:

1-(2-Chloro-4-nitro-1H-imidazol-1-yl)-2-methyl-3-(2-phenyl-7,8-dihydro-1,6-naphthyridin-6(5H)-yl)propan-2-ol

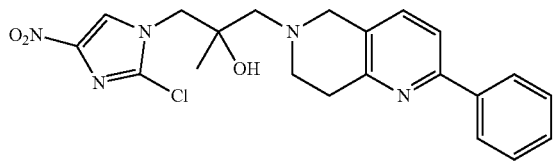 [SMILES: CC(O)(CN1CCc2nc(-c3ccccc3)ccc2C1)Cn1cc([N+](=O)[O-])nc1Cl]

2-Chloro-1-((2-methyloxiran-2-yl)methyl)-4-nitro-1H-imidazole (672.69 mg, 3.09 mmol) was added to a solution of 2-phenyl-5,6,7,8-tetrahydro-1,6-naphthyridine hydrochloride (500.00 mg, 2.38 mmol) in ethanol (5 mL), the mixture was stirred at 70° C. for 6 hours. The mixture was concentrated and the residue was purified by silica gel chromatography (petroleum ether ethyl acetate=20/1, 2/1) to deliver 1-(2-chloro-4-nitro-1H-imidazol-1-yl)-2-methyl-3-(2-phenyl-7,8-dihydro-1,6-naphthyridin-6(5H)-yl)propan-2-ol (600.00 mg, crude) as a yellow oil. LCMS (ESI) m/z: 428 (M+1).

Step 4:

2-Methyl-6-nitro-2-((2-phenyl-7,8-dihydro-1,6-naphthyridin-6(5H)-yl)methyl)-2,3-dihydroimidazo[2,1-b]oxazole

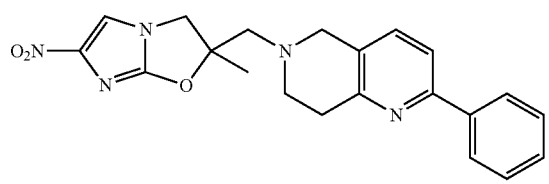

Compound 1A
Compound 1B

NaH (67.20 mg, 2.80 mmol) was added to a solution of 1-(2-chloro-4-nitro-1H-imidazol-1-yl)-2-methyl-3-(2-phenyl-7,8-dihydro-1,6-naphthyridin-6(5H)-yl)propan-2-ol (600.00 mg, 1.40 mmol) in DMF (10 mL) at 0° C. under the nitrogen gas atmosphere. The mixture was stirred at 0° C. for 1 hour. The mixture was added to stirred water (40 mL) and the precipitated solid was filtered and recrystallized from ethyl acetate (50 mL) to deliver a white solid, which was resolved by chiral SFC (Chiralpak AD 250×30 mm I.D. Sum, Supercritical $CO_2$/EtOH (0.2% $NH_3H_2O$)=60/40, 80 mL/min, 220 nm) to obtain two chiral isomers. The first compound of 2-methyl-6-nitro-2-((2-phenyl-7,8-dihydro-1,6-naphthyridin-6(5H)-yl)methyl)-2,3-dihydroimidazo[2,1-b]oxazole was named compound 1A (40.60 mg, 7.19%) and the resulting second compound of 2-methyl-6-nitro-2-((2-phenyl-7,8-dihydro-1,6-naphthyridin-6(5H)-yl)methyl)-2,3-dihydroimidazo[2,1-b]oxazole was named compound 1B (48.10 mg, 8.48%). The nuclear magnetic were the same: $^1$H NMR (400 MHz, $CDCl_3$): δ 7.94 (d, J=7.2 Hz, 2H), 7.53-7.36 (m, 6H), 4.45 (d, J=10.0 Hz, 1H), 3.97-3.86 (m, 3H), 3.16-2.99 (m, 5H), 2.81 (d, J=14.8 Hz, 1H), 1.69 (s, 3H). LCMS (ESI) m/z: 392 (M+1).

Embodiment 2

2-Methyl-6-nitro-2-((2-(4-(trifluoromethoxy)phenyl)-7,8-dihydro-1,6-naphthyridin-6(5H)-yl)methyl)-2,3-dihydroimidazo[2,1-b]oxazole

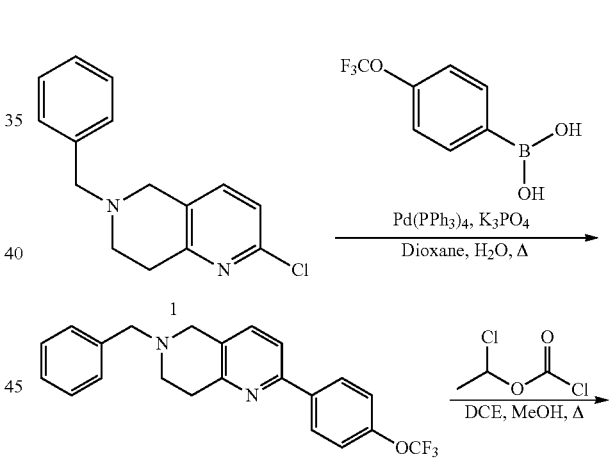

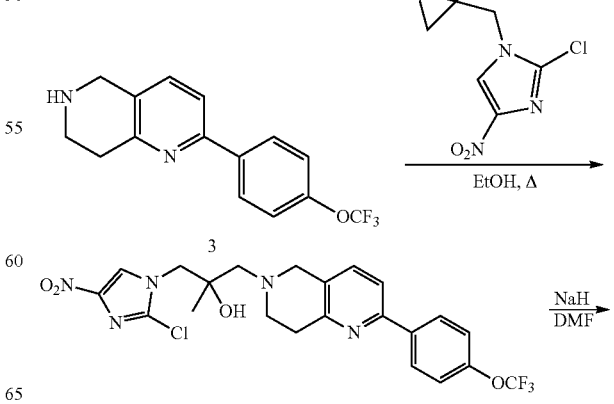

-continued

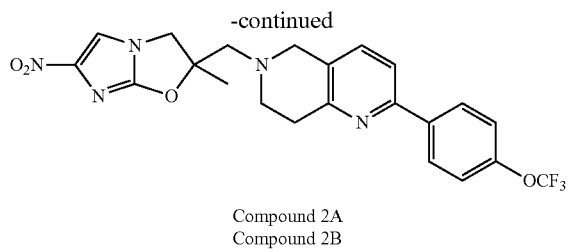

Compound 2A
Compound 2B

Step 1:

6-Benzyl-2-(4-(trifluoromethoxy)phenyl)-5,6,7,8-tetrahydro-1,6-naphthyridine

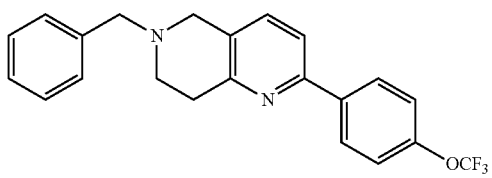 [SMILES: FC(F)(F)Oc1ccc(-c2ccc3c(n2)CCN(Cc2ccccc2)C3)cc1]

Potassium phosphate (2.46 g, 11.60 mmol, 2.50 eq) was added to a mixed solution of key intermediate A (1.20 g, 4.64 mmol, 1.00 eq) in dioxane (5 mL) and water (0.5 mL), Pd(PPh$_3$)$_4$ (536.18 mg, 464.00 μmol, 0.10 eq), (4-(trifluoromethoxy)phenyl)boronic acid (1.43 g, 6.96 mmol, 1.50 eq) were added at 0° C. under the nitrogen gas atmosphere. The mixture was stirred at 120° C. for 3 hours. The mixture was cooled and concentrated under reduced pressure at 50° C. The residue was purified by silica gel chromatography (petroleum ether/ethyl acetate=50/1, 15/1) to deliver 6-benzyl-2-(4-(trifluoromethoxy)phenyl)-5,6,7,8-tetrahydro-1,6-naphthyridine (1.30 g, 3.38 mmol, 72.89% yield) as a yellow solid. LCMS (ESI) m/z: 385 (M+1).

Step 2:

2-(4-(Trifluoromethoxy)phenyl)-5,6,7,8-tetrahydro-1,6-naphthyridine

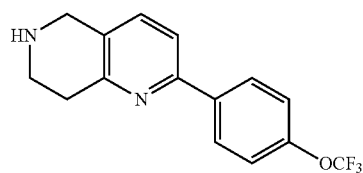 [SMILES: FC(F)(F)Oc1ccc(-c2ccc3c(n2)CCNC3)cc1]

1-Chloroethyl carbonochloridate (725.28 mg, 5.07 mmol, 1.50 eq) was added to a solution of 6-benzyl-2-(4-(trifluoromethoxy)phenyl)-5,6,7,8-tetrahydro-1,6-naphthyridine (1.30 g, 3.38 mmol) in dichloroethane (20 mL) at 0° C. under the nitrogen gas atmosphere. The mixture was stirred at 15° C. for 0.5 hour and then heated to 80° C. for 12 hours. Methanol (5 mL) was added to the mixture, and the mixture was stirred for another 4 hours and then cooled. The mixture was concentrated under reduced pressure at 50° C. The residue was purified by silica gel chromatography (dichloromethane/methanol=50/1, 1/10) to deliver 2-(4-(trifluoromethoxy)phenyl)-5,6,7,8-tetrahydro-1,6-naphthyridine (500.00 mg, 1.70 mmol, 50.27% yield) as a yellow solid. LCMS (ESI) m/z: 295 (M+1).

Step 3:

1-(2-Chloro-4-nitro-1H-imidazol-1-yl)-2-methyl-3-(2-(4-(trifluoromethoxy)phenyl)-7,8-dihydro-1,6-naphthyridin-6(5H)-yl)propan-2-ol

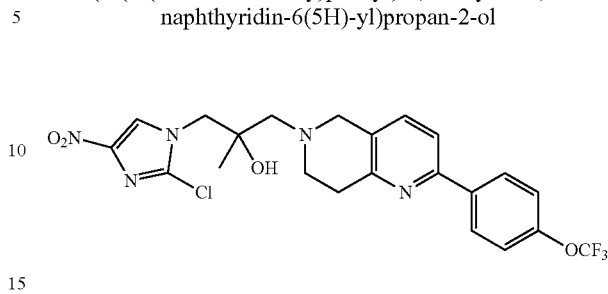

DIPEA (74.00 mg, 572.58 μmol, 0.42 eq) was added to a solution of 2-(4-(trifluoromethoxy)phenyl)-5,6,7,8-tetrahydro-1,6-naphthyridine (400.00 mg, 1.36 mmol, 1.00 eq) and 2-chloro-1-[(2-methyloxiran-2-yl)methyl]-4-nitroimidazole (591.90 mg, 2.72 mmol, 2.00 eq) in ethanol (10 mL). The mixture was stirred at 80° C. for 12 hours. The mixture was cooled and concentrated under reduced pressure at 50° C. The residue was purified by silica gel chromatography (petroleum ether/ethyl acetate=15/1, 1/1) to deliver 1-(2-chloro-4-nitro-1H-imidazol-1-yl)-2-methyl-3-(2-(4-(trifluoromethoxy)phenyl)-7,8-dihydro-1,6-naphthyridin-6(5H)-yl)propan-2-ol (500.00 mg, crude) as a yellow solid. LCMS (ESI) m/z: 512 (M+1).

Step 4:

2-Methyl-6-nitro-2-((2-(4-(trifluoromethoxy)phenyl)-7,8-dihydro-1,6-naphthyridin-6(5H)-yl)methyl)-2,3-dihydroimidazo[2,1-b]oxazole NaH (28.13 mg, 1.17 mmol, 2.00 eq) was added to a solution of 1-(2-chloro-4-nitro-1H-imidazol-1-yl)-2-methyl-3-(2-(4-(trifluoromethoxy)phenyl)-7,8-dihydro-1,6-naphthyridin-6(5H)-yl)propan-2-ol (300.00 mg, 586.07 μmol, 1.00 eq) in DMF (5.00 mL). The mixture was stirred at 0° C. for 0.5 hour and the color of the solution turned red. The mixture was added to water (10 mL) at 0° C. and the aqueous phase was extracted with ethyl acetate (50 mL×4). The combined organic phases were washed with saturated brine (20 mL×2), dried over anhydrous sodium sulfate, filtered and concentrated in vacuo. The residue was purified by preparative chromatography (GX-D; Boston Symmetrix C18 ODS-R 150*30 mm*5 μm; acetonitrile 24%-54%; water (0.225% NH$_4$OH); 25 mL/min) to give a mixture of two isomers (90 mg) which was seperated by chiral SFC (Chiralpak AD 250×30 mm I.D. Sum, Supercritical CO$_2$/EtOH (0.2% NH$_3$H$_2$O)=60/40, 70 mL/min, 220 nm) to deliver two chiral isomers, the first compound of 2-methyl-6-nitro-2-((2-(4-(trifluoromethoxy)phenyl)-7,8-dihydro-1,6-naphthyridin-6(5H)-yl)methyl)-2,3-dihydroimidazo[2,1-b]oxazole obtained was named compound 2A (48.20 mg, 97.33 μmol, 16.61% yield, 96% purity), and the second compound of 2-methyl-6-nitro-2-((2-(4-(trifluoromethoxy)phenyl)-7,8-dihydro-1,6-naphthyridin-6(5H)-yl)methyl)-2,3-dihydroimidazo[2,1-b]oxazole obtained was named compound 2B (33.40 mg, 67.02 μmol, 11.44% yield, 95.4% purity). The nuclear magnetic were the same: $^1$H NMR (400 MHz, CDCl$_3$): δ 7.98 (d, J=8.8 Hz, 2H), 7.56-7.45 (m, 2H), 7.42-7.36 (m, 1H), 7.30 (d, J=8.4 Hz, 2H), 4.43 (d, J=9.6 Hz, 1H), 4.01-3.78 (m, 3H), 3.21-2.92 (m, 5H), 2.81 (d, J=14.8 Hz, 1H), 1.69 (s, 3H). LCMS (ESI) m/z: 476 (M+1).

Embodiment 3

(S)-2-Methyl-6-nitro-2-((2-(3-(trifluoromethoxy) phenyl)-7,8-dihydro-1,6-naphthyridin-6(5H)-yl) methyl)-2,3-dihydroimidazo[2,1-b]oxazole Compound 3

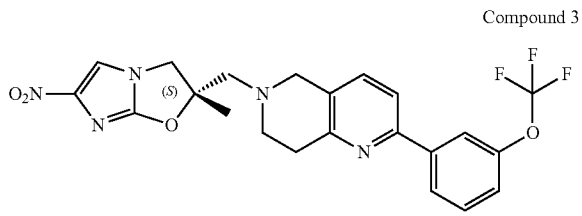

The key intermediate B (120.00 mg, 343.08 μmol, 1.00 eq) and [3-(trifluoromethoxy)phenyl]boronic acid (70.65 mg, 343.08 μmol, 1.00 eq) were dissolved in dioxane (5.00 mL) and water (500.00 μL), Pd(dppf)Cl$_2$ (25.10 mg, 34.31 μmol, 0.10 eq), sodium carbonate (90, 91 mg, 857.70 μmol, 2.5 eq) were added to the solution at 30° C. under the nitrogen gas atmosphere. The mixture was stirred at 110° C. for 12 hours. After the reaction, the mixture was cooled to 30° C. and concentrated under reduced pressure at 45° C. The residue was poured into water (10 mL) and stirred for 5 minutes. The aqueous phase was extracted with ethyl acetate (30 mL×3). The combined organic phases were washed with saturated brine (10 mL×2), dried over anhydrous sodium sulfate, filtered and concentrated in vacuo. The residue was purified by preparative thin layer chromatography (petroleum ether/ethyl acetate=1/2.5) and preparative chromatography (GX-D; Boston Symmetrix C18 ODS-R 150*30 mm*5 μm; acetonitrile 24%-54%; water (0.225% fomic acid) 25 mL/min) to deliver (S)-2-methyl-6-nitro-2-((2-(3-(trifluoromethoxy)phenyl)-7,8-dihydro-1,6-naphthyridin-6(5H)-yl)methyl)-2,3-dihydroimidazo[2,1-b]oxazole compound 3 (12.00 mg, 24.62 μmol, 7.18% yield, 97.54% purity). $^1$H NMR (400 MHz, CDCl$_3$): δ 7.89-7.87 (d, J=8.03 Hz, 1H), 7.84 (s, 1H), 7.52 (s, 1H), 7.51-7.46 (m, 2H), 7.41 (d, J=8.16 Hz, 1H), 7.27 (d, J=8.16 Hz, 1H), 4.44 (d, J=9.66 Hz, 1H), 3.97 (d, J=9.66 Hz, 1H), 3.95-3.84 (m, 2H), 3.18-3.01 (m, 5H), 2.82 (d, J=14.81 Hz, 1H), 1.69 (s, 3H). LCMS (ESI) m/z: 476 (M+1).

Embodiment 4

(S)-2-Methyl-6-nitro-2-((2-(2-(trifluoromethoxy) phenyl)-7,8-dihydro-1,6-naphthyridin-6(5H)-yl) methyl)-2,3-dihydroimidazo[2,1-b]oxazole Compound 4

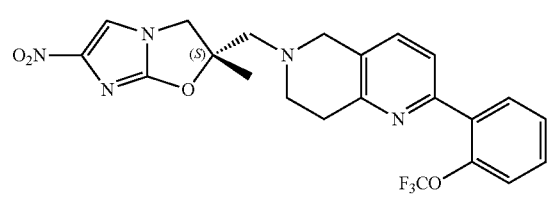

The key intermediate B (100.00 mg, 285.90 μmol, 1.00 eq) and (2-(trifluoromethoxy)phenyl)boronic acid (70.65 mg, 343.08 μL, 1.20 eq) were dissolved in dioxane (5.00 mL) and water (500.00 μL). Sodium carbonate (60.61 mg, 571.80 μmol, 2.00 eq), Pd(dppf)Cl$_2$ (20.92 mg, 28.59 μmol, 0.10 eq) were added to the mixture at 15° C. under the nitrogen gas atmosphere. The mixed solution was stirred at 120° C. for 12 hours. After the reaction, the mixed solution was cooled to 15° C., filtered and the filtrate was concentrated in vacuo. The residue was purified by preparative chromatography (GX-D; Boston Symmetrix C18 ODS-R 150*30 mm*5 um; acetonitrile 24%-54%; water (0.225% fomic acid); 25 mL/min) to deliver (S)-2-methyl-6-nitro-2-((2-(2-(trifluoromethoxy)phenyl)-7,8-dihydro-1,6-naphthyridin-6(5H)-yl)methyl)-2,3-dihydroimidazo[2,1-b]oxazole compound 4 (15.00 mg, 29.97 μmol, 10.48% yield, 95% purity). $^1$H NMR (400 MHz, CDCl$_3$): δ 7.77 (d, J=2.8 Hz, 1H), 7.55 (s, 1H), 7.49-7.31 (m, 5H), 4.45 (d, J=9.6 Hz, 1H), 4.01-3.82 (m, 3H), 3.23-2.93 (m, 5H), 2.83 (d, J=14.8 Hz, 1H), 1.70 (s, 3H). LCMS (ESI) m/z: 476 (M+1).

Embodiment 5

(S)-2-((2-(2-Fluorophenyl)-7,8-dihydro-1,6-naphthyridin-6(5H)-yl)methyl)-2-methyl-6-nitro-2,3-dihydroimidazo[2,1-b]oxazole

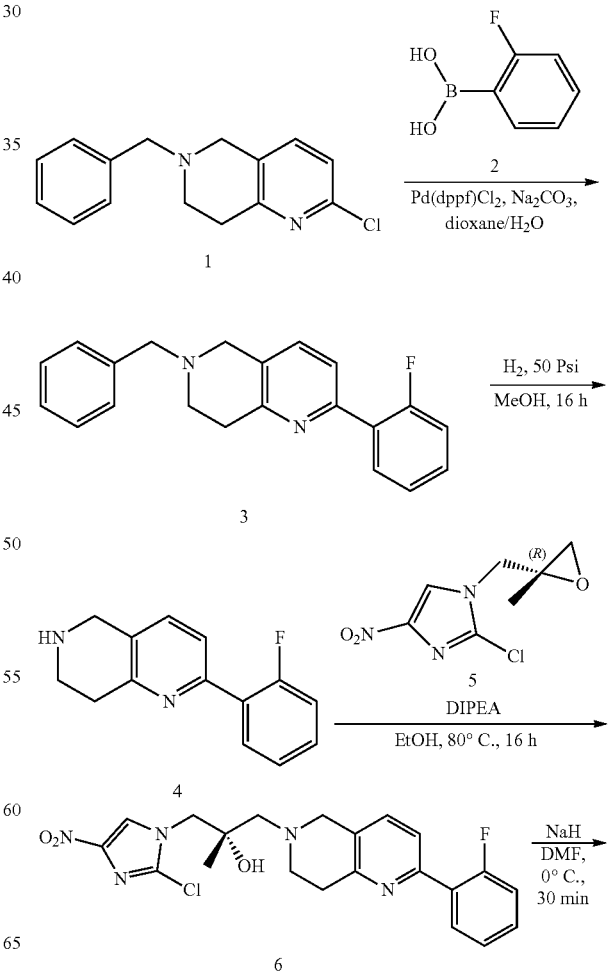

-continued

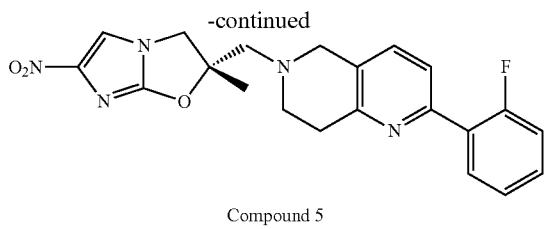

Compound 5

Step 1:

6-Benzyl-2-(2-fluorophenyl)-5,6,7,8-tetrahydro-1,6-naphthyridine

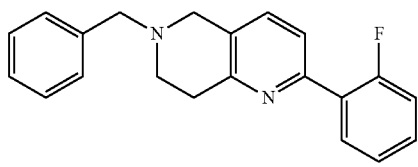 [SMILES: Fc1ccccc1-c1ccc2c(n1)CCN(Cc1ccccc1)C2]

The key intermediate A (1.50 g, 5.80 mmol, 1.00 eq) and (2-fluorophenyl) boronic acid (973.84 mg, 6.96 mmol, 1.20 eq) were dissolved in dioxane (20.00 mL) and water (5.00 mL), Pd(dppf)Cl$_2$ (424.39 mg, 580.00 μmol, 0.10 eq) and sodium carbonate (1.23 g, 11.60 mmol, 2.00 eq) were added to the mixture under the nitrogen gas atmosphere. The mixed solution was then stirred at 100° C. for 12 hours. The reaction solution was concentrated under reduced pressure to remove the solvent, and the residue was diluted with water 20 mL and extracted with ethyl acetate (10 mL×3). The combined organic layers were washed with saturated brine (10 mL×2), dried over sodium sulfate, filtered and concentrated under reduced pressure to deliver 6-benzyl-2-(2-fluorophenyl)-5,6,7,8-tetrahydro-1,6-naphthyridine (1.39 g, 4.37 mmol, 75.27% yield) as a brown solid.

Step 2:

2-(2-Fluorophenyl)-5,6,7,8-tetrahydro-1,6-naphthyridine

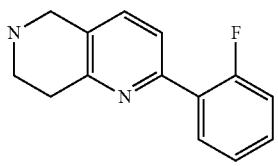 [SMILES: Fc1ccccc1-c1ccc2c(n1)CCNC2]

6-Benzyl-2-(2-fluorophenyl)-5,6,7,8-tetrahydro-1,6-naphthyridine (1.39 g, 4.37 mmol, 1.00 eq) was dissolved in methanol (20.00 mL), Pd(OH)$_2$/C (10%, 139 mg) was added under the nitrogen gas atmosphere. The mixed solution was replaced with hydrogen three times. The mixed solution was heated to 50° C. and stirred for 12 hours under H$_2$ (50 psi). The reaction mixture was filtered and the filtrate was concentrated under reduced pressure to deliver the crude 2-(2-fluorophenyl)-5,6,7,8-tetrahydro-1,6-naphthyridine (1.05 g, crude). The crude product was used in the next step without further purification.

Step 3:

(S)-1-(2-Chloro-4-nitro-1H-imidazol-1-yl)-3-(2-(2-fluorophenyl)-7,8-dihydro-1,6-naphthyridin-6(5H)-yl)-2-methylpropan-2-ol

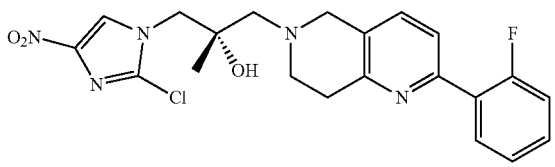 [SMILES: C[C@](O)(CN1CCc2nc(-c3ccccc3F)ccc2C1)Cn1cc([N+](=O)[O-])nc1Cl]

2-(2-Fluorophenyl)-5,6,7,8-tetrahydro-1,6-naphthyridine (300.00 mg, 1.31 mmol, 1.00 eq), (R)-2-chloro-1-((2-methyloxiran-2-yl)methyl)-4-nitro-1H-imidazole (286.00 mg, 1.31 mmol, 1.00 eq) and DIPEA (507.91 mg, 3.93 mmol, 3.00 eq) were dissolved in ethanol (20.00 mL). The mixed solution was replaced with nitrogen three times. The mixed solution was then stirred at 80° C. for 12 hours under the nitrogen gas atmosphere. The reaction mixture was concentrated under reduced pressure to remove the solvent. The residue was purified by silica gel chromatography (silica, petroleum ether/ethyl acetate=5/1, 1/1) to deliver (S)-1-(2-chloro-4-nitro-1H-imidazol-1-yl)-3-(2-(2-fluorophenyl)-7,8-dihydro-1,6-naphthyridin-6(5H)-yl)-2-methylpropan-2-ol (300.00 mg, 672.84 μmol, 51.36% yield) as a yellow solid.

Step 4:

(S)-2-((2-(2-Fluorophenyl)-7,8-dihydro-1,6-naphthyridin-6(5H)-yl)methyl)-2-methyl-6-nitro-2,3-dihydroimidazo[2,1-b]oxazole Compound 5

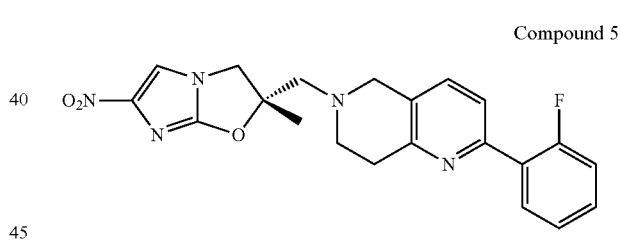

(S)-1-(2-Chloro-4-nitro-1H-imidazol-1-yl)-3-(2-(2-fluorophenyl)-7,8-dihydro-1,6-naphthyridin-6(5H)-yl)-2-methylpropan-2-ol (300.00 mg, 672.84 μmol, 1.00 eq) was dissolved in DMF (5.00 mL). NaH (32.30 mg, 807.41 μmol, 1.20 eq) was added to the mixed solution at 0° C. and stirred at the temperature for 30 minutes. Saturated ammonium chloride solution (20 mL) was added to the reaction mixture at 0° C. and the reaction mixture was then diluted with 20 mL of water and extracted with DCM (10 mL×3). The combined organic layers were washed with saturated brine (10 mL×2), dried over sodium sulfate, filtered and concentrated under reduced pressure to give a residue. The residue was purified by preparative chromatography (GX-E; Innoval C18 150*30 mm*5 um; acetonitrile 12%-42%; water (0.225% fomic acid); 25 mL/min) to deliver (S)-2-((2-(2-fluorophenyl)-7,8-dihydro-1,6-naphthyridin-6(5H)-yl) methyl)-2-methyl-6-nitro-2,3-dihydroimidazo[2,1-b]oxazole compound 5 (101.80 mg, 248.65 μmol, 36.96% yield). $^1$H NMR (400 MHz, CDCl$_3$): δ 7.94-7.87 (m, 1H), 7.57-7.54 (m, 1H), 7.53 (s, 1H), 7.42-7.33 (m, 2H), 7.28-7.23 (m, 1H), 7.19-7.11 (m, 1H), 4.44 (d, J=8.0 Hz, 1H), 3.96 (d, J=8.0 Hz, 1H), 3.92-3.83 (m, 2H), 3.22-3.08 (m, 2H), 3.08-2.94 (m, 3H), 2.82 (d, J=12.0 Hz, 1H), 1.69 (s, 3H). LCMS (ESI) m/z: 409 (M+1).

Embodiment 6

(S)-2-((2-(3-Fluorophenyl)-7,8-dihydro-1,6-naphthyridin-6(5H)-yl)methyl)-2-methyl-6-nitro-2,3-dihydroimidazo[2,1-b]oxazole

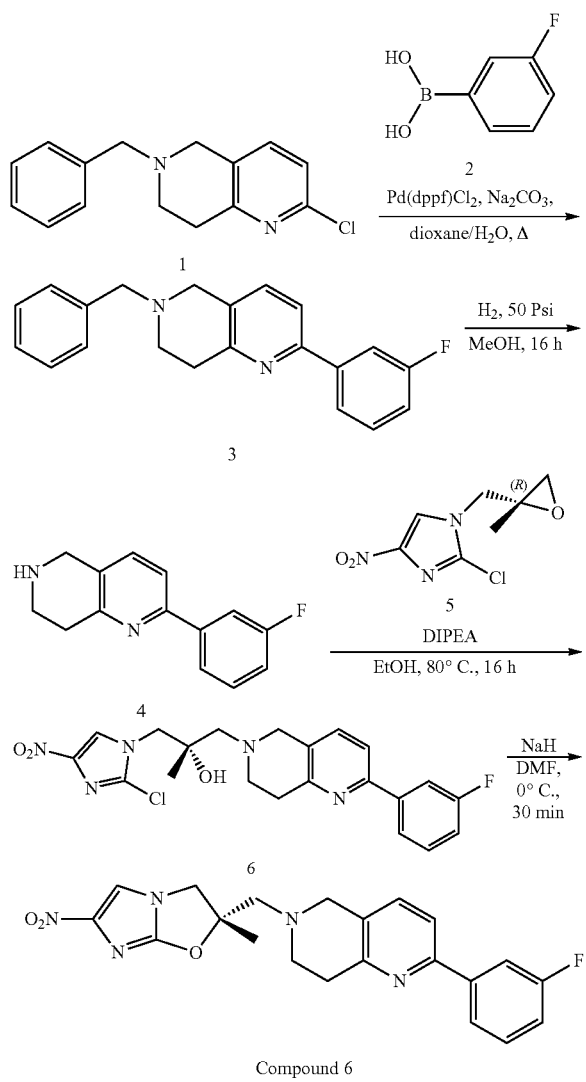

Step 1:

6-Benzyl-2-(3-fluorophenyl)-5,6,7,8-tetrahydro-1,6-naphthyridine

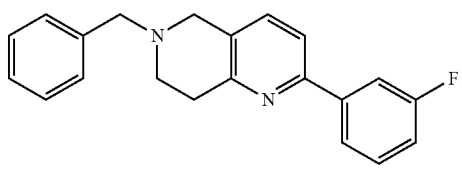 [SMILES: Fc1cccc(-c2ccc3c(n2)CCN(Cc2ccccc2)C3)c1]

The key intermediate A (1.50 g, 5.80 mmol, 1.00 eq), (3-fluorophenyl) boronic acid (973.36 mg, 6.96 mmol, 1.20 eq) were dissolved in dioxane (20.00 mL) and water (5.00 mL), Pd(dppf)Cl$_2$ (424.17 mg, 579.71 μmol, 0.10 eq) and sodium carbonate (1.23 g, 11.59 mmol, 2.00 eq) were added to the mixed solution under the nitrogen gas atmosphere. The mixture was then stirred at 100° C. for 12 hours under the nitrogen gas atmosphere. The reaction mixture was concentrated under reduced pressure to remove the solvent. The residue was diluted with water 20 mL and extracted with ethyl acetate (10 mL×3). The combined organic layers were washed with saturated brine (10 mL×2), dried over sodium sulfate, filtered and concentrated under reduced pressure to deliver 6-benzyl-2-(3-fluorophenyl)-5,6,7,8-tetrahydro-1,6-naphthyridine (1.40 g, 4.40 mmol, 75.81% yield) as a brown solid.

Step 2:

2-(3-Fluorophenyl)-5,6,7,8-tetrahydro-1,6-naphthyridine

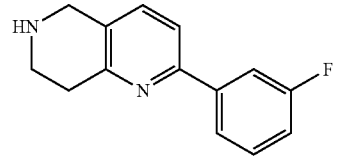 [SMILES: Fc1cccc(-c2ccc3c(n2)CCNC3)c1]

6-Benzyl-2-(3-fluorophenyl)-5,6,7,8-tetrahydro-1,6-naphthyridine (1.40 g, 4.40 mmol, 1.00 eq) was dissolved in methanol (20.00 mL). Pd(OH)$_2$/C (10%, 140 mg) was added under the nitrogen gas atmosphere. The mixed solution was replaced with hydrogen three times. The mixture was heated to 50° C. under H$_2$ (50 psi) for 12 hours. The mixture was filtered and the filtrate was concentrated under reduced pressure to deliver crude 2-(3-fluorophenyl)-5,6,7,8-tetrahydro-1,6-naphthyridine (1.10 g, crude). The crude product was used directly in the next step. The crude product was used in the next step without further purification.

Step 3:

(S)-1-(2-Chloro-4-nitro-1H-imidazol-1-yl)-3-(2-(3-fluorophenyl)-7,8-dihydro-1,6-naphthyridin-6(5H)-yl)-2-methylpropan-2-ol

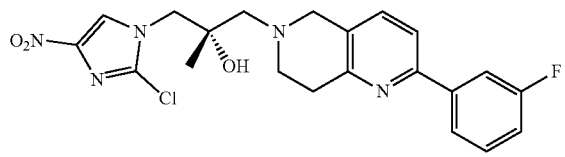 [SMILES: C[C@](O)(CN1CCc2nc(-c3cccc(F)c3)ccc2C1)Cn1cc([N+](=O)[O-])nc1Cl]

2-(3-Fluorophenyl)-5,6,7,8-tetrahydro-1,6-naphthyridine (300.00 mg, 1.31 mmol, 1.00 eq), (R)-2-chloro-1-((2-methyloxiran-2-yl)methyl)-4-nitro-1H-imidazole (286.00 mg, 1.31 mmol, 1.00 eq), DIPEA (507.91 mg, 3.93 mmol, 3.00 eq) were dissolved in ethanol (20.00 mL). The mixture was stirred at 80° C. for 12 hours under the nitrogen gas atmosphere. The reaction mixture was concentrated under reduced pressure. The residue was purified by silica gel chromatography (silica, petroleum ether/ethyl acetate=5/1, 1/1) to deliver (S)-1-(2-chloro-4-nitro-1H-imidazol-1-yl)-3-(2-(3-fluorophenyl)-7,8-dihydro-1,6-naphthyridin-6(5H)-yl)-2-methylpropan-2-ol (300.00 mg, 672.84 μmol, 51.36% yield) as a yellow solid.

Step 4:

(S)-2-((2-(3-Fluorophenyl)-7,8-dihydro-1,6-naphthyridin-6(5H)-yl)methyl)-2-methyl-6-nitro-2,3-dihydroimidazo[2,1-b]oxazole Compound 6

(S)-1-(2-Chloro-4-nitro-1H-imidazol-1-yl)-3-(2-(3-fluorophenyl)-7,8-dihydro-1,6-naphthyridin-6(5H)-yl)-2-methylpropan-2-ol (300.00 mg, 672.84 μmol, 1.00 eq) was dissolved in DMF (5.00 mL). NaH (32.30 mg, 807.41 μmol, 1.20 eq) was added to the mixed solution at 0° C. and stirred for 30 minutes. The reaction mixture was quenched with saturated ammonium chloride solution (20 mL) at 0° C., then diluted with water (20 mL) and extracted with DCM (10 mL×3). The combined organic layers were washed with saturated brine (10 mL×2), dried over sodium sulfate, filtered and concentrated under reduced pressure to give a residue. The residue was purified by preparative chromatography to deliver (GX-E; Phenomenex Synergi C18 150*30 mm*4 um; acetonitrile 15%-45%; water (0.13% HCl); 25 mL/min) (S)-2-((2-(3-fluorophenyl)-7,8-dihydro-1,6-naphthyridin-6(5H)-yl)methyl)-2-methyl-6-nitro-2,3-dihydroimidazo[2,1-b]oxazole compound 6 (161.80 mg, 395.20 μmol, 58.74% yield). $^1$H NMR (400 MHz, CDCl$_3$): δ 7.76-7.66 (m, 2H), 7.53 (s, 1H), 7.50 (d, J=8.0 Hz, 1H), 7.46-7.37 (m, 2H), 7.14-7.06 (m, 1H), 4.44 (d, J=8.0 Hz, 1H), 3.97 (d, J=12.0 Hz, 1H), 3.92-3.82 (m, 2H), 3.20-3.08 (m, 2H), 3.07-2.95 (m, 3H), 2.82 (d, J=12.0 Hz, 1H), 1.69 (s, 3H). LCMS (ESI) m/z: 409 (M+1).

Embodiment 7

(S)-2-((2-(4-Fluorophenyl)-7,8-dihydro-1,6-naphthyridin-6(5H)-yl)methyl)-2-methyl-6-nitro-2,3-dihydroimidazo[2,1-b]oxazole

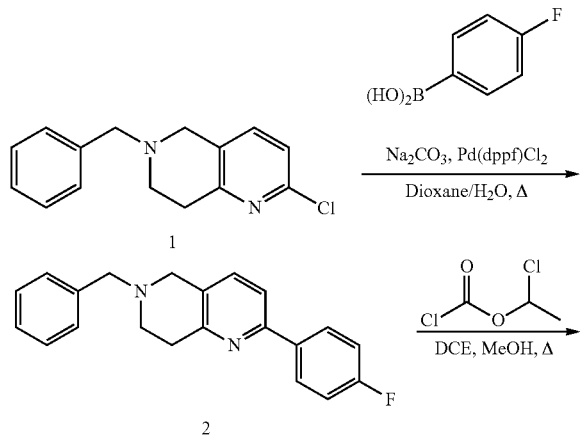

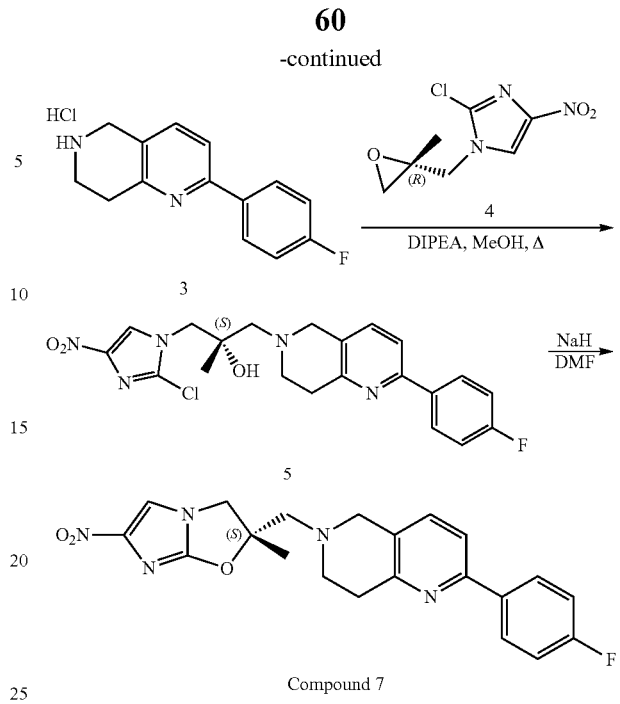

Step 1:

6-Benzyl-2-(4-fluorophenyl)-5,6,7,8-tetrahydro-1,6-naphthyridine

The key intermediate A (2.00 g, 7.73 mmol, 1.00 eq) and (4-fluorophenyl)boronic acid (1.08 g, 7.73 mmol, 1.00 eq) were dissolved in dioxane (20.00 mL) and water (2.00 mL). Sodium carbonate (1.64 g, 15.46 mmol, 2.00 eq), Pd(dppf)Cl$_2$ (565.60 mg, 773.00 μmol, 0.10 eq) was added at 15° C. under the nitrogen gas atmosphere. The mixed solution was stirred at 110° C. for 12 hours under the nitrogen gas atmosphere. After the reaction, the mixed solution was cooled to 15° C. and concentrated under reduced pressure at 50° C. Water (20 mL) was added to the residue and the aqueous phase was extracted with dichloromethane (100 mL×4). The combined organic phases were washed with saturated brine (50 mL), dried over anhydrous sodium sulfate, filtered and concentrated in vacuo. The residue was purified by silica gel chromatography (petroleum ether/ethyl acetate=20/1, 5/1) to deliver 6-benzyl-2-(4-fluorophenyl)-5,6,7,8-tetrahydro-1,6-naphthyridine (1.86 g, 5.84 mmol, 75.57% yield) as a yellow solid. $^1$H NMR (400 MHz, CDCl$_3$): δ 8.00-7.89 (m, 2H), 7.47-7.30 (m, 7H), 7.15 (t, J=8.8 Hz, 2H), 3.76 (s, 2H), 3.68 (s, 2H), 3.19-3.07 (m, 2H), 2.92 (t, J=6.0 Hz, 2H).

Step 2:

2-(4-Fluorophenyl)-5,6,7,8-tetrahydro-1,6-naphthyridine hydrochloride

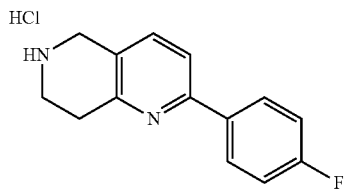 [SMILES: Cl ; Fc1ccc(-c2ccc3c(n2)CCNC3)cc1]

6-Benzyl-2-(4-fluorophenyl)-5,6,7,8-tetrahydro-1,6-naphthyridine (1.86 g, 5.84 mmol, 1.00 eq) was dissolved in dichloroethane (20.00 mL). 1-Chloroethyl carbonochloridate (1.25 g, 8.76 mmol, 1.50 eq) was added at 0° C. under the nitrogen gas atmosphere. The mixture was stirred at 0° C. for 0.5 hour and then heated to 85° C. and stirred for 12 hours. The mixture was then concentrated to remove the solvent, methanol (20.00 mL) was added to the residue, and the mixture was stirred at 85° C. for 2 hours. The mixed solution was filtered and dried to deliver 2-(4-fluorophenyl)-5,6,7,8-tetrahydro-1,6-naphthyridine hydrochloride (1.54 g, crude) as a yellow solid, which was used directly in the next step.

Step 3:

(S)-1-(2-Chloro-4-nitro-1H-imidazol-1-yl)-3-(2-(4-fluorophenyl)-7,8-dihydro-1,6-naphthyridin-6(5H)-yl)-2-methylpropan-2-ol

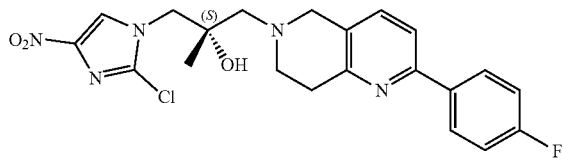

2-(4-Fluorophenyl)-5,6,7,8-tetrahydro-1,6-naphthyridine hydrochloride (1.44 g, 6.75 mmol, 1.00 eq) and 2-chloro-1-[[(2R)-2-methyloxiran-2-yl]methyl]-4-nitroimidazole (1.47 g, 6.75 mmol, 1.00 eq) were dissolved in ethanol (20.00 mL). DIPEA (2.18 g, 16.88 mmol, 2.50 eq) was added at 15° C. under the nitrogen gas atmosphere. After the mixture was stirred at 80° C. for 12 hours, the mixture was cooled to 15° C. and concentrated under reduced pressure at 60° C. The residue was purified by silica gel chromatography (silica, petroleum ether/ethyl acetate=20/1, 1/3) to deliver (S)-1-(2-chloro-4-nitro-1H-imidazol-1-yl)-3-(2-(4-fluorophenyl)-7,8-dihydro-1,6-naphthyridin-6(5H)-yl)-2-methylpropan-2-ol (1.20 g, 2.69 mmol, 39.87% yield) as a yellow solid.

Step 4:

(S)-2-((2-(4-Fluorophenyl)-7,8-dihydro-1,6-naphthyridin-6(5H)-yl)methyl)-2-methyl-6-nitro-2,3-dihydroimidazo[2,1-b]oxazole Compound 7

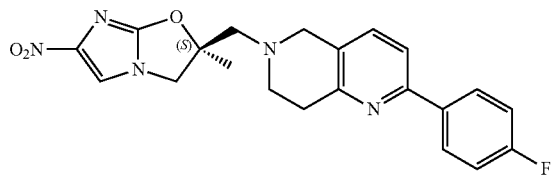

(S)-1-(2-Chloro-4-nitro-1H-imidazol-1-yl)-3-(2-(4-fluorophenyl)-7,8-dihydro-1,6-naphthyridin-6(5H)-yl)-2-methylpropan-2-ol (1.20 g, 2.69 mmol, 1.00 eq) was dissolved in DMF (10.00 mL). NaH (129.12 mg, 5.38 mmol, 2.00 eq) was added to the mixed solution under the nitrogen gas atmosphere. The mixed solution was then stirred at −20° C. for 10 minutes and then at −5° C. for 10 minutes and at 15° C. for 10 minutes. The residue was purified by silica gel chromatography (petroleum ether/ethyl acetate=20/1, 1/3) and the resulting product was stirred in methanol (20 mL) at 75° C. for 0.5 hour and then cooled to 15° C., filtered and dried to deliver (S)-2-((2-(4-Fluorophenyl)-7,8-dihydro-1,6-naphthyridin-6(5H)-yl)methyl)-2-methyl-6-nitro-2,3-dihydroimidazo[2,1-b]oxazole compound 7 (711.10 mg, 1.72 mmol, 63.99% yield, 99.1% purity). $^1$H NMR (400 MHz, CDCl$_3$): δ 7.93 (dd, J=8.8, 5.5 Hz, 2H), 7.52 (s, 1H), 7.48-7.42 (m, 1H), 7.40-7.33 (m, 1H), 7.14 (t, J=8.7 Hz, 2H), 4.43 (d, J=9.6 Hz, 1H), 4.02-3.78 (m, 3H), 3.22-2.90 (m, 5H), 2.81 (d, J=15.1 Hz, 1H), 1.69 (s, 3H). LCMS (ESI) m/z: 410 (M+1).

Embodiment 8

(S)-2-((2-(4-Chlorophenyl)-7,8-dihydro-1,6-naphthyridin-6(5H)-yl)methyl)-2-methyl-6-nitro-2,3-dihydroimidazo[2,1-b]oxazole Compound 8

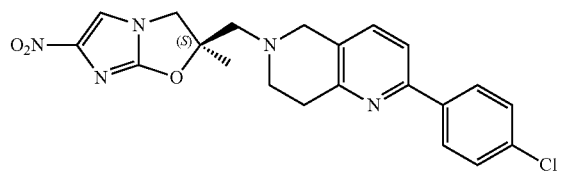

The key intermediate B (100.00 mg, 285.90 μmol, 1.00 eq) and (4-chlorophenyl) boronic acid (53.65 mg, 343.08 μmol, 1.20 eq) were dissolved in dioxane (5.00 mL) and water (500.00 μL) at 15° C. under the nitrogen gas atmosphere. The mixture was stirred at 120° C. for 12 hours and then cooled to 15° C., filtered. The filtrate was concentrated at 50° C. under reduced pressure and the residue was purified by preparative chromatography (GX-D; Boston Symmetrix C18 ODS-R 150*30 mm*5 um; acetonitrile 24%-54%; water (0.225% fomic acid); 25 mL/min) to deliver (S)-2-((2-(4-chlorophenyl)-7,8-dihydro-1,6-naphthyridin-6(5H)-yl)methyl)-2-methyl-6-nitro-2,3-dihydroimidazo[2,1-b]oxazole compound 8 (10.80 mg, 24.26 μmol, 8.49% yield, 95.67% purity). $^1$H NMR (400 MHz, CDCl$_3$): δ 7.90 (d, J=8.4 Hz, 2H), 7.55-7.34 (m, 5H), 4.43 (d, J=9.5 Hz, 1H), 4.03-3.79 (m, 3H), 3.24-2.92 (m, 5H), 2.81 (d, J=14.8 Hz, 1H), 1.69 (s, 3H). LCMS (ESI) m/z: 426 (M+1).

Embodiment 9

(S)-4-(6-((2-Methyl-6-nitro-2,3-dihydroimidazo[2,1-b]oxazol-2-yl)methyl)-5,6,7,8-tetrahydro-1,6-naphthyridin-2-yl)benzonitrile

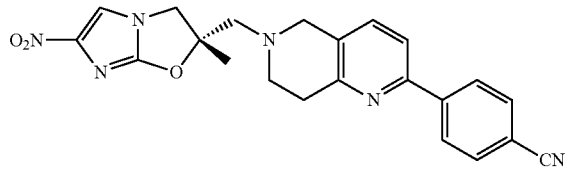

Compound 9

The key intermediate B (120.00 mg, 343.08 µmol, 1.00 eq) and (4-cyanophenyl) boronic acid (60.49 mg, 411.70 µmol, 1.20 eq) were dissolved in dioxane (5.00 mL). Pd(dppf)Cl₂ (25.10 mg, 34.31 µmol, 0.10 eq), sodium carbonate (90.91 mg, 857.70 µmol, 2.5 eq) were added to the solution at 30° C. under the nitrogen gas atmosphere. The mixture was stirred at 110° C. for 12 hours, then cooled to 30° C. and concentrated at 45° C. under reduced pressure, and water (10 mL) was added to the residue. The aqueous phase was extracted with ethyl acetate (20 mL×3). The combined organic phases were washed with saturated brine (10 mL×2), dried over anhydrous sodium sulfate, filtered and concentrated in vacuo. The residue was subjected to preliminary treatment by thin layer chromatography (petroleum ether/ethyl acetate=1/2.5), and then separated and purified by preparative chromatographic (GX-D; Boston Symmetrix C18 ODS-R 150*30 mm*5 um; acetonitrile 24%-54%; water (0.225% fomic acid); 25 mL/min) to deliver (S)-4-(6-((2-methyl-6-nitro-2,3-dihydroimidazo[2,1-b]oxazol-2-yl)methyl)-5,6,7,8-tetrahydro-1,6-naphthyridin-2-yl)benzonitrile compound 9 (9.60 mg, 23.05 µmol, 6.72% yield, 99.3% purity). $^1$H NMR (400 MHz, CDCl₃): δ 8.09-8.07 (d, J=8.28 Hz, 2H), 7.76-7.74 (d, J=8.41 Hz, 2H), 7.55 (d, J=8.03 Hz, 1H), 7.52 (s, 1H), 7.43-7.41 (d, J=8.03 Hz, 1H), 4.43-4.41 (d, J=9.66 Hz, 1H), 3.98-3.96 (d, J=9.54 Hz, 1H), 3.92-3.84 (m, 2H), 3.17-3.00 (m, 5H), 2.82 (d, J=14.81 Hz, 1H), 1.69 (s, 3H). LCMS (ESI) m/z: 417 (M+1).

Embodiment 10

(S)-2-Methyl-6-nitro-2-((2-(4-(trifluoromethyl)phenyl)-7,8-dihydro-1,6-naphthyridin-6(5H)-yl)methyl)-2,3-dihydroimidazo[2,1-b]oxazole

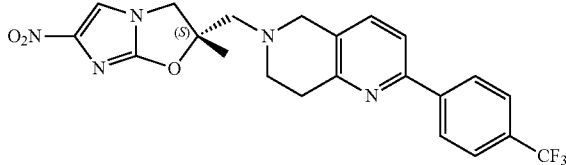

Compound 10

The key intermediate B (120.00 mg, 343.08 µmol, 1.00 eq) and [4-(trifluoromethyl) phenyl]boronic acid (65.16 mg, 343.08 µmol, 1.00 eq) were dissolved in dioxane (5.00 mL) and water (500.00 µL), sodium carbonate (72.73 mg, 686.17 µmol, 2.00 eq), Pd(dppf)Cl₂ (25.10 mg, 34.31 µmol, 0.10 eq) were added at 15° C. under the nitrogen gas atmosphere. The mixed solution was stirred at 110° C. for 12 hours and purified by preparative chromatography (Boston Symmetrix C18 ODS-R 150*30 mm*5 µm; acetonitrile 24%-54%; water (0.225% fomic acid); 25 mL/min) to deliver (S)-2-methyl-6-nitro-2-((2-(4-(trifluoromethyl)phenyl)-7,8-dihydro-1,6-naphthyridin-6(5H)-yl)methyl)-2,3-dihydroimidazo[2,1-b]oxazole compound 10 (16.40 mg, 34.16 µmol, 9.96% yield, 95.7% purity). $^1$H NMR (400 MHz, CDCl₃): δ 8.07 (d, J=8.0 Hz, 2H), 7.72 (d, J=8.2 Hz, 2H), 7.59-7.48 (m, 2H), 7.42 (d, J=8.0 Hz, 1H), 4.44 (d, J=9.8 Hz, 1H), 4.04-3.81 (m, 3H), 3.23-2.93 (m, 5H), 2.82 (d, J=14.8 Hz, 1H), 1.70 (s, 3H). LCMS (ESI) m/z: 460 (M+1).

Embodiment 11

(S)-2-((2-(3-Fluoro-4-(trifluoromethoxy)phenyl)-7,8-dihydro-1,6-naphthyridin-6(5H)-yl)methyl)-2-methyl-6-nitro-2,3-dihydroimidazo[2,1-b]oxazole

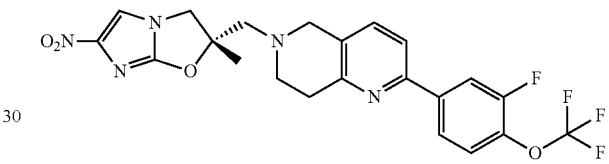

Compound 11

The key intermediate B (62.32 mg, 178.17 µmol, 1.00 eq.) and [3-fluoro-4-(trifluoromethoxy)phenyl]boronic acid (39.90 mg, 178.17 µmol, 1.00 eq) were dissolved in dioxane (5.00 mL), Pd(dppf)Cl₂ (13.04 mg, 17.82 µmol, 0.10 eq), sodium carbonate (47.21 mg, 445.42 µmol, 2.5 eq) were added at 30° C. under the nitrogen gas atmosphere. The mixed solution was stirred at 110° C. for 12 hours and then cooled and concentrated under reduced pressure at 45° C. The residue was poured into water (10 mL) and stirred for 5 minutes. The aqueous phase was extracted with ethyl acetate (30 mL×3). The combined organic phases were washed with saturated brine (10 mL×2), dried over anhydrous sodium sulfate, filtered and concentrated in vacuo. The residue was subjected to preliminary treatment by thin layer chromatography (petroleum ether/ethyl acetate=1/2.5) and then separated and purified by preparative chromatography (GX-E; Column: Innoval C18 150*30 mm*5 µm; acetonitrile 30%-60%; water (0.225% fomic acid); 25 mL/min) to deliver (S)-2-((2-(3-fluoro-4-(trifluoromethoxy)phenyl)-7,8-dihydro-1,6-naphthyridin-6(5H)-yl)methyl)-2-methyl-6-nitro-2,3-dihydroimidazo[2,1-b]oxazole compound 11 (10.70 mg, 20.82 µmol, 11.68% yield, 96% purity). $^1$H NMR (400 MHz, CDCl₃): δ 7.86 (dd, J=11.36, 2.07 Hz, 1H), 7.85 (d, J=8.53 Hz, 1H), 7.72 (s, 1H), 7.52-7.49 (m, 1H), 7.47-7.39 (m, 2H), 4.43 (d, J=9.66 Hz, 1H), 3.96 (d, J=9.66 Hz, 1H), 3.91-3.83 (m, 2H), 3.20-2.99 (m, 5H), 2.82 (d, J=14.93 Hz, 1H), 1.69 (s, 3H). LCMS (ESI) m/z: 494 (M+1).

Embodiment 12

(S)-2-((2-(3,4-Difluorophenyl)-7,8-dihydro-1,6-naphthyridin-6(5H)-yl)methyl)-2-methyl-6-nitro-2,3-dihydroimidazo[2,1-b]oxazole

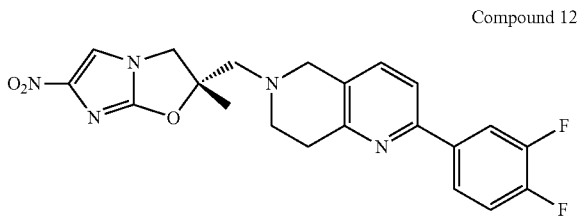 [SMILES: C[C@]1(CN2CCc3nc(-c4ccc(F)c(F)c4)ccc3C2)Cn2cc([N+](=O)[O-])nc2O1]

Compound 12

The key intermediate B (300.00 mg, 857.71 μmol, 1.00 eq) and (3,4-difluorophenyl) boronic acid (162.53 mg, 1.03 mmol, 1.20 eq) were dissolved in dioxane (5.00 mL) and water (500.00 μL). Sodium carbonate (113.64 mg, 1.07 mmol, 2.50 eq), Pd(dppf)Cl$_2$ (62.76 mg, 85.77 μmol, 0.10 eq) were added at 30° C. under the nitrogen gas atmosphere. The mixture was heated to 100° C. and stirred for 12 hours, and cooled, water (10 mL) was added to the mixed solution and the aqueous phase was extracted with ethyl acetate (30 mL×3). The combined organic phases were washed with saturated brine (20 mL), dried over anhydrous sodium sulfate, filtered and concentrated in vacuo. The residue was subjected to preliminary treatment by thin layer chromatography (petroleum ether/ethyl acetate=1/1, 0/1) and then separated and purified by preparative chromatography (GX-D; Boston Symmetrix C18 ODS-R 150*30 mm*5 um; acetonitrile 24%-54%; water (0.225% fomic acid), 25 mL/min) to deliver (S)-2-((2-(3,4-difluorophenyl)-7,8-dihydro-1,6-naphthyridin-6(5H)-yl)methyl)-2-methyl-6-nitro-2,3-dihydroimidazo[2,1-b]oxazole compound 12 (5.70 mg, 13.34 μmol, 3.11% yield, 95.0% purity). $^1$H NMR (400 MHz, CDCl$_3$): δ 7.85 (ddd, J=11.83, 7.83, 2.13 Hz, 1H), 7.83 (br. s., 1H), 7.52 (s, 1H), 7.46-7.44 (m, 1H), 7.39-7.37 (m, 1H), 7.26-7.21 (m, 1H), 4.43 (d, J=9.66 Hz, 1H), 3.96 (d, J=9.54 Hz, 1H), 3.90-3.82 (m, 2H), 3.11 (d, J=14.93 Hz, 2H), 3.01-2.99 (m, 3H), 2.83-2.79 (d, J=14.81 Hz, 1H), 1.69 (s, 3H). LCMS (ESI) m/z: 428 (M+1).

Embodiment 13

(S)-2-((2-(2,4-Difluorophenyl)-7,8-dihydro-1,6-naphthyridin-6(5H)-yl)methyl)-2-methyl-6-nitro-2,3-dihydroimidazo[2,1-b]oxazole

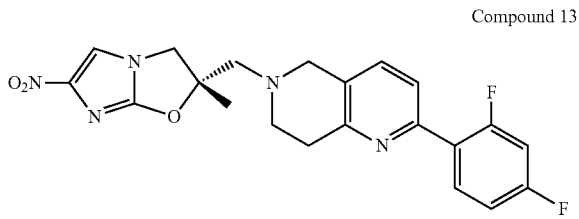 [SMILES: C[C@]1(CN2CCc3nc(-c4ccc(F)cc4F)ccc3C2)Cn2cc([N+](=O)[O-])nc2O1]

Compound 13

The key intermediate B (300.00 mg, 857.71 μmol, 1.00 eq) and (2,4-difluorophenyl) boronic acid (162.53 mg, 1.03 mmol, 1.20 eq) were dissolved in dioxane (5.00 mL) and water (500.00 μL). Then sodium carbonate (113.64 mg, 1.07 mmol, 2.50 eq), Pd(dppf)Cl$_2$ (62.76 mg, 85.77 μmol, 0.10 eq) were added at 30° C. under the nitrogen gas atmosphere. Then the mixture was heated to 100° C. and stirred for 12 hours. The mixture was cooled to 30° C. Water (10 mL) was added to the mixture and extracted with ethyl acetate (30 mL×3). The combined organic phases were washed with saturated brine (20 mL), dried over anhydrous sodium sulfate, filtered and concentrated in vacuo. The residue was purified by silica gel chromatography (petroleum ether/ethyl acetate=1/1, 0/1), and then purified by preparative chromatography (GX-D; Boston Symmetrix C18 ODS-R 150*30 mm*5 um; acetonitrile 24%-54%; water (0.225% fomic acid), 25 mL/min) to deliver (S)-2-((2-(2,4-difluorophenyl)-7,8-dihydro-1,6-naphthyridin-6(5H)-yl)methyl)-2-methyl-6-nitro-2,3-dihydroimidazo[2,1-b]oxazole compound 13 (35.70 mg, 83.53 μmol, 19.48% yield, 97.0% purity). $^1$H NMR (400 MHz, CDCl$_3$): δ 7.95-7.93 (td, J=8.78, 6.65 Hz, 1H), 7.53-7.50 (m, 2H), 7.38-7.36 (d, J=8.16 Hz, 1H), 7.00-6.99 (td, J=8.03, 2.76 Hz, 1H), 6.93-6.88 (ddd, J=11.11, 8.72, 2.51 Hz, 1H), 4.43 (d, J=9.66 Hz, 1H), 3.96 (d, J=9.66 Hz, 1H), 3.90-3.87 (m, 2H), 3.17-3.09 (m, 2H), 3.03-2.99 (m, 3H), 2.81 (d, J=14.81 Hz, 1H), 1.69 (s, 3H). LCMS (ESI) m/z: 428 (M+1).

Embodiment 14

(S)-2-((2-(3,5-Difluorophenyl)-7,8-dihydro-1,6-naphthyridin-6(5H)-yl)methyl)-2-methyl-6-nitro-2,3-dihydroimidazo[2,1-b]oxazole

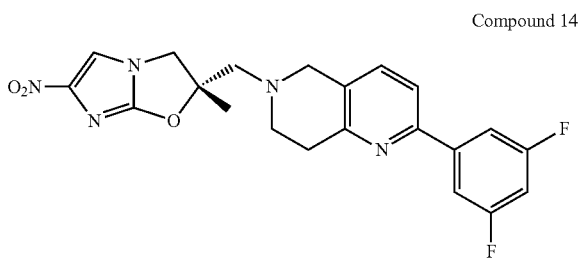 [SMILES: C[C@]1(CN2CCc3nc(-c4cc(F)cc(F)c4)ccc3C2)Cn2cc([N+](=O)[O-])nc2O1]

Compound 14

The key intermediate B (200 mg, 571.80 μmol, 1.00 eq) and (3,5-difluorophenyl) boronic acid (628.98 μmol, 1.10 eq) were dissolved in dioxane (5.00 mL), Pd(dppf)Cl$_2$ (42 mg, 57.18 μmol, 0.10 eq) and cesium fluoride (217 mg, 1.43 mmol, 2.50 eq) were added under the nitrogen gas atmosphere. The mixture was heated to 110° C. and stirred for 2 hours. The mixture was cooled to 20° C. and concentrated under reduced pressure. The residue was diluted with water and the aqueous phase was extracted with ethyl acetate (20 mL×3). The combined organic phases were washed with saturated brine (20 mL), dried over anhydrous sodium sulfate, filtered and concentrated in vacuo. The residue was purified by silica gel chromatography (column height: 250 mm, diameter: 100 mm, 100-200 mesh silica gel, petroleum ether/ethyl acetate=2/1, 1/1) to deliver (S)-2-((2-(3,5-difluorophenyl)-7,8-dihydro-1,6-naphthyridin-6(5H)-yl)methyl)-2-methyl-6-nitro-2,3-dihydroimidazo[2,1-b]oxazole compound 14 (26.00 mg, 59.62 μmol, 10.43% yield). $^1$H NMR (400 MHz, CDCl$_3$): δ 7.52-7.46 (m, 4H), 7.41-7.39 (m, 1H), 6.84 (tt, J=8.67, 2.31 Hz, 1H), 4.43 (d, J=9.66 Hz, 1H), 4.98-3.87 (m, 3H), 3.17-2.84 (m, 5H), 2.80 (d, J=14.81 Hz, 1H), 1.69 (s, 3H). LCMS (ESI) m/z: 428 (M+1).

Embodiment 15

(S)-2-((2-(5-Chloro-2-fluorophenyl)-7,8-dihydro-1,6-naphthyridin-6(5H)-yl)methyl)-2-methyl-6-nitro-2,3-dihydroimidazo[2,1-b]oxazole Compound 15

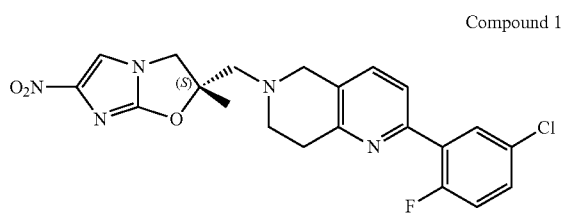

The key intermediate B (200.00 mg, 571.80 μmol, 1.00 eq) and (5-chloro-2-fluoro-phenyl) boronic acid (119.64 mg, 686.17 μmol, 1.20 eq) were dissolved in water (500.00 μL) and dioxane (3.00 mL), and then Pd(dppf)Cl$_2$ (41.84 mg, 57.18 μmol, 0.10 eq) and cesium fluoride (260.57 mg, 1.72 mmol, 3.00 eq) were added. The mixture was stirred at 110° C. for 16 hours under the nitrogen gas atmosphere. The mixture was concentrated in vacuo, and the residue was purified by preparative chromatography (GX-D; Boston Green ODS 150*30 5u; acetonitrile 40%-70%; water (0.225% fomic acid); 25 mL/min) to deliver (S)-2-((2-(5-chloro-2-fluorophenyl)-7,8-dihydro-1,6-naphthyridin-6(5H)-yl)methyl)-2-methyl-6-nitro-2,3-dihydroimidazo[2,1-b]oxazole compound 15 (40.09 mg, 88.24 μmol, 15.43% yield, 97.7% purity). $^1$H NMR (400 MHz, CDCl$_3$): δ 7.94 (dd, J=6.78, 2.76 Hz, 1H), 7.53-7.56 (m, 2H), 7.39 (d, J=8.00 Hz, 1H), 7.32 (ddd, J=8.75, 4.17, 2.76 Hz, 1H), 7.10 (dd, J=10.42, 8.78 Hz, 1H), 4.44 (d, J=9.66 Hz, 1H), 4.00-3.82 (m, 3H), 2.93-3.22 (m, 5H), 2.82 (d, J=14.81 Hz, 1H), 1.69 (s, 3H). LCMS (ESI) m/z: 444.0 (M+1).

Embodiment 16

(S)-2-((2-(2,3-Difluorophenyl)-7,8-dihydro-1,6-naphthyridin-6(5H)-yl)methyl)-2-methyl-6-nitro-2,3-dihydroimidazo[2,1-b]oxazole Compound 16

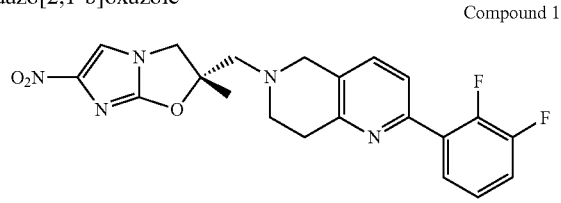

The key intermediate B (200.00 mg, 571.80 μmol, 1.00 eq) and (2,3-difluorophenyl) boronic acid (135.44 mg, 857.70 μmol, 1.50 eq), cesium fluoride (173.71 mg, 1.14 mmol, 2.00 eq) were dissolved in water (300.00 μL) and dioxane (3.00 mL). The mixed solution was replaced with nitrogen three times and Pd(dppf)Cl$_2$ (41.84 mg, 57.18 μmol, 0.10 eq) was added and stirred at 110° C. for 12 hours. The residue was purified by preparative chromatography (GX-A; Phenomenex Gemini C18 250*50 10u; acetonitrile 38%-68%; H$_2$O (0.2% NH$_3$.H$_2$O); 25 mL/min) to deliver (S)-2-((2-(2,3-difluorophenyl)-7,8-dihydro-1,6-naphthyridin-6(5H)-yl)methyl)-2-methyl-6-nitro-2,3-dihydroimidazo[2,1-b]oxazole compound 16 (28.00 mg, 65.51 μmol, 11.46% yield). $^1$H NMR (400 MHz, DMSO-d$_6$) δ 8.11 (s, 1H), 7.73-7.43 (m, 4H), 7.37-7.22 (m, 1H), 4.29 (s, 1H), 4.10 (d, J=10.54 Hz, 1H), 3.85 (d, J=14.05 Hz, 2H), 2.98 (d, J=3.76 Hz, 6H), 1.60 (s, 3H). LCMS (ESI) m/z: 428.0 (M+1).

Embodiment 17

(S)-2-((2-(2,5-Difluorophenyl)-7,8-dihydro-1,6-naphthyridin-6(5H)-yl)methyl)-2-methyl-6-nitro-2,3-dihydroimidazo[2,1-b]oxazole Compound 17

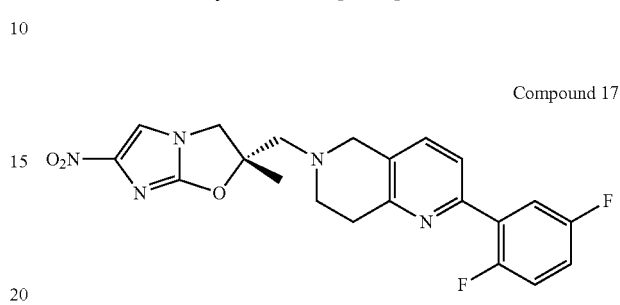

The key intermediate B (200.00 mg, 571.80 μmol, 1.00 eq) and (2,5-difluorophenyl) boronic acid (108.3 mg, 686.16 μmol, 1.20 eq) were dissolved in toluene (5.00 mL) and water (500.00 μL), cesium fluoride (260.57 mg, 1.72 mmol, 3.00 eq) and Pd(dppf)Cl$_2$ (41.84 mg, 57.18 μmol, 0.10 eq) were added to the mixed solution at 30° C. under the nitrogen gas atmosphere, and then heated to 100° C. and stirred for 12 hours. The mixture was cooled to 30° C., and water (10 mL) was added to the mixture, the aqueous phase was extracted with ethyl acetate (30 mL×3). The combined organic phases were washed with saturated brine (20 mL), dried over anhydrous sodium sulfate, filtered and concentrated in vacuo. The residue was subjected to preliminary treatment by silica gel chromatography (petroleum ether/ethyl acetate=1/1, 0/1) and then separated and purified by preparative chromatography (GX-D; Boston Symmetrix C18 ODS-R 150*30 mm*5 um; acetonitrile 24%-54%; water (0.225% fomic acid),25 mL/min) to deliver (S)-2-((2-(2,5-difluorophenyl)-7,8-dihydro-1,6-naphthyridin-6(5H)-yl)methyl)-2-methyl-6-nitro-2,3-dihydroimidazo[2,1-b]oxazole compound 17 (51.50 mg, 118.69 μmol, 20.76% yield, 98.5% purity). $^1$H NMR (400 MHz, CDCl$_3$): δ 7.71-7.60 (ddd, J=9.22, 6.02, 3.20 Hz, 1H), 7.59 (dd, J=8.03, 2.26 Hz, 1H), 7.53 (s, 1H), 7.38 (d, J=8.03 Hz, 1H), 7.12-7.05 (m, 2H), 4.44 (d, J=9.66 Hz, 1H), 3.98 (d, J=9.66 Hz, 1H), 3.91-3.84 (m, 2H), 3.16-3.09 (m, 2H), 3.04-3.00 (m, 3H), 2.83-2.80 (d, J=14.81 Hz, 1H), 1.69 (s, 3H). LCMS (ESI) m/z: 428 (M+1).

Embodiment 18

(S)-2-((2-(3-Chloro-4-fluorophenyl)-7,8-dihydro-1,6-naphthyridin-6(5H)-yl)methyl)-2-methyl-6-nitro-2,3-dihydroimidazo[2,1-b]oxazole Compound 18

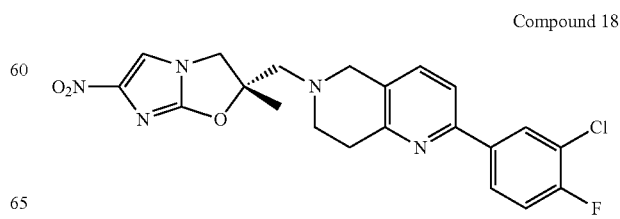

The key intermediate B (300.00 mg, 857.71 μmol, 1.00 eq), (3-chloro-4-fluoro-phenyl) boronic acid (224.32 mg, 1.29 mmol, 1.50 eq), cesium fluoride (260.57 mg, mmol, 2.00 eq) were dissolved in water (500.00 μL) and dioxane (5.00 mL), Pd(dppf)Cl$_2$ (62.76 mg, 85.77 μmol, 0.10 eq) was added under the nitrogen gas atmosphere, and the mixture was stirred at 110° C. for 12 hours. The mixture was concentrated, and purified by preparative chromatography (GX-G, Phenomenex Synergi C18 150*30 mm*4 um, acetonitrile 45%-75%; H$_2$O (+0.0022 NH$_3$.H$_2$O); 25 mL/min) to deliver (S)-2-((2-(3-chloro-4-fluorophenyl)-7,8-dihydro-1,6-naphthyridin-6(5H)-yl)methyl)-2-methyl-6-nitro-2,3-dihydroimidazo[2,1-b]oxazole compound 18 (90.00 mg, 202.77 μmol, 23.64% yield). $^1$H NMR (400 MHz, DMSO-d$_6$): δ 8.27-8.18 (m, 1H), 8.10 (s, 1H), 8.09-8.03 (m, 1H), 7.84-7.75 (m, 1H), 7.63-7.43 (m, 2H), 4.30 (d, J=10.67 Hz, 1H), 4.16-4.06 (m, 1H), 3.82 (d, J=12.67 Hz, 2H), 2.97 (d, J=3.51 Hz, 6H), 1.60 (s, 3H). LCMS (ESI) m/z: 444.1 (M+1).

Embodiment 19

(S)-2-((2-(3-Chloro-2-fluorophenyl)-7,8-dihydro-1,6-naphthyridin-6(5H)-yl)methyl)-2-methyl-6-nitro-2,3-dihydroimidazo[2,1-b]oxazole

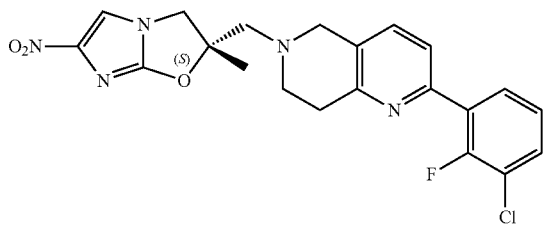

Compound 19

The key intermediate B (200.00 mg, 571.80 μmol, 1.00 eq) and (3-chloro-2-fluoro-phenyl) boronic acid (99.70 mg, 571.80 μmol, 1.00 eq) were dissolved in dioxane (3.00 mL) and water (500.00 μL), Pd(dppf)Cl$_2$ (41.84 mg, 57.18 μmol, 0.10 eq) and cesium fluoride (260.57 mg, 1.72 mmol, 3.00 eq) were added. The mixture was stirred at 110° C. for 16 hours under the nitrogen gas atmosphere, and then concentrated. The residue was purified by preparative chromatography (GX-D; Boston Green ODS 150*30 5u; acetonitrile 40%-70%; water (0.225% fomic acid); 25 mL/min) to deliver (S)-2-((2-(3-chloro-2-fluorophenyl)-7,8-dihydro-1,6-naphthyridin-6(5H)-yl)methyl)-2-methyl-6-nitro-2,3-dihydroimidazo[2,1-b]oxazole compound 19 (47.80 mg, 101.12 μmol, 17.68% yield, 93.9% purity). $^1$H NMR (400 MHz, CDCl$_3$) δ 7.83-7.74 (m, 1H), 7.56-7.50 (m, 2H), 7.47-7.37 (m, 2H), 7.19 (td, J=7.91, 0.88 Hz, 1H), 4.43 (d, J=9.66 Hz, 1H), 3.99-3.86 (m, 3H), 3.24-2.91 (m, 5H), 2.82 (d, J=14.81 Hz, 1H), 1.69 (s, 3H). LCMS (ESI) m/z: 444.1 (M+1).

Embodiment 20

(S)-2-((2-(4-Chloro-3-fluorophenyl)-7,8-dihydro-1,6-naphthyridin-6(5H)-yl)methyl)-2-methyl-6-nitro-2,3-dihydroimidazo[2,1-b]oxazole

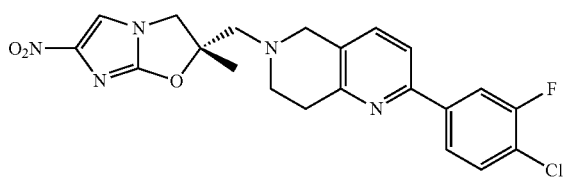

Compound 20

The key intermediate B (200 mg, 571.80 μmol, 1.00 eq) and (4-chloro-3-fluoro-phenyl) boronic acid (628.98 μmol, 1.10 eq) were dissolved in dioxane (5.00 mL), Pd(dppf)Cl$_2$ (42 mg, 57.18 μmol, 0.10 eq) and cesium fluoride (217 mg, 1.43 mmol, 2.50 eq) were added under the nitrogen gas atmosphere. The mixture was heated to 110° C. and stirred for 2 hours. The mixture was cooled to 20° C. and concentrated under reduced pressure. The residue was diluted with water and the aqueous phase was extracted with ethyl acetate (20 mL×3). The combined organic phases were washed with saturated brine (20 mL), dried over anhydrous sodium sulfate, filtered and concentrated in vacuo. The residue was purified by preparative chromatography (Instrument: GX-D; Column: Boston Symmetrix C18 ODS-R 150*30 mm*5 um; Mobile phase: MeCN: 25%-55%; H$_2$O (+0.0023 HCOOH), Rate: 25 mL/min; Monitored Wavelength: 220 nm/254 nm; Run length: 10 min/15 min; Column temperature: 20° C.) to deliver (S)-2-((2-(4-chloro-3-fluorophenyl)-7,8-dihydro-1,6-naphthyridin-6(5H)-yl)methyl)-2-methyl-6-nitro-2,3-dihydroimidazo[2,1-b]oxazole compound 20 (26.00 mg, 52.72 μmol, 9.22% yield). $^1$H NMR (400 MHz, CDCl$_3$): δ 7.81 (d, J=10.29 Hz, 1H), 7.68 (d, J=8.78 Hz, 1H), 7.52-7.38 (m, 4H), 4.43 (d, J=9.54 Hz, 1H), 3.98-3.66 (m, 3H), 3.16-2.79 (m, 6H), 1.69 (s, 1H). LCMS (ESI) m/z: 444 (M+1).

Embodiment 21

(S)-2-((2-(3-Chloro-5-fluorophenyl)-7,8-dihydro-1,6-naphthyridin-6(5H)-yl)methyl)-2-methyl-6-nitro-2,3-dihydroimidazo[2,1-b]oxazole

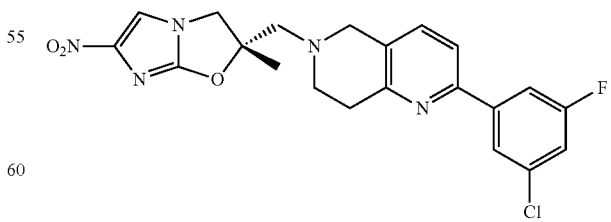

Compound 21

The key intermediate B (200 mg, 571.80 μmol, 1.00 eq) and (3-chloro-5-fluoro-phenyl) boronic acid (628.98 μmol, 1.10 eq) were dissolved in dioxane (5.00 mL), Pd(dppf)Cl$_2$ (42 mg, 57.18 μmol, 0.10 eq) and cesium fluoride (217 mg, 1.43 mmol, 2.50 eq) were added under the nitrogen gas atmosphere. The mixed solution was heated to 110° C. and stirred for 2 hours and then cooled to 20° C. The mixture was concentrated under reduced pressure. The residue was diluted with water and the aqueous phase was extracted with ethyl acetate (20 ml×3). The combined organic phases were washed with saturated brine (20 mL), dried over anhydrous sodium sulfate, filtered and concentrated in vacuo. The residue was purified by preparative chromatography (Instrument: GX-D; Column: Boston Symmetrix C18 ODS-R 150*30 mm*5 um; Mobile phase: MeCN: 15%-45%; $H_2O$ (+0.0023 HCOOH), Rate: 25 mL/min; Monitored Wavelength: 220 nm/254 nm; Run length: 10 min/15 min; Column temperature: 20° C.) to deliver (S)-2-((2-(3-chloro-5-fluorophenyl)-7,8-dihydro-1,6-naphthyridin-6(5H)-yl) methyl)-2-methyl-6-nitro-2,3-dihydroimidazo[2,1-b] oxazole compound 21 (88.00 mg, 193.70 µmol, 33.88% yield). $^1$H NMR (400 MHz, $CDCl_3$): δ 7.76 (s, 1H), 7.59 (dt, J=9.47, 1.98 Hz, 1H), 7.53 (s, 1H), 7.50-7.43 (m, 1H), 7.43-7.35 (m, 1H), 7.12 (dt, J=8.16, 2.07 Hz, 1H), 4.43 (d, J=9.66 Hz, 1H), 3.98-3.68 (m, 3H), 3.34-2.88 (m, 5H), 2.82 (d, J=14.81 Hz, 1H), 1.69 (s, 3H). LCMS (ESI) m/z: 444 (M+1).

Embodiment 22

(S)-2-((2-(2-Chloro-5-fluorophenyl)-7,8-dihydro-1, 6-naphthyridin-6(5H)-yl)methyl)-2-methyl-6-nitro-2, 3-dihydroimidazo[2,1-b]oxazole Compound 22

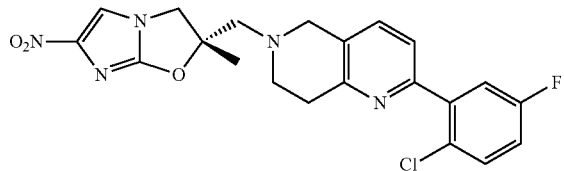

The key intermediate B (200 mg, 571.80 µmol, 1.00 eq) and (2-chloro-5-fluoro-phenyl) boronic acid (628.98 µmol, 1.10 eq) were dissolved in dioxane (5.00 mL), $Pd(dppf)Cl_2$ (42 mg, 57.18 µmol, 0.10 eq) and cesium fluoride (217 mg, 1.43 mmol, 2.50 eq) were added under the nitrogen gas atmosphere. The mixture was heated to 110° C. and stirred for 2 hours. The mixture was cooled to 20° C. and concentrated under reduced pressure. The residue was diluted with water and the aqueous phase was extracted with ethyl acetate (20 mL×3). The combined organic phases were washed with saturated brine (20 mL), dried over anhydrous sodium sulfate, filtered and concentrated in vacuo. The residue was purified by preparative chromatography (Instrument: GX-D; Column: Boston Symmetrix C18 ODS-R 150*30 mm*5 um; Mobile phase: MeCN: 35%-75%; $H_2O$ (+0.0023 HCOOH), Rate: 25 mL/min; Monitored Wavelength: 220 nm/254 nm; Run length: 10 min/15 min; Column temperature: 20° C.) to deliver (S)-2-((2-(2-chloro-5-fluorophenyl)-7,8-dihydro-1,6-naphthyridin-6(5H)-yl) methyl)-2-methyl-6-nitro-2,3-dihydroimidazo[2,1-b] oxazole compound 22 (30.00 mg, 66.91 µmol, 11.70% yield). $^1$H NMR (400 MHz, $CDCl_3$): δ 7.54 (s, 1H), 7.47-7.36 (m, 3H), 7.31 (dd, J=8.97, 3.07 Hz, 1H), 7.04 (td, J=8.22, 3.14 Hz, 1H), 4.44 (d, J=9.66 Hz, 1H), 4.12-3.68 (m, 3H), 3.36-2.91 (m, 5H), 2.83 (d, J=14.81 Hz, 1H), 1.69 (s, 3H). LCMS (ESI) m/z: 444 (M+1).

Embodiment 23

(S)-2-((2-(4-Chloro-2-fluorophenyl)-7,8-dihydro-1, 6-naphthyridin-6(5H)-yl)methyl)-2-methyl-6-nitro-2, 3-dihydroimidazo[2,1-b]oxazole Compound 23

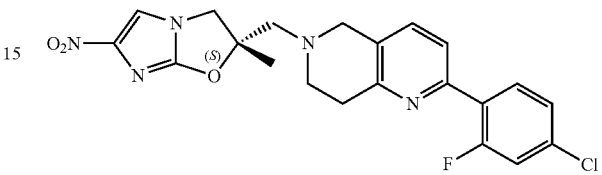

The key intermediate B (200.00 mg, 571.80 µmol, 1.00 eq) and (4-chloro-2-fluoro-phenyl) boronic acid (119.64 mg, 686.16 µmol, 1.20 eq) were dissolved in dioxane (3.00 mL) and water (500.00 µL). $Pd(dppf)Cl_2$ (41.84 mg, 57.18 µmol, 0.10 eq) and cesium fluoride (260.57 mg, 1.72 mmol, 3.00 eq) were added under the nitrogen gas atmosphere. The mixture was stirred at 110° C. for 16 hours and concentrated. The residue was separated and purified by preparative chromatography (GX-G; Phenomenex Synergi C18 150*30 mm*4 um; acetonitrile 24%-54%; water (0.225% fomic acid); 25 mL/min) to deliver (S)-2-((2-(2-chloro-5-fluoro-phenyl)-7,8-dihydro-1,6-naphthyridin-6(5H)-yl)methyl)-2-methyl-6-nitro-2,3-dihydroimidazo[2,1-b]oxazole compound 23 (56.26 mg, 125.10 µmol, 21.88% yield, 98.7% purity). $^1$H NMR (400 MHz, $CDCl_3$): δ 7.92 (t, J=8.41 Hz, 1H), 7.57-7.50 (m, 2H), 7.38 (d, J=8.03 Hz, 1H), 7.27-7.22 (m, 1H), 7.22-7.16 (m, 1H), 4.43 (d, J=9.66 Hz, 1H), 4.0-3.81 (m, 3H), 3.23-2.90 (m, 5H), 2.81 (d, J=14.81 Hz, 1H), 1.69 (s, 3H). LCMS (ESI) m/z: 444.0 (M+1).

Embodiment 24

(S)-2-((2-(Furan-3-yl)-7,8-dihydro-1,6-naphthyridin-6(5H)-yl)methyl)-2-methyl-6-nitro-2,3-dihydroimidazo[2,1-b]oxazole Compound 24

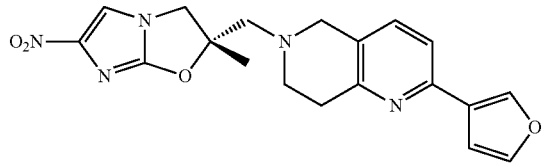

The key intermediate B (200.00 mg, 571.80 µmol, 1.00 eq) and 3-furylboronic acid (76.77 mg, 686.16 µmol, 1.20 eq) were dissolved in dioxane (5.00 mL) and water (500.00 µL), sodium carbonate (121.21 mg, 1.14 mmol, 2.00 eq), $Pd(PPh_3)_4$ (66.07 mg, 57.18 µmol, 0.10 eq) were added under the nitrogen gas atmosphere. The mixture was stirred at 90° C. for 12 hours. The mixture was cooled to 30° C. and concentrated under reduced pressure at 45° C. The residue was subjected to preliminary treatment by silica gel chromatography (petroleum ether/ethyl acetate=10/1, 1/1), and then separated and purified by preparative chromatography (GX-D; Boston Symmetrix C18 ODS-R 150*30 mm*5 um; MeCN: 24%-54%; H₂O (+0.0025 FA); 25 mL/min) to deliver (S)-2-((2-(furan-3-yl)-7,8-dihydro-1,6-naphthyridin-6(5H)-yl)methyl)-2-methyl-6-nitro-2,3-dihydroimidazo[2,1-b]oxazole compound 24 (56.67 mg, 142.65 μmol, 24.95% yield, 96% purity). ¹H NMR (400 MHz, CDCl₃): δ 7.99 (s, 1H), 7.51 (s, 1H), 7.48 (t, J=1.69 Hz, 1H), 7.31-7.29 (m, 1H), 7.28-7.24 (m, 1H), 6.87 (d, J=1.13 Hz, 1H), 4.43 (d, J=9.66 Hz, 1H), 3.95 (d, J=9.66 Hz, 1H), 3.81 (m, 2H), 3.14-3.07 (m, 2H), 2.99-2.96 (m, 3H), 2.79 (d, J=14.81 Hz, 1H), 1.68 (s, 3H). LCMS (ESI) m/z: 382 (M+1).

Embodiment 25

(S)-2-((2-(Furan-2-yl)-7,8-dihydro-1,6-naphthyridin-6(5H)-yl)methyl)-2-methyl-6-nitro-2,3-dihydroimidazo[2,1-b]oxazole

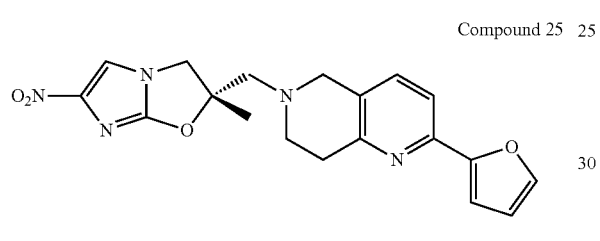

Compound 25

The key intermediate B (150.00 mg, 428.85 μmol, 1.00 eq) and tributyl(2-furyl)stannane (229.73 mg, 643.28 μmol, 1.50 eq) were dissolved in dichloroethane (10.00 mL), Pd(dppf)Cl₂ (31.38 mg, 42.89 μmol, 0.10 eq), lithium chloride (6.09 mg, 143.76 μmol, 1.00 eq) was added at 30° C. under the nitrogen gas atmosphere. The mixture was then heated to 120° C. and stirred for 12 hours. The mixture was cooled and concentrated under reduced pressure at 45° C. Water (10 mL) was added to the mixture and stirred for 5 minutes. The aqueous phase was extracted with ethyl acetate (30 ml×3). The combined organic phases were washed with saturated brine (10 mL×2), dried over anhydrous sodium sulfate, filtered and concentrated in vacuo. The residue was subjected to preliminary treatment by silica gel chromatography (ethyl acetate), and then separated and purified by preparative chromatography (Instrument: GX-D; Boston Symmetrix C18 ODS-R 150*30 mm*5 um; acetonitrile 24%-54%; water (0.225% fomic acid); 25 mL/min) to deliver (S)-2-((2-(furan-2-yl)-7,8-dihydro-1,6-naphthyridin-6(5H)-yl)methyl)-2-methyl-6-nitro-2,3-dihydroimidazo[2,1-b]oxazole compound 25 (31.70 mg, 83.12 μmol, 19.38% yield). ¹H NMR (400 MHz, CDCl₃): δ 7.53 (m, 1H), 7.52 (s, 1H), 7.47 (d, J=8.16 Hz, 1H), 7.33 (d, J=8.16 Hz, 1H), 6.99 (d, J=3.39 Hz, 1H), 6.52 (dd, J=3.39, 1.76 Hz, 1H), 4.43 (d, J=9.54 Hz, 1H), 3.95 (d, J=9.66 Hz, 1H), 3.85 (d, J=14.18 Hz, 2H), 3.09 (d, J=14.81 Hz, 2H), 3.01-2.97 (m, 3H), 2.79 (d, J=14.81 Hz, 1H), 1.69 (s, 3H). LCMS (ESI) m/z: 382 (M+1).

Embodiment 26

(S)-2-((2-Cyclopropyl-7,8-dihydro-1,6-naphthyridin-6(5H)-yl)methyl)-2-methyl-6-nitro-2,3-dihydroimidazo[2,1-b]oxazole

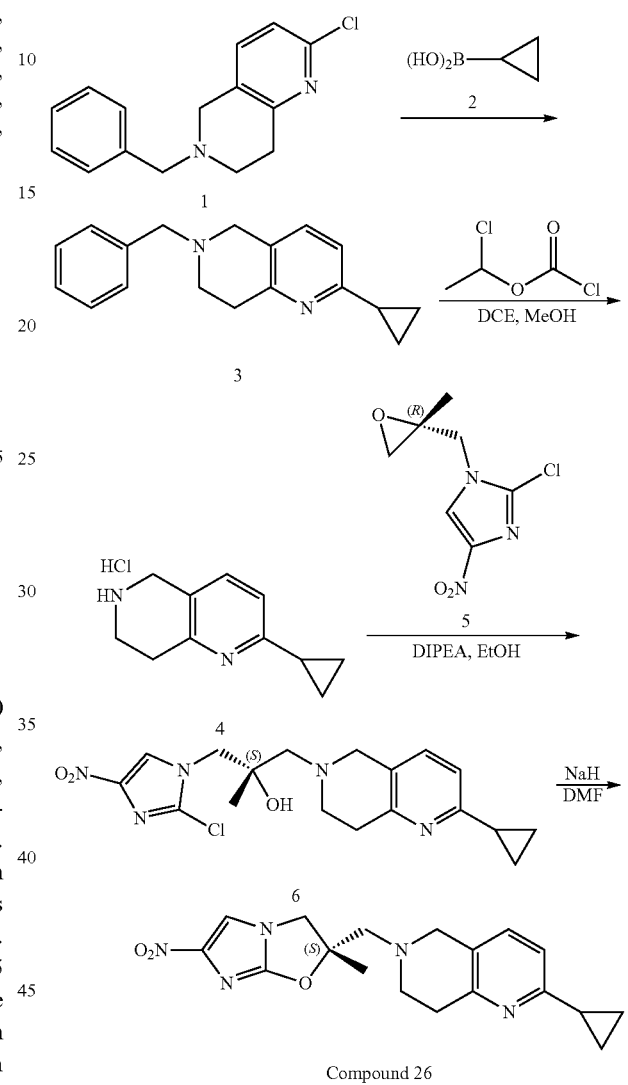

Step 1:

6-Benzyl-2-cyclopropyl-5,6,7,8-tetrahydro-1,6-naphthyridine

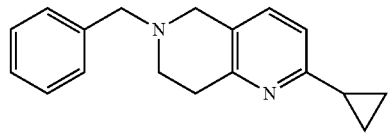 [SMILES: c1ccc(CN2CCc3nc(C4CC4)ccc3C2)cc1]

The key intermediate A (1.50 g, 5.80 mmol, 1.00 eq) and cyclopropylboronic acid (647.69 mg, 7.54 mmol, 1.30 eq) were dissolved in toluene (10.00 mL), di(adamantan-1-yl)(butyl)phosphine (415.91 mg, 1.16 mmol, 0.20 eq), cesium carbonate (3.78 g, 11.60 mmol, 2.00 eq) and Pd(OAc)$_2$ (130.22 mg, 580.00 μmol, 0.10 eq) were added at 30° C. under the nitrogen gas atmosphere. The mixture was then heated to 100° C. and stirred for 12 hours. The residue was purified by silica gel chromatography (petroleum ether/ethyl acetate=30/1) to deliver 6-benzyl-2-cyclopropyl-7,8-dihydro-5H-1-1,6-naphthyridine (1.30 g, 4.92 mmol, 84.79% yield) as a yellow solid. $^1$H NMR (300 MHz, CDCl$_3$): δ 7.35-7.29 (m, 2H), 7.27 (s, 1H), 7.25-7.21 (m, 1H), 7.21-7.17 (m, 1H), 7.05 (d, J=7.9 Hz, 1H), 6.71 (d, J=7.9 Hz, 1H), 3.62 (s, 2H), 3.49 (s, 2H), 2.93-2.85 (m, 2H), 2.79-2.71 (m, 2H), 1.99-1.87 (m, 1H), 0.92-0.85 (m, 2H), 0.84-0.80 (m, 2H). LCMS (ESI) m/z: 265 (M+1).

Step 2:

2-Cyclopropyl-5,6,7,8-tetrahydro-1,6-naphthyridine hydrochloride

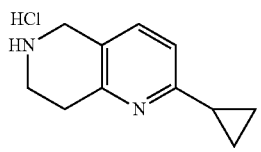 [SMILES: Cl ; c1cc2c(nc1C1CC1)CCNC2]

6-Benzyl-2-cyclopropyl-7,8-dihydro-5H-1,6-naphthyridine (200.00 mg, 756.54 μmol, 1.00 eq) was dissolved in dichloroethane (10.00 mL), 1-chlorocarbonyl chloride (162.24 mg, 1.13 mmol, 1.50 eq) was added at 0° C. under the nitrogen gas atmosphere. The mixture was stirred at 0° C. for 20 minutes and then heated to 80° C. and stirred for 12 hours. After the mixture was concentrated, methanol (10.00 mL) was added to the mixture and stirred at 75° C. for an additional 2 hours. The mixture was cooled and concentrated under reduced pressure at 45° C. The residue was washed with dichloromethane (20 mL×3), filtered and the cake was dried to deliver 2-cyclopropyl-5,6,7,8-tetrahydro-1,6-naphthyridine hydrochloride (170.00 mg, crude) as a yellow solid which was used in the next step without further purification.

Step 3:

(2S)-1-(2-Chloro-4-nitroimidazol-1-yl)-3-(2-cyclopropyl-7,8-dihydro-5H-1,6-naphthyridin-6-yl)-2-methylpropan-2-ol

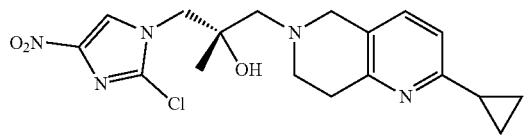 [SMILES: C[C@](O)(CN1CCc2nc(C3CC3)ccc2C1)Cn1cc([N+](=O)[O-])nc1Cl]

2-Cyclopropyl-5,6,7,8-tetrahydro-1,6-naphthyridine hydrochloride (550.00 mg, 3.16 mmol, 1.00 eq) and 2-chloro-1-[[(2R)-2-methyloxiran-2-yl]methyl]-4-nitroimidazole (893.94 mg, 4.11 mmol, 1.30 eq) were dissolved in ethanol (20.00 mL), DIPEA (1.02 g, 7.90 mmol, 2.50 eq) was added at 30° C. under the nitrogen gas atmosphere. The mixture was stirred at this temperature for 10 minutes and then heated to 80° C. and stirred for 12 hours. The mixture was diluted with water (20 mL) and the aqueous phase was extracted with ethyl acetate (20 mL×3). The combined organic phases were washed with saturated brine (10 mL×2), dried over anhydrous sodium sulfate, filtered and concentrated in vacuo. The residue was purified by silica gel chromatography (petroleum ether/ethyl acetate=10/1, 2/1) to deliver (2S)-1-(2-chloro-4-nitroimidazol-1-yl)-3-(2-cyclopropyl-7,8-dihydro-5H-1,6-naphthyridin-6-yl)-2-methylpropan-2-ol (400.00 mg, crude) as a yellow solid. LCMS (ESI) m/z: 392 (M+1).

Step 4:

(S)-2-((2-Cyclopropyl-7,8-dihydro-1,6-naphthyridin-6(5H)-yl)methyl)-2-methyl-6-nitro-2,3-dihydroimidazo[2,1-b]oxazole Compound 26

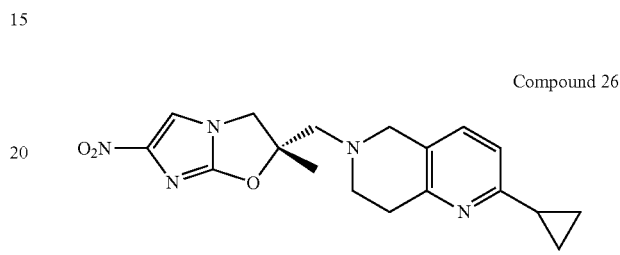

(2S)-1-(2-chloro-4-nitroimidazol-1-yl)-3-(2-cyclopropyl-7,8-dihydro-5H-1,6-naphthyridin-6-yl)-2-methylpropan-2-ol (440.00 mg, 1.12 mmol, 1.0 eq) was dissolved in DMF (5.00 mL), NaH (67.37 mg, 1.68 mmol, 1.50 eq) was added at −45° C. under the nitrogen gas atmosphere. The mixture was stirred at −45 to −15° C. for 2 hours. The residue was poured into a saturated aqueous ammonium chloride solution (20 mL) and stirred at 0° C. for 20 minutes. The aqueous phase was extracted with ethyl acetate (30 mL×3). The combined organic phases were washed with saturated brine (10 mL×2), dried over anhydrous sodium sulfate, filtered and concentrated in vacuo. The residue was separated and purified by preparative chromatography (GX-D; Boston Symmetrix C18 ODS-R 150*30 mm*5 um; acetonitrile 20%-54%; water (0.225% fomic acid); 25 mL/min) to deliver (S)-2-((2-cyclopropyl-7,8-dihydro-1,6-naphthyridin-6(5H)-yl)methyl)-2-methyl-6-nitro-2,3-dihydroimidazo[2,1-b]oxazole compound 26 (157.10 mg, 442.05 μmol, 39.47% yield). $^1$H NMR (400 MHz, CDCl$_3$): δ 7.51 (s, 1H), 7.16 (d, J=7.91 Hz, 1H), 6.82 (d, J=8.03 Hz, 1H), 4.42 (d, J=9.66 Hz, 1H), 3.93 (d, J=9.54 Hz, 1H), 3.79 (q, J=14.89 Hz, 2H), 3.07-3.04 (m, 2H), 2.94-2.85 (m, 3H), 2.76 (d, J=14.81 Hz, 1H), 2.03-2.01 (m, 1H), 1.66 (s, 3H), 0.98-0.96 (m, 2H), 0.92-0.90 (m, 2H). LCMS (ESI) m/z: 356 (M+1).

Embodiment 27

(S)-2-Methyl-6-nitro-2-((2-(trifluoromethyl)-7,8-dihydro-1,6-naphthyridin-6(5H)-yl)methyl)-2,3-dihydroimidazo[2,1-b]oxazole

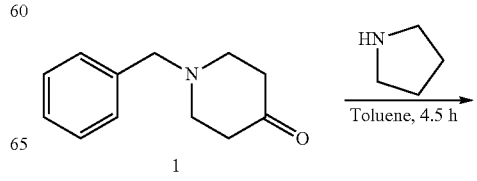

1

-continued

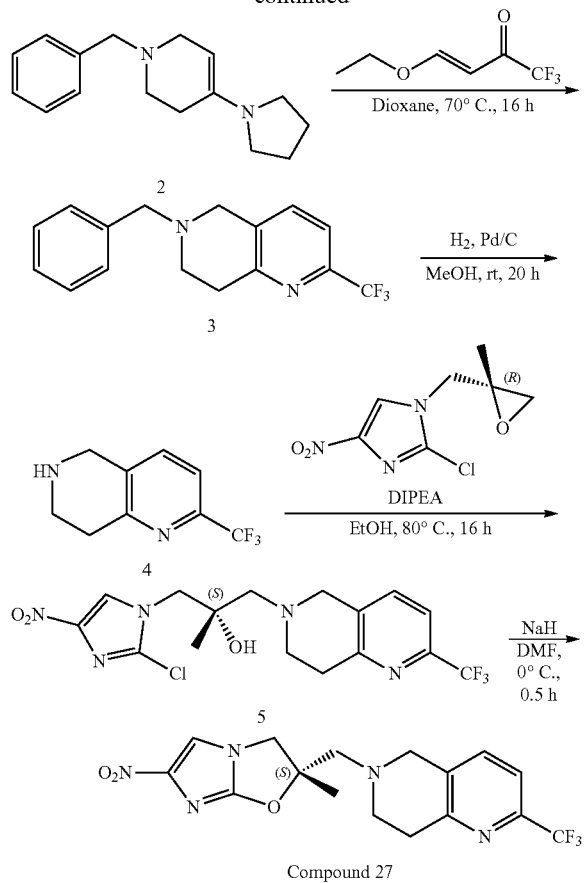

Compound 27

Step 1:

1-Benzyl-4-pyrrolidin-1-yl-3,6-dihydro-2H-pyridine

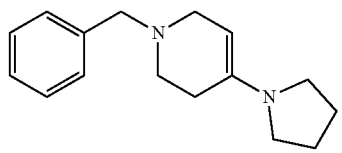 [SMILES: C1=C(N2CCCC2)CCN(Cc2ccccc2)C1]

1-Benzyl-4-one (10.00 g, 52.84 mmol, 1.00 eq) and pyrrolidine (4.51 g, 63.41 mmol, 1.20 eq) were dissolved in toluene (100 mL), water was removed by a water separator at 110° C. for 4.5 hours. The mixture was cooled and concentrated to deliver 1-benzyl-4-pyrrolidin-1-yl-3,6-dihydro-2H-pyridine (10.50 g, crude) as a yellow oil which was used in the next step without further purification.

Step 2:

6-Benzyl-2-(trifluoromethyl)-7,8-dihydro-5H-1,6-naphthyridine

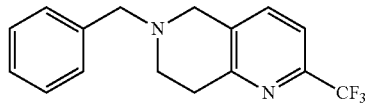 [SMILES: FC(F)(F)c1ccc2c(n1)CCN(Cc1ccccc1)C2]

1-Benzyl-4-pyrrolidin-1-yl-3,6-dihydro-2H-pyridine (2.50 g, 10.32 mmol, 1.00 eq) and (E)-4-ethoxy-1,1,1-trifluoro-but-3-en-2-one (2.08 g, 12.38 mmol, 1.20 eq) were dissolved in dioxane (30.00 mL). The mixture was heated to 100° C. and stirred for 4 hours. Ammonium acetate (2.39 g, 30.96 mmol, 3.00 eq) was then added and stirred for an additional 16 hours. The mixture was cooled and diluted with water. The aqueous phase was extracted with ethyl acetate (100 mL×3). The combined organic phases were washed with saturated brine (100 mL), dried over anhydrous sodium sulfate, filtered and concentrated in vacuo. The residue was purified by silica gel chromatography (column height: 300 mm, diameter 40 mm, 100-200 mesh silica gel, petroleum ether/ethyl acetate=30/1) to deliver 6-benzyl-2-(trifluoromethyl)-7,8-dihydro-5H-1,6-naphthyridine (1.50 g, 5.13 mmol, 49.73% yield) as a yellow oil. $^1$H NMR (400 MHz, CDCl$_3$) δ 7.46-7.29 (m, 7H), 3.75 (s, 2H), 3.70 (s, 2H), 3.15 (t, J=5.90 Hz, 2H), 2.92 (t, J=5.96 Hz, 2H).

Step 3:

2-(Trifluoromethyl)-5,6,7,8-tetrahydro-1,6-naphthyridine

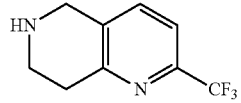

6-Benzyl-2-(trifluoromethyl)-7,8-dihydro-5H-1,6-naphthyridine (1.50 g, 5.13 mmol, 1.00 eq) was dissolved in methanol (20.00 ml) and Pd/C (100.00 mg) was added to the solution. The mixture was stirred at H$_2$ (50 psi) for 16 hours. The mixture was filtered and concentrated to deliver 2-(trifluoromethyl)-5,6,7,8-tetrahydro-1,6-naphthyridine (850.00 mg, crude) as an off-white solid which was used in the next step without further purification.

Step 4:

(S)-1-(2-Chloro-4-nitro-1H-imidazol-1-yl)-2-methyl-3-(2-(trifluoromethyl)-7,8-dihydro-1,6-naphthyridin-6(5H)-yl)propan-2-ol

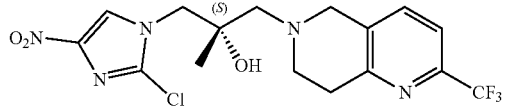

2-(Trifluoromethyl)-5,6,7,8-tetrahydro-1,6-naphthyridine (200.00 mg, 989.22 µmol, 1.00 eq) and (R)-2-chloro-1-((2-methyloxiran-2-yl)methyl)-4-nitro-1H-imidazole (322.90 mg, 1.48 mmol, 1.50 eq) were dissolved in ethanol (10.00 mL) and DIPEA (127.85 mg, 989.22 µmol, 1.00 eq) was added under the nitrogen gas atmosphere. The mixture was heated to 80° C. and stirred for 16 hours. The mixture was cooled and concentrated under reduced pressure. The residue was poured into water (50 mL) and extracted with ethyl acetate (50 mL×3). The combined organic phases were washed with saturated brine (50 mL), dried over anhydrous sodium sulfate, filtered and concentrated in vacuo to deliver (S)-1-(2-chloro-4-nitro-1H-imidazol-1-yl)-2-methyl-3-(2-

(trifluoromethyl)-7,8-dihydro-1,6-naphthyridin-6(5H)-yl) propan-2-ol (310.00 mg, crude) as a brown oil. LCMS (ESI) m/z: 420.1 (M+1).

Step 5:

(S)-2-Methyl-6-nitro-2-((2-(trifluoromethyl)-7,8-dihydro-1,6-naphthyridin-6(5H)-yl)methyl)-2,3-dihydroimidazo[2,1-b]oxazole Compound 27

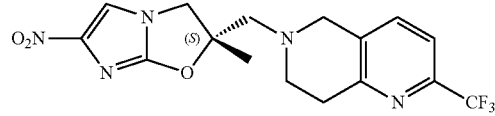

(S)-1-(2-Chloro-4-nitro-1H-imidazol-1-yl)-2-methyl-3-(2-(trifluoromethyl)-7,8-dihydro-1,6-naphthyridin-6(5H)-yl)propan-2-ol (100.00 mg, 238.21 µmol, 1.00 eq) was dissolved in DMF (2.00 mL), NaH (19.06 mg, 476.42 µmol, 2.00 eq) was added at −20° C. under the nitrogen gas atmosphere. The mixture was stirred at −20° C. for 1 hour. The mixture was poured into ice-water (w/w=1/1) (10 mL) and stirred for 5 minutes. The aqueous phase was extracted with ethyl acetate (10 mL×3). The combined organic phases were dried over anhydrous Na$_2$SO$_4$, filtered and concentrated in vacuo. The residue was separated and purified by preparative chromatography (Instrument: GX-G; Column: Phenomenex Synergi C18 150*30 mm*4 um; Mobile phase: MeCN: 20%-60%; H$_2$O (+0.0025 FA); Rate: 25 mL/min; Monitored Wavelength: 220 nm/254 nm; Run length: 10 min/15 min; Column temperature: 30° C.) to deliver (S)-2-methyl-6-nitro-2-((2-(trifluoromethyl)-7,8-dihydro-1,6-naphthyridin-6(5H)-yl)methyl)-2,3-dihydroimidazo[2,1-b]oxazole compound 27 (42.00 mg, 108.47 µmol, 45.54% yield, 99% purity). $^1$H NMR (300 MHz, CDCl$_3$) δ 7.52-7.47 (m, 3H), 4.39 (d, J=9.8 Hz, 1H), 3.99-3.89 (m, 3H), 3.14-3.84 (m, 5H), 2.82 (d, J=14.7 Hz, 1H), 1.68 (s, 3H). LCMS (ESI) m/z: 384 (M+1).

Embodiment 28

(S)-2-Methyl-6-nitro-2-((2-(piperidin-1-yl)-7,8-dihydro-1,6-naphthyridin-6(5H)-yl)methyl)-2,3-dihydroimidazo[2,1-b]oxazole

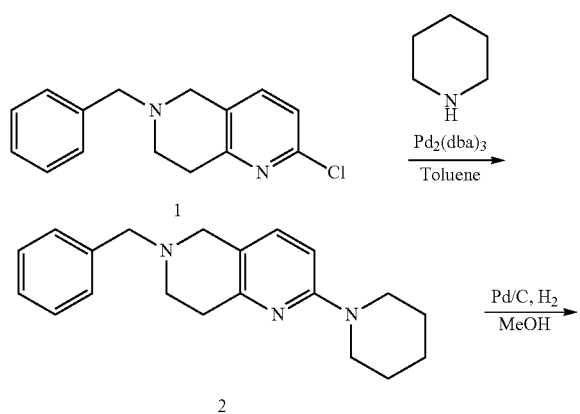

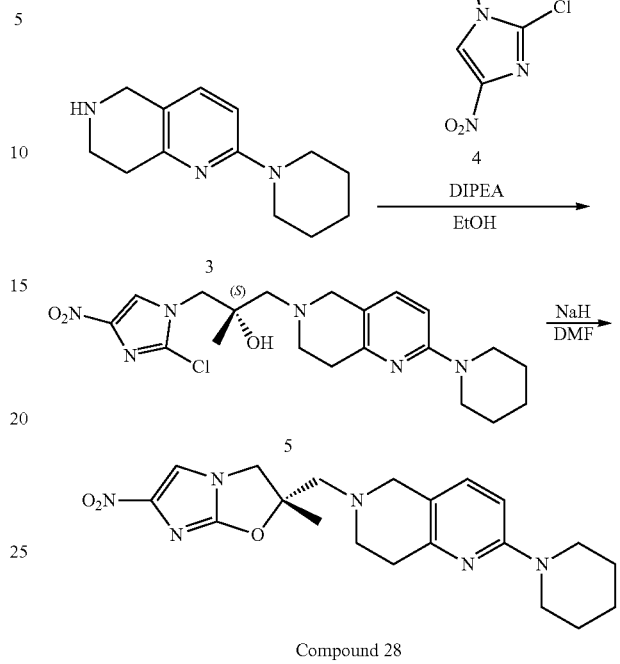

Step 1:

6-Benzyl-2-(1-piperidinyl)-7,8-dihydro-5H-1,6-naphthyridine

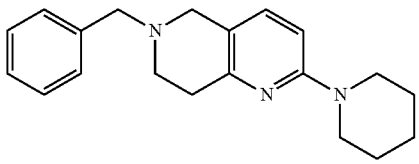 [SMILES: c1ccc(CN2CCc3nc(N4CCCCC4)ccc3C2)cc1]

The key intermediate A (500.00 mg, 1.93 mmol, 1.00 eq) and piperidine (328.68 mg, 3.86 mmol, 2.00 eq) were dissolved in toluene (5.00 mL), sodium tert-butoxide (370.95 mg, 3.86 mmol, 2.00 eq), Pd$_2$(dba)$_3$ (88.37 mg, 96.5 µmol, 0.05 eq), Xphos (92.01 mg, 193.00 µmol, 0.10 eq) were added at 30° C. under the nitrogen gas atmosphere. The mixture was stirred at 100° C. for 12 hours, then cooled and concentrated under reduced pressure at 45° C. The residue was purified by silica gel chromatography (petroleum ether/ethyl acetate=20/1, 5/1) to deliver 6-benzyl-2-(1-piperidinyl)-7,8-dihydro-5H-1,6-naphthyridine (550.00 mg, 1.79 mmol, 92.70% yield) as a yellow solid. $^1$H NMR (400 MHz, CDCl$_3$) δ 7.43-7.39 (m, 2H), 7.39-7.33 (m, 2H), 7.33-7.29 (m, 1H), 7.09 (d, J=8.5 Hz, 1H), 6.47 (d, J=8.5 Hz, 1H), 3.71 (s, 2H), 3.52 (s, 2H), 3.51-3.46 (m, 4H), 2.91-2.87 (m, 2H), 2.84-2.80 (m, 2H), 1.67-1.61 (m, 6H). LCMS (ESI) m/z: 308 (M+1).

Step 2:

2-(1-Piperidinyl)-5,6,7,8-tetrahydro-1,6-naphthyridine

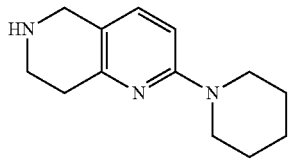 [SMILES: c1cc2c(nc1N1CCCCC1)CCNC2]

6-Benzyl-2-(1-piperidinyl)-7,8-dihydro-5H-1,6-naphthyridine (500.00 mg, 1.63 mmol, 1.00 eq) was dissolved in methanol (20.00 mL), Pd/C (100.00 mg, 1.63 mmol, 1.00 eq) was added at 30° C. under the nitrogen gas atmosphere. The mixture was stirred at H$_2$ (50 psi) at 30° C. for 18 hours. The mixture was filtered and concentrated under reduced pressure at 45° C. to deliver 2-(1-piperidinyl)-5,6,7,8-tetrahydro-1,6-naphthyridine (410.00 mg, crude) as a yellow solid which was used in the next step without further purification.

Step 3:

(2S)-1-(2-Chloro-4-nitroimidazol-1-yl)-2-methyl-3-(2-(1-piperidinyl)-7,8-dihydro-5H-1,6-naphthyridin-6-yl)propan-2-ol

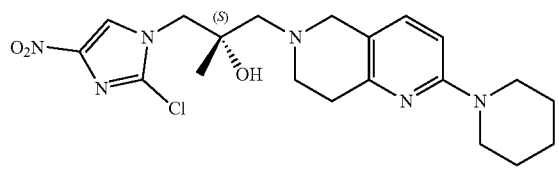

2-(1-Piperidinyl)-5,6,7,8-tetrahydro-1,6-naphthyridine (200.00 mg, 920.34 μmol, 1.00 eq) and (R)-2-chloro-1-((2-methyloxiran-2-yl)methyl)-4-nitro-1H-imidazole (300.41 mg, 1.38 mmol, 1.50 eq) were dissolved in ethanol (3.00 mL), DIPEA (59.47 mg, 460.17 μmol, 0.50 eq) was added at 30° C. under the nitrogen gas atmosphere. The mixture was stirred at 80° C. for 12 hours, cooled and concentrated under reduced pressure at 45° C. The residue was purified by silica gel chromatography (petroleum ether/ethyl acetate=10/1, 1/1) to deliver (2S)-1-(2-chloro-4-nitroimidazol-1-yl)-2-methyl-3-(2-(1-piperidinyl)-7,8-dihydro-5H-1,6-naphthyridin-6-yl)propan-2-ol (200.00 mg, crude) as a yellow solid.

Step 4:

(S)-2-Methyl-6-nitro-2-((2-(piperidin-1-yl)-7,8-dihydro-1,6-naphthyridin-6(5H)-yl)methyl)-2,3-dihydroimidazo[2,1-b]oxazole Compound 28

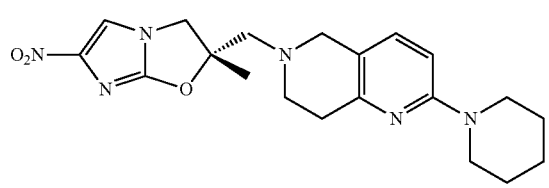

(2S)-1-(2-Chloro-4-nitroimidazol-1-yl)-2-methyl-3-(2-(1-piperidinyl)-7,8-dihydro-5H-1,6-naphthyridin-6-yl)propan-2-ol (139.00 mg, 319.60 μmol, 1.00 eq) was dissolved in DMF (5.00 mL) and NaH (25.57 mg, 639.20 μmol, 2.00 eq) was added at −45° C. under the nitrogen gas atmosphere. After the mixture was stirred at −45 to −15° C. for 1 hour, water (3 mL) was added and the mixture was stirred for 5 minutes. The aqueous phase was extracted with dichloromethane (20 mL×3). The combined organic phases were washed with saturated brine (10 mL×2), dried over anhydrous sodium sulfate, filtered and concentrated in vacuo. The residue was treated by thin layer chromatography (petroleum ether/ethyl acetate=1/2.5) and then purified by preparative chromatography (GX-D; Boston Symmetrix C18 ODS-R 150*30 mm*5 um; acetonitrile 24%-54%; water (0.225% fomic acid); 25 mL/min) to deliver (S)-2-methyl-6-nitro-2-((2-(piperidin-1-yl)-7,8-dihydro-1,6-naphthyridin-6(5H)-yl)methyl)-2,3-dihydroimidazo[2,1-b]oxazole compound 28 (5.40 mg, 13.55 μmol, 4.24% yield). $^1$H NMR (400 MHz, CDCl$_3$): δ 7.51 (s, 1H), 7.07 (d, J=8.66 Hz, 1H), 6.46 (d, J=8.53 Hz, 1H), 4.43 (d, J=9.66 Hz, 1H), 3.91 (d, J=9.54 Hz, 1H), 3.73-3.66 (m, 2H), 3.48 (br. S., 4H), 3.08-3.02 (m, 2H), 2.90-2.89 (m, 2H), 2.72 (d, J=14.81 Hz, 2H), 1.65 (s, 3H), 1.63 (br. s., 6H). LCMS (ESI) m/z: 399 (M+1).

Embodiment 29

(S)-2-Methyl-6-nitro-2-((2-(tetrahydro-2H-pyran-4-yl)-7,8-dihydro-1,6-naphthyridin-6(5H)-yl)methyl)-2,3-dihydroimidazo[2,1-b]oxazole

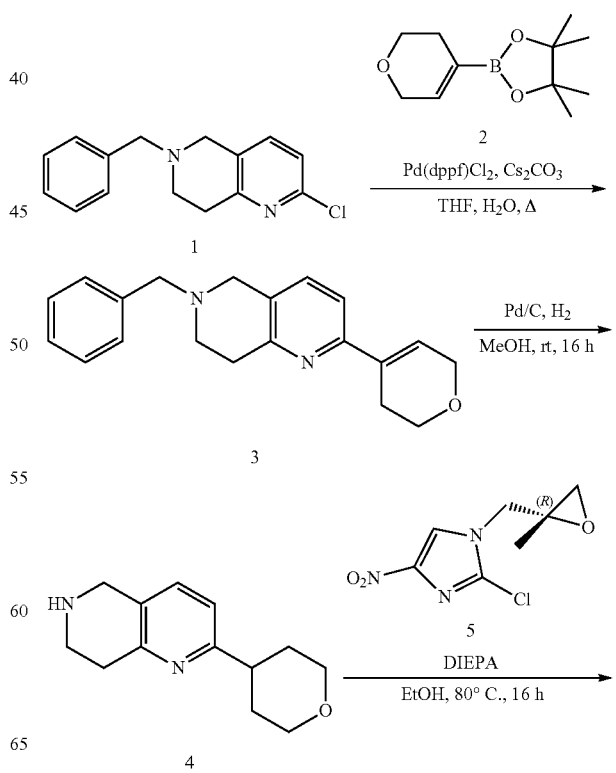

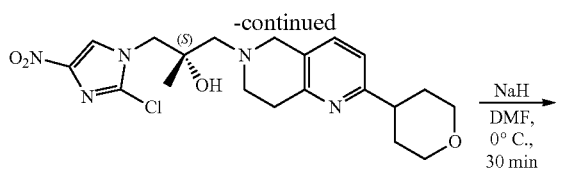

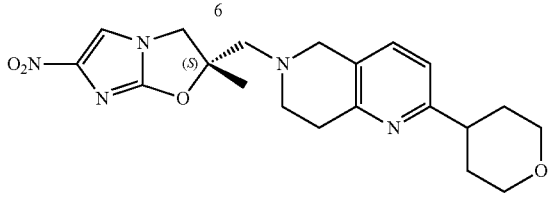

Compound 29

Step 1:

6-Benzyl-2-(3,6-dihydro-2H-pyran-4-yl)-5,6,7,8-tetrahydro-1,6-naphthyridine

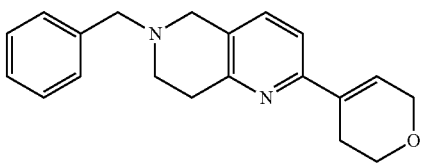 [SMILES: C1=C(c2ccc3c(n2)CCN(Cc2ccccc2)C3)CCOC1]

The key intermediate A (1.33 g, 5.14 mmol, 1.20 eq), 2-(3,6-dihydro-2H-pyran-4-yl)-4,4,5,5-tetramethyl-1,3,2-dioxaborolane (900.00 mg, 4.28 mmol, 1.00 eq) were dissolved in THF (20.00 mL) and water (5.00 mL), Pd(dppf)Cl₂ (313.17 mg, 428.00 μmol, 0.10 eq) and cesium carbonate (2.79 g, 8.56 mmol, 2.00 eq) were added to the mixed solution under the nitrogen gas atmosphere. The mixture was then stirred at 80° C. for 12 hours. The reaction mixture was concentrated under reduced pressure to remove the solvent, and the residue was diluted with water (20 mL) and extracted with ethyl acetate (10 ml×3). The combined organic layers were washed with saturated brine (10 ml×2), dried over sodium sulfate, filtered and concentrated under reduced pressure to give a residue which was purified by silica gel chromatography (silica, PE: ethyl acetate=5:1) to deliver 6-benzyl-2-(3,6-dihydro-2H-pyran-4-yl)-5,6,7,8-tetrahydro-1,6-naphthyridine (960.00 mg, 3.13 mmol, 73.20% yield) as a white solid. LCMS (ESI) m/z: 308 (M+1).

Step 2:

2-(Tetrahydro-2H-pyran-4-yl)-5,6,7,8-tetrahydro-1,6-naphthyridine

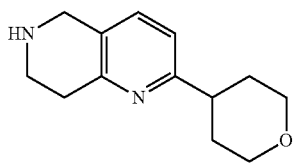

6-Benzyl-2-(3,6-dihydro-2H-pyran-4-yl)-5,6,7,8-tetrahydro-1,6-naphthyridine (500.00 mg, 1.62 mmol, 1.00) was dissolved in methanol (10.00 mL) and Pd/C (10%, 0.05 g) was added under the nitrogen gas atmosphere. The mixed solution was replaced with hydrogen three times and stirred at 28° C., H₂ (50 psi) for 12 hours. The reaction mixture was filtered and the filtrate was concentrated under reduced pressure to deliver crude 2-(tetrahydro-2H-pyran-4-yl)-5,6,7,8-tetrahydro-1,6-naphthyridine (400.00 mg, crude) as a colorless oil which was used in the next step without further purification. LCMS (ESI) m/z: 219 (M+1).

Step 3:

(S)-2-Methyl-2-((2-morpholino-7,8-dihydro-1,6-naphthyridin-6(5H)-yl)methyl-6-nitro-2,3-dihydroimidazo[2,1-b]oxazole

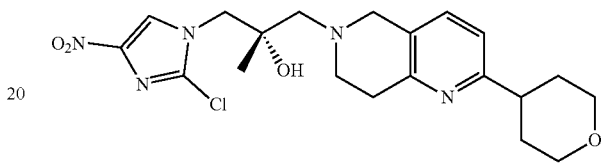

2-(Tetrahydro-2H-pyran-4-yl)-5,6,7,8-tetrahydro-1,6-naphthyridine (350.00 mg, 1.60 mmol, 1.00 eq), (R)-2-chloro-1-((2-methyloxiran-2-yl)methyl)-4-nitro-1H-imidazole (417.81 mg, 1.92 mmol, 1.20 eq), DIPEA (620.35 mg, 4.80 mmol, 3.00 eq) were added to ethanol (10.00 mL), the mixture was stirred at 80° C. for 12 hours under the nitrogen gas atmosphere. The reaction mixture was concentrated under reduced pressure and the residue was purified by silica gel chromatography (silica, dichloromethane/methanol=20/1) to deliver (S)-2-methyl-2-((2-morpholino-7,8-dihydro-1,6-naphthyridin-6(5H)-yl)methyl-6-nitro-2,3-dihydroimidazo[2,1-b]oxazole (530.00 mg, 1.22 mmol, 75.99% yield) as a yellow solid. ¹H NMR (400 MHz, CDCl₃) δ 8.06 (s, 1H), 7.29 (d, J=8.0 Hz, 1H), 7.01 (d, J=8.0 Hz, 1H), 4.13-4.07 (m, 2H), 4.06 (s, 2H), 3.92-3.72 (m, 2H), 3.62-3.49 (m, 2H), 3.15-2.89 (m, 5H), 2.74-2.50 (m, 2H), 1.89-1.84 (m, 4H), 1.21 (s, 3H). LCMS (ESI) m/z: 436/438 (M+1).

Step 4:

(S)-2-Methyl-6-nitro-2-((2-(tetrahydro-2H-pyran-4-yl)-7,8-dihydro-1,6-naphthyridin-6(5H)-yl)methyl)-2,3-dihydroimidazo[2,1-b]oxazole Compound 29

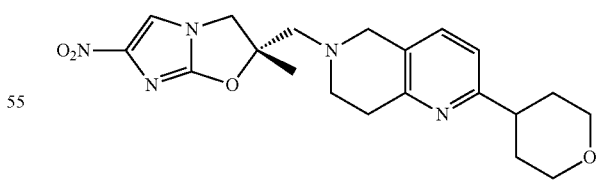

(S)-2-Methyl-2-((2-morpholino-7,8-dihydro-1,6-naphthyridin-6(5H)-yl)methyl-6-nitro-2,3-dihydroimidazo[2,1-b]oxazole (530.00 mg, 1.22 mmol, 1.00 eq) was dissolved in DMF (5.00 mL), NaH (58.56 mg, 1.46 mmol, 1.20 eq) was added at 0° C. The mixture was stirred at 0° C. for 20 minutes and quenched with a saturated ammonium chloride solution (30 mL) and then diluted with water (10 mL) and extracted with DCM (10 mL×3). The combined organic layers were washed with saturated brine (10 mL×2), dried over sodium sulfate, filtered and concentrated under reduced pressure. The residue was separated and purified by preparative chromatography (GX-G; Phenomenex Synergi C18 150*30 mm*4 um; acetonitrile 0%-30%; water (0.225% fomic acid); 25 mL/min) to deliver (S)-2-methyl-6-nitro-2-((2-(tetrahydro-2H-pyran-4-yl)-7,8-dihydro-1,6-naphthyridin-6(5H)-yl)methyl)-2,3-dihydroimidazo[2,1-b]oxazole compound 29 (300.00 mg, 751.05 μmol, 61.56% yield). $^1$H NMR (400 MHz, CDCl$_3$): δ 7.52 (s, 1H), 7.27 (d, J=8.0 Hz, 1H), 6.98 (d, J=8.0 Hz, 1H), 4.42 (d, J=8.0 Hz, 1H), 4.13-4.06 (m, 2H), 3.95 (d, J=12.0 Hz, 1H), 3.89-3.75 (m, 2H), 3.60-3.51 (m, 2H), 3.15-3.04 (m, 2H), 3.01-2.87 (m, 4H), 2.79 (d, J=12.0 Hz, 1H), 1.90-1.81 (m, 4H), 1.68 (s, 3H). LCMS (ESI) m/z: 399(M+1).

Embodiment 30

(S)-2-Methyl-2-((2-morpholino-7,8-dihydro-1,6-naphthyridin-6(5H)-yl)methyl)-6-nitro-2,3-dihydroimidazo[2,1-b]oxazole

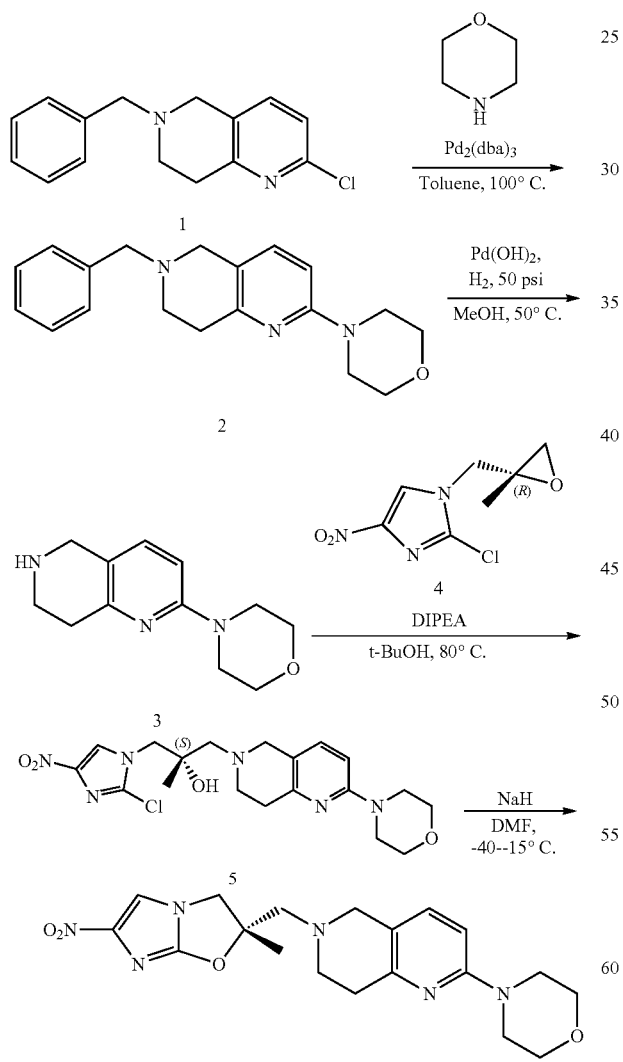

Compound 30

Step 1:

4-(6-Benzyl-7,8-dihydro-5H-1,6-naphthyridin-2-yl) morpholine

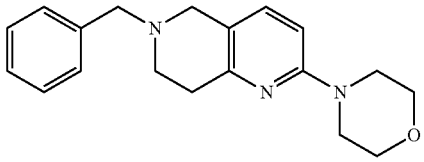 [SMILES: c1ccc(CN2CCc3nc(N4CCOCC4)ccc3C2)cc1]

The key intermediate A (1.00 g, 3.86 mmol, 1.00 eq), and morpholine (672.57 mg, 7.72 mmol, 2.00 eq), Pd$_2$(dba)$_3$ (176.73 mg, 193.00 μmol, 0.05 eq), sodium tert-butoxide (741.92 mg, 7.72 mmol, 2.00 eq), Xphos (184.01 mg, 386.00 μmol, 0.10 eq) were dissolved in toluene (20.00 mL) at 30° C. under the nitrogen gas atmosphere. The mixture was then heated to 100° C. and stirred for 12 hours. The mixture was cooled and concentrated under reduced pressure at 45° C. The residue was purified by silica gel chromatography (petroleum ether/ethyl acetate=20/1, 1/1) to deliver 4-(6-benzyl-7,8-dihydro-5H-1,6-naphthyridin-2-yl) morpholine (1.10 g, 3.56 mmol, 92.11% yield) as a yellow solid. $^1$H NMR (400 MHz, CDCl$_3$) δ 7.43-7.39 (m, 2H), 7.36 (t, J=7.3 Hz, 2H), 7.31 (d, J=7.0 Hz, 1H), 7.15 (d, J=8.4 Hz, 1H), 6.45 (d, J=8.5 Hz, 1H), 3.86-3.81 (m, 4H), 3.72 (s, 2H), 3.54 (s, 2H), 3.49-3.44 (m, 4H), 2.92-2.87 (m, 2H), 2.85-2.81 (m, 2H). LCMS (ESI) m/z: 310 (M+1).

Step 2:

4-(6-Benzyl-5,6,7,8-tetrahydro-1,6-naphthyridin-2-yl) morpholine

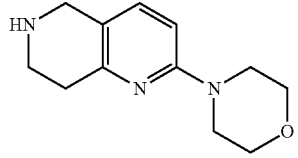 [SMILES: c1cc2c(nc1N1CCOCC1)CCNC2]

4-(6-Benzyl-7,8-dihydro-5H-1,6-naphthyridin-2-yl) morpholine (700.00 mg, 2.26 mmol, 1.00 eq) was dissolved in methanol (20.00 mL), then Pd(OH)$_2$/C (10%, 20 mg) was added. The mixed solution was replaced with hydrogen three times and then stirred at 50° C. and H$_2$ (50 psi) for 12 hours. The reaction mixture was filtered and the filtrate was concentrated to deliver 4-(5,6,7,8-tetrahydro-1,6-naphthyridin-2-yl) morpholine (400.00 mg, crude) as a yellow solid. LCMS (ESI) m/z: 220 (M+1).

Step 3:

(2S)-1-(2-Chloro-4-nitroimidazol-1-yl)-2-methyl-3-(2-morpholino-7,8-dihydro-5H-1,6-naphthyridin-6-yl)propan-2-ol

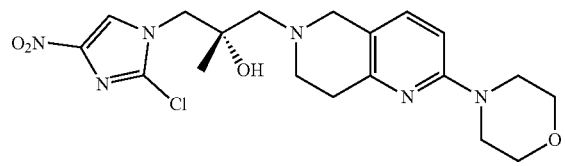 [SMILES: C[C@](O)(CN1CCc2nc(N3CCOCC3)ccc2C1)Cn1cc([N+](=O)[O-])nc1Cl]

4-(5,6,7,8-Tetrahydro-1,6-naphthyridin-2-yl) morpholine (250.00 mg, 1.14 mmol, 1.00 eq) and (R)-2-chloro-1-((2-methyloxiran-2-yl) methyl)-4-nitro-1H-imidazole (198.46 mg, 912.00 μmol, 0.80 eq) were dissolved in tert-butanol (3.00 mL) at 30° C. under the nitrogen gas atmosphere. Then DIPEA (147.34 mg, 1.14 mmol, 1.00 eq) was added. The mixture was stirred at 80° C. for 12 hours, cooled and concentrated under reduced pressure at 45° C. The residue was purified by silica gel chromatography (petroleum ether/ethyl acetate=10/1, 2/1) to deliver (2S)-1-(2-chloro-4-nitroimidazol-1-yl)-2-methyl-3-(2-morpholino-7,8-dihydro-5H-1,6-naphthyridin-6-yl)propan-2-ol (200.00 mg, 457.78 μmol, 40.16% yield) as a yellow solid. LCMS (ESI) m/z: 437 (M+1).

Step 4:

(S)-2-Methyl-2-((2-morpholino-7,8-dihydro-1,6-naphthyridin-6(5H)-yl)methyl)-6-nitro-2,3-dihydroimidazo[2,1-b]oxazole Compound 30

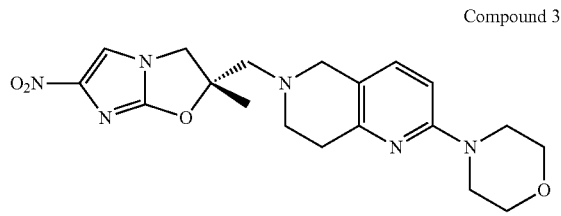

(2S)-1-(2-Chloro-4-nitroimidazol-1-yl)-2-methyl-3-(2-morpholino-7,8-dihydro-5H-1,6-naphthyridin-6-yl)propan-2-ol (200.00 mg, 457.78 μmol, 1.00 eq) was dissolved in DMF (5.00 mL), NaH (36.62 mg, 915.56 μmol, 2.00 eq) was added at −45° C. under the nitrogen gas atmosphere. The mixture was stirred at −45 to 15° C. for 2 hours, then quenched with ammonium chloride (20 mL). The aqueous phase was extracted with ethyl acetate (30 mL×3). The combined organic phases were washed with saturated brine (20 mL), dried over anhydrous sodium sulfate, filtered and concentrated in vacuo. The residue was purified by preparative chromatography (GX-A; Phenomenex Gemini C18 250*50 10u; (0.05% ammonia-ACN); 25 mL/min) to deliver (S)-2-methyl-2-((2-morpholino-7,8-dihydro-1,6-naphthyridin-6(5H)-yl)methyl)-6-nitro-2,3-dihydroimidazo[2,1-b]oxazole compound 30 (39.10 mg, 97.06 μmol, 21.2% yield, 99.4% purity). $^1$H NMR (400 MHz, CDCl$_3$): δ 7.51 (s, 1H), 7.13 (d, J=8.53 Hz, 1H), 6.45 (d, J=8.53 Hz, 1H), 4.43 (d, J=9.66 Hz, 1H), 3.93 (d, J=9.54 Hz, 1H), 3.83-3.81 (m, 4H), 3.72-3.68 (m, 2H), 3.47-3.44 (m, 4H), 3.07-3.04 (m, 2H), 2.76 (ddd, J=12.02, 7.18, 4.77 Hz, 1H) 2.75-2.71 (m, 3H) 1.66 (s, 3H). LCMS (ESI) m/z: 401 (M+1).

Embodiment 31

(S)-2-((2-(4,4-Difluoropiperidin-1-yl)-7,8-dihydro-1,6-naphthyridin-6(5H)-yl)methyl)-2-methyl-6-nitro-2,3-dihydroimidazo[2,1-b]oxazole

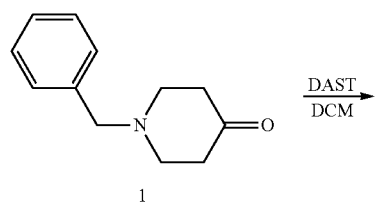

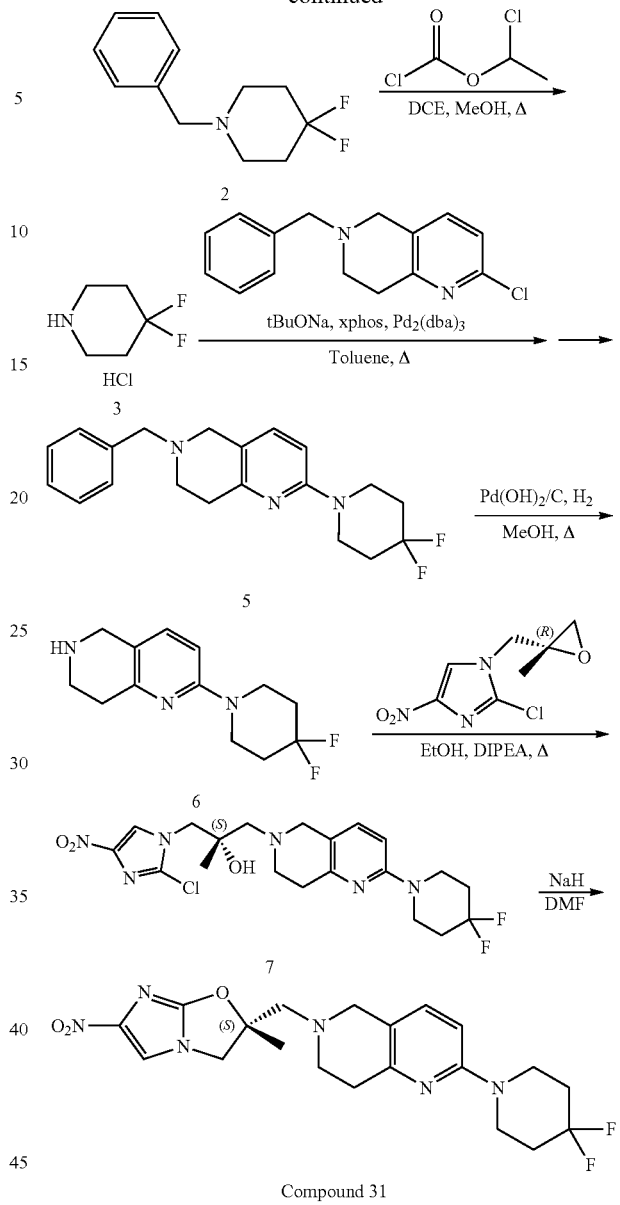

Compound 31

Step 1:

Benzyl-4,4-difluoropiperidine

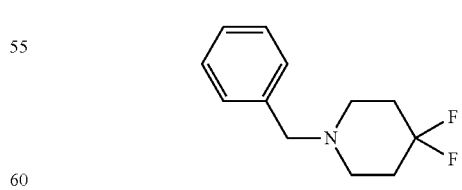

1-Benzyl-4-one (1.00 g, 5.28 mmol, 1.00 eq) was dissolved in DCM (10.00 mL) and DAST (2.56 g, 15.85 mmol, 3.00 eq) was added at 0° C. under the nitrogen gas atmosphere. The mixture was stirred at 0° C. for 0.5 hour, then warmed to 15° C. and stirred for 12 hours. The mixture was added to a saturated sodium bicarbonate solution (60 mL) at 0° C. and the mixture was extracted with DCM (100 mL×4). The combined organic phases were washed with saturated brine (40 mL), dried over anhydrous sodium sulfate, filtered and concentrated in vacuo to deliver 1-benzyl-4,4-difluoropiperidine (1.20 g, crude) as a black solid which is used in the next step without further purification. $^1$H NMR (400 MHz, CDCl$_3$): δ 7.39-7.29 (m, 5H), 3.66-3.52 (m, 2H), 2.57 (t, J=5.3 Hz, 4H), 2.02 (ddd, J=19.7, 13.7, 5.8 Hz, 4H).

Step 2:

4,4-Difluoropiperidine hydrochloride

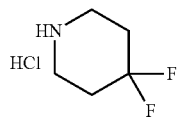

1-Benzyl-4,4-difluoro-piperidine (1.20 g, 5.68 mmol, 1.00 eq) was dissolved in dichloroethane (10.00 mL), 1-chloroethyl carbonochloridate (1.22 g, 8.52 mmol, 1.50 eq) was added at 0° C. under the nitrogen gas atmosphere. The mixture was stirred at this temperature for 0.5 h, then heated to 85° C. and stirred for 12 hours. The mixture was concentrated and the residue was added with methanol (10.00 mL) and the mixture was stirred at 85° C. for an additional 2 hours. The mixture was cooled and concentrated under reduced pressure at 60° C. to deliver 4,4-difluoropiperidine hydrochloride (580.00 mg, crude) as a black solid which was used in the next step without further purification.

Step 3:

6-Benzyl-2-(4,4-difluoropiperidin-1-yl)-5,6,7,8-tetrahydro-1,6-naphthyridine

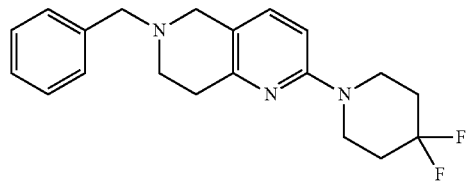 [SMILES: FC1(F)CCN(c2ccc3c(n2)CCN(Cc2ccccc2)C3)CC1]

6-Benzyl-2-chloro-7,8-dihydro-5H-1,6-naphthyridine (1.03 g, 3.98 mmol, 1.00 eq) and 4,4-difluoropiperidine (960.00 mg, 7.93 mmol, 1.99 eq) were dissolved in toluene (15.00 mL) at 15° C. under the nitrogen gas atmosphere. And then sodium tert-butoxide (956.36 mg, 9.95 mmol, 2.50 eq), dicyclohexyl-[2-(2,4,6-triisopropyl) phenyl]phosphine (284.65 mg, 597.10 μmol, 0.15 eq) and Pd$_2$(dba)$_3$ (291.61 mg, 318.45 μmol, 0.08 eq) were added. The mixture was stirred at 110° C. for 12 hours, cooled and concentrated under reduced pressure at 60° C. The residue was added with water (20 mL) and the aqueous phase was extracted with dichloromethane (100 mL×4). The combined organic phases were washed with saturated brine (50 mL), dried over anhydrous sodium sulfate, filtered and concentrated in vacuo to deliver 6-benzyl-2-(4,4-difluoropiperidin-1-yl)-5,6,7,8-tetrahydro-1,6-naphthyridine (700.00 mg, 1.67 mmol, 41.92% yield) as a yellow solid. $^1$H NMR (400 MHz, CDCl$_3$): δ 7.49-7.30 (m, 5H), 7.21-7.06 (m, 1H), 6.58-6.47 (m, 1H), 3.78-3.66 (m, 5H), 3.64-3.46 (m, 2H), 2.86 (dd, J=18.7, 5.4 Hz, 3H), 2.10-1.95 (m, 3H), 1.40-1.20 (m, 2H), 1.03-0.79 (m, 2H). LCMS (ESI) m/z: 344 (M+1).

Step 4:

2-(4,4-Difluoropiperidin-1-yl)-5,6,7,8-tetrahydro-1,6-naphthyridine

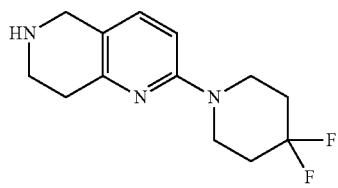 [SMILES: FC1(F)CCN(c2ccc3c(n2)CCNC3)CC1]

6-Benzyl-2-(4,4-difluoropiperidin-1-yl)-5,6,7,8-tetrahydro-1,6-naphthyridine (600.00 mg, 1.75 mmol, 1.00 eq) was dissolved in methanol (30.00 mL) and Pd(OH)$_2$/C (24.22 mg, 174.98 lama 0.10 eq) was added at 15° C. And the mixture was stirred for 12 hours at 60° C., H$_2$ (50 psi). The mixture was filtered and the filtrate was concentrated and the residue was purified by silica gel chromatography (petroleum ether/ethyl acetate=10/1, 1/10) to deliver 2-(4,4-difluoropiperidin-1-yl)-5,6,7,8-tetrahydro-1,6-naphthyridine (250.00 mg, 987.01 μmol, 56.40% yield) as a yellow solid. LCMS (ESI) m/z: 254 (M+1).

Step 5:

(S)-1-(2-Chloro-4-nitro-1H-imidazol-1-yl)-3-(2-(4,4-difluoropiperidin-1-yl)-7,8-dihydro-1,6-naphthyridin-6(5H)-yl)-2-methylpropan-2-ol

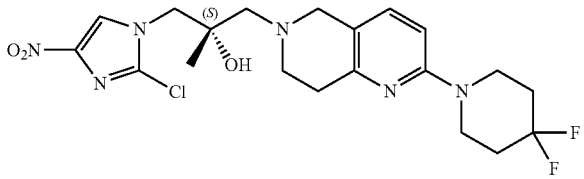

2-(4,4-Difluoropiperidin-1-yl)-5,6,7,8-tetrahydro-1,6-naphthyridine (100.00 mg, 394.80 μmol, 1.00 eq), and 2-chloro-1-[[(2R)-2-methyloxiran-2-yl]methyl]-4-nitroimidazole (85.91 mg, 394.80 μmol, 1.00 eq), DIPEA (127.56 mg, 987.00 μmol, 2.50 eq) were dissolved in tert-butanol (5.00 mL) at 15° C. under the nitrogen gas atmosphere. The mixture was stirred at 85° C. for 12 hours, cooled and concentrated at 60° C. The residue was purified by silica gel chromatography (petroleum ether/ethyl acetate=20/1, 1/2) to deliver (S)-1-(2-chloro-4-nitro-1H-imidazol-1-yl)-3-(2-(4,4-difluoropiperidin-1-yl)-7,8-dihydro-1,6-naphthyridin-6(5H)-yl)-2-methylpropan-2-ol (200.00 mg, crude) as a yellow oil. LCMS (ESI) m/z: 471 (M+1).

Step 6:

(S)-2-((2-(4,4-Difluoropiperidin-1-yl)-7,8-dihydro-1,6-naphthyridin-6(5H)-yl)methyl)-2-methyl-6-nitro-2,3-dihydroimidazo[2,1-b]oxazole

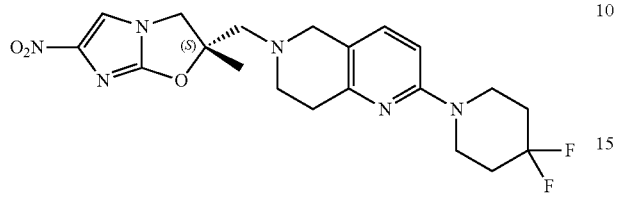

Compound 31

(S)-1-(2-Chloro-4-nitro-1H-imidazol-1-yl)-3-(2-(4,4-difluoropiperidin-1-yl)-7,8-dihydro-1,6-naphthyridin-6(5H)-yl)-2-methylpropan-2-ol (200.00 mg, 424.72 µmol, 1.00 eq) was dissolved in DMF (5.00 mL) and NaH (20.39 mg, 849.44 µmol, 2.00 eq) was added at −20° C. under the nitrogen gas atmosphere. The mixture was stirred at −20° C. for 10 minutes and then raised to 0° C. and stirred for 10 minutes. The mixture was then stirred at 15° C. for an additional 10 minutes and quenched with a saturated aqueous ammonium chloride solution (50 mL). The mixture was filtered and the crude was dried to give the crude product which was purified by preparative chromatography (GX-D; Boston Symmetrix C18 ODS-R 150*30 mm*5 um; acetonitrile 24%-54%; water (0.225% fomic acid); 25 mL/min) to deliver (S)-2-((2-(4,4-difluoropiperidin-1-yl)-7,8-dihydro-1,6-naphthyridin-6(5H)-yl)methyl)-2-methyl-6-nitro-2,3-dihydroimidazo[2,1-b]oxazole compound 31 (15.00 mg, 33.88 µmol, 7.98% yield, 98.12% purity). $^1$H NMR (400 MHz, METHANOL-d4): δ 7.81 (s, 1H), 7.21 (d, J=8.4 Hz, 1H), 6.67 (d, J=8.4 Hz, 1H), 4.40 (d, J=10.3 Hz, 1H), 4.11 (d, J=10.3 Hz, 1H), 3.75-3.61 (m, 6H), 3.11-2.98 (m, 2H), 2.95-2.85 (m, 2H), 2.77-2.67 (m, 1H), 2.66-2.55 (m, 1H), 2.06-1.91 (m, 4H), 1.66 (s, 3H). LCMS (ESI) m/z: 435 (M+1).

Embodiment 32

(S)-2-Methyl-6-nitro-2-((2-(3,4,5-trifluorophenyl)-7,8-dihydro-1,6-naphthyridin-6(5H)-yl)methyl)-2,3-dihydroimidazo[2,1-b]oxazole

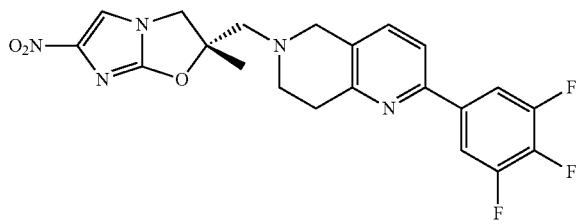

Compound 32

The synthesis method was as in Embodiment 29.
(S)-2-Methyl-6-nitro-2-((2-(3,4,5-trifluorophenyl)-7,8-dihydro-1,6-naphthyridin-6(5H)-yl)methyl)-2,3-dihydroimidazo[2,1-b]oxazole compound 32 (123.50 mg, 272.34 µmol, 52.49% yield, 98.216% purity). $^1$H NMR (400 MHz, CDCl$_3$) δ 7.68-7.59 (m, 2H), 7.52 (s, 1H), 7.46-7.37 (m, 2H), 4.43 (d, J=12.0 Hz, 1H), 3.97 (d, J=8.0 Hz, 1H), 3.95-3.81 (m, 2H), 3.24-2.92 (m, 5H), 2.82 (d, J=12.0 Hz, 1H), 1.69 (s, 3H). LCMS (ESI) m/z: 446(M+1).

Embodiment 33

(S)—N-(4-Fluorophenyl)-6-((2-methyl-6-nitro-2,3-dihydroimidazo[2,1-b]oxazol-2-yl)methyl)-5,6,7,8-tetrahydro-1,6-naphthyridin-2-amine

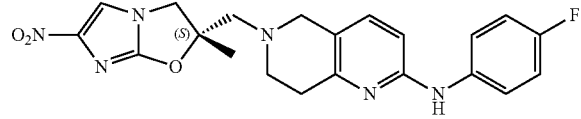

Compound 33

The synthesis method was as in Embodiment 30.

(S)—N-(4-Fluorophenyl)-6-((2-methyl-6-nitro-2,3-dihydroimidazo[2,1-b]oxazol-2-yl)methyl)-5,6,7,8-tetrahydro-1,6-naphthyridin-2-amine compound 33 (9.50 mg, 22.09 µmol, 6.79% yield, 98.7% purity). $^1$H NMR (400 MHz, CDCl$_3$): δ 8.47 (s, 1H), 7.97 (br. s., 1H), 7.53 (s, 1H), 7.25 (d, J=4.6 Hz, 1H), 7.18 (d, J=8.5 Hz, 1H), 7.05 (t, J=8.5 Hz, 2H), 6.63 (d, J=8.5 Hz, 1H), 4.41 (d, J=9.5 Hz, 1H), 3.96 (d, J=9.8 Hz, 1H), 3.79-3.65 (m, 2H), 3.12-3.04 (m, 2H), 2.94 (dd, J=6.3, 11.4 Hz, 1H), 2.88-2.73 (m, 3H), 1.67 (s, 3H). LCMS (ESI) m/z: 425 (M+1).

Embodiment 34

(S)-2-((2-(4-Fluorophenoxy)-7,8-dihydro-1,6-naphthyridin-6(5H)-yl)methyl)-2-methyl-6-nitro-2,3-dihydroimidazo[2,1-b]oxazole

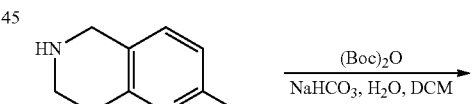

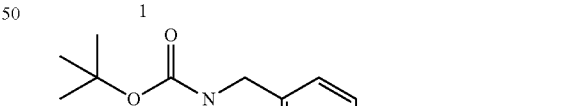

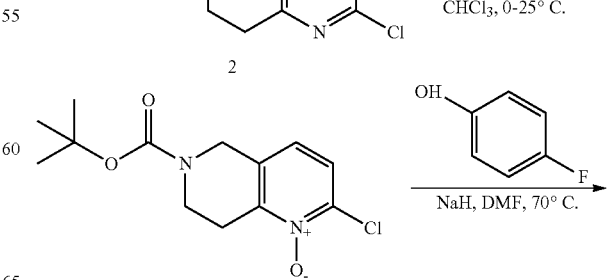

-continued

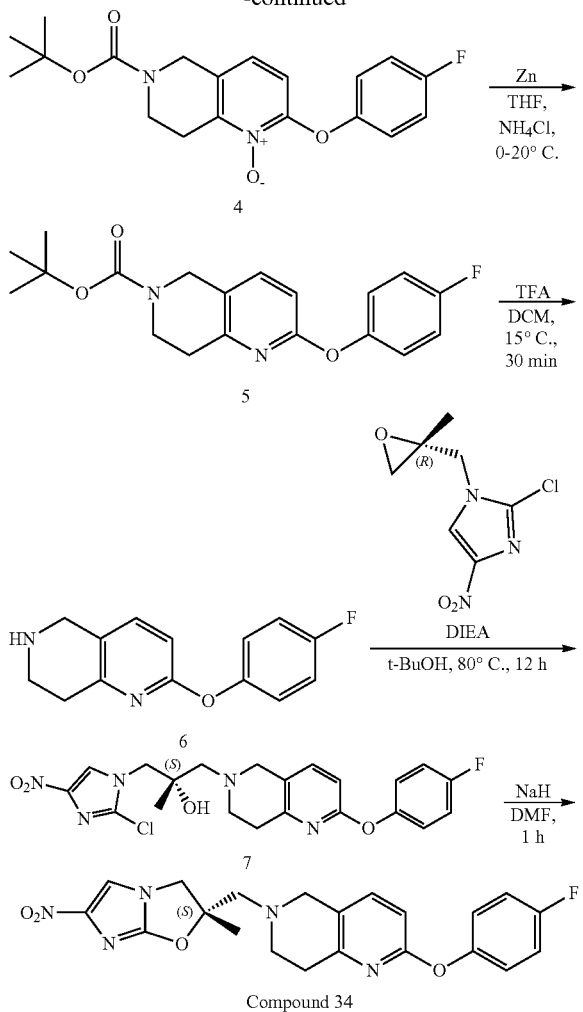

Compound 34

Step 1:

tert-Butyl-2-chloro-7,8-dihydro-1,6-naphthyridin-6(5H)-carboxylate

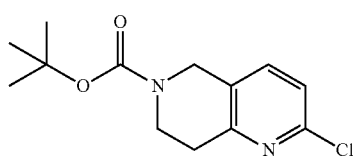 [SMILES: CC(C)(C)OC(=O)N1CCc2nc(Cl)ccc2C1]

2-Chloro-5,6,7,8-tetrahydro-1,6-naphthyridine (850.00 mg, 4.14 mmol, 1.00 eq) and Di-tert-butyl dicarbonate (1.36 g, 6.22 mmol, 1.50 eq) were dissolved in a mixed solution of dichloromethane (15.00 mL) and water (15.00 mL), sodium bicarbonate (1.04 g, 12.43 mmol, 3.00 eq) was added at 15° C. The mixture was stirred at 15° C. for 2 hours. The mixture was poured into water (30 mL) and the aqueous phase was extracted with ethyl acetate (50 mL×3). The combined organic phases were washed with saturated brine (30 mL), dried over anhydrous sodium sulfate, filtered and concentrated in vacuo. The residue was purified by silica gel chromatography (petroleum ether/ethyl acetate=50/1, 30/1) to deliver tert-butyl-2-chloro-7,8-dihydro-1,6-naphthyridin-6(5H)-carboxylate (1.00 g, 3.72 mmol, 89.75% yield) as a white solid.

Step 2:

tert-Butyl-2-chloro-1-oxo-7,8-dihydro-5H-1,6-naphthyridin-1-onium-6-carboxylate

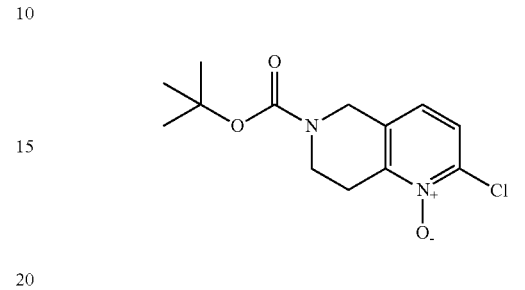

tert-Butyl-2-chloro-7,8-dihydro-1,6-naphthyridin-6(5H)-carboxylate (1.20 g, 4.47 mmol, 1.00 eq) was dissolved in chloroform (20.00 mL) and m-chloroperbenzoic acid (1.45 g, 6.71 mmol, 1.50 eq) was added to the mixture at 0° C. The mixture was stirred at 25° C. for 12 hours. The mixture was then quenched with a saturated sodium sulfate solution (20 mL) and extracted with dichloromethane (40 ml×3). The combined organic phases were washed with saturated brine (20 mL), dried over anhydrous sodium sulfate, filtered and concentrated in vacuo to deliver tert-butyl-2-chloro-1-oxo-7,8-dihydro-5H-1,6-naphthyridin-1-onium-6-carboxylate (1.00 g, 3.51 mmol, 78.52% yield) as a yellow solid which was used directly in the next step. LCMS (ESI) m/z: 285 (M+1).

Step 3:

6-(tert-Butoxycarbonyl)-2-(4-fluorophenoxy)-5,6,7,8-tetrahydro-1,6-naphthyridine 1-oxide

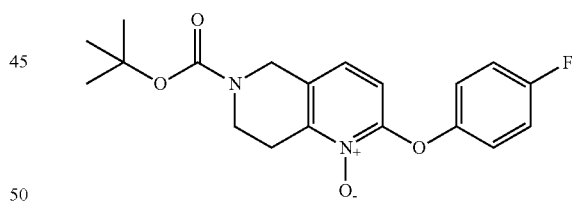

tert-Butyl-2-chloro-1-oxo-7,8-dihydro-5H-1,6-naphthyridin-1-onium-6-carboxylate (600.00 mg, 2.11 mmol, 1.00 eq) and 4-fluorophenol (283.46 mg, 2.53 mmol, 1.20 eq) were dissolved in DMF (3.00 mL), NaH (168.57 mg, 4.21 mmol, 2.00 eq) was added at 0° C. under the nitrogen gas atmosphere. The mixture was stirred at 70° C. for 12 hours and then cooled. The residue was poured into water (15 mL) and extracted with ethyl acetate (30 mL×3). The combined organic phases were washed with saturated brine (20 mL), dried over anhydrous sodium sulfate, filtered and concentrated in vacuo, and the residue was purified by silica gel chromatography (petroleum ether/ethyl acetate=5/1, 1/3) to deliver 6-(tert-butoxycarbonyl)-2-(4-fluorophenoxy)-5,6,7,8-tetrahydro-1,6-naphthyridine 1-oxide (510.00 mg, 1.42 mmol, 67.07% yield) as a yellow solid.

Step 4:

tert-Butyl 2-(4-fluorophenoxy)-7,8-dihydro-1,6-naphthyridine-6(5H)-carboxylate

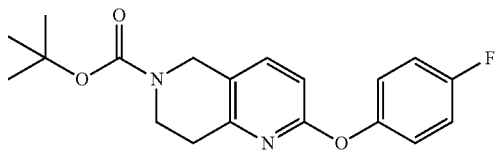 [SMILES: CC(C)(C)OC(=O)N1CCc2nc(Oc3ccc(F)cc3)ccc2C1]

6-(tert-Butoxycarbonyl)-2-(4-fluorophenoxy)-5,6,7,8-tetrahydro-1,6-naphthyridine 1-oxide (410.00 mg, 1.14 mmol, 1.00 eq) was dissolved in ammonium chloride (3.00 mL) and THF (3.00 ml), and zinc (745.45 mg, 11.40 mmol, 10.00 eq) was added at 0° C. under the nitrogen gas atmosphere. The mixture was stirred at 15° C. for 2 hours. The mixture was filtered and the filtrate was extracted with ethyl acetate (30 ml×3). The combined organic phases were washed with saturated brine (20 mL), dried over anhydrous sodium sulfate, filtered and concentrated in vacuo. The residue was then purified by silica gel chromatography (petroleum ether/ethyl acetate=20/1, 10/1) to deliver tert-butyl 2-(4-fluorophenoxy)-7,8-dihydro-1,6-naphthyridine-6(5H)-carboxylate (420.00 mg, crude) as a white solid. $^1$H NMR (400 MHz, CDCl$_3$): δ 7.41 (d, J=8.4 Hz, 1H), 7.12-7.05 (m, 4H), 6.66 (d, J=8.4 Hz, 1H), 4.55 (s, 2H), 3.72 (t, T=5.8 Hz, 2H), 2.92-2.81 (m, 2H), 1.51 (s, 9H).

Step 5:

2-(4-Fluorophenoxy)-5,6,7,8-tetrahydro-1,6-naphthyridine

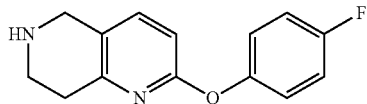 [SMILES: Fc1ccc(Oc2ccc3c(n2)CCNC3)cc1]

tert-Butyl 2-(4-fluorophenoxy)-7,8-dihydro-1,6-naphthyridine-6(5H)-carboxylate (200.00 mg, 580.75 μmol, 1.00 eq) was dissolved in dichloromethane (1.00 mL), and TFA (66.24 mg, 580.75 μmol, 1.00 eq) was added at 15° C. and the mixture was stirred for 1 hour. The mixture was then concentrated under reduced pressure to deliver 2-(4-fluorophenoxy)-5,6,7,8-tetrahydro-1,6-naphthyridine (177.00 mg, crude, TFA salt) as a yellow oil.

Step 6:

(2S)-1-(2-Chloro-4-nitroimidazol-1-yl)-3-(2-(4-fluorophenoxy)-7,8-dihydro-5H-1,6-naphthyridin-6-yl)-2-methylpropan-2-ol

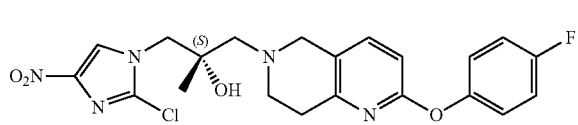

2-(4-Fluorophenoxy)-5,6,7,8-tetrahydro-1,6-naphthyridine (177.00 mg, 494.01 μmol, 1.00 eq, TFA salt) was dissolved in tert-butanol (2.00 mL), DIPEA (191.54 mg, 1.48 mmol, 3.00 eq), 2-chloro-1-[[(2R)-2-methyloxiran-2-yl]methyl]-4-nitroimidazole (129.00 mg, 592.81 μmol, 1.20 eq) were added at 15° C. The mixture was stirred at 70° C. for 12 hours, cooled and concentrated under reduced pressure at 45° C. The residue was purified by silica gel chromatography (petroleum ether/ethyl acetate=10/1, 3/1) to deliver (2S)-1-(2-chloro-4-nitroimidazol-1-yl)-3-(2-(4-fluorophenoxy)-7,8-dihydro-5H-1,6-naphthyridin-6-yl)-2-methylpropan-2-ol (130.00 mg, 281.46 μmol, 56.97% yield) as a yellow solid. LCMS (ESI) m/z: 462 (M+1).

Step 7:

(S)-2-((2-(4-Fluorophenoxy)-7,8-dihydro-1,6-naphthyridin-6(5H)-yl)methyl)-2-methyl-6-nitro-2,3-dihydroimidazo[2,1-b]oxazole Compound 34

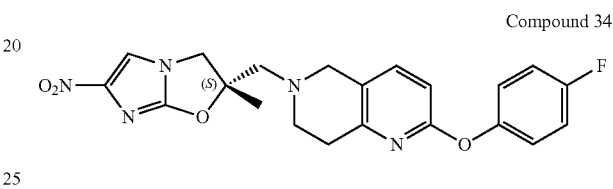

(2S)-1-(2-Chloro-4-nitroimidazol-1-yl)-3-(2-(4-fluorophenoxy)-7,8-dihydro-5H-1,6-naphthyridin-6-yl)-2-methylpropan-2-ol (160.00 mg, 346.42 μmol, 1.00 eq) was dissolved in DMF (2.00 mL), NaH (27.71 mg, 692.84 μmol, 2.00 eq) was added at −45° C. under the nitrogen gas atmosphere. The mixture was stirred at −45 to 15° C. for 1 hour. And the mixture was quenched with a saturated ammonium chloride solution (20 mL) and stirred for 5 minutes. The aqueous phase was extracted with ethyl acetate (40 mL×3). The combined organic phases were washed with saturated brine (30 mL), dried over anhydrous sodium sulfate, filtered and concentrated in vacuo. The residue was separated and purified by preparative chromatography (GX-G; Phenomenex Synergi Max-RP 250*80 10u; acetonitrile 30%-60%; water (0.225% fomic acid); 25 mL/min) to deliver (S)-2-((2-(4-fluorophenoxy)-7,8-dihydro-1,6-naphthyridin-6(5H)-yl)methyl)-2-methyl-6-nitro-2,3-dihydroimidazo[2,1-b]oxazole compound 34 (56.00 mg, 129.00 μmol, 37.24% yield, 98% purity). $^1$H NMR (400 MHz, CDCl$_3$): δ 7.52 (s, 1H), 7.30 (br. s., 1H), 7.09 (s, 2H), 7.07 (d, J=1.9 Hz, 2H), 6.60 (d, J=8.3 Hz, 1H), 4.41 (d, J=9.8 Hz, 1H), 3.95 (d, J=9.7 Hz, 1H), 3.79 (q, J=14.9 Hz, 2H), 3.11-3.03 (m, 2H), 2.93 (td, J=6.0, 11.6 Hz, 1H), 2.84-2.74 (m, 3H), 1.68 (s, 3H). LCMS (ESI) m/z: 426 (M+1).

Embodiment 35

(S)-2-(3,4-Difluorophenyl)-6-((2-methyl-6-nitro-2,3-dihydroimidazo[2,1-b]oxazol-2-yl)methyl)-5,6,7,8-tetrahydro-1,6-naphthyridine-3-carbonitrile

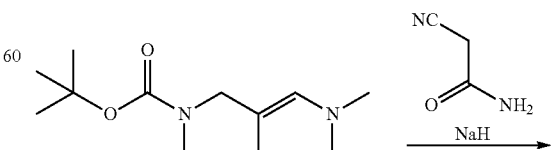

1

-continued

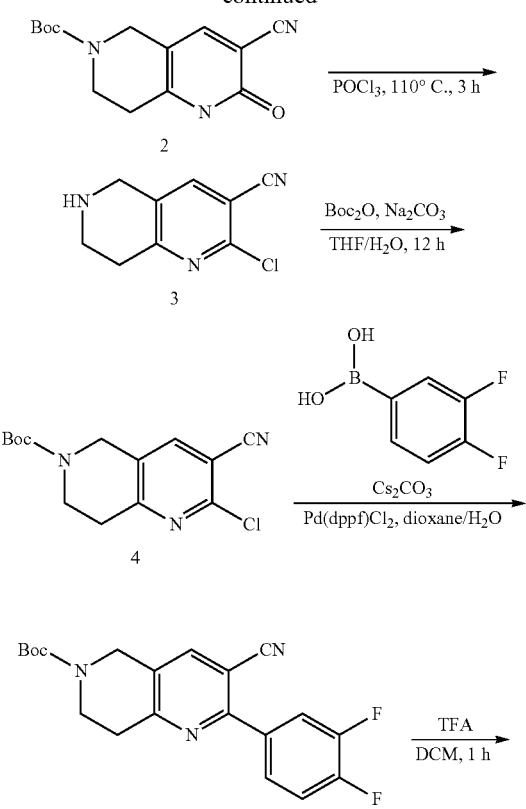

Step 1:

tert-Butyl 3-cyano-2-oxo-1,2,7,8-tetrahydro-1,6-naphthyridine-6(5H)-carboxylate

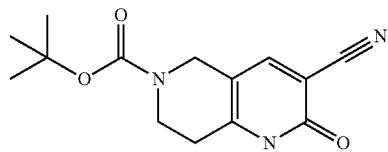 [SMILES: CC(C)(C)OC(=O)N1CCc2[nH]c(=O)c(C#N)cc2C1]

(Z)-tert-Butyl 3-((dimethylamino)methylene)-4-oxopiperidine-1-carboxylate (16.00 g, 62.91 mmol, 1.00 eq) was dissolved in DMF (120.00 mL), NaH (5.03 g, 125.82 mmol, 2.00 eq) was added in portions at 0° C. and stirred for 1 hour. After the addition, the mixture was stirred at this temperature for an additional 30 minutes, then 2-cyanoacetamide (5.55 g, 66.06 mmol, 1.05 eq) was dissolved in DMF (80.00 mL) which was added dropwise to the mixed solution and kept the temperature constant. The resulting mixture was stirred at 28° C. for 12 hours. The resulting mixture was concentrated under reduced pressure, and the residue was purified by silica gel chromatography (silica, DCM/ethyl acetate=1/1, 1:5) to deliver tert-butyl 3-cyano-2-oxo-1,2,7,8-tetrahydro-1,6-naphthyridine-6(5H)-carboxylate (1.00 g, 3.63 mmol, 5.77% yield) as a dark brown solid. $^1$H NMR (400 MHz, DMSO-$d_6$) δ 8.04 (s, 1H), 4.24 (s, 2H), 3.55 (t, J=4.0 Hz, 2H), 2.64 (t, J=4.0 Hz, 2H), 1.42 (s, 9H).

Step 2:

2-Chloro-5,6,7,8-tetrahydro-1,6-naphthyridine-3-carbonitrile

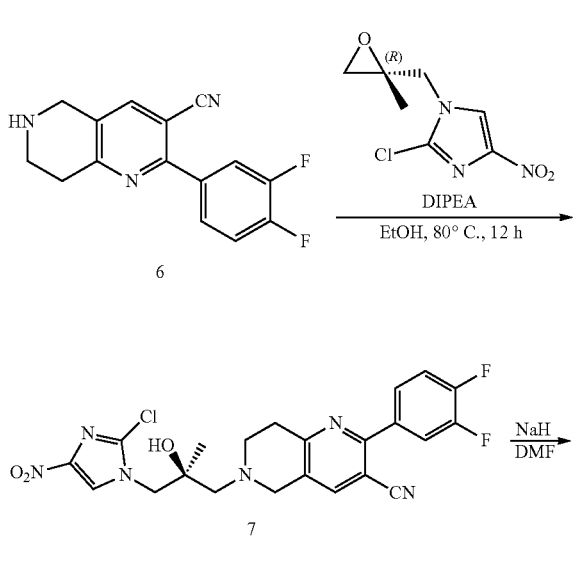

tert-Butyl 3-cyano-2-oxo-1,2,7,8-tetrahydro-1,6-naphthyridine-6(5H)-carboxylate (2.00 g, 7.26 mmol, 1.00 eq) was added to phosphorous oxychloride (28.22 g, 184.05 mmol, 25.35 eq). The mixture was stirred at 110° C. for 3 hours. The reaction mixture was poured into water (1500 mL) with the temperature 28° C. and then the pH was adjusted to 10 by the addition of sodium carbonate. The mixture was extracted with DCM (500 mL×3). The combined organic layers were washed with saturated brine (500 mL×2), dried over sodium sulfate, filtered and concentrated under reduced pressure to deliver crude product 2-chloro-5,6,7,8-tetrahydro-1,6-naphthyridine-3-carbonitrile (2.00 g, crude) which was used directly in the next step.

Step 3:

tert-Butyl 2-chloro-3-cyano-7,8-dihydro-1,6-naphthyridine-6(5H)-carboxylate

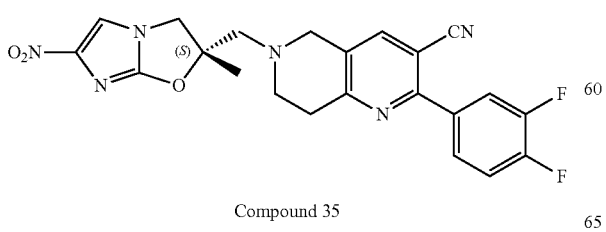

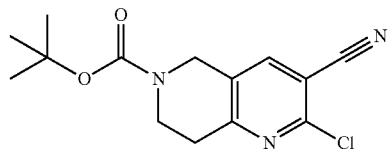 [SMILES: CC(C)(C)OC(=O)N1CCc2nc(Cl)c(C#N)cc2C1]

Compound 35

2-Chloro-5,6,7,8-tetrahydro-1,6-naphthyridine-3-carbonitrile (1.40 g, 7.23 mmol, 1.00 eq) was dissolved in THF (20.00 mL) and water (10.00 mL), di-tert-butyl dicarbonate (3.16 g, 14.46 mmol, 2.00 eq) and sodium carbonate (2.30 g, 21.69 mmol, 3.00 eq) were added. The mixture was stirred at 25° C. for 12 hours. The reaction mixture was concentrated under reduced pressure and the residue was diluted with DCM (20 mL) and extracted with DCM (20 mL×3). The combined organic layers were washed with saturated brine (20 mL×2), dried over sodium sulfate, filtered and concentrated under reduced pressure. The residue was purified by silica gel chromatography (silica, petroleum ether/ethyl acetate=10/1, 5/1) to deliver tert-butyl 2-chloro-3-cyano-7,8-dihydro-1,6-naphthyridine-6(5H)-carboxylate (700.00 mg, 2.38 mmol, 32.96% yield) as a yellow solid. $^1$H NMR (300 MHz, CDCl$_3$) δ 7.74 (s, 1H), 4.61 (s, 2H), 3.75 (t, J=8.0 Hz, 2H), 3.03 (t, J=8.0 Hz, 2H), 1.48 (s, 9H).

Step 4:

tert-Butyl 3-cyano-2-(3,4-difluorophenyl)-7,8-dihydro-1,6-naphthyridine-6(5H)-carboxylate

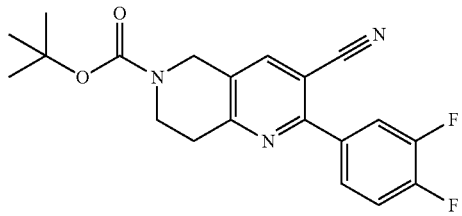 [SMILES: CC(C)(C)OC(=O)N1CCc2nc(-c3ccc(F)c(F)c3)c(C#N)cc2C1]

tert-Butyl 2-chloro-3-cyano-7,8-dihydro-1,6-naphthyridine-6(5H)-carboxylate (350.00 mg, 1.19 mmol, 1.00 eq), (3,4-difluorophenyl) boronic acid (225.50 mg, 1.43 mmol, 1.20 eq), cesium carbonate (775.45 mg, 2.38 mmol, 2.00 eq) were dissolved in a mixed solution of dioxane (10.00 mL) and water (4.00 mL), Pd(dppf)Cl$_2$ (87.07 mg, 119.00 μmol, 0.10 eq) was added under the nitrogen gas atmosphere. The mixture was then stirred at 110° C. for 12 hours. The reaction mixture was concentrated under reduced pressure and the residue was diluted with DCM (20 mL) and extracted with DCM (20 mL×3). The combined organic phases were washed with saturated brine (20 mL×2), dried over sodium sulfate, filtered and concentrated under reduced pressure. The residue was purified by silica gel chromatography (silica, petroleum ether/ethyl acetate=10/1, 5/1) to deliver tert-butyl 3-cyano-2-(3,4-difluorophenyl)-7,8-dihydro-1,6-naphthyridine-6(5H)-carboxylate (420.00 mg, 1.13 mmol, 95.04% yield) as a yellow solid. $^1$H NMR (400 MHz, CDCl$_3$) δ 8.53 (s, 1H), 8.32-8.25 (m, 1H), 8.24-8.19 (m, 1H), 7.31-7.22 (m, 1H), 4.65 (s, 2H), 3.81 (t, J=6.0 Hz, 2H), 3.03 (t, J=6.0 Hz, 2H), 1.53 (s, 9H).

Step 5:

2-(3,4-Difluorophenyl)-5,6,7,8-tetrahydro-1,6-naphthyridine-3-carbonitrile

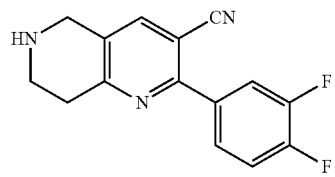 [SMILES: N#Cc1cc2c(nc1-c1ccc(F)c(F)c1)CCNC2]

tert-Butyl 3-cyano-2-(3,4-difluorophenyl)-7,8-dihydro-1,6-naphthyridine-6(5H)-carboxylate (246.00 mg, 662.39 μmol, 1.00 eq) was dissolved in DCM (2.00 mL), and TFA (75.52 mg, 662.39 μmol, 1.00 eq) was then added and the mixture was stirred at 25° C. for 1 hour. The mixture was concentrated under reduced pressure to deliver the product 2-(3,4-difluorophenyl)-5,6,7,8-tetrahydro-1,6-naphthyridine-3-carbonitrile (250.00 mg, crude) and which was used directly in the next step without purification.

Step 6:

(S)-6-(3-(2-Chloro-4-nitro-1H-imidazol-1-yl)-2-hydroxy-2-methylpropyl)-2-(3,4-difluorophenyl)-5,6,7,8-tetrahydro-1,6-naphthyridine-3-carbonitrile

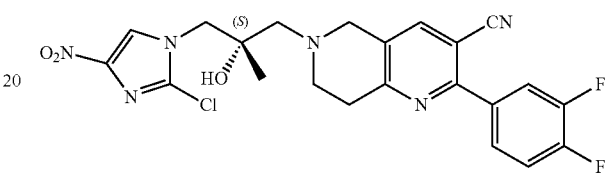

2-(3,4-Difluorophenyl)-5,6,7,8-tetrahydro-1,6-naphthyridine-3-carbonitrile (180.00 mg, 663.57 μmol, 1.00 eq) and (R)-2-chloro-1-((2-methyloxiran-2-yl) methyl)-4-nitro-1H-imidazole (173.28 mg, 796.28 μmol, 1.20 eq) were dissolved in tert-butanol (10.00 mL), then DIPEA (257.28 mg, 1.99 mmol, 3.00 eq) was added. The mixture was stirred at 80° C. for 12 hours. The reaction mixture was concentrated under reduced pressure and the residue was purified by silica gel chromatography (silica, petroleum ether/ethyl acetate=5/1, 1:1) to deliver (S)-6-(3-(2-chloro-4-nitro-1H-imidazol-1-yl)-2-hydroxy-2-methylpropyl)-2-(3,4-difluorophenyl)-5,6,7,8-tetrahydro-1,6-naphthyridine-3-carbonitrile (230.00 mg, 470.47 μmol, 70.90% yield) as a yellow solid. LCMS (ESI) m/z: 489/491 (M+1/M+3).

Step 7:

(S)-2-(3,4-Difluorophenyl)-6-((2-methyl-6-nitro-2,3-dihydroimidazo[2,1-b]oxazol-2-yl)methyl)-5,6,7,8-tetrahydro-1,6-naphthyridine-3-carbonitrile Compound 35

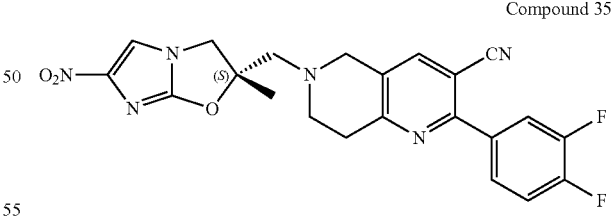

(S)-6-(3-(2-Chloro-4-nitro-1H-imidazol-1-yl)-2-hydroxy-2-methylpropyl)-2-(3,4-difluorophenyl)-5,6,7,8-tetrahydro-1,6-naphthyridine-3-carbonitrile (230.00 mg, 470.47 μmol, 1.00 eq) was dissolved in DMF (5.00 mL), NaH (22.58 mg, 564.56 mmol, 1.20 eq) was added at 0° C. The mixture was stirred at 0° C. for 10 minutes, quenched with a saturated ammonium chloride solution (20 mL), then diluted with water (20 mL) and extracted with DCM (20 mL×3). The combined organic phases were washed with saturated brine (20 mL×2), dried over sodium sulfate, filtered and concentrated under reduced pressure. The residue was separated and purified by preparative chromatography (GX-F; Welch Ultimate AQ-C18 150*30 mm*5 um; acetonitrile 43%-73%; water (0.225% fomic acid); 25 mL/min) to deliver (S)-2-(3,4-difluorophenyl)-6-((2-methyl-6-nitro-2,3-dihydroimidazo[2,1-b]oxazol-2-yl)methyl)-5,6,7,8-tetrahydro-1,6-naphthyridine-3-carbonitrile compound 35 (20.90 mg, 42.91 mmol, 9.12% yield, 92.884% purity). $^1$H NMR (400 MHz, CDCl$_3$) δ 7.80-7.66 (m, 3H), 7.53 (s, 1H), 7.36-7.29 (m, 1H), 4.37 (d, J=12.0 Hz, 1H), 4.00 (d, J=8.0 Hz, 1H), 3.93 (d, J=13.2 Hz, 2H), 3.25-2.98 (m, 5H), 2.84 (d, J=16.0 Hz, 1H), 1.70 (s, 3H). LCMS (ESI) m/z: 453(M+1).

Embodiment 36

(S)-2-((3-Chloro-2-(3,4-difluorophenyl)-7,8-dihydro-1,6-naphthyridin-6(5H)-yl)methyl)-2-methyl-6-nitro-2,3-dihydroimidazo[2,1-b]oxazole

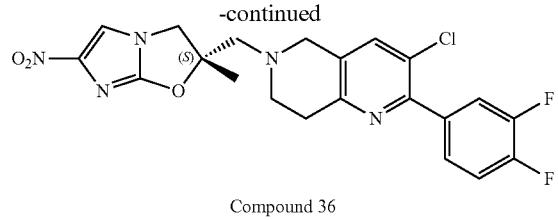

Compound 36

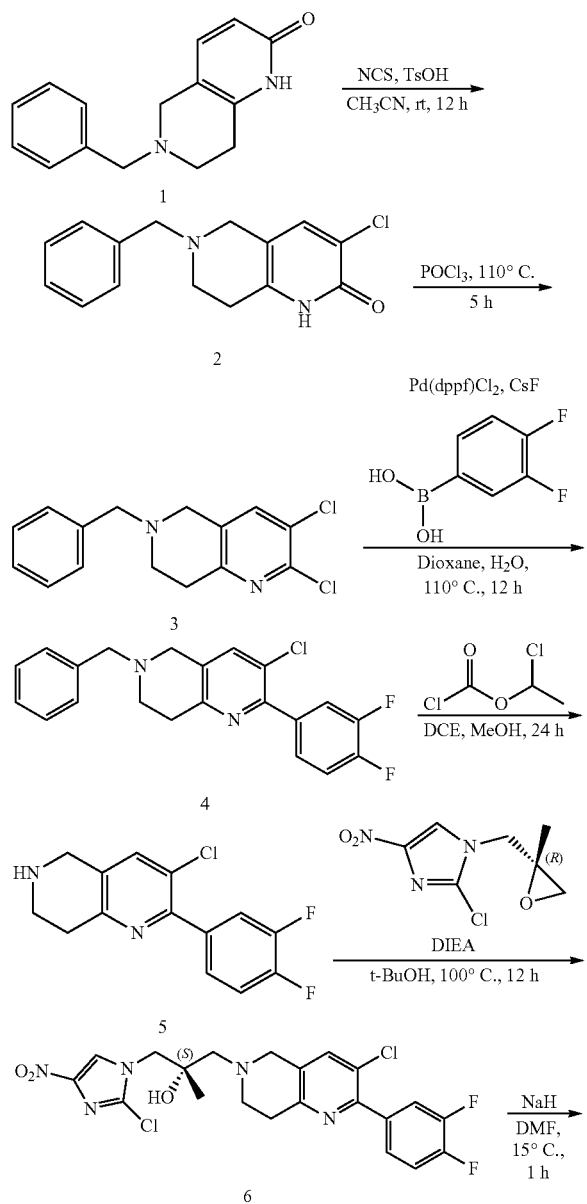

Step 1:

6-Benzyl-3-chloro 1,5,7,8-tetrahydro-1,6-naphthyridin-2-one

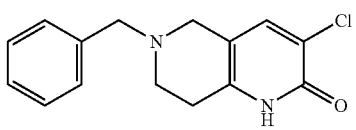 [SMILES: O=c1[nH]c2c(cc1Cl)CN(Cc1ccccc1)CC2]

4-Methylbenzenesulfonic acid (4.30 g, 24.98 mmol, 1.50 eq) and 6-benzyl 1,5,7,8-tetrahydro-1,6-naphthyridin-2-one (4.00 g, 16.65 mmol, 1.00 eq) were dissolved in acetonitrile (30.00 mL), then NCS (3.33 g, 24.98 mmol, 1.50 eq) was added. The mixture was stirred at 25° C. for 12 hours. The reaction mixture was quenched with water and the reaction mixture was extracted with ethyl acetate (250 mL×2). The combined organic phases were concentrated under reduced pressure and the residue was purified by silica gel chromatography (silica, petroleum ether/ethyl acetate=3/1, dichloromethane/methanol=10/1) to deliver 6-benzyl-3-chloro-5,6,7,8-tetrahydro-1,6-naphthyridin-2(1H)-one (220.00 mg, 750.37 μmol, 29.43% yield) as a white solid. LCMS (ESI) m/z: 275.1 (M+1).

Step 2:

6-Benzyl-2,3-dichloro-7,8-dihydro-5H-1,6-naphthyridine

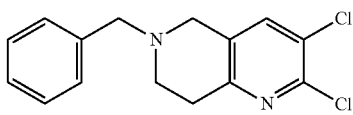 [SMILES: Clc1cc2c(nc1Cl)CCN(Cc1ccccc1)C2]

6-Benzyl-3-chloro-1,5,7,8-tetrahydro-1,6-naphthyridin-2-one (700.00 mg, 2.55 mmol, 1.00 eq) and phosphorus oxychloride (3.33 g, 21.73 mmol, 8.53 eq) were dissolved in toluene (5.00 mL), the mixture was heated at 100° C. for 5 hours. The reaction mixture was poured into water (100 mL) at 25° C. and the pH was adjusted to about 9 by the gradually addition of a sodium carbonate solution, and extracted with ethyl acetate (200 mL×2). The combined organic phases were concentrated under reduced pressure and the residue was purified by silica gel chromatography (silica, petroleum ether/ethyl acetate=80/1, 20/1) to deliver 6-benzyl-2,3-dichloro-7,8-dihydro-5H-1,6-naphthyridine (220.00 mg, 750.37 μmol, 29.43% yield) as a white solid. LCMS (ESI) m/z: 293.0 (M+1).

Step 3:

6-Benzyl-3-chloro-2-(3,4-difluorophenyl)-7,8-dihydro-5H-1,6-naphthyridine

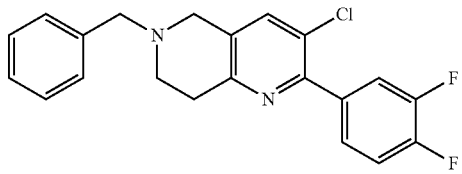 [SMILES: Fc1ccc(-c2nc3c(cc2Cl)CN(Cc2ccccc2)CC3)cc1F]

6-Benzyl-2,3-dichloro-7,8-dihydro-5H-1,6-naphthyridine (200.00 mg, 682.15 μmol, 1.00 eq), (3,4-difluorophenyl) boronic acid (0.295 mg, 613.94 μmol, 0.90 eq), cesium fluoride (207.24 mg, 1.36 mmol, 2.00 eq) were dissolved in dioxane (3 mL) and water (300.00 μL), Pd(dppf)Cl$_2$ (49.91 mg, 68.22 μmol, 0.10 eq) was added under the nitrogen gas atmosphere, and the mixture was stirred at 110° C. for 12 hours. The mixture was concentrated in vacuo and the residue was purified by silica gel chromatography (silica, petroleum ether/ethyl acetate=50/1, 20:1) to deliver 6-benzyl-3-chloro-2-(3,4-difluorophenyl)-7,8-dihydro-5H-1,6-naphthyridine (170.00 mg, 458.44 μmol, 67.21% yield) as a white solid. LCMS (ESI) m/z: 370.9 (M+1).

Step 4:

3-Chloro-2-(3,4-difluorophenyl)-5,6,7,8-tetrahydro-1,6-naphthyridine hydrochloride

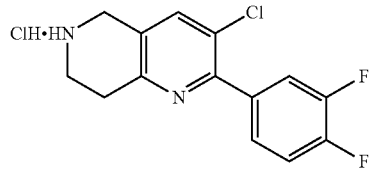

6-Benzyl-3-chloro-2-(3,4-difluorophenyl)-7,8-dihydro-5H-1,6-naphthyridine (70.00 g, 377.54 μmol, 1.00 eq) and 1-chloroethyl carbonochloridate (70.17 mg, 490.80 μmol, 1.30 eq) were dissolved in dichloroethane (100.00 mL). The mixture was stirred at 80° C. for 12 hours. The reaction mixture was concentrated under reduced pressure, methanol (100.00 mL) was added to the reaction mixture, and the mixture was stirred at 80° C. for 12 hours. The reaction mixture was concentrated under reduced pressure to deliver the crude product 3-chloro-2-(3,4-difluorophenyl)-5,6,7,8-tetrahydro-1,6-naphthyridine hydrochloride (140.00 mg, crude, hydrochloric acid) which was used in the next step without further purification. LCMS (ESI) m/z: 280.9 (M+1).

Step 5:

(2S)-1-(3-Chloro-2-(3,4-difluorophenyl)-7,8-dihydro-5H-1,6-naphthyridin-6-yl)-3-(2-chloro-4-nitroimidazol-1-yl)-2-methylpropan-2-ol

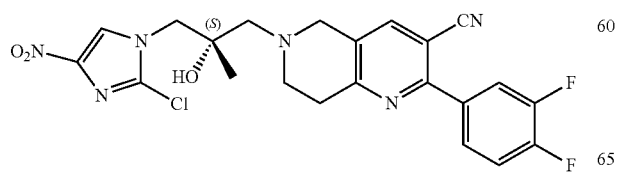

3-Chloro-2-(3,4-difluorophenyl)-5,6,7,8-tetrahydro-1,6-naphthyridine hydrochloride (140.00 mg, 498.75 μmol, 1.00 eq) was dissolved in t-butanol (5.00 mL), and then DIPEA (161.15 mg, 1.25 mmol, 2.50 eq) and 2-chloro-1-[[(2R)-2-methyloxiran-2-yl]methyl]-4-nitroimidazole (130.24 mg, 598.50 μmol, 1.20 eq) were added. The mixture was stirred at 100° C. for 12 hours. The reaction mixture was concentrated under reduced pressure and the residue was purified by silica gel chromatography (silica, petroleum ether/ethyl acetate=20/1, 1/3) to deliver (2S)-1-[3-chloro-2-(3,4-difluorophenyl)-7,8-dihydro-5H-1,6-naphthyridin-6-yl]-3-(2-chloro-4-nitroimidazol-1-yl)-2-methylpropan-2-ol (80.00 mg, 160.54 μmol, 32.19% yield) as a yellow solid. LCMS (ESI) m/z: 499.8 (M+1).

Step 6:

(S)-2-((3-Chloro-2-(3,4-difluorophenyl)-7,8-dihydro-1,6-naphthyridin-6(5H)-yl)methyl)-2-methyl-6-nitro-2,3-dihydroimidazo[2,1-b]oxazole Compound 36

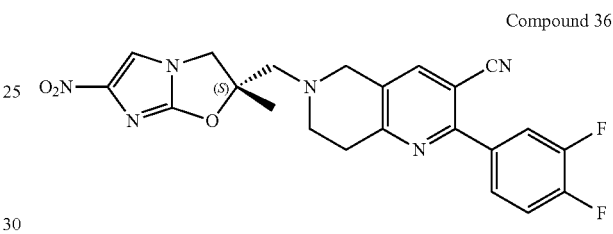

(2S)-1-[3-Chloro-2-(3,4-difluorophenyl)-7,8-dihydro-5H-1,6-naphthyridin-6-yl]-3-(2-chloro-4-nitroimidazol-1-yl)-2-methylpropan-2-ol (80.00 mg, 160.54 μmol, 1.00 eq) was dissolved in DMF (2.00 mL), NaH (3.85 mg, 160.54 μmol, 1.00 eq) was added at −20° C. and stirred for 30 minutes, and then the mixture was stirred at 15° C. for 1 hour. The reaction mixture was quenched by adding to water (15 mL) at 0° C. and then extracted with ethyl acetate (100 mL×2). The combined organic phases were concentrated under reduced pressure and the residue was purified by preparative chromatography (GX-A, Phenomenex Gemini C18 250*50 mm*10 um, acetonitrile 50%-80%; 0.05% ammonia-ACN; 25 mL/min) to deliver (S)-2-((3-Chloro-2-(3,4-difluorophenyl)-7,8-dihydro-1,6-naphthyridin-6(5H)-yl)methyl)-2-methyl-6-nitro-2,3-dihydroimidazo[2,1-b]oxazole compound 36 (17.80 mg, 38.38 μmol, 23.91% yield, 99.580% purity). $^1$H NMR (400 MHz, CDCl$_3$) δ 7.53 (s, 1H), 7.45 (s, 1H), 7.28-7.20 (m, 1H), 4.40 (d, J=9.8 Hz, 1H), 4.03-3.79 (m, 3H), 3.22-3.07 (m, 2H), 3.05-2.75 (m, 4H), 1.69 (s, 3H) LCMS (ESI) m/z: 462.1 (M+1).

Embodiment 37

(S)-2-((2-(3,4-Difluorophenyl)-4-methyl-7,8-dihydro-1,6-naphthyridin-6(5H)-yl)methyl)-2-methyl-6-nitro-2,3-dihydroimidazo[2,1-b]oxazole

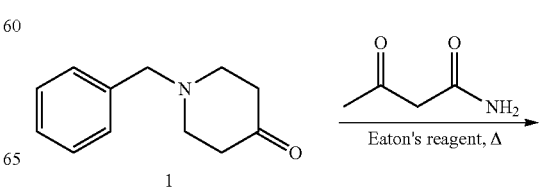

1

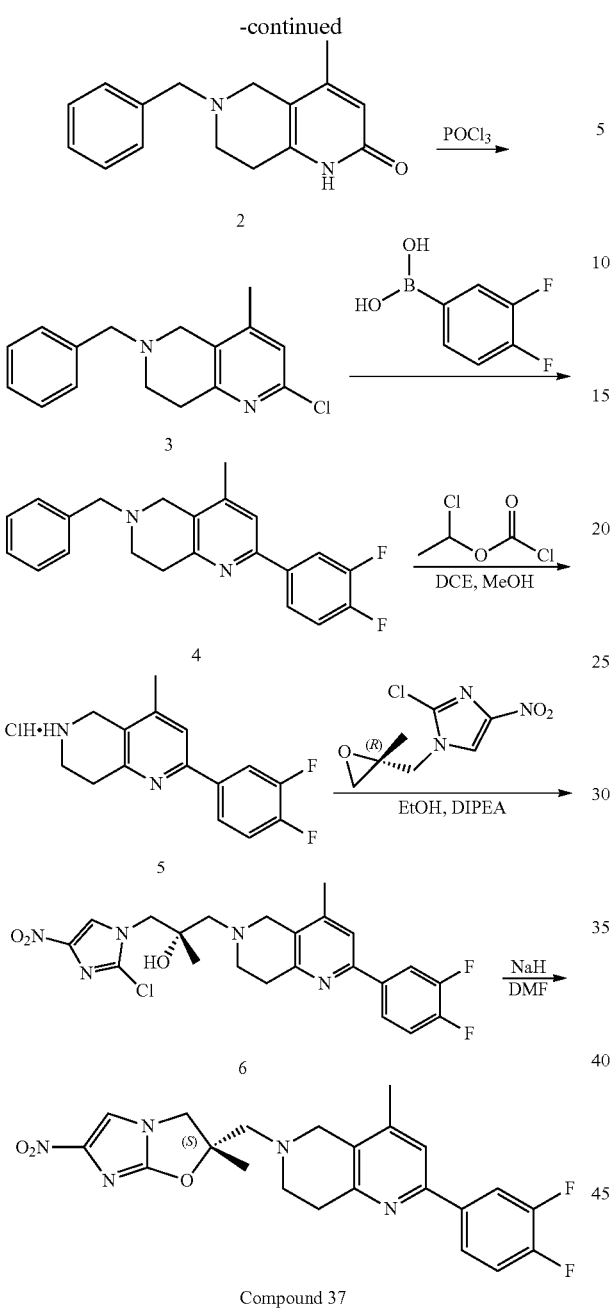

Compound 37

Step 1:

6-Benzyl-4-methyl-5,6,7,8-tetrahydro-1,6-naphthyridin-2(1H)-one

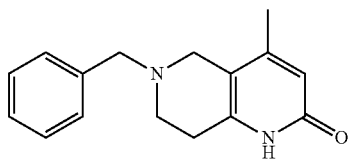 [SMILES: Cc1cc(=O)[nH]c2c1CN(Cc1ccccc1)CC2]

A mixture of 1-benzyl-4-one (10.00 g, 52.84 mmol, 1.00 eq) and 3-oxobutanamide (5.88 g, 58.12 mmol, 1.10 eq) in EATON'S REAGENT (20.00 mL) was stirred at 110° C. for 12 hours. The mixture was added to a saturated aqueous sodium bicarbonate solution (300 mL) to adjust the pH>7, and the aqueous phase was extracted with ethyl acetate (200 mL×4). The combined organic phases were washed with saturated brine (100 mL), dried over anhydrous sodium sulfate, filtered and concentrated in vacuo. The residue was poured into acetone (100 mL) and then filtered and the cake was dried to deliver 6-benzyl-4-methyl-5,6,7,8-tetrahydro-1,6-naphthyridin-2(1H)-one (7.00 g, 27.52 mmol, 52.09% yield) as a white solid. $^1$H NMR (400 MHz, CDCl$_3$): δ 7.46-7.25 (m, 5H), 6.25 (br, s, 1H), 3.76 (s, 2H), 3.42 (br, s, 2H), 2.84-2.64 (m, 4H), 2.10 (s, 3H).

Step 2:

6-Benzyl-2-chloro-4-methyl-7,8-dihydro-5H-1,6-naphthyridine

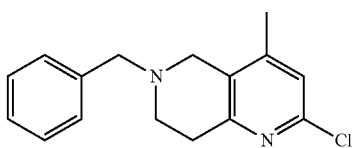 [SMILES: Cc1cc(Cl)nc2c1CN(Cc1ccccc1)CC2]

6-Benzyl-4-methyl-5,6,7,8-tetrahydro-1,6-naphthyridin-2(1H)-one (7.80 g, 30.67 mmol, 1.00 eq) was added to phosphorus oxychloride (97.44 g, 635.49 mmol, 20.72 eq). The mixture was stirred at 110° C. for 12 hours and cooled. The mixture was quenched by adding to the water (300 mL) and stirred for 30 minutes. The aqueous layer was then basified to pH>7 with aqueous sodium bicarbonate solution. The mixture was extracted with DCM (200 mL×4), dried over anhydrous sodium sulfate, filtered and concentrated in vacuo to deliver 6-benzyl-2-chloro-4-methyl-7,8-dihydro-5H-6-naphthyridine (5.00 g, crude) as a yellow solid. LCMS (ESI) m/z: 273 (M+1).

Step 3:

6-Benzyl-2-(3,4-difluorophenyl)-4-methyl-5,6,7,8-tetrahydro-1,6-naphthyridine

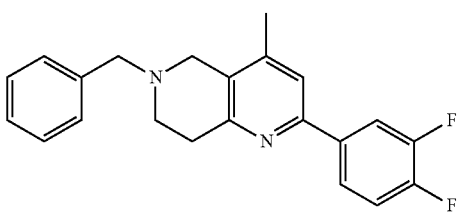 [SMILES: Cc1cc(-c2ccc(F)c(F)c2)nc2c1CN(Cc1ccccc1)CC2]

6-Benzyl-2-chloro-4-methyl-7,8-dihydro-5H-1,6-naphthyridine (1.87 g, 6.86 mmol, 1.00 eq) and (3,4-difluorophenyl) boronic acid (1.30 g, 8.23 mmol, 1.20 eq), cesium fluoride (3.13 g, 20.58 mmol, 3.00 eq) were dissolved in dioxane (25.00 mL) and water (2.50 mL) at 15° C. under the nitrogen gas atmosphere, and then Pd(dppf)Cl$_2$ (501.95 mg, 686.00 μmol, 0.10 eq) was added and the mixture was stirred at 110° C. for 12 hours. The mixture was added to water (10 mL) and the mixture was extracted with dichloromethane (100 mL×4). The combined organic phases were washed with saturated brine (100 mL), dried over anhydrous sodium sulfate, filtered and concentrated in vacuo. The residue was purified by silica gel chromatography (petroleum ether/ethyl acetate=20/1, 5/1) to deliver 6-benzyl-2-(3,4-difluorophenyl)-4-methyl-5,6,7,8-tetrahydro-1,6-naphthyridine (1.30 g, 3.71 mmol, 54.08% yield) as a yellow solid. $^1$H NMR (400 MHz, CDCl$_3$): δ 7.83 (ddd, J=2.1, 7.8, 11.7 Hz, 1H), 7.66 (ddd, J=2.0, 4.2, 6.3 Hz, 1H), 7.46-7.30 (m, 6H), 7.27-7.18 (m, 1H), 3.83-3.78 (m, 2H), 3.64 (s, 2H), 3.11 (t, J=5.8 Hz, 2H), 2.87 (t, J=5.9 Hz, 2H), 2.23 (s, 3H).

Step 4:

2-(3,4-Difluorophenyl)-4-methyl-5,6,7,8-tetrahydro-1,6-naphthyridine hydrochloride

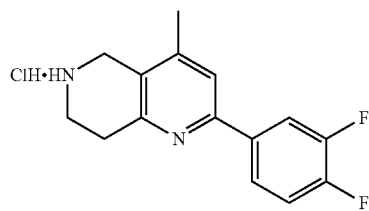

6-Benzyl-2-(3,4-difluorophenyl)-4-methyl-5,6,7,8-tetrahydro-1,6-naphthyridine (1.30 g, 3.71 mmol, 1.00 eq) was dissolved in dichloroethane (20.00 mL) and 1-chlorocarbonyl chloride (795.63 mg, 5.57 mmol, 1.50 eq) was added at 15° C. under the nitrogen gas atmosphere, and the mixture was stirred at 85° C. for 12 hours. The mixture was then concentrated and the residue was added with methanol (20.00 mL) and the resulting mixture was stirred at 85° C. for 2 hours. The mixture was filtered and the cake was collected and dried to deliver 2-(3,4-difluorophenyl)-4-methyl-5,6,7,8-tetrahydro-1,6-naphthyridine hydrochloride (800.00 mg, 2.70 mmol, 72.67% yield) as a white solid which was used directly in the next step.

Step 5:

(S)-1-(2-Chloro-4-nitro-1H-imidazol-1-yl)-3-(2-(3,4-difluorophenyl)-4-methyl-7,8-dihydro-1,6-naphthyridin-6(5H)-yl)-2-methylpropan-2-ol

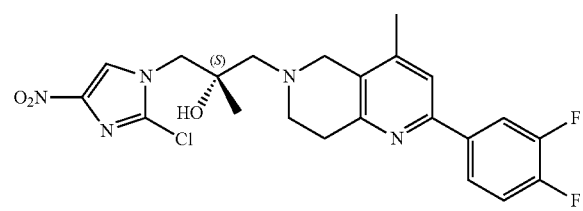

2-(3,4-Difluorophenyl)-4-methyl-5,6,7,8-tetrahydro-1,6-naphthyridine hydrochloride (800.00 mg, 2.70 mmol, 1.00 eq) and 2-chloro-1-[[(2R)-2-methyloxiran-2-yl]methyl]-4-nitroimidazole (705.06 mg, 3.24 mmol, 1.20 eq) were dissolved in ethanol (20.00 mL), DIPEA (872.37 mg, 6.75 mmol, 2.50 eq) was added at 15° C. under the nitrogen gas atmosphere. The mixture was stirred at 80° C. for 12 hours, cooled and concentrated at 60° C. under reduced pressure and the residue was added to water (10 mL). The aqueous phase was extracted with dichloromethane (50 mL×4), dried over anhydrous sodium sulfate, filtered and concentrated in vacuo. The residue was purified by silica gel chromatography (column height: 250 mm, diameter: 100 mm, 100 to 200 mesh silica gel, petroleum ether/ethyl acetate=20/1, 1/1) to deliver (S)-1-(2-chloro-4-nitro-1H-imidazol-1-yl)-3-(2-(3,4-difluorophenyl)-4-methyl-7,8-dihydro-1,6-naphthyridin-6(5H)-yl)-2-methylpropan-2-ol (800.00 mg, 1.67 mmol, 62.00% yield) as a yellow solid. LCMS (ESI) m/z: 478 (M+1).

Step 6:

(S)-2-((2-(3,4-Difluorophenyl)-4-methyl-7,8-dihydro-1,6-naphthyridin-6(5H)-yl)methyl)-2-methyl-6-nitro-2,3-dihydroimidazo[2,1-b]oxazole Compound 37

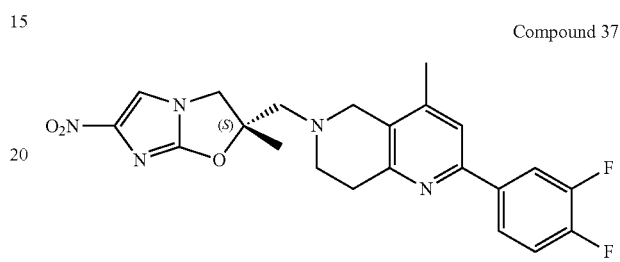

(S)-1-(2-Chloro-4-nitro-1H-imidazol-1-yl)-3-(2-(3,4-difluorophenyl)-4-methyl-7,8-dihydro-1,6-naphthyridin-6(5H)-yl)-2-methylpropan-2-ol (400.00 mg, 837.01 μmol, 1.00 eq) was dissolved in DMF (5.00 mL) and NaH (40.18 mg, 1.67 mmol, 2.00 eq) was added at −20° C. under the nitrogen gas atmosphere. The mixture was stirred for 10 minutes and then warmed to −5° C. for 10 minutes. The mixture was then stirred at 15° C. for an additional 10 minutes. The mixture was cooled to 0° C. and quenched with a saturated aqueous ammonium chloride solution (30 mL). The mixture was then filtered and the filter cake was collected and dried to give the crude product which was purified by preparative chromatography (GX-D; Boston Symmetrix C18 ODS-R 150*30 mm*5 um; acetonitrile 24%-54%; water (0.225% fomic acid); 25 mL/min) to deliver (S)-2-((2-(3,4-difluorophenyl)-4-methyl-7,8-dihydro-1,6-naphthyridin-6(5H)-yl)methyl)-2-methyl-6-nitro-2,3-dihydroimidazo[2,1-b]oxazole compound 37 (97.50 mg, 215.7 μmol, 25.78% yield, 97.7% purity). $^1$H NMR (400 MHz, METHANOL-d$_4$): δ 7.88-7.78 (m, 2H), 7.71 (d, J=8.5 Hz, 1H), 7.46 (s, 1H), 7.38-7.30 (m, 1H), 4.45 (d, J=10.5 Hz, 1H), 4.14 (d, J=10.3 Hz, 1H), 3.84 (s, 2H), 3.18-3.08 (m, 2H), 3.05-2.90 (m, 3H), 2.88-2.78 (m, 1H), 2.30 (s, 3H), 1.69 (s, 3H). LCMS (ESI) m/z: 442 (M+1).

Embodiment 38

2-(3,4-Difluorophenyl)-6-((2-methyl-6-nitro-2,3-dihydroimidazo[2,1-b]oxazol-2-yl)methyl)-7,8-dihydro-1,6-naphthyridin-5(6H)-one

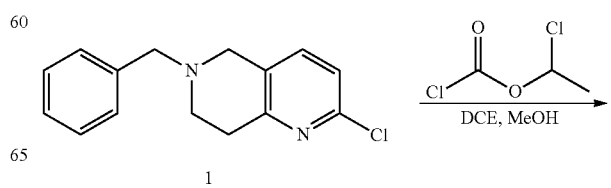

1

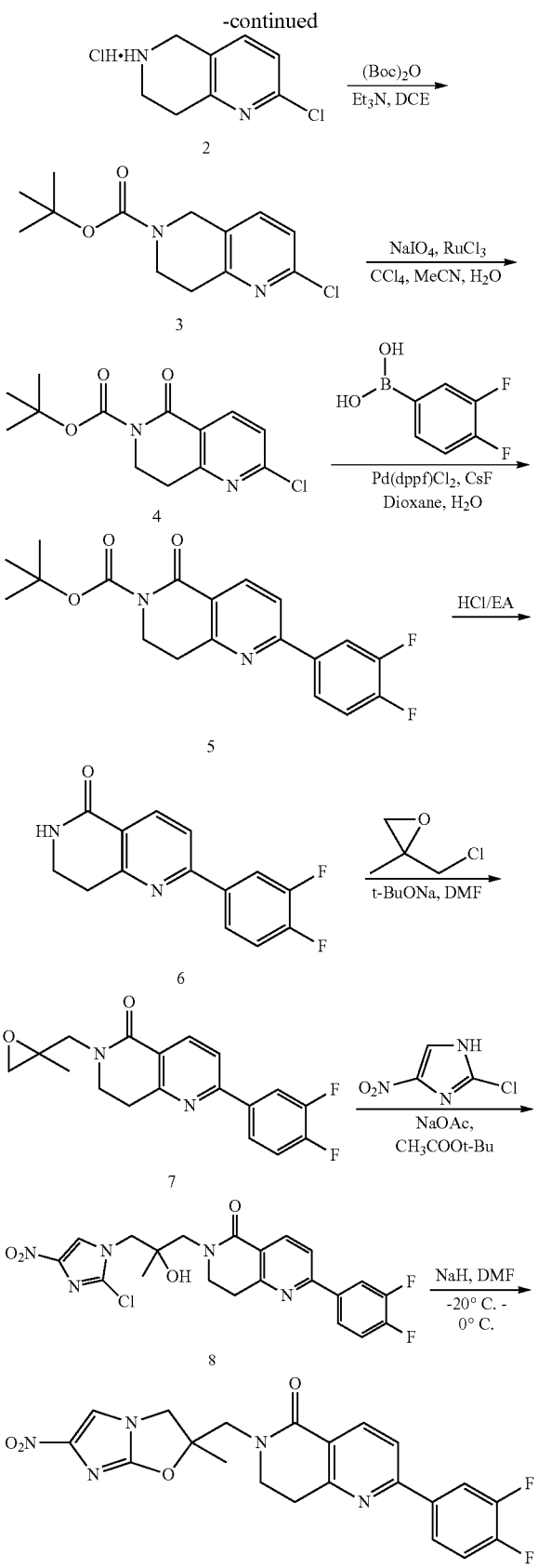

Compound 38

Step 1:

2-Chloro-5,6,7,8-tetrahydro-1,6-naphthyridine hydrochloride

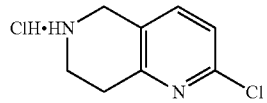

6-Benzyl-2-chloro-7,8-dihydro-5H-1,6-naphthyridine (2.70 g, 10.43 mmol, 1.00 eq) was dissolved in dichloroethane (50.00 mL), 1-chloroethyl carbonochloridate (2.24 g, 15.65 mmol, 1.50 eq) was added at 15° C. under the nitrogen gas atmosphere. The mixture was stirred at 85° C. for 12 hours. The mixture was then concentrated to remove the solvent. Methanol (50.00 mL) was added to the residue, and then heated to 80° C. and stirred for 2 hours. The mixture was filtered and the cake was collected and dried to deliver 2-chloro-5,6,7,8-tetrahydro-1,6-naphthyridine hydrochloride (2.00 g, 9.75 mmol, 93.50% yield) as a white solid which was used directly in the next step.

Step 2:

tert-Butyl 2-chloro-7,8-dihydro-1,6-naphthyridine-6 (5H)-carboxylate

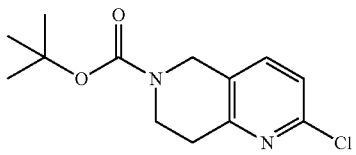 [SMILES: CC(C)(C)OC(=O)N1CCc2nc(Cl)ccc2C1]

2-Chloro-5,6,7,8-tetrahydro-1,6-naphthyridine hydrochloride (2.00 g, 9.75 mmol, 1.00 eq) was dissolved in DCM (20.00 mL) and triethylamine (2.47 g, 24.38 mmol, 2.50 eq) and di-tert-butyl dicarbonate (3.19 g, 14.63 mmol, 1.50 eq) were added at 15° C. under the nitrogen gas atmosphere. The mixture was stirred at 15° C. for 12 hours. The mixture was poured into water (30 mL) and the aqueous phase was extracted with dichloromethane (100 mL×4). The combined organic phases were washed with saturated brine (100 mL), dried over anhydrous sodium sulfate, filtered and concentrated in vacuo to deliver tert-butyl 2-chloro-7,8-dihydro-5H-1,6-naphthyridine-6-carboxylate (2.50 g, 9.30 mmol, 95.41% yield) as a white solid. LCMS (ESI) m/z: 269 (M+1).

Step 3:

tert-Butyl 2-chloro-5-oxo-7,8-dihydro-1,6-naphthyridine-6(5H)-carboxylate

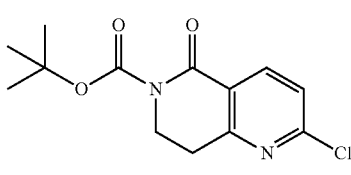 [SMILES: CC(C)(C)OC(=O)N1CCc2nc(Cl)ccc2C1=O]

Sodium pentachlorate (5.49 g, 25.68 mmol, 3.00 eq) and RuCl$_3$ (532.58 mg, 2.57 mmol, 0.30 eq) were added to a mixed solution of tert-butyl 2-chloro-7,8-dihydro-5H-1,6- naphthyridine-6-carboxylate (2.30 g, 8.56 mmol, 1.00 eq) in acetonitrile (740.00 μL) and carbon tetrachloride (37.00 mL) and water (14.80 mL) at 15° C. under the nitrogen gas atmosphere. The mixture was stirred at 15° C. for 12 hours. The mixture was poured into water (20 mL) and then extracted with dichloromethane (100 mL×4). The combined organic phases were washed with saturated brine (100 mL), dried over anhydrous sodium sulfate, filtered and concentrated in vacuo. The residue was purified by silica gel chromatography (column height: 250 mm, diameter: 100 mm, 100 to 200 mesh silica gel, petroleum ether/ethyl acetate=20/1 to 10/1) to deliver tert-butyl 2-chloro-5-oxo-7,8-dihydro-1,6-naphthyridine-6(5H)-carboxylate (1.80 g, 6.37 mmol, 74.38% yield) as a white solid. $^1$H NMR (400 MHz, CDCl$_3$): δ 8.38 (d, J=8.3 Hz, 1H), 7.37 (d, J=8.0 Hz, 1H), 4.13-4.04 (m, 2H), 3.24-3.12 (m, 2H), 1.60 (s, 9H). LCMS (ESI) m/z: 283 (M+1).

Step 4:

tert-Butyl 2-(3,4-difluorophenyl)-5-oxo-7,8-dihydro-1,6-naphthyridine-6(5H)-carboxylate

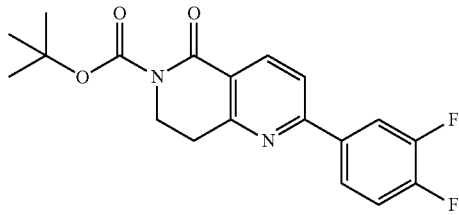 [SMILES: CC(C)(C)OC(=O)N1CCc2nc(-c3ccc(F)c(F)c3)ccc2C1=O]

tert-Butyl 2-chloro-5-oxo-7,8-dihydro-1,6-naphthyridine-6(5H)-carboxylate (1.80 g, 6.37 mmol, 1.00 eq) was dissolved in dioxane (30.00 mL) and water (3.00 mL), and then (3,4-difluorophenyl) boronic acid (1.21 g, 7.64 mmol, 1.20 eq), cesium fluoride (2.90 g, 19.11 mmol, 3.00 eq) were added. Pd(dppf)Cl$_2$ (466.09 mg, 637.00 μmol, 0.10 eq) was added at 15° C. under the nitrogen gas atmosphere. The mixture was stirred at 110° C. for 12 hours. The mixture was cooled to 15° C. and concentrated under reduced pressure. Water (20 mL) was added to the residue and the aqueous phase was extracted with dichloromethane (100 mL×4). The combined organic phases were washed with saturated brine (100 mL), dried over anhydrous sodium sulfate, filtered and concentrated in vacuo. The residue was purified by silica gel chromatography (column height: 250 mm, diameter: 100 mm, 100 to 200 mesh silica gel, petroleum ether/ethyl acetate=20/1, 10/1) to deliver tert-butyl 2-(3,4-difluorophenyl)-5-oxo-7,8-dihydro-1,6-naphthyridine-6-carboxylate (1.40 g, 3.89 mmol, 60.99% yield) as a white solid. $^1$H NMR (400 MHz, CDCl$_3$): δ 8.49 (d, J=8.3 Hz, 1H), 7.99 (ddd, J=2.0, 7.8, 11.5 Hz, 1H), 7.82 (ddd, J=2.0, 4.1, 6.4 Hz, 1H), 7.73 (d, J=8.3 Hz, 1H), 7.35-7.29 (m, 1H), 4.18-4.08 (m, 2H), 3.28 (t, J=6.4 Hz, 2H), 1.62 (s, 10H).

Step 5:

2-(3,4-Difluorophenyl)-7,8-dihydro-1,6-naphthyridin-5(6H)-one

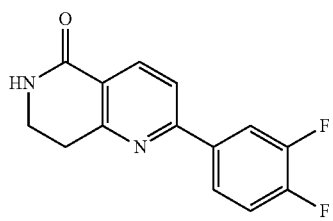 [SMILES: O=C1NCCc2nc(-c3ccc(F)c(F)c3)ccc21]

tert-Butyl 2-(3,4-difluorophenyl)-5-oxo-7,8-dihydro-1,6-naphthyridine-6-carboxylate (500.00 mg, 1.39 mmol, 1.00 eq) was dissolved in hydrochloric acid/ethyl acetate (10.00 mL) and the solution was stirred at 15° C. for 1 hour. The mixture was concentrated to dry to deliver 2-(3,4-difluorophenyl)-7,8-dihydro-6H-1,6-naphthyridin-5-one (350.00 mg, 1.34 mmol, 96.76% yield) as a white solid. LCMS (ESI) m/z: 261 (M+1).

Step 6:

2-(3,4-Difluorophenyl)-6-((2-methyloxiran-2-yl)methyl)-7,8-dihydro-1,6-naphthyridin-5(6H)-one

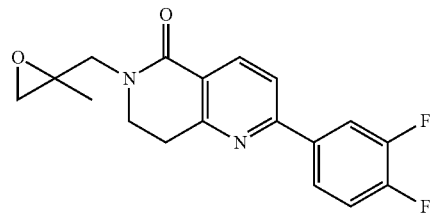 [SMILES: CC1(CN2CCc3nc(-c4ccc(F)c(F)c4)ccc3C2=O)CO1]

Potassium tert-butoxide (215.59 mg, 1.92 mmol, 2.00 eq) was added to a solution of 2-(3,4-difluorophenyl)-7,8-dihydro-6H-1,6-naphthyridin-5-one (250.00 mg, 960.65 μmol, 1.00 eq) and 2-(chloromethyl)-2-methyl-oxirane (153.54 mg, 1.44 mmol, 1.50 eq) in DMF (3.00 mL) at 15° C. under the nitrogen gas atmosphere. The mixture was stirred at 110° C. for 3 hours. Water (10 mL) was added to the mixture, and the mixture was extracted with ethyl acetate (50 mL×4). The combined organic phases were washed with brine (50 mL), dried over anhydrous sodium sulfate, filtered and concentrated in vacuo. The residue was purified by silica gel chromatography (column height: 250 mm, 10 mm diameter, 100 to 200 mesh silica gel, petroleum ether/ethyl acetate=20/1, 1/1) to deliver 2-(3,4-difluorophenyl)-6-((2-methyloxiran-2-yl)methyl)-7,8-dihydro-1,6-naphthyridin-5(6H)-one (240.00 mg, crude) as a yellow solid. LCMS (ESI) m/z: 331 (M+1).

Step 7:

6-(3-(2-Chloro-4-nitro-1H-imidazol-1-yl)-2-hydroxy-2-methylpropyl)-2-(3,4-difluorophenyl)-7,8-dihydro-1,6-naphthyridin-5(6H)-one

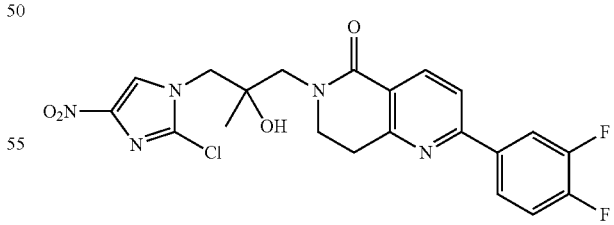

2-(3,4-Difluorophenyl)-6-((2-methyloxiran-2-yl)methyl)-7,8-dihydro-1,6-naphthyridin-5(6H)-one (150.00 mg, 454.09 μmol, 1.00 eq) and 2-chloro-4-nitro-1H-imidazole (66.99 mg, 454.09 μmol, 1.00 eq) were dissolved in t-butyl acetate (5.00 mL), sodium acetate (37.25 mg, 454.09 μmol, 1.00 eq) was added at 15° C. under the nitrogen gas atmosphere. The mixture was stirred at 110° C. for 3 hours. The mixture was cooled and concentrated under reduced pressure at 70° C. The residue was purified by preparative thin layer chromatography (petroleum ether/ethyl acetate=1/1) to deliver 6-(3-(2-chloro-4-nitro-1H-imidazol-1-yl)-2-hydroxy-2-methylpropyl)-2-(3,4-difluorophenyl)-7,8-dihydro-1,6-naphthyridin-5 (6H)-one (40 mg, crude) as a white solid. LCMS (ESI) m/z: 478 (M+1).

Step 8:

2-(3,4-Difluorophenyl)-6-((2-methyl-6-nitro-2,3-dihydroimidazo[2,1-b]oxazol-2-yl)methyl)-7,8-dihydro-1,6-naphthyridin-5(6H)-one Compound 38

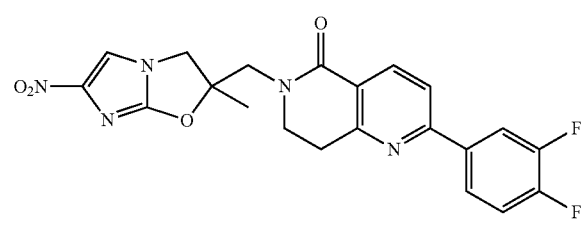

6-(3-(2-Chloro-4-nitro-1H-imidazol-1-yl)-2-hydroxy-2-methylpropyl)-2-(3,4-difluorophenyl)-7,8-dihydro-1,6-naphthyridin-5(6H)-one (30.00 mg, 83.71 μmol, 1.00 eq) was dissolved in DMF (2.00 mL), NaH (4.02 mg, 167.42 μmol, 2.00 eq) was added at −20° C. under the nitrogen gas atmosphere. The mixture was stirred at −20° C. for 10 minutes and then warmed to 0° C. and stirred for 10 minutes and then stirred at 15° C. for 10 minutes. The mixture was cooled to 0° C. and quenched with a saturated aqueous ammonium chloride solution (20 mL). The mixture was extracted with ethyl acetate (30 mL×4). The combined organic phases were washed with brine (20 mL), dried over anhydrous sodium sulfate, filtered and concentrated in vacuo, and the residue was purified by preparative chromatography (GX-D; Boston Symmetrix C18 ODS-R 150*30 mm*5 um; acetonitrile 24%-54%; water (0.225% fomic acid); 25 mL/min) to deliver 2-(3,4-difluorophenyl)-6-((2-methyl-6-nitro-2,3-dihydroimidazo[2,1-b]oxazol-2-yl)methyl)-7,8-dihydro-1,6-naphthyridin-5(6H)-one compound 38 (8.00 mg, 18.12 μmol, 21.65% yield). $^1$H NMR (400 MHz, METHANOL-$d_4$): δ 8.35 (d, J=8.3 Hz, 1H), 8.13-8.02 (m, 1H), 7.91 (d, J=8.3 Hz, 2H), 7.84 (s, 1H), 7.46-7.35 (m, 1H), 4.68-4.47 (m, 1H), 4.34-4.16 (m, 2H), 3.96-3.78 (m, 2H), 3.31-3.14 (m, 2H), 3.08-2.96 (m, 1H), 1.76 (s, 3H). LCMS (ESI) m/z: 442 (M+1).

Embodiment 39

(S)-2-((2-(4-Fluorophenyl)-6,7-dihydrothiazolo[5,4-c]pyridin-5(4H)-yl)methyl)-2-methyl-6-nitro-2,3-dihydroimidazo[2,1-b]oxazole

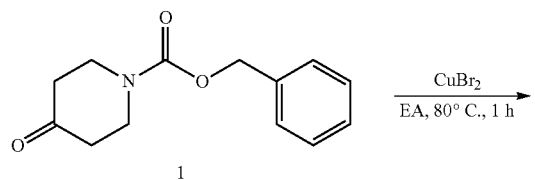

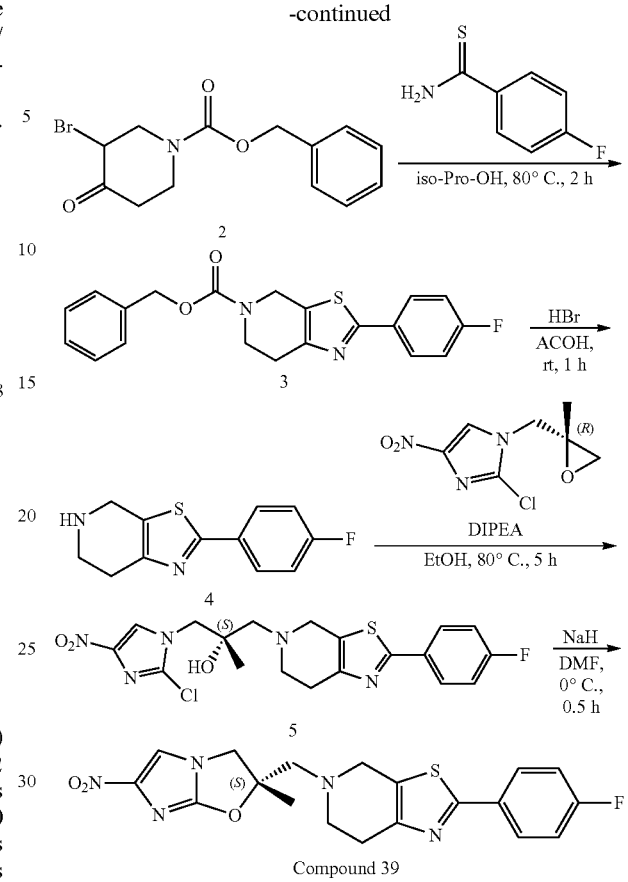

Compound 39

Step 1:

Benzyl 3-bromo-4-oxopiperidine-1-carboxylate

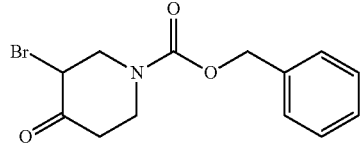 [SMILES: O=C1CCN(C(=O)OCc2ccccc2)CC1Br]

Copper bromide (3.83 g, 17.14 mmol, 2.00 eq) was added to a solution of benzyl 4-oxopiperidine-1-carboxylate (2.00 g, 8.57 mmol, 1.00 eq) in ethyl acetate (10.00 mL) under the nitrogen gas atmosphere. The mixture was stirred at 80° C. for 1 hour. The mixture was filtered and concentrated under reduced pressure to deliver benzyl 3-bromo-4-oxopiperidine-1-carboxylate (2.40 g, crude) which was used directly in the next step.

Step 2:

Benzyl 2-(4-fluorophenyl)-6,7-dihydrothiazolo[5,4-c]pyridine-5(4H)-carboxylate

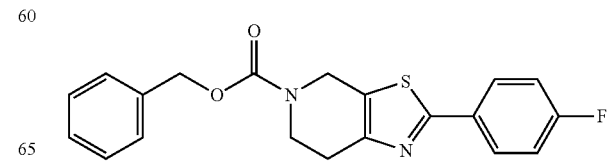

Benzyl 3-bromo-4-oxopiperidine-1-carboxylate (2.40 g, 7.69 mmol, 1.00 eq) and 4-fluorothiobenzamide (1.19 g, 7.69 mmol, 1.00 eq) were dissolved in isopropanol (20.00 mL) and heated to 80° C. and stirred for 2 hours. The mixture was concentrated under reduced pressure, and the residue was purified by silica gel chromatography (column height: 300 mm, diameter: 50 mm, 100 to 200 mesh silica gel, petroleum ether/ethyl acetate=30/1, 5/1) to deliver benzyl 2-(4-fluorophenyl)-6,7-dihydrothiazolo[5,4-c]pyridine-5(4H)-carboxylate (1.20 g, 3.26 mmol, 42.36% yield) as a white solid. $^1$H NMR (400 MHz, CDCl$_3$): δ 8.12-7.73 (m, 2H), 7.49-7.31 (m, 5H), 7.19-7.06 (m, 2H), 5.22 (s, 2H), 4.78 (br. s., 2H), 3.89 (br. s., 2H), 2.98 (br. s., 2H).

Step 3:

2-(4-Fluorophenyl)-4,5,6,7-tetrahydrothiazolo[5,4-c]pyridine

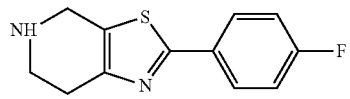 [SMILES: Fc1ccc(-c2nc3c(s2)CNCC3)cc1]

Benzyl 2-(4-fluorophenyl)-6,7-dihydrothiazolo[5,4-c]pyridine-5(4H)-carboxylate (1.20 g, 3.26 mmol, 1.00 eq) was dissolved in AcOH (5.00 mL). A solution of HBr in acetic acid (48%, 5 mL) was added at 20° C. and stirred for 1 hour. The mixture was filtered and the filter cake was washed with ethyl acetate and dried in vacuo to deliver 2-(4-fluorophenyl)-4,5,6,7-tetrahydrothiazolo[5,4-c]pyridine (800.00 mg, 2.54 mmol, 77.85% yield) as a yellow solid which was used directly in the next step.

Step 4:

(2S)-1-(2-Chloro-4-nitroimidazol-1-yl)-3-(2-(4-fluorophenyl)-6,7-dihydro-4H-thiazolo[5,4-c]pyridin-5-yl)-2-methylpropan-2-ol 2-Chloro-1-[[(2R)-2-methyloxiran-2-yl]methyl]-4-nitroimidazole (150.00 mg, 689.31 μmol, 1.10 eq) and 2-(4-fluorophenyl)-4,5,6,7-tetrahydrothiazolo[5,4-c]pyridine (197.52 mg, 626.64 μmol, 1.00 eq) were dissolved in ethanol (5.00 mL), then DIPEA (202.47 mg, 1.57 mmol, 2.50 eq) was added. The mixed solution was stirred at 80° C. for 5 hours, cooled and concentrated under reduced pressure. The residue was diluted with water and extracted with ethyl acetate (30 mL×3). The combined organic phases were washed with saturated brine (30 mL), dried over anhydrous sodium sulfate, filtered and concentrated in vacuo to deliver (2S)-1-(2-chloro-4-nitroimidazol-1-yl)-3-(2-(4-fluorophenyl)-6,7-dihydro-4H-thiazolo[5,4-c]pyridin-5-yl)-2-methylpropan-2-ol (250.00 mg, crude) and which was used directly in the next step.

Step 5:

(S)-2-((2-(4-Fluorophenyl)-6,7-dihydrothiazolo[5,4-c]pyridin-5(4H)-yl)methyl)-2-methyl-6-nitro-2,3-dihydroimidazo[2,1-b]oxazole Compound 39

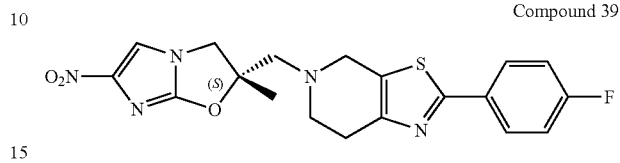

(2S)-1-(2-chloro-4-nitroimidazol-1-yl)-3-(2-(4-fluorophenyl)-6,7-dihydro-4H-thiazolo[5,4-c]pyridin-5-yl)-2-methylpropan-2-ol (150.00 mg, 331.93 μmol, 1.00 eq) was dissolved in DMF (3.00 mL), NaH (26.55 mg, 663.86 μmol, 2.00 eq) was added at 0° C. under the nitrogen gas atmosphere and stirred for 30 minutes. The mixture was poured into ice-water (w/w=1/1) (20 mL) and stirred for 10 minutes. The aqueous phase was extracted with ethyl acetate (20 mL×3). The combined organic phases were washed with saturated brine (20 mL), dried over anhydrous sodium sulfate, filtered and concentrated in vacuo. The residue was separated and purified by preparative chromatography (GX-A; Phenomenex Gemini C18 250*50 10u; 0.225% FA-ACN; Begin from 25 to 55; Flow Rate (25 mL/min)) to deliver (S)-2-((2-(4-fluorophenyl)-6,7-dihydrothiazolo[5,4-c]pyridin-5 (4H)-yl)methyl)-2-methyl-6-nitro-2,3-dihydroimidazo[2,1-b]oxazole compound 39 (20.00 mg, 47.18 μmol, 14.21% yield, 98% purity). $^1$H NMR (400 MHz, CDCl$_3$): δ 7.99-7.79 (m, 1H), 7.55 (s, 1H), 7.12 (t, J=8.7 Hz, 2H), 4.42 (d, J=9.7 Hz, 1H), 4.08-3.84 (m, 3H), 3.24-3.10 (m, 2H), 3.09-2.95 (m, 1H), 2.94-2.69 (m, 3H), 1.67 (s, 3H); LCMS (ESI) m/z: 416 (M+1).

Embodiment 40

(2S)-2-((2-(3,4-Difluorophenyl)-6,7-dihydro-4H-thiazolo[5,4-c]pyridin-5-yl)methyl)-2-methyl-6-nitro-3H-imidazo[2,1-b]oxazole Compound 40

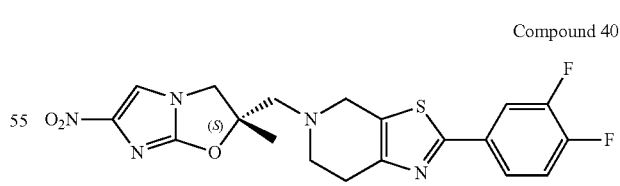

The synthesis method is as in Embodiment 39.

(2S)-2-((2-(3,4-Difluorophenyl)-6,7-dihydro-4H-thiazolo[5,4-c]pyridin-5-yl)methyl)-2-methyl-6-nitro-3H-imidazo[2,1-b]oxazole compound 40 (30.00 mg, 92.29 μmol, 43.37%). $^1$H NMR (300 MHz, CDCl$_3$): δ 7.78-7.71 (m, 1H), 7.65-7.56 (m, 2H), 7.26-7.20 (m, 1H), 4.41 (d, J=9.8 Hz, 1H), 4.06-3.85 (m, 3H), 3.23-2.95 (m, 3H), 2.93-2.68 (m, 3H), 1.67 (s, 3H); LCMS (ESI) m/z: 434 (M+1).

Embodiment 41
(S)-2-(3,4-Difluorophenyl)-5-((2-methyl-6-nitro-2,3-dihydroimidazo[2,1-b]oxazol-2-yl)methyl)-4,5,6,7-tetrahydrooxazolo[5,4-c]pyridine
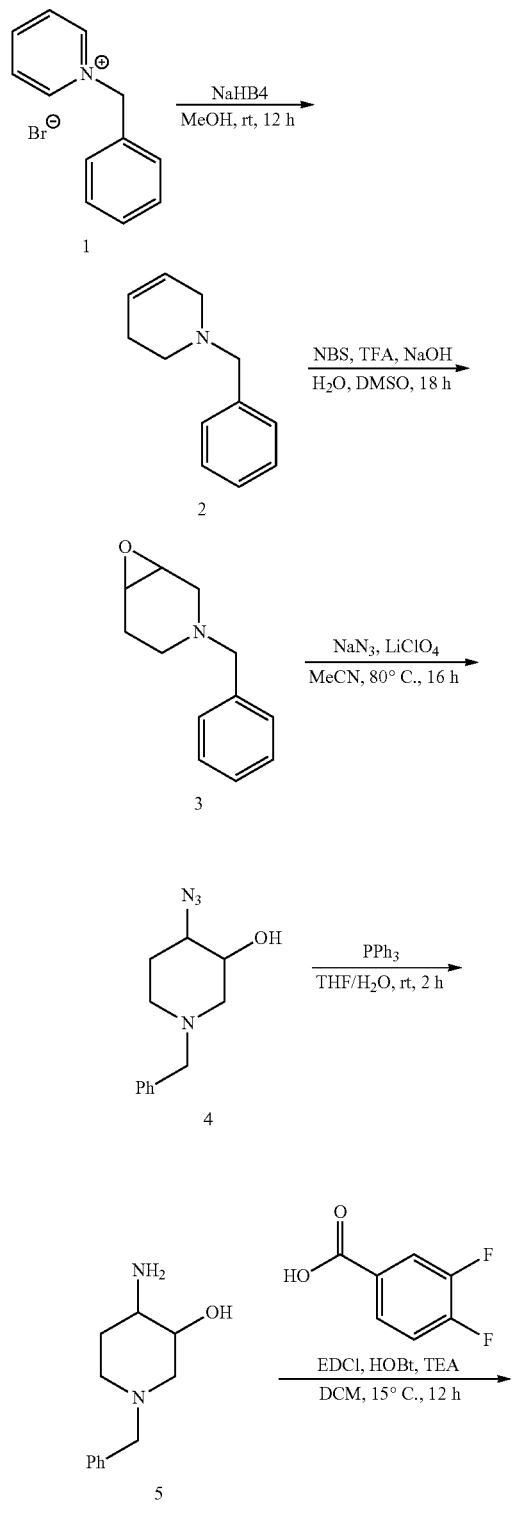
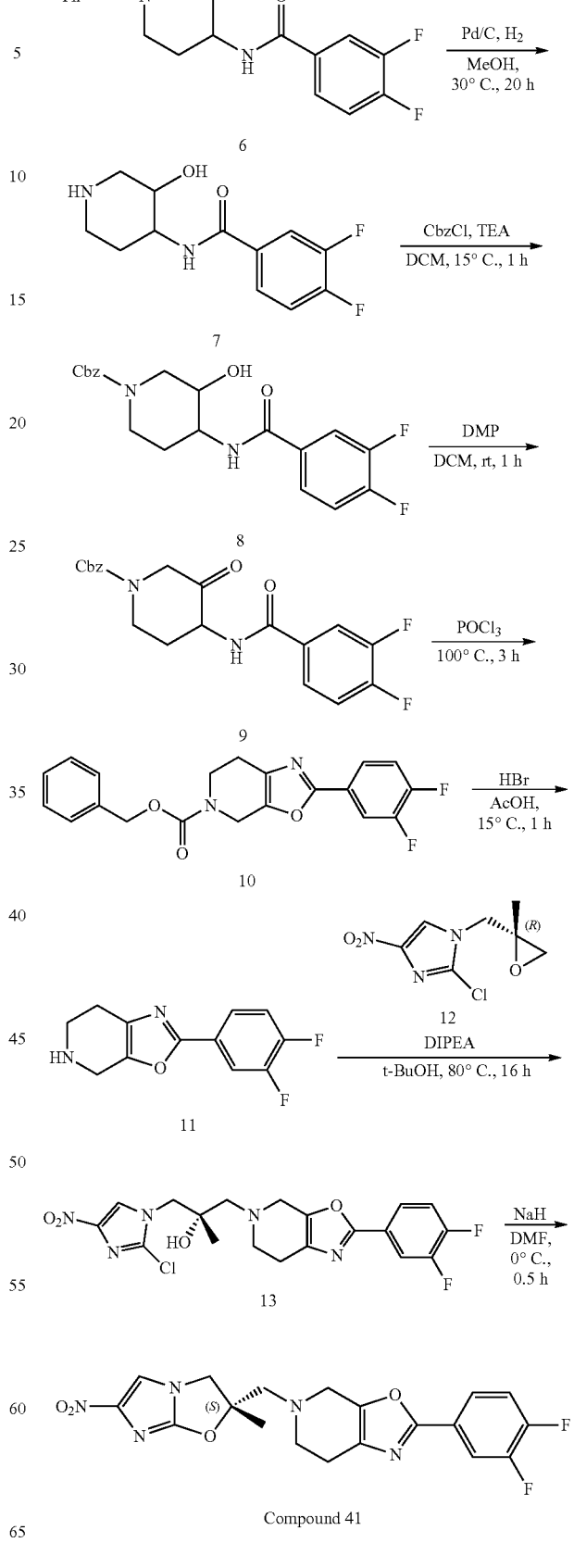
Compound 41

Step 1:

1-Benzyl-3,6-dihydro-2H-pyridine

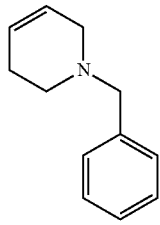 [SMILES: C1=CCN(Cc2ccccc2)CC1]

1-Benzylpyridin-1-ium bromide (53.00 g, 211.89 mmol, 1.00 eq) was dissolved in methanol (500.00 mL), sodium borohydride (12.02 g, 317.83 mmol, 1.50 eq) was added. The mixture was stirred at 25° C. for 12 hours and concentrated under reduced pressure. The residue was diluted with water (250 mL) and extracted with ethyl acetate (500 mL×2). The combined organic layers were concentrated under reduced pressure to deliver 1-benzyl-3,6-dihydro-2H-pyridine (30.00 g, crude) and which was used directly in the next step.

Step 2:

4-Benzyl-7-oxa-4-azabicyclo[4.1.0]heptane

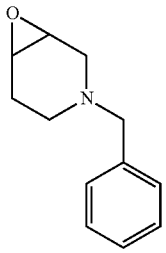

1-Benzyl-3,6-dihydro-2H-pyridine (10.00 g, 57.72 mmol, 1.00 eq) was dissolved in water (190.00 mL) and trifluoroacetic acid (24.02 g, 210.68 mmol, 3.65 eq) at 25° C. and stirred at this temperature for 1 hour. The mixture was then heated to 35° C. and bromosuccinimide (20.55 g, 115.44 mmol, 2.00 eq) was added and then the mixed solution was stirred for 5 hours, cooled to 25° C., and sodium hydroxide (2.31 g, 57.72 mmol, 1.00 eq) and acetonitrile (50.00 mL) were added to the mixed solution and then the mixed solution was stirred for 12 hours and concentrated under reduced pressure to remove the solvent. The residue was extracted with ethyl acetate (500 mL×2). The combined organic layers were concentrated under reduced pressure and the residue was purified by silica gel chromatography (silica, petroleum ether/ethyl acetate=10/1, 3:1) to deliver 4-benzyl-7-oxa-4-azabicyclo[4.1.0]heptane (5.00 g, 26.42 mmol, 45.77% yield) as a yellow solid.

Step 3:

4-Azido-1-benzylpiperidin-3-ol

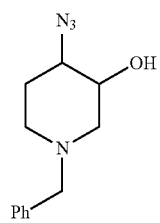

4-Benzyl-7-oxa-4-azabicyclo[4.1.0]heptane (5.00 g, 26.42 mmol, 1.00 eq) and lithium perchlorate (2.81 g, 26.42 mmol, 1.00 eq) were dissolved in acetonitrile (30.00 mL), sodium azide (2.23 g, 34.35 mmol, 1.30 eq) was added under the nitrogen gas atmosphere, and the mixture was warmed to 80° C. stirred for 16 hours. The mixture was poured into aqueous sodium bicarbonate (50 mL) and stirred for 10 minutes. The aqueous phase was extracted with ethyl acetate (50 mL×3). The combined organic phases were washed with saturated brine (50 mL), dried over anhydrous sodium sulfate, filtered and concentrated in vacuo to deliver 4-azido-1-benzyl-piperidin-3-ol (5.50 g, crude) which was used directly in the next step.

Step 4:

4-Amino-1-benzylpiperidin-3-ol

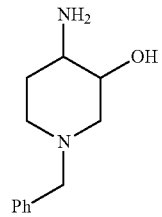

4-Azido-1-benzyl-piperidin-3-ol (5.50 g, 23.68 mmol, 1.00 eq) was dissolved in tetrahydrofuran (50.00 mL) and water (2.00 mL), triphenylphosphine (12.42 g, 47.36 mmol, 2.00 eq) was added in portions at 15° C. and the mixture was stirred for 16 hours and then concentrated in vacuo. The residue was purified by silica gel separation (column height: 300 mm, diameter: 50 mm, 100 to 200 mesh silica gel, dichloromethane/methanol=50/1) to deliver 4-amino-1-benzyl-piperidin-3-ol (3.40 g, 16.48 mmol, 69.60% yield) as a yellow solid.

Step 5:

N-(1-Benzyl-3-hydroxy-4-piperidinyl)-3,4-difluorobenzamide

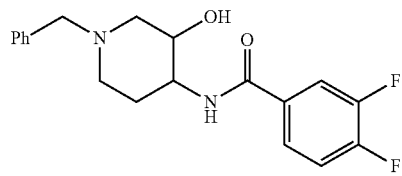 [SMILES: O=C(NC1CCN(Cc2ccccc2)CC1O)c1ccc(F)c(F)c1]

4-Amino-1-benzyl-piperidin-3-ol (2.00 g, 9.70 mmol, 1.00 eq) and 3,4-difluorobenzoic acid (1.53 g, 9.70 mmol, 1.00 eq) were dissolved in dichloromethane (30.00 mL), then EDCI (3.72 g, 19.40 mmol, 2.00 eq), HOBT (2.62 g, 19.40 mmol, 2.00 eq), triethylamine (3.93 g, 38.80 mmol, 4.00 eq) were added at 15° C. and the mixture was stirred for 12 hours. Then the mixture was diluted with water (20 mL) and the aqueous phase was extracted with ethyl acetate (40 mL×3). The combined organic phases were washed with brine (20 mL), dried over anhydrous sodium sulfate, filtered and concentrated in vacuo. The residue was separated and purified by thin layer chromatography (petroleum ether/ethyl acetate=10/1, 1/3) to deliver N-(1-benzyl-3-hydroxy-4-piperidinyl)-3,4-difluorobenzamide (1.70 g, 4.91 mmol, 50.62% yield) as a white solid. ¹H NMR (400 MHz, CDCl₃): δ 7.71-7.64 (m, 1H), 7.58-7.47 (m, 1H), 7.38-7.30 (m, 4H), 7.27-7.21 (m, 1H), 6.11 (d, J=6.1 Hz, 1H), 3.92-3.82 (m, 1H), 3.66 (dt, J=4.3, 9.3 Hz, 1H), 3.59 (s, 2H), 3.13 (dd, J=3.2, 11.2 Hz, 1H), 2.87 (d, J=11.8 Hz, 1H), 2.21-2.13 (m, 1H), 2.11-2.03 (m, 2H), 1.66 (dq, J=4.3, 11.8 Hz, 1H). LCMS (ESI) m/z: 347 (M+1).

Step 6:

3,4-Difluoro-N-(3-hydroxypiperidin-4-yl)benzamide

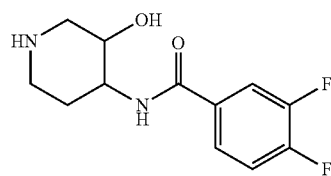 [SMILES: O=C(NC1CCNCC1O)c1ccc(F)c(F)c1]

N-(1-Benzyl-3-hydroxy-4-piperidinyl)-3,4-difluorobenzamide (1.70 g, 4.91 mmol, 1.00 eq) was dissolved in methanol (50.00 mL), Pd(OH)₂/C (10%, 0.05 g) was added under the nitrogen gas atmosphere. Then the mixture was replaced with hydrogen three times, and the mixture was stirred at H₂ (50 PSI) at 50° C. for 12 hours. The reaction mixture was filtered and the filtrate was concentrated to deliver 3,4-difluoro-N-(3-hydroxy-4-piperidinyl) benzamide (1.20 g, crude) which was used in the next step without further purification. LCMS (ESI) m/z: 257 (M+1).

Step 7:

Benzyl 4-(3,4-difluorobenzamido)-3-hydroxypiperidine-1-carboxylate

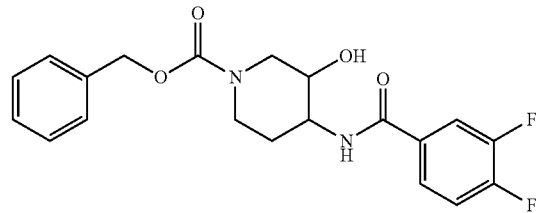 [SMILES: O=C(NC1CCN(C(=O)OCc2ccccc2)CC1O)c1ccc(F)c(F)c1]

Carbobenzoxy chloride (878.75 mg, 5.15 mmol, 1.10 eq), 3,4-difluoro-N-(3-hydroxy-4-piperidinyl) benzamide (1.20 g, 4.68 mmol, 1.00 eq) were dissolved in dichloromethane (30.00 mL), triethylamine (1.42 g, 14.04 mmol, 3.00 eq) was added at 15° C. and the mixture was stirred for 10 hours. Water (20 mL) was added to the mixture and the aqueous phase was extracted with ethyl acetate (40 mL×3). The combined organic phases were washed with brine (30 mL), dried over anhydrous sodium sulfate, filtered and concentrated in vacuo. The residue was separated and purified by silica gel chromatography (petroleum ether/ethyl acetate=10/1, 1/1) to deliver benzyl 4-(3,4-difluorobenzamido)-3-hydroxypiperidine-1-carboxylate (1.25 g, 3.20 mmol, 68.42% yield) as a white solid. LCMS (ESI) m/z: 391 (M+1).

Step 8:

Benzyl 4-(3,4-difluorobenzamido)-3-oxopiperidine-1-carboxylate

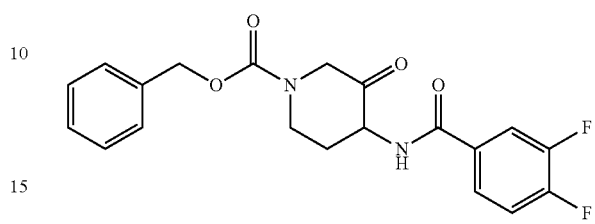

Benzyl 4-(3,4-difluorobenz amido)-3-hydroxypiperidine-1-carboxylate (920.00 mg, 2.36 mmol, 1.00 eq) was dissolved in dichloromethane (30.00 mL), DMP (3.00 g, 7.08 mmol, 3.00 eq) was added at 15° C. and the mixture was stirred for 3 hours. The residue was then poured into an sodium hydroxide aqueous solution (0.5N, 40 mL) and the aqueous phase was extracted with dichloromethane (60 mL×3). The combined organic phases were washed with brine (30 mL), dried over anhydrous sodium sulfate, filtered and concentrated in vacuo. The residue was purified by silica gel chromatography (petroleum ether/ethyl acetate=10/1, 1/3) to deliver benzyl 4-(3,4-difluorobenzamido)-3-oxopiperidine-1-carboxylate (1.00 g, crude) as a yellow oil.

Step 9:

Benzyl 2-(3,4-difluorophenyl)-6,7-dihydro-4H-oxazolo[5,4-c]pyridine-5-carboxylate

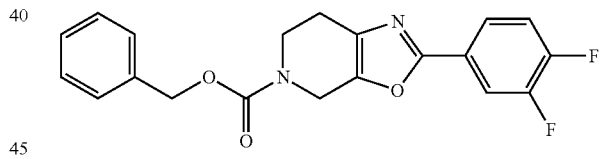

Benzyl 4-(3,4-difluorobenzamido)-3-oxopiperidine-1-carboxylate (1.20 g, 3.09 mmol, 1.00 eq) was added to a solution of phosphorus oxychloride (2.55 g, 16.63 mmol, 5.38 eq) in dioxane (20.00 mL) at 15° C. under the nitrogen gas atmosphere. Then the mixture was heated to 110° C. and stirred for 3 hours. The residue was then poured into water (50 mL) and stirred for 5 minutes. The aqueous phase was extracted with ethyl acetate (60 mL×3) and the combined organic phases were washed with brine (30 mL×2), dried over anhydrous sodium sulfate, filtered and concentrated in vacuo. The residue was purified by silica gel chromatography (silica, petroleum ether/ethyl acetate=1/0, 10/1) to deliver benzyl 2-(3,4-difluorophenyl)-6,7-dihydro-4H-oxazolo[5,4-d]pyridine-5-carboxylate (800.00 mg, 2.16 mmol, 69.90% yield) as a yellow oil. ¹H NMR (400 MHz, CDCl₃): δ 7.89-7.69 (m, 2H), 7.42-7.39 (m, 4H), 7.39-7.34 (m, 1H), 7.28-7.22 (m, 1H), 5.21 (s, 2H), 4.68 (br. s., 2H), 3.86 (br. s., 2H), 2.87-2.67 (m, 2H). LCMS (ESI) m/z: 371 (M+1).

Step 10:

2-(3,4-Difluorophenyl)-4,5,6,7-tetrahydrooxazolo[5,4-c]pyridine

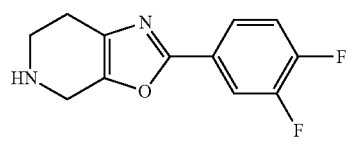 [SMILES: Fc1ccc(-c2nc3c(o2)CNCC3)cc1F]

Benzyl 2-(3,4-difluorophenyl)-6,7-dihydro-4H-oxazolo[5,4-c]pyridine-5-carboxylate (800.00 mg, 2.16 mmol, 1.00 eq) was dissolved in hydrobromic acid/acetic acid (20 mL) and stirred at 15° C. for 3 hours. The mixture was filtered and the filter cake was concentrated in vacuo to deliver 2-(3,4-difluorophenyl)-4,5,6,7-tetrahydrooxazolo[5,4-c]pyridine (450.00 mg, 1.42 mmol, 65.69% yield, hydrobromide) as a yellow solid. LCMS (ESI) m/z: 237 (M+1).

Step 11:

(2S)-1-(2-Chloro-4-nitroimidazol-1-yl)-3-(2-(3,4-difluorophenyl)-6,7-dihydro-4H-oxazolo[5,4-c]pyridin-5-yl)-2-methylpropan-2-ol

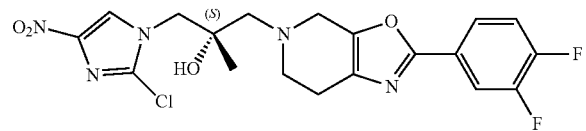

2-(3,4-Difluorophenyl)-4,5,6,7-tetrahydrooxazolo[5,4-c]pyridine (200.00 mg, 630.66 iunol, 1.00 eq, hydrobromide) and 2-chloro-1-[[(2R)-2-methyloxiran-2-yl]methyl]-4-nitroimidazole (137.24 mg, 630.66 μmol, 1.00 eq) were dissolved in t-butanol (15.00 mL), then DIPEA (244.52 mg, 1.89 mmol, 3.00 eq) was added. The mixture was stirred at 80° C. for 12 hours and then cooled, concentrated at 45° C. and the residue was purified by silica gel chromatography (petroleum ether/ethyl acetate=10/1, 3/1) to deliver (2S)-1-(2-Chloro-4-nitroimidazol-1-yl)-3-(2-(3,4-difluorophenyl)-6,7-dihydro-4H-oxazolo[5,4-c]pyridin-5-yl)-2-methylpropan-2-ol (166.00 mg, 365.78 μmol, 58.00% yield) as a yellow oil. LCMS (ESI) m/z: 454 (M+1).

Step 12:

(S)-2-(3,4-Difluorophenyl)-5-((2-methyl-6-nitro-2,3-dihydroimidazo[2,1-b]oxazol-2-yl)methyl)-4,5,6,7-tetrahydrooxazolo[5,4-c]pyridine Compound 41

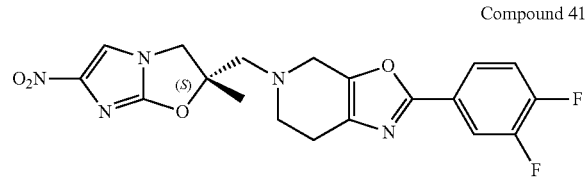

(2S)-1-(2-Chloro-4-nitroimidazol-1-yl)-3-(2-(3,4-difluorophenyl)-6,7-dihydro-4H-oxazolo[5,4-c]pyridin-5-yl)-2-methylpropan-2-ol (166.00 mg, 365.78 μmol, 1.00 eq) was dissolved in DMF (3.00 mL) and NaH (29.26 mg, 731.56 μmol, 2.00 eq) was added at −45° C. under the nitrogen gas atmosphere. The mixture was stirred at −45 to −15° C. for 2 hours. The mixture was then quenched with a saturated ammonium chloride solution (20 mL). The aqueous phase was extracted with ethyl acetate (50 mL×2). The combined organic phases were washed with brine (20 mL×2), dried over anhydrous sodium sulfate, filtered and concentrated in vacuo. The residue was then purified by preparative chromatography (GX-D; Boston Green ODS 150*30 5u; acetonitrile 42%-72%; water (0.225% fomic acid); 25 mL/min) to deliver (S)-2-(3,4-difluorophenyl)-5-((2-methyl-6-nitro-2,3-dihydroimidazo[2,1-b]oxazol-2-yl)methyl)-4,5,6,7-tetrahydrooxazolo[5,4-c]pyridine compound 41 (49.40 mg, 115.64 μmol, 31.61% yield, 97.7% purity). $^1$H NMR (400 MHz, CDCl$_3$): δ 7.85-7.78 (m, 1H), 7.74 (dd, J=3.1, 7.7 Hz, 1H), 7.55 (s, 1H), 7.27-7.20 (m, 1H), 4.40 (d, J=9.7 Hz, 1H), 3.97 (d, J=9.7 Hz, 1H), 3.87 (s, 2H), 3.17-3.07 (m, 2H), 3.02-2.94 (m, 1H), 2.80 (d, J=14.9 Hz, 1H), 2.65 (d, J=1.9 Hz, 2H), 1.67 (s, 3H). LCMS (ESI) m/z: 418 (M+1).

Embodiment 42

(S)-2-((2-(4-Fluorophenyl)-5,6-dihydroimidazo[1,2-c]pyrazin-7(8H)-yl)methyl)-2-methyl-6-nitro-2,3-dihydroimidazo[2,1-b]oxazole

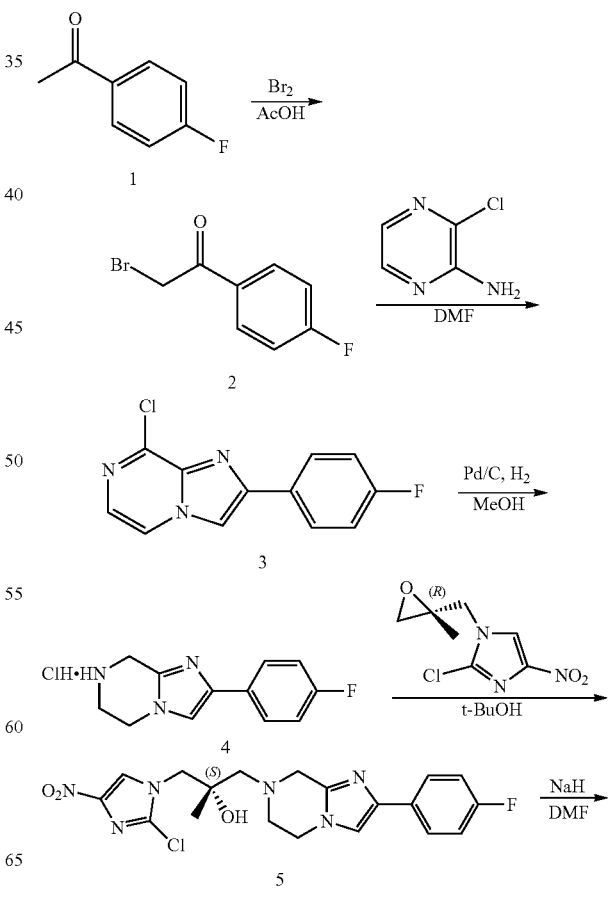

-continued

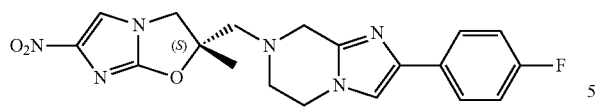

Compound 42

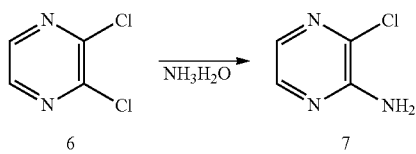

Step 1:

2-Bromo-1-(4-fluorophenyl)ethanone

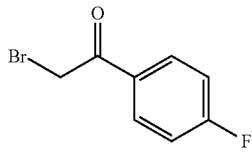

1-(4-Fluorophenyl)ethanone (9.00 g, 65.15 mmol, 1.00 eq) was dissolved in acetic acid (100.00 mL), liquid bromine (10.41 g, 65.15 mmol, 1.00 eq) was added at 15° C. and the mixture was stirred for 20 minutes. The resulting mixture was then stirred at 50° C. for 12 hours, concentrated under reduced pressure, and the pH of the mixture was adjusted to 9 with a sodium carbonate solution. The mixture was extracted with ethyl acetate (200 mL×2). The combined organic layers were concentrated under reduced pressure to give a residue which was purified by silica gel chromatography (column height: 250 mm, diameter: 100 mm, 100 to 200 mesh silica gel, petroleum ether/ethyl acetate=1/0) to deliver 2-bromo-1-(4-fluorophenyethanone (6.30 g, 29.03 mmol, 44.56% yield) as a white solid. LCMS (ESI) m/z: 218.8 (M+1).

Step 2:

3-Chloropyrazine-2-amine

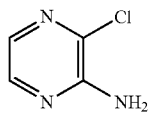

2,3-Dichloropyrazine (5.00 g, 33.56 mmol, 1.00 eq) was mixed with ammonia (68.27 g, 1.95 mol, 58.04 eq). The mixture was stirred at 85° C. for 12 hours, concentrated under reduced pressure. The residue was purified by silica gel chromatography (column height: 250 mm, diameter: 100 mm, 100 to 200 mesh silica gel, petroleum ether/ethyl acetate=50/1, 20/1) to deliver 3-chloropyrazine-2-amine (700.00 mg, 5.40 mmol, 16.09% yield) as a white solid.

Step 3:

8-Chloro-2-(4-fluorophenyl)imidazo[1,2-a]pyrazine

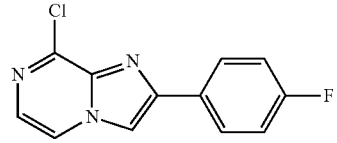 [SMILES: Fc1ccc(-c2cn3ccnc(Cl)c3n2)cc1]

2-Bromo-1-(4-fluorophenyl)ethanone (3.02 g, 13.90 mmol, 1.20 eq) and 3-chloropyrazine-2-amine (1.50 g, 11.58 mmol, 1.00 eq) were dissolved in ethylene glycol dimethyl ether (20.00 mL), and the mixture was heated to 35° C. and stirred for 12 hours. The mixture was concentrated and purified by silica gel chromatography (column height: 250 mm, diameter: 100 mm, 100 to 200 mesh silica gel, petroleum ether/ethyl acetate=20/1, 5/1) to deliver 8-chloro-(4-fluorophenyl)imidazo[1,2-a]pyrazine (900.00 mg, 3.63 mmol, 31.38% yield) as a white solid. LCMS (ESI) m/z: 247.9 (M+1).

Step 4:

2-(4-Fluorophenyl)-5,6,7,8-tetrahydroimidazo[1,2-a]pyrazine hydrochloride

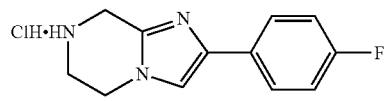

8-chloro-(4-fluorophenyl)imidazo[1,2-a]pyrazine (900.00 mg, 3.63 mmol, 1.00 eq) was dissolved in methanol (20.00 mL) and Pd/C was added under the nitrogen gas atmosphere. The mixed solution was then stirred at 50° C., $H_2$ (50 psi) for 12 hours. The reaction mixture was concentrated under reduced pressure to deliver 2-(4-fluorophenyl)-5,6,7,8-tetrahydroimidazo[1,2-a]pyrazine hydrochloride (850.00 mg, 2.93 mmol, 80.70% yield) which was used directly in the next step.

Step 5:

(2S)-1-(2-Chloro-4-nitroimidazol-1-yl)-3-(2-(4-fluorophenyl)-6,8-dihydro-5H-imidazo[1,2-a]pyrazin-7-yl)-2-methylpropan-2-ol

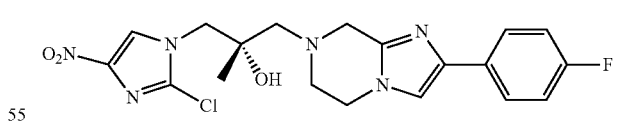

2-(4-Fluorophenyl)-5,6,7,8-tetrahydroimidazo[1,2-a]pyrazine hydrochloride (400.00 mg, 1.58 mmol, 1.00 eq) was dissolved in tert-butanol (10.00 mL), and then DIPEA (509.42 mg, 3.94 mmol, 2.50 eq) and 2-chloro-1-[[(2R)-2-methyloxiran-2-yl]methyl]-4-nitroimidazole (514.65 mg, 2.36 mmol, 1.50 eq) were added. The mixture was warmed to 100° C. and stirred for 12 hours. The reaction solution was poured into water (20 mL) and then extracted with ethyl acetate (50 mL×2). The combined organic layers were concentrated to dryness. The residue was purified by silica gel chromatography (column height: 250 mm, diameter: 100 mm, 100 to 200 mesh silica gel, petroleum ether/ethyl acetate=5/1, 1/3) to deliver (2S)-1-(2-chloro-4-nitroimidazol-1-yl)-3-(2-(4-fluorophenyl)-6,8-dihydro-5H-imidazo[1,2-c]pyrazin-7-yl)-2-methylpropan-2-ol (200 mg, 459.93 μmol, 29.17% yield) as a white solid. LCMS (ESI) m/z: 435.0 (M+1).

Step 6:

(S)-2-((2-(4-Fluorophenyl)-5,6-dihydroimidazo[1,2-c]pyrazin-7(8H)-yl)methyl)-2-methyl-6-nitro-2,3-dihydroimidazo[2,1-b]oxazole Compound 42

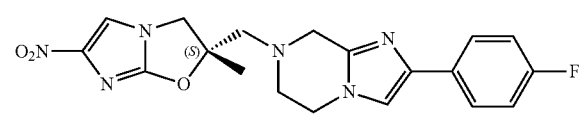

(2S)-1-(2-Chloro-4-nitroimidazol-1-yl)-3-(2-(4-fluorophenyl)-6,8-dihydro-5H-imidazo[1,2-c]pyrazin-7-yl)-2-methylpropan-2-ol (200.00 mg, 459.93 μmol, 1.00 eq) was dissolved in DMF (3.00 mL), NaH (11.04 mg, 459.93 μmol, 1.00 eq) was added at -25° C. and the mixture was stirred for 1 hour. The mixture was poured into water (15 mL) at 0° C. and then extracted with ethyl acetate (30 mL×2). The combined organic layers were concentrated to dry. The residue was purified by preparative chromatography (GX-B, Phenomenex Synergi C18 150*30 mm*4 um, acetonitrile 20%-50%; 0.1% TFA-ACN; 25 mL/min) to deliver (S)-2-((2-(4-fluorophenyl)-5,6-dihydroimidazo[1,2-c]pyrazin-7(8H)-yl)methyl)-2-methyl-6-nitro-2,3-dihydroimidazo[2,1-b]oxazole compound 42 (70.60 mg, 176.28 μmol, 38.33% yield, 99.476% purity). $^1$H NMR (400 MHz, METHANOL-$d_4$): δ 7.86 (s, 1H), 7.78 (s, 1H), 7.71 (dd, J=5.0, 8.7 Hz, 2H), 7.29 (t, J=8.7 Hz, 2H), 4.47-4.38 (m, 1H), 4.31-4.05 (m, 5H), 3.30-3.09 (m, 3H), 1.70 (s, 3H). LCMS (ESI) m/z: 399.0 (M+1).

Embodiment 43

(S)-2-((2-(3,4-Difluorophenyl)-5,6-dihydroimidazo[1,2-c]pyrazin-7(8H)-yl)methyl)-2-methyl-6-nitro-2,3-dihydroimidazo[2,1-b]oxazole Compound 43

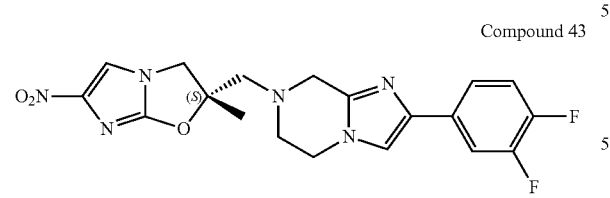

The synthesis method is as in Embodiment 42.
(S)-2-((2-(3,4-Difluorophenyl)-5,6-dihydroimidazo[1,2-c]pyrazin-7(8H)-yl)methyl)-2-methyl-6-nitro-2,3-dihydroimidazo[2,1-b]oxazole compound 43 (82.00 mg, 192.51 μmol, 21.79% yield, 97.753% purity) as a yellow solid. $^1$H NMR (400 MHz, METHANOL-$d_4$): δ 7.85 (d, J=11.9 Hz, 2H), 7.69-7.62 (m, 1H), 7.54-7.40 (m, 2H), 4.42 (d, J=10.7 Hz, 1H), 4.31-4.06 (m, 5H), 3.30-3.09 (m, 3H), 1.70 (s, 3H). LCMS (ESI) m/z: 417.0 (M+1).

Embodiment 44

(S)-2-Methyl-6-nitro-2-((2-phenyl-7,8-dihydropyrido[4,3-d]pyrimidin-6(5H)-yl)methyl)-2,3-dihydroimidazo[2,1-b]oxazole

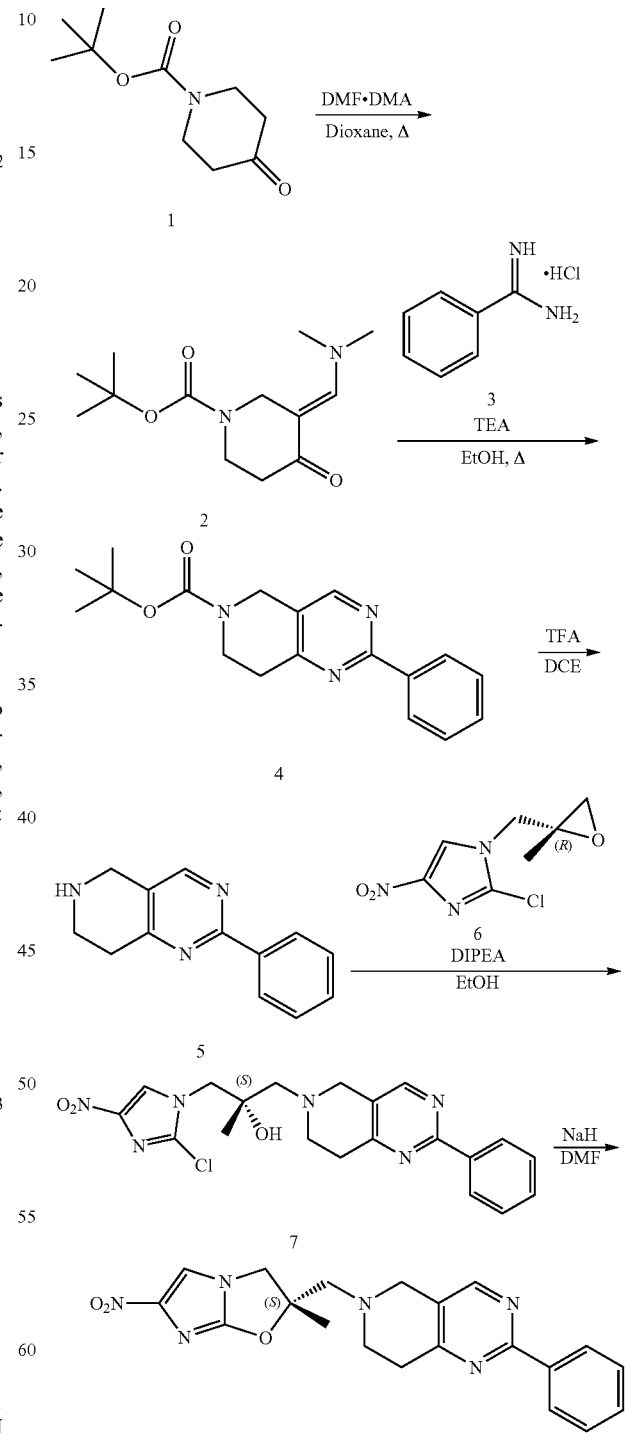

Compound 44

Step 1:

tert-Butyl (3E)-3-((dimethylamino)methylene)-4-oxopiperidine-1-carboxylate

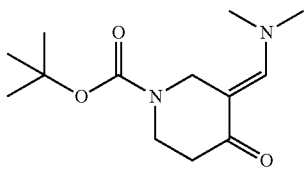 [SMILES: CN(C)/C=C1\CN(C(=O)OC(C)(C)C)CCC1=O]

tert-Butyl 4-oxopiperidine-1-carboxylate (5.00 g, 25.09 mmol, 1.00 eq) was dissolved in dioxane (30.00 mL), then 1,1-dimethoxy-N,N-dimethylmethylamine (11.96 g, 100.36 mmol, 4.00 eq) was added. The mixture was stirred at 120° C. for 16 hours, cooled and concentrated under reduced pressure at 50° C. The residue was diluted with water (50 mL) and stirred for 20 minutes. The aqueous phase was extracted with ethyl acetate (50 mL×3). The combined organic phases were washed with saturated brine (50 mL×2), dried over anhydrous sodium sulfate, filtered and concentrated in vacuo. The residue was purified by silica gel chromatography (ethyl acetate/methanol=20/1) to deliver tert-butyl (3E)-3-((dimethylamino)methylene)-4-oxopiperidine-1-carboxylate (3.00 g, 11.80 mmol, 47.02% yield) as a yellow oil. $^1$H NMR (400 MHz, CDCl$_3$): δ 7.51 (s, 1H), 4.57 (s, 2H), 3.62 (t, J=4.0 Hz, 1H), 3.13 (s, 7H), 2.46 (t, T=4.0 Hz, 1H), 1.49 (s, 9H).

Step 2:

tert-Butyl 2-phenyl-7,8-dihydro-5H-pyrido[4,3-d]pyrimidine-6-carboxylate

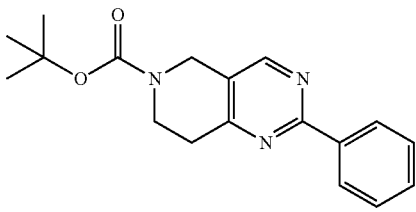 [SMILES: CC(C)(C)OC(=O)N1CCc2nc(-c3ccccc3)ncc2C1]

tert-Butyl (3E)-3-((dimethylamino)methylene)-4-oxopiperidine-1-carboxylate (3.00 g, 11.80 mmol, 1.00 eq) and benzamidine (1.85 g, 11.80 mmol, 1.00 eq) were dissolved in ethanol (30.00 mL), then triethylamine (3.58 g, 35.40 mmol, 3.00 eq) was added. The mixture was stirred at 80° C. for 2 hours, cooled and concentrated under reduced pressure. The residue was diluted with water (30 mL) and stirred for 20 minutes. The aqueous phase was extracted with ethyl acetate (30 mL×3). The combined organic phases were washed with saturated brine (30 mL×2), dried over anhydrous sodium sulfate, filtered and concentrated in vacuo. The residue was purified by silica gel chromatography (petroleum ether/ethyl acetate=3/1) to deliver tert-butyl 2-phenyl-7,8-dihydro-5H-pyrido[4,3-d]pyrimidine-6-carboxylate (2.10 g, 6.74 mmol, 57.15% yield) as a yellow solid. $^1$H NMR (400 MHz, CDCl$_3$): δ 8.54 (s, 1H), 8.46-8.36 (m, 2H), 7.54-7.44 (m, 3H), 4.64 (s, 2H), 3.80 (t, J=4.0 Hz, 2H), 3.03 (t, J=4.0 Hz, 2H), 1.53 (s, 9H). LCMS (ESI) m/z: 312(M+1).

Step 3:

2-Phenyl-5,6,7,8-tetrahydropyrido[4,3-d]pyrimidine

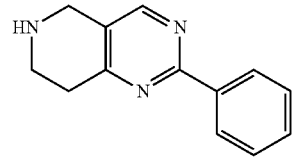 [SMILES: c1ccc(-c2ncc3c(n2)CCNC3)cc1]

tert-Butyl 2-phenyl-7,8-dihydro-5H-pyrido[4,3-d]pyrimidine-6-carboxylate (500.00 mg, 1.61 mmol, 1.00 eq) was dissolved in dichloromethane (1.00 mL), trifluoroacetic acid (183.09 mg, 1.61 mmol, 1.00 eq) was added. The mixture was stirred at 28° C. for 2 hours and concentrated under reduced pressure at 50° C. to deliver 2-phenyl-5,6,7,8-tetrahydropyrido[4,3-d]pyrimidine trifluoroacetic acid salt (800.00 mg, crude) as a yellow oil. The product was used in the next step without further purification.

Step 4:

(S)-1-(2-Chloro-4-nitro-1H-imidazol-1-yl)-2-methyl-3-(2-phenyl-7,8-dihydropyrido[4,3-d]pyrimidin-6(5H)-yl)propan-2-ol

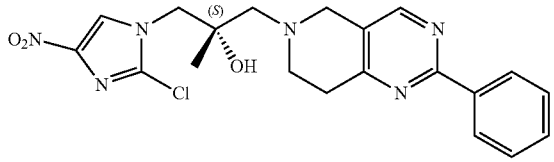

2-Phenyl-5,6,7,8-tetrahydropyrido[4,3-d]pyrimidine (340.00 mg, 1.61 mmol, 1.00 eq) and (R)-2-chloro-1-((2-methyloxiran-2-yl)methyl)-4-nitro-1H-imidazol (420.42 mg, 1.93 mmol, 1.20 eq) were dissolved in ethanol (10.00 mL), and then DIPEA (623.99 mg, 4.83 mmol, 3.00 eq) was added. The mixture was stirred at 80° C. for 12 hours, cooled and concentrated under reduced pressure at 50° C. The residue was purified by silica gel chromatography (petroleum ether ethyl acetate=2/1) to deliver (S)-1-(2-chloro-4-nitro-1H-imidazol-1-yl)-2-methyl-3-(2-phenyl-7,8-dihydropyrido[4,3-d]pyrimidin-6(5H)-yl)propan-2-ol (650.00 mg, 1.52 mmol, 94.14%) as a yellow oil. $^1$H NMR (400 MHz, CDCl$_3$) δ 8.46 (s, 1H), 8.43-8.36 (m, 2H), 8.06 (s, 1H), 7.52-7.45 (m, 3H), 4.10-4.06 (m, 2H), 3.96-3.78 (m, 2H), 3.19-2.99 (m, 4H), 2.77-2.56 (m, 2H), 1.22 (s, 3H). LCMS (ESI) m/z: 429/431 (M+1).

Step 5:

(S)-2-Methyl-6-nitro-2-((2-phenyl-7,8-dihydropyrido[4,3-d]pyrimidin-6(5H)-yl)methyl)-2,3-dihydroimidazo[2,1-b]oxazole Compound 44

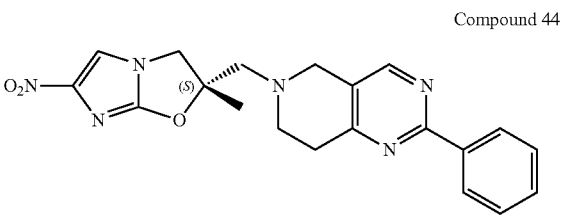

(S)-1-(2-Chloro-4-nitro-1H-imidazol-1-yl)-2-methyl-3-(2-phenyl-7,8-dihydropyrido[4,3-d]pyrimidin-6(5H)-yl)propan-2-ol (350.00 mg, 816.10 μmol, 1.00 eq) was dissolved in DMF (5.00 mL), NaH (39.17 mg, 979.32 μmol, 1.20 eq) was added at 0° C. under the nitrogen gas atmosphere and the mixture was stirred for 30 min. The reaction mixture was quenched with a saturated ammonium chloride solution (20 mL), then diluted with water (10 mL) and extracted with dichloromethane (10 mL×3). The combined organic layers were washed with saturated brine (10 mL×2), dried over sodium sulfate, filtered and concentrated under reduced pressure. The residue was purified by preparative chromatography (GX-E; Diamonsil 150*25 mm*5 um; acetonitrile 20%-50%; water (0.225% fomic acid); 25 mL/min) to deliver (S)-2-methyl-6-nitro-2-((2-phenyl-7,8-dihydropyrido[4,3-d]pyrimidin-6(5H)-yl)methyl)-2,3-dihydroimidazo[2,1-b]oxazole compound 44 (23.10 mg, 58.87 μmol, 7.21% yield). $^1$H NMR (400 MHz, CDCl$_3$): δ 8.45 (s, 1H), 8.43-8.36 (m, 2H), 7.53 (s, 1H), 7.51-7.46 (m, 3H), 4.43-3.95 (m, 2H), 3.93-3.82 (m, 2H), 3.25-3.17 (m, 1H), 3.12 (d, J=16.0 Hz, 1H), 3.05-2.89 (m, 3H), 2.83 (d, J=12.0 Hz, 1H), 1.70 (s, 3H). LCMS (ESI) m/z: 393(M+1).

Embodiment 45

(S)-2-((2-(4-Fluorophenyl)-7,8-dihydropyrido[4,3-d]pyrimidin-6(5H)-yl)methyl)-2-methyl-6-nitro-2,3-dihydroimidazo[2,1-b]oxazole

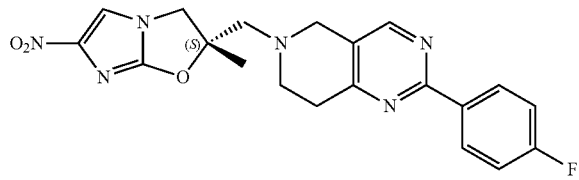

Compound 45

The synthesis method was as in Embodiment 44.
(S)-2-((2-(4-Fluorophenyl)-7,8-dihydropyrido[4,3-d]pyrimidin-6(5H)-yl)methyl)-2-methyl-6-nitro-2,3-dihydroimidazo[2,1-b]oxazole compound 45 (100.00 mg, 243.66 μmol, 27.22% yield). $^1$H NMR (400 MHz, CDCl$_3$): δ 8.44-8.37 (m, 3H), 7.53 (s, 1H), 7.19-7.12 (m, 2H), 4.42-3.96 (m, 2H), 3.89-3.85 (m, 2H), 3.24-3.16 (m, 1H), 3.12 (d, J=16.0 Hz, 1H), 3.03-2.87 (m, 3H), 2.83 (d, J=16.0 Hz, 1H), 1.70 (s, 3H). LCMS (ESI) m/z: 411(M+1).

Embodiment 46

(S)-2-((2-(3,4-Difluorophenyl)-7,8-dihydropyrido[4,3-d]pyrimidin-6(5H)-yl)methyl)-2-methyl-6-nitro-2,3-dihydroimidazo[2,1-b]oxazole

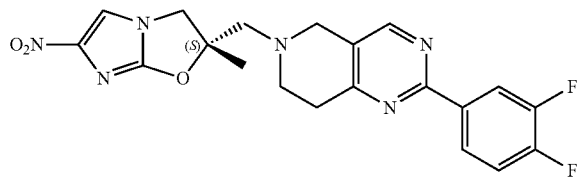

Compound 46

The synthesis method was as in Embodiment 44.
(S)-2-((2-(3,4-Difluorophenyl)-7,8-dihydropyrido[4,3-d]pyrimidin-6(5H)-yl)methyl)-2-methyl-6-nitro-2,3-dihydroimidazo[2,1-b]oxazole compound 46 (20.80 mg, 47.05 μmol, 7.06% yield, 96.9% purity). $^1$H NMR (400 MHz, CDCl$_3$) δ 8.42 (s, 1H), 8.31-8.16 (m, 2H), 7.53 (s, 1H), 7.27-7.21 (m, 1H), 4.39 (d, J=12.0 Hz, 1H), 3.99 (d, J=12.0 Hz, 1H), 3.93-3.82 (m, 2H), 3.26-3.16 (m, 1H), 3.12 (d, J=16.0 Hz, 1H), 3.04-2.88 (m, 3H), 2.83 (d, J=16.0 Hz, 1H), 1.70 (s, 3H). LCMS (ESI) m/z: 429(M+1).

Embodiment 47

(S)-2-Methyl-6-nitro-2-((2-(4-(trifluoromethoxy)phenyl)-7,8-dihydropyrido[4,3-d]pyrimidin-6(5H)-yl)methyl)-2,3-dihydroimidazo[2,1-b]oxazole

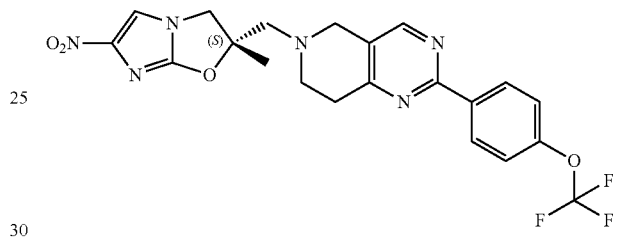

Compound 47

The synthesis method was as in Embodiment 44.
(S)-2-Methyl-6-nitro-2-((2-(4-(trifluoromethoxy)phenyl)-7,8-dihydropyrido[4,3-d]pyrimidin-6(5H)-yl)methyl)-2,3-dihydroimidazo[2,1-b]oxazole compound 47 (26.70 mg, 56.04 μmol, 5.75% yield). $^1$H NMR (400 MHz, CDCl$_3$): δ 8.49-8.41 (m, 3H), 7.53 (s, 1H), 7.31 (d, J=8.0 Hz, 2H), 4.43-3.95 (m, 2H), 3.94-3.82 (m, 2H), 3.25-3.16 (m, 1H), 3.12 (d, J=16.0 Hz, 1H), 3.04-2.89 (m, 3H), 2.83 (d, J=16.0 Hz, 1H), 1.70 (s, 3H). LCMS (ESI) m/z: 477(M+1).

Embodiment 48

(S)-2-((2-(3,5-Difluorophenyl)-7,8-dihydropyrido[4,3-d]pyrimidin-6(5H)-yl)methyl)-2-methyl-6-nitro-2,3-dihydroimidazo[2,1-b]oxazole

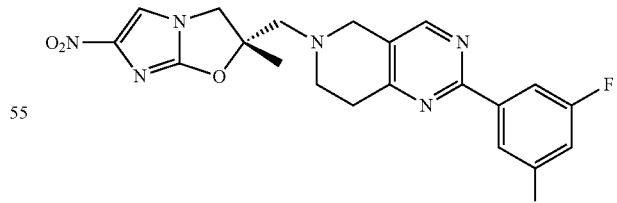

Compound 48

The synthesis method was as in Embodiment 44.
(S)-2-((2-(3,5-Difluorophenyl)-7,8-dihydropyrido[4,3-d]pyrimidin-6(5H)-yl)methyl)-2-methyl-6-nitro-2,3-dihydroimidazo[2,1-b]oxazole compound 48 (25.20 mg, 57.67 μmol, 15.77% yield, 98.030% purity). $^1$H NMR (400 MHz, CDCl$_3$) δ 8.35 (s, 1H), 7.91-7.83 (m, 2H), 7.43 (s, 1H), 6.86-6.78 (m, 1H), 4.29 (d, J=8.0 Hz, 1H), 3.89 (d, J=8.0 Hz, 1H), 3.85-3.74 (m, 2H), 3.14-3.07 (m, 1H), 3.03 (d, J=16.0 Hz, 1H), 2.96-2.79 (m, 3H), 2.75 (d, J=16.0 Hz, 1H), 1.61 (s, 3H). LCMS (ESI) m/z: 429(M+1).

Embodiment 49

(S)-2-((2-(3,5-Difluorophenyl)-4-methoxy-7,8-dihydropyrido[4,3-d]pyrimidin-6(5H)-yl)methyl)-2-methyl-6-nitro-2,3-dihydroimidazo[2,1-b]oxazole

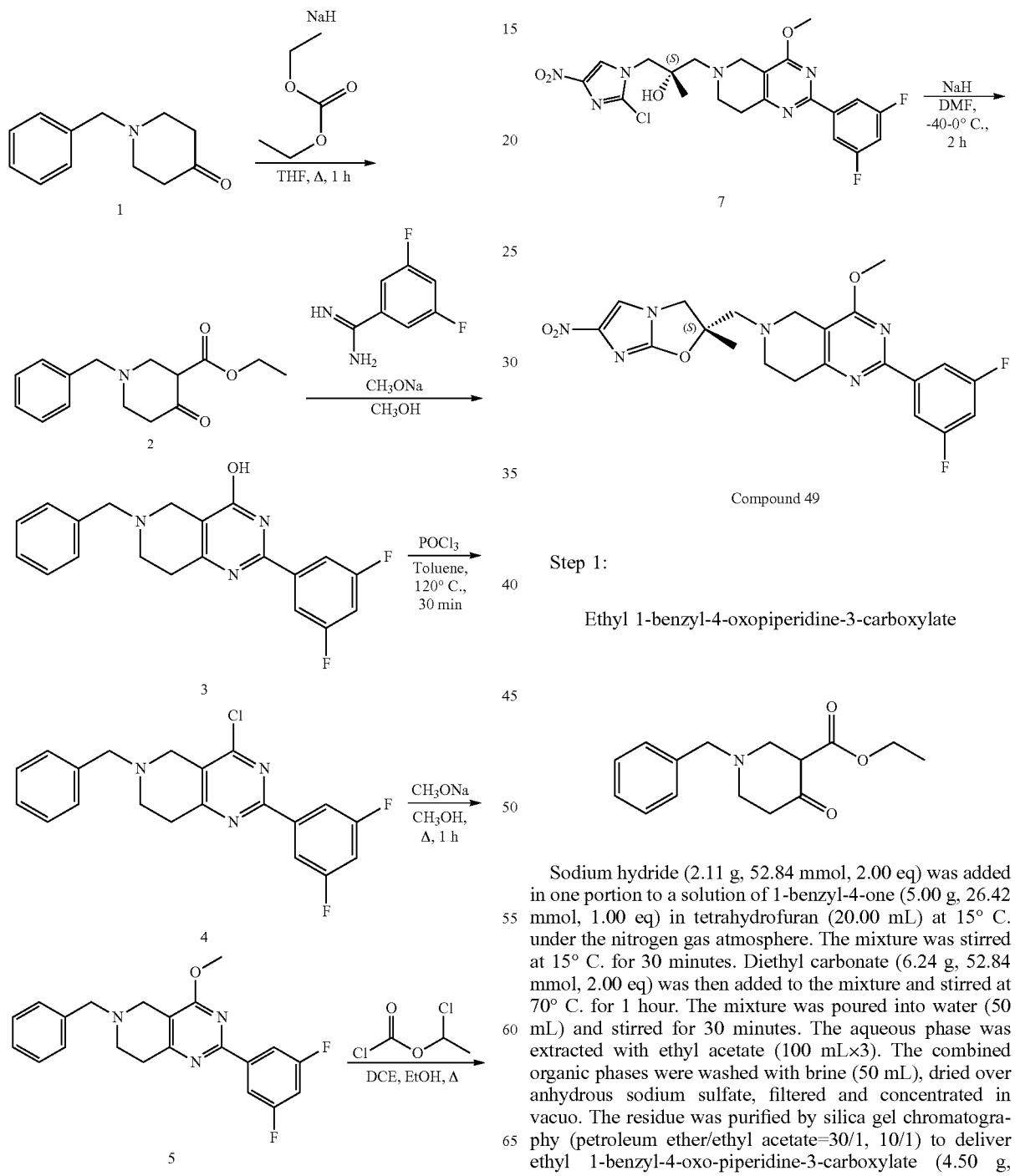

Step 1:

Ethyl 1-benzyl-4-oxopiperidine-3-carboxylate

Sodium hydride (2.11 g, 52.84 mmol, 2.00 eq) was added in one portion to a solution of 1-benzyl-4-one (5.00 g, 26.42 mmol, 1.00 eq) in tetrahydrofuran (20.00 mL) at 15° C. under the nitrogen gas atmosphere. The mixture was stirred at 15° C. for 30 minutes. Diethyl carbonate (6.24 g, 52.84 mmol, 2.00 eq) was then added to the mixture and stirred at 70° C. for 1 hour. The mixture was poured into water (50 mL) and stirred for 30 minutes. The aqueous phase was extracted with ethyl acetate (100 mL×3). The combined organic phases were washed with brine (50 mL), dried over anhydrous sodium sulfate, filtered and concentrated in vacuo. The residue was purified by silica gel chromatography (petroleum ether/ethyl acetate=30/1, 10/1) to deliver ethyl 1-benzyl-4-oxo-piperidine-3-carboxylate (4.50 g, 17.22 mmol, 65.18% yield) as a yellow oil.

Step 2:

6-Benzyl-2-(3,5-difluorophenyl)-7,8-dihydro-5H-pyrido[4,3-d]pyrimidin-4-ol

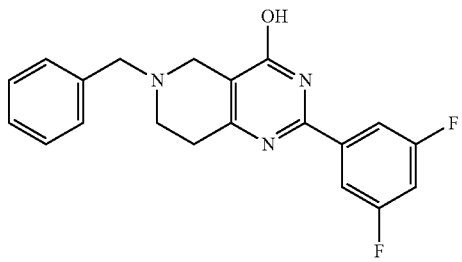 [SMILES: Fc1cc(F)cc(-c2nc(Cl)c3c(n2)CCN(Cc2ccccc2)C3)c1]

Sodium methoxide (496.13 mg, 9.18 mmol, 2.00 eq) was added to a solution of ethyl 1-benzyl-4-oxo-piperidine-3-carboxylate (1.20 g, 4.59 mmol, 1.00 eq) and 3,5-difluorobenzamidine (931.63 mg, 5.97 mmol, 1.30 eq) in methanol (15.00 mL). The mixture was stirred at 80° C. for 2 hours. The mixture was concentrated under reduced pressure at 45° C. and the residue was poured into water (50 mL) and ethyl acetate (30 mL) and stirred for 5 minutes. The filtrate was filtered and the cake was dried to deliver 6-benzyl-2-(3,5-difluorophenyl)-7,8-dihydro-5H-pyrido[4,3-d]pyrimidin-4-ol (400.00 mg, 1.13 mmol, 24.66% yield) as a white solid. LCMS (ESI) m/z: 354.1 (M+1).

Step 3:

6-Benzyl-4-chloro-2-(3,5-difluorophenyl)-7,8-dihydro-5H-pyrido[4,3-d]pyrimidine

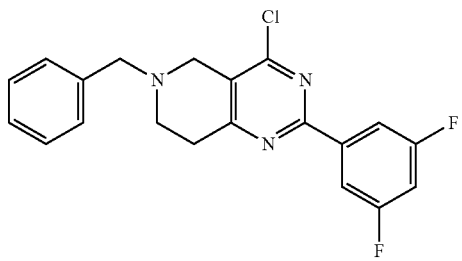

Phosphorus oxychloride (2.77 g, 18.07 mmol, 8.86 eq) was added to a solution of 6-benzyl-2-(3,5-difluorophenyl)-7,8-dihydro-5H-pyrido[4,3-d]pyrimidin-4-ol (720.00 mg, 2.04 mmol, 1.00 eq) in toluene (5.00 mL). The mixture was stirred at 120° C. for 2 hours and the mixture was poured into a mixed solution of water (50 mL) and ethyl acetate (50 mL). The mixture was stirred for 5 minutes, filtered and the filtrate was dried to deliver 6-benzyl-(3,5-difluorophenyl)-7,8-dihydro-5H-1-pyrido[4,3-d]pyrimidine (540.00 mg, 1.45 mmol, 71.08% yield) as a white solid.

Step 4:

6-Benzyl-2-(3,5-difluorophenyl)-4-methoxy-7,8-dihydro-5H-pyrido[4,3-d]pyrimidine

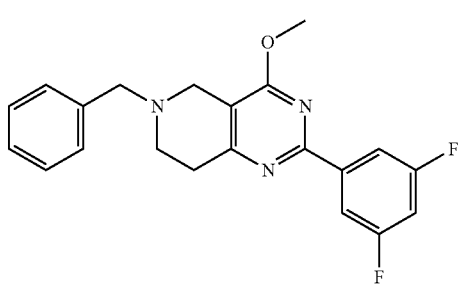 [SMILES: COc1nc(-c2cc(F)cc(F)c2)nc2c1CN(Cc1ccccc1)CC2]

Sodium methoxide (783.29 mg, 14.50 mmol, 10.00 eq) was added to a solution of 6-benzyl-(3,5-difluorophenyl)-7,8-dihydro-5H-1-pyrido[4,3-d]pyrimidine (540.00 mg, 1.45 mmol, 1.00 eq) in methanol (10.00 mL). The mixture was stirred at 70° C. for 8 hours and water (50 mL) was added to the mixed solution and stirred for 5 minutes. The mixture was filtered and the filter cake was dried to deliver 6-benzyl-2-(3,5-difluorophenyl)-4-methoxy-7,8-dihydro-5H-pyrido[4,3-d]pyrimidine (410.00 mg, 1.12 mmol, 76.96% yield) as a white solid. $^1$H NMR (400 MHz, CDCl$_3$) δ 7.90-7.83 (m, 2H), 7.34-7.29 (m, 3H), 7.27-7.16 (m, 2H), 6.80 (tt, J=2.4, 8.7 Hz, 1H), 3.98 (s, 3H), 3.68 (s, 2H), 3.48 (s, 2H), 2.92-2.85 (m, 2H), 2.78-2.70 (m, 2H).

Step 5:

2-(3,5-Difluorophenyl)-4-methoxy-5,6,7,8-tetrahydropyrido[4,3-d]pyrimidine

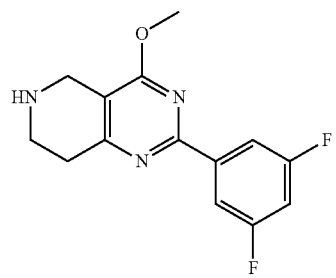 [SMILES: COc1nc(-c2cc(F)cc(F)c2)nc2c1CNCC2]

1-Chloroethyl carbonochloridate (240.19 mg, 1.68 mmol, 1.50 eq) was added to a solution of 6-benzyl-2-(3,5-difluorophenyl)-4-methoxy-7,8-dihydro-5H-pyrido[4,3-d]pyrimidine (410.00 mg, 1.12 mmol, 1.00 eq) in dichloroethane (15.00 mL) at 0° C. under the nitrogen gas atmosphere. The mixture was stirred at 0° C. for 30 minutes and heated to 90° C. After stirring for 11.5 hours, the mixture was concentrated at 45° C. under reduced pressure, methanol (15 mL) was added and stirred at 90° C. for 2 hours. The mixture was then concentrated under reduced pressure at 45° C., dichloromethane (30 mL) was added to the residue and stirred for 30 minutes. The filter cake was collected to deliver 2-(3,5-difluorophenyl)-4-methoxy-5,6,7,8-tetrahydropyrido[4,3-d]pyrimidine (286.00 mg, 911.61 μmol, 81.39% yield, hydrochloride) as a white solid.

Step 6:

(2S)-1-(2-Chloro-4-nitroimidazol-1-yl)-3-(2-(3,5-difluorophenyl)-4-methoxy-7,8-dihydro-5H-1-pyrido[4,3-d]pyrimidin-6-yl)-2-methylpropan-2-ol

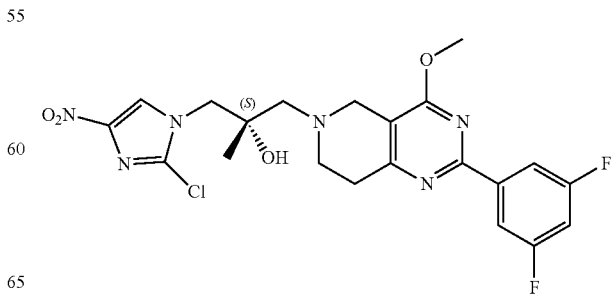

2-(3,5-Difluorophenyl)-4-methoxy-5,6,7,8-tetrahydropyrido[4,3-d]pyrimidine (286.00 mg, 911.61 mmol, 1.00 eq., hydrochloride) and 2-chloro-1-[[(2R)-2-methyloxiran-2-yl]methyl]-4-nitroimidazole (238.05 mg, 1.09 mmol, 1.20 eq) were dissolved in tert-butanol (6.00 mL), diisopropylamine (235.63 mg, 1.82 mmol, 2.00 eq) was added under the nitrogen gas atmosphere. The mixture was stirred at 80° C. for 12 hours. The mixture was cooled to 15° C. and concentrated under reduced pressure at 45° C. The residue was purified by silica gel chromatography (diameter: 250 mm, column height: 100 mm, 100 to 200 mesh silica gel, petroleum ether/ethyl acetate=10/1, 2/1) to deliver (2S)-1-(2-chloro-4-nitroimidazol-1-yl)-3-(2-(3,5-difluorophenyl)-4-methoxy-7,8-dihydro-5H-1-pyrido[4,3-d]pyrimidin-6-yl)-2-methylpropan-2-ol (400.00 mg, 808.28 μmol, 88.66% yield) as a yellow solid. $^1$H NMR (400 MHz, CDCl$_3$) δ 8.02 (s, 1H), 8.00-7.91 (m, 2H), 6.92 (tt, T=2.3, 8.6 Hz, 1H), 4.11 (s, 3H), 4.07 (s, 2H), 3.82-3.67 (m, 2H), 3.63-3.51 (m, 2H), 3.02-2.98 (m, 2H), 2.77-2.57 (m, 2H), 1.35 (s, 3H).

Step 7:

(S)-2-((2-(3,5-Difluorophenyl)-4-methoxy-7,8-dihydropyrido[4,3-d]pyrimidin-6(5H)-yl)methyl)-2-methyl-6-nitro-2,3-dihydroimidazo[2,1-b]oxazole Compound 49

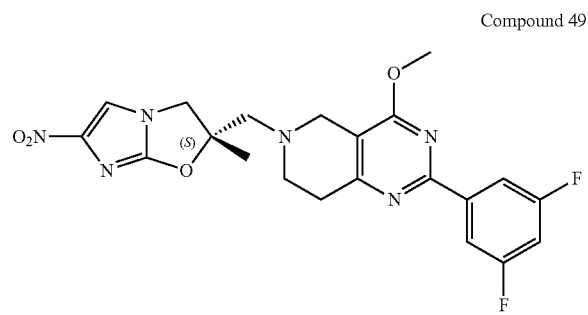

Sodium hydride (32.33 mg, 808.28 μmol, 2.00 eq) was added to a solution of (2S)-1-(2-chloro-4-nitroimidazol-1-yl)-3-(2-(3,5-difluorophenyl)-4-methoxy-7,8-dihydro-5H-pyrido[4,3-d]pyrimidin-6-yl)-2-methylpropan-2-ol (200.00 mg, 404.14 μmol, 1.00 eq) in DMF (3.00 mL) at −45° C. under the nitrogen gas atmosphere. The mixture was stirred at −45° C. to 0° C. for 1 hour. The mixture was poured into a saturated ammonium chloride solution (50 mL) and stirred for 5 minutes. The aqueous phase was extracted with ethyl acetate (100 mL×2). The combined organic phases were washed with brine (30 mL), dried over anhydrous sodium sulfate, filtered and concentrated in vacuo. The residue was washed with methanol (30 mL×2), filtered and the cake was collected to deliver (S)-2-((2-(3,5-difluorophenyl)-4-methoxy-7,8-dihydropyrido[4,3-d]pyrimidin-6(5H)-yl)methyl)-2-methyl-6-nitro-2,3-dihydroimidazo[2,1-b]oxazole compound 49 (39.00 mg, 81.08 μmol, 20.06% yield, 95.3% purity). $^1$H NMR (400 MHz, CDCl$_3$) δ 7.85 (d, J=7.7 Hz, 2H), 7.43 (s, 1H), 6.80 (t, J=8.0 Hz, 1H), 4.29 (d, J=9.5 Hz, 1H), 4.00 (s, 3H), 3.87 (d, J=9.3 Hz, 1H), 3.72-3.56 (m, 2H), 3.11-2.98 (m, 2H), 2.89-2.67 (m, 4H), 1.60 (s, 3H). LCMS (ESI) nth: 459.1 (M+1).

Embodiment 50

(S)-2-((2-(3,5-Difluorophenyl)-5,6-dihydro-[1,2,4]triazolo[1,5-α]pyrazin-7(8H)-yl)methyl)-2-methyl-6-nitro-2,3-dihydroimidazo[2,1-b]oxazole

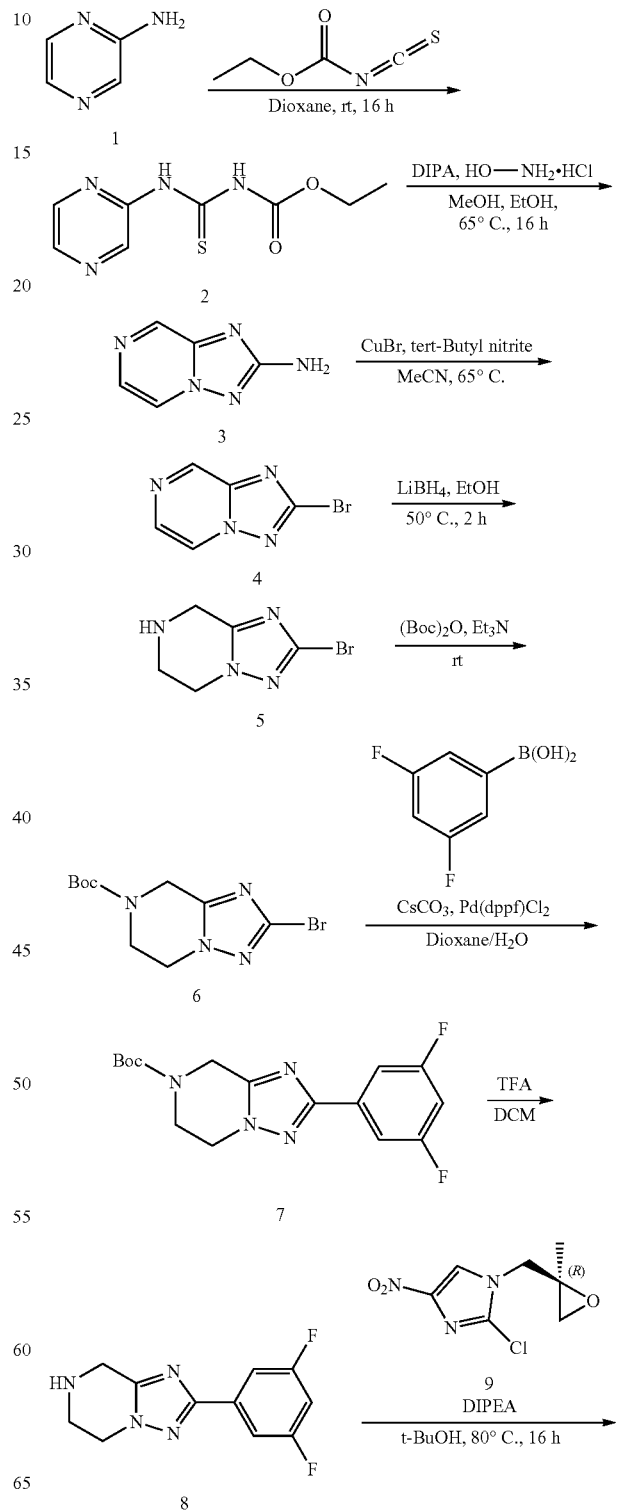

-continued

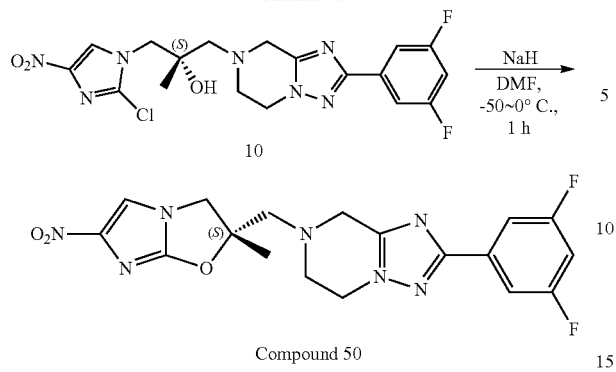

Compound 50

Step 1:

Ethyl-N-(pyrazin-2-ylthiocarbamoyl) carbamate

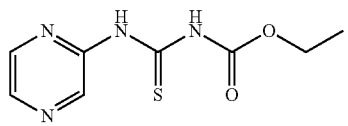

Ethyl-N-(thiomethylene)carbamic acid (17.05 g, 130.00 mmol, 1.24 eq) was added dropwise to a solution of pyrazin-2-amine (10.00 g, 105.15 mmol, 1.00 eq) in dioxane (200.00 mL) at 0° C. to 5° C. under the nitrogen gas atmosphere. The mixture was stirred at 15° C. for 16 hours. The resulting suspension was filtered and washed with dichloromethane (200 mL) to deliver Ethyl-N-(pyrazin-2-ylthiocarbamoyl) carbamate (13.60 g, 60.11 mmol, 57.16% yield) as a pale yellow solid. $^1$H NMR (400 MHz, DMSO-$d_6$) δ 12.08 (s, 1H), 11.79 (s, 1H), 9.68 (s, 1H), 8.51 (s, 2H), 4.24 (m, 2H), 1.27 (m, 3H).

Step 2:

[1,2,4]Triazolo[1,5-α]pyrazin-2-amine

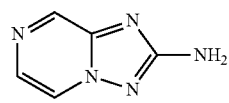

Hydroxylamine hydrochloride (6.97 g, 100.24 mmol, 1.80 eq) and diisopropylamine (17.76 g, 137.55 mmol, 2.47 eq) were added to a solution of ethyl-N-(pyrazin-2-ylthiocarbamoyl)carbamate (12.60 g, 55.69 mmol, 1.00 eq) in methanol (80.00 mL) and ethanol (80.00 mL). The mixture was stirred at 65° C. for 16 hours. The reaction mixture was concentrated under reduced pressure to a volume of about 20 mL. The resulting suspension was filtered and the solid was collected and washed with dichloromethane:ethanol (60:1, 90 mL) to deliver [1,2,4]triazolo[1,5-α]pyrazin-2-amine (5.30 g, 39.22 mmol, 70.43% yield) as a white solid. $^1$H NMR (400 MHz, DMSO-$d_6$) δ 8.83 (s, 1H), 8.69-8.68 (d, J=4.3 Hz, 1H), 7.97-7.96 (d, J=4.3 Hz, 1H), 6.46 (s, 2H).

Step 3:

2-Bromo-[1,2,4]triazolo[1,5-α]pyrazine

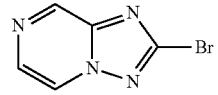

[1,2,4]Triazolo[1,5-α]pyrazin-2-amine (1.00 g, 7.40 mmol, 1.00 eq) was added to a solution of copper bromide (1.98 g, 8.88 mmol, 1.20 eq) and t-butyl nitrite (1.14 g, 11.10 mmol, 1.50 eq) in acetonitrile (30 mL) at 65° C. After the addition, the mixture was stirred at this temperature for 2 hours. The reaction mixture was concentrated under reduced pressure. The residue was diluted with ethyl acetate (150 mL) and washed with 1N hydrochloric acid (100 mL) and a saturated ammonium chloride solution (100 mL). The organic layer was dried over anhydrous $Na_2SO_4$, filtered and concentrated under reduced pressure to give a residue which was purified by silica gel chromatography (silica, petroleum ether/ethyl acetate=1:1) to deliver 2-bromo-[1,2,4]triazolo [1,5-α]pyrazine (350.00 mg, 1.76 mmol, 23.77% yield) as a pale yellow solid. $^1$H NMR (300 MHz, DMSO-$d_6$) δ 9.38 (s, 1H), 9.10-9.09 (d, J=4.3 Hz, 1H), 8.33-8.32 (d, J=4.3 Hz, 1H).

Step 4:

2-Bromo-5,6,7,8-tetrahydro[1,2,4]triazolo[1,5-α] pyrazine

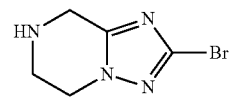

Lithium borohydride (154.00 mg, 7.08 mmol, 4.02 eq) was added to a solution of 2-bromo-[1,2,4]triazolo[1,5-α] pyrazine (350.00 mg, 1.76 mmol, 1.00 eq) in ethanol (10.00 mL). The mixture was stirred at 50° C. for 2 hours. The reaction mixture was concentrated under reduced pressure to give the crude product as a white solid which was used directly in the next step. LCMS (ESI) m/z: 203/205 (M+1)/(M+2).

Step 5:

tert-Butyl 2-bromo-5,6-dihydro-[1,2,4]triazolo[1,5-α]pyrazine-7(8H)-carboxylate

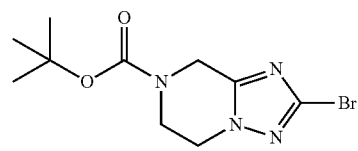 [SMILES: CC(C)(C)OC(=O)N1CCn2nc(Br)nc2C1]

Sodium bicarbonate (144.82 mg, 1.72 mmol, 1.00 eq) and $Boc_2O$ (379.98 mg, 1.74 mmol, 1.01 eq) were added to an aqueous solution (15 mL) of 2-bromo-5,6,7,8-tetrahydro[1,2,4]triazolo[1,5-α]pyrazine (350.00 mg, 1.72 mmol, 1.00 eq). The mixture was stirred at 10° C. to 20° C. for 0.5 hour. Water (50 mL) was added to the reaction mixture and extracted with ethyl acetate (30 mL×3). The combined organic layers were dried over anhydrous sodium sulfate, filtered and concentrated under reduced pressure to deliver tert-butyl 2-bromo-6,8-dihydro-5H-[1,2,4]triazolo[1,5-α] pyrazine-7-carboxylate (600.00 mg, crude) as a pale yellow solid. ¹H NMR (300 MHz, CDCl₃) δ 4.72 (s, 2H), 4.23-4.13 (m, 2H), 3.99-3.89 (m, 2H), 1.50 (s, 9H).

Step 6:

tert-Butyl 2-(3,5-difluorophenyl)-5,6-dihydro-[1,2,4]triazolo[1,5-α]pyrazine-7(8H)-carboxylate

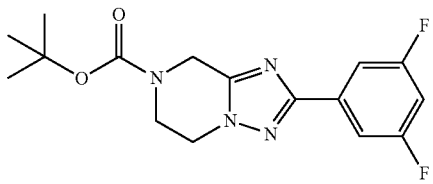 [SMILES: CC(C)(C)OC(=O)N1CCn2nc(-c3cc(F)cc(F)c3)nc2C1]

Cesium carbonate (1.08 g, 3.30 mmol, 2.00 eq) and Pd(dppf)Cl₂ (60.00 mg, 82.00 µmol, 0.05 eq) were added in one portion to a mixed solution of tert-butyl 2-bromo-6,8-dihydro-5H-[1,2,4]triazolo[1,5-α]pyrazine-7-carboxylate (500.00 mg, 1.65 mmol, 1.00 eq) and (3,5-difluorophenyl) boronic acid (260.00 mg, 1.65 mmol, 1.00 eq) in dioxane (10.00 mL) and water (1.00 mL) under the nitrogen gas atmosphere. The mixture was heated to 80° C. and stirred for 16 hours. The mixture was washed with water (30 mL) and the aqueous phase was extracted with ethyl acetate (30 mL×2). The combined organic phases were dried over anhydrous Na₂SO₄, filtered and concentrated in vacuo to give a residue. The residue was purified by silica gel chromatography (SiO₂, petroleum ether/ethyl acetate=20/1 to 5:1) to deliver tert-butyl 2-(3,5-difluorophenyl)-6,8-dihydro-5H-[1,2,4]triazolo[1,5-α]pyrazine-7-carboxylate (310.00 mg, 921.69 µmol, 55.86% yield) as a pale yellow solid. LCMS (ESI) m/z: 337.1 (M+1).

Step 7:

2-(3,5-Difluorophenyl)-5,6,7,8-tetrahydro-[1,2,4]triazolo[1,5-α]pyrazine

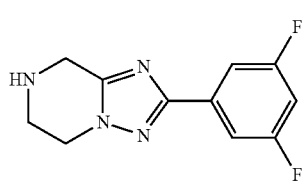 [SMILES: Fc1cc(F)cc(-c2nc3n(n2)CCNC3)c1]

Trifluoroacetic acid (3.06 g, 26.84 mmol, 29.12 eq) was added to a solution of tert-butyl 2-(3,5-difluorophenyl)-6,8-dihydro-5H-[1,2,4]triazolo[1,5-α]pyrazine-7-carboxylate (310.00 mg, 921.69 µmol, 1.00 eq) in dichloromethane (10.00 mL). The mixture was stirred at 15° C. for 12 hours. The reaction mixture was concentrated under reduced pressure to give a residue as a dark brown solid which was used directly in the next step. LCMS (ESI) m/z: 237.1 (M+1).

Step 8:

(S)-1-(2-Chloro-4-nitro-1H-imidazol-1-yl)-3-(2-(3,5-difluorophenyl)-5,6-dihydro-[1,2,4]triazolo[1,5-α]pyrazin-7(8H)-yl)-2-methylpropan-2-ol

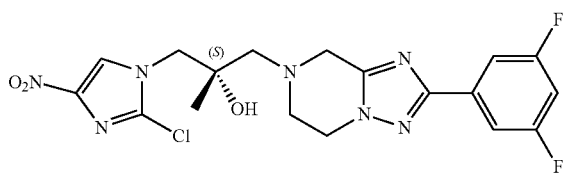

2-Chloro-1-[[(2R)-2-methyloxiran-2-yl]methyl]-4-nitroimidazole (250.00 mg, 1.15 mmol, 0.73 eq) and diisopropylamine (1.01 g, 7.85 mmol, 5.00 eq) were added to a solution of 2-(3,5-difluorophenyl)-5,6,7,8-tetrahydro-[1,2,4]triazolo[1,5-α]pyrazine (550.00 mg, 1.57 mmol, 1.00 eq, trifluoroacetate) in tert-butanol (10.00 mL). The mixture was stirred at 80° C. for 16 hours. The reaction mixture was washed with water (50 mL) and extracted with ethyl acetate (30 mL×2). The combined organic layers were dried over anhydrous sodium sulfate, filtered and concentrated under reduced pressure to give a residue. The residue was purified by silica gel chromatography (SiO₂, petroleum ether/ethyl acetate=3/1 to 1/5) to deliver (S)-1-(2-chloro-4-nitro-1H-imidazol-1-yl)-3-(2-(3,5-difluorophenyl)-5,6-dihydro-[1,2,4]triazolo[1,5-a]pyrazin-7(8H)-yl)-2-methylpropan-2-ol (250.00 mg, 550.87 µmol, 35.09% yield) as a pale yellow oil. LCMS (ESI) m/z: 454.1 (M+1).

Step 9:

(S)-2-((2-(3,5-Difluorophenyl)-5,6-dihydro-[1,2,4]triazolo[1,5-α]pyrazin-7(8H)-yl)methyl)-2-methyl-6-nitro-2,3-dihydroimidazo[2,1-b]oxazole Compound 50

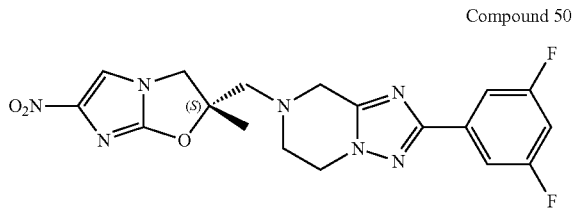

Sodium hydrogen (20.00 mg, 500.00 µmol, 2.27 eq) was added to a solution of (2S)-1-(2-chloro-4-nitro-1H-imidazol-1-yl)-3-(2-(3,5-difluorophenyl)-5,6-dihydro-[1,2,4]triazolo[1,5-α]pyrazin-7(8H)-yl)-2-methylpropan-2-ol (100.00 mg, 220.35 µmol, 1.00 eq) in DMF (5.00 mL) at −50° C. under the nitrogen gas atmosphere. The mixture was stirred at −50° C. for 0.5 hour. The mixture was then heated to 0° C. and stirred for an additional 0.5 hour. The reaction mixture was poured into a saturated ammonium chloride solution (40 mL) and then extracted with ethyl acetate (30 mL×2). The combined organic layers were filtered over anhydrous sodium sulfate, and concentrated under reduced pressure to give a residue. The residue was purified by preparative separation chromatography to deliver (S)-2-((2-(3,5-difluorophenyl)-5,6-dihydro-[1,2,4]triazolo[1,5-α]pyrazin-7 (8H)-yl)methyl)-2-methyl-6-nitro-2,3-dihydroimidazo[2,1-b]oxazole (11.25 mg, 26.36 µmol, 11.96% yield, 97.79% purity). ¹H NMR (400 MHz, DMSO-d₆) δ 8.42 (br. s., 1H), 8.10 (s, 1H), 7.55 (d, J=6.5 Hz, 2H), 7.31

(br. s., 1H), 4.31 (d, J=10.8 Hz, 1H), 4.22-4.15 (m, 1H), 4.10 (d, J=10.5 Hz, 1H), 4.02-3.90 (m, 3H), 3.19-3.15 (m, 2H), 3.08-3.04 (m, 2H), 1.59 (s, 3H). LCMS (ESI) m/z: 418.2 (M+1).

Embodiment 51

(S)-2-((2-(3,5-Dichlorophenyl)-7,8-dihydro-1,6-naphthyridin-6(5H)-yl)methyl)-2-methyl-6-nitro-2,3-dihydroimidazo[2,1-b]oxazole Compound 51

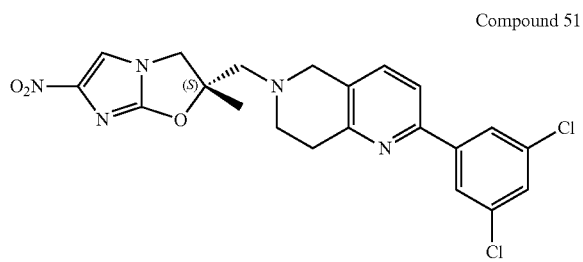

Pd(dppf)Cl$_2$ (20.92 mg, 28.59 μmol, 0.05 eq), cesium fluoride (260.57 mg, 1.72 mmol, 3.00 eq) were added in one portion to a mixed solution of the key intermediate B (200.00 mg, 571.80 μmol, 1.00 eq) and (3,5-dichlorophenyl) boronic acid (109.11 mg, 571.80 μmol, 1.00 eq) in dioxane (5.00 mL) and water (500.00 μL) under the nitrogen gas atmosphere. The mixture was stirred at 100° C. for 6 hours. The mixture was diluted with ethyl acetate, filtered and concentrated. The residue was separated by preparative separation chromatography (GX-F; Phenomenex Synergi C18 150*25*10 um; 0.225% FA-ACN; Begin from 52 to 82; Flow Rate (25 mL/min) to deliver (S)-2-((2-(3,5-dichlorophenyl)-7,8-dihydro-1,6-naphthyridin-6(5H)-yl)methyl)-2-methyl-6-nitro-2,3-dihydroimidazo[2,1-b]oxazole compound 51 (50.00 mg, 107.54 μmol, 18.81% yield, 99% purity). $^1$H NMR (400 MHz, CDCl$_3$) δ 7.86 (d, J=1.9 Hz, 2H), 7.53 (s, 1H), 7.50-7.44 (m, 1H), 7.43-7.35 (m, 2H), 4.43 (d, J=9.7 Hz, 1H), 4.07-3.66 (m, 3H), 3.30-2.88 (m, 5H), 2.82 (d, J=14.9 Hz, 1H), 1.69 (s, 3H); LCMS (ESI) m/z: 460 (M+1).

Embodiment 52

(S)-2-((2-(3,5-Difluorophenyl)-4-methyl-7,8-dihydro-1,6-naphthyridin-6(5H)-yl)methyl)-2-methyl-6-nitro-2,3-dihydroimidazo[2,1-b]oxazole

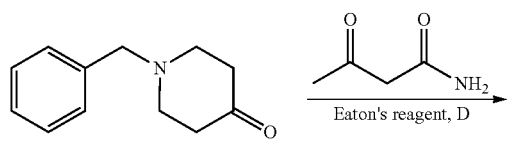

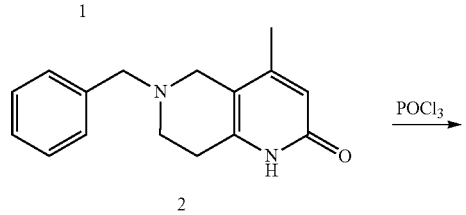

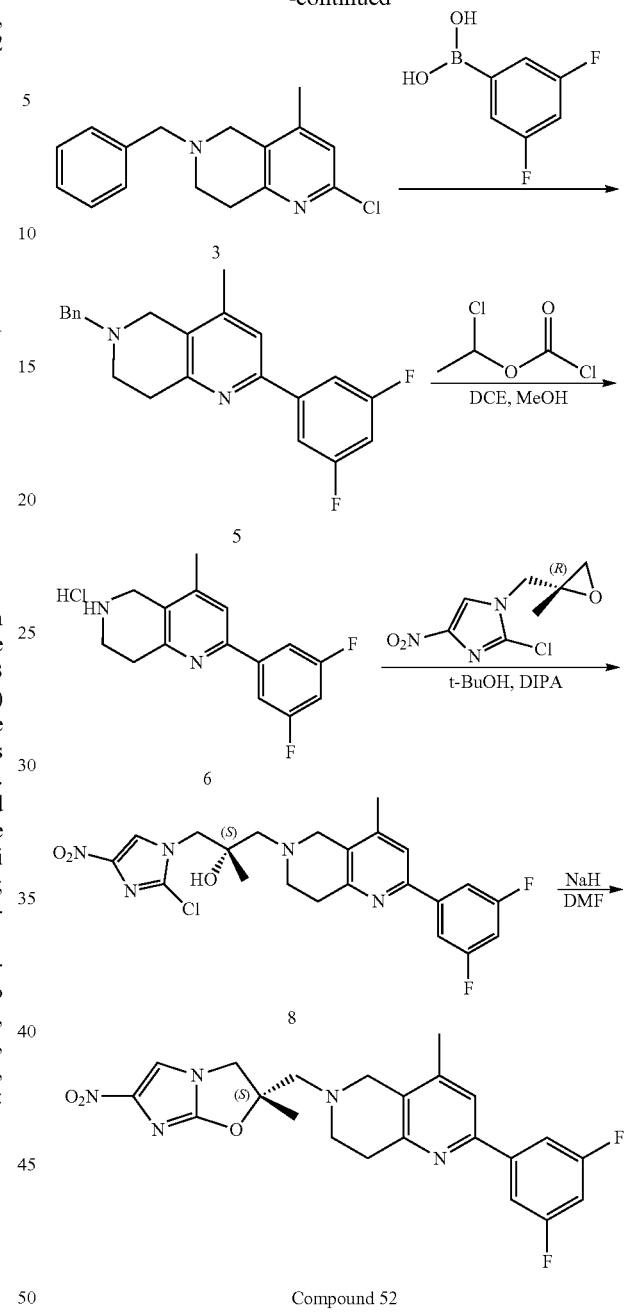

Compound 52

Step 1:

6-Benzyl-4-methyl-1,5,7,8-tetrahydro-1,6-naphthyridin-2-one

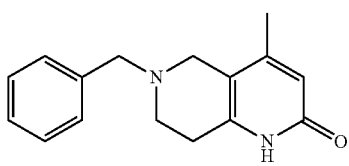 [SMILES: Cc1cc(=O)[nH]c2c1CN(Cc1ccccc1)CC2]

1-Benzyl-4-one (4.00 g, 21.14 mmol, 1.00 eq) and 3-oxobutanamide (2.35 g, 23.25 mmol, 1.10 eq) were dissolved in Eaton's reagent (8.00 mL). The mixture was stirred for 12 hours. The mixture was added to a saturated aqueous sodium bicarbonate solution (100 mL) to control pH>7, and the aqueous layer was extracted with ethyl acetate (100 mL×4). The combined organic phases were washed with saturated brine (100 mL), dried over anhydrous sodium sulfate, filtered and concentrated in vacuo. The residue was washed with acetone (60 mL) and then filtered to collect the cake to deliver 6-benzyl-4-methyl-1,5,7,8-tetrahydro-1,6-naphthyridin-2-one (2.80 g, 11.01 mmol, 52.08% yield) as a white solid. $^1$H NMR (400 MHz, DMSO-$d_6$): δ 11.25 (br, s, 1H), 7.34 (d, J=4.3 Hz, 4H), 7.27 (qd, J=4.1, 8.6 Hz, 1H), 5.99 (s, 1H), 3.66 (s, 2H), 3.26 (s, 2H), 2.61-2.52 (m, 4H), 1.95 (s, 3H).

Step 2:

6-Benzyl-2-chloro-4-methyl-7,8-dihydro-5H-1,6-naphthyridine

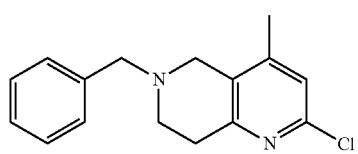 [SMILES: Cc1cc(Cl)nc2c1CN(Cc1ccccc1)CC2]

6-Benzyl-4-methyl-1,5,7,8-tetrahydro-1,6-naphthyridin-2-one (2.80 g, 11.01 mmol, 1.00 eq) and phosphorus oxychloride (9.00 ml) were mixed and stirred at 110° C. for 12 hours. The mixture was added dropwise to ice water (100 mL), and the mixture was stirred at 15° C. for 0.5 hour. A saturated aqueous sodium bicarbonate solution (100 mL) was added to the mixture until pH>7. The mixture was extracted with dichloromethane (100 mL×4). The combined organic phases were washed with brine (100 mL) and the organic phase was dried over anhydrous sodium sulfate, filtered and concentrated in vacuo to deliver 6-benzyl-2-chloro-4-methyl-7,8-dihydro-5H-1-1,6-naphthyridine (3.50 g, crude) as a yellow solid. LCMS (ESI) m/z: 273 (M+1).

Step 3:

6-Benzyl-2-(3,5-difluorophenyl)-4-methyl-7,8-dihydro-5H-1,6-naphthyridine

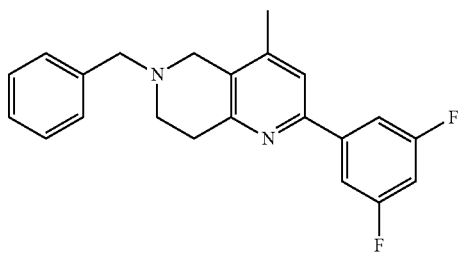 [SMILES: Cc1cc(-c2cc(F)cc(F)c2)nc2c1CN(Cc1ccccc1)CC2]

Cesium fluoride (694.94 mg, 4.58 mmol, 2.50 eq) and Pd(dppf)Cl$_2$ (133.90 mg, 183.00 μmol, 0.10 eq) were added in one portion to a mixed solution of 6-benzyl-2-chloro-4-methyl-7,8-dihydro-5H-1,6-naphthyridine (500.00 mg, 1.83 mmol, 1.00 eq) and (3,5-difluorophenyl) boronic acid (346.77 mg, 2.20 mmol, 1.20 eq) in dioxane (10.00 mL) and water (1.00 mL) under the nitrogen gas atmosphere. The mixture was stirred at 110° C. for 5 hours. Water (10 mL) was added to the mixture, and then extracted with dichloromethane (100 mL×3). The combined organic phases were washed with brine (100 mL), dried over anhydrous sodium sulfate, filtered and concentrated in vacuo. The residue was purified by silica gel chromatography (column height: 250 mm, diameter: 100 mm, 100 to 200 mesh silica gel, petroleum ether/ethyl acetate=40/1 to 15/1) to deliver 6-benzyl-2-(3,5-difluorophenyl)-4-methyl-7,8-dihydro-5H-1,6-naphthyridine (580.00 mg, 1.66 mmol, 90.45% yield) as white solid. $^1$H NMR (300 MHz, CDCl$_3$): δ 7.41 (d, J=6.8 Hz, 2H), 7.32 (br, s, 3H), 7.27-7.16 (m, 3H), 6.78-6.65 (m, 1H), 3.70 (s, 2H), 3.55 (s, 2H), 3.08-2.95 (m, 2H), 2.83-2.71 (m, 2H), 2.14 (s, 3H).

Step 4:

2-(3,5-Difluorophenyl)-4-methyl-5,6,7,8-tetrahydro-1,6-naphthyridine hydrochloride

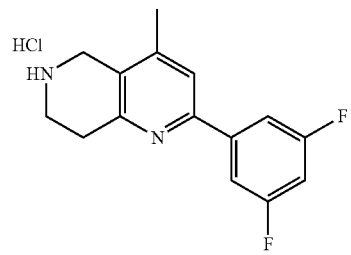 [SMILES: Cl ; Cc1cc(-c2cc(F)cc(F)c2)nc2c1CNCC2]

1-Chlorocarbonyl chloride (354.98 mg, 2.48 mmol, 1.50 eq) was added in one portion to a solution of 6-benzyl-2-(3,5-difluorophenyl)-4-methyl-7,8-dihydro-5H-1,6-naphthyridine (580.00 mg, 1.66 mmol, 1.00 eq) in dichloroethane (15.00 mL) at −15° C. under the nitrogen gas atmosphere. The mixture was stirred at 90° C. for 12 hours. The mixture was then concentrated to dry and methanol (10.00 mL) was added to the residue. And the resulting mixture was stirred at 90° C. for an additional hour. The mixture was concentrated to dry to deliver 2-(3,5-difluorophenyl)-4-methyl-5,6,7,8-tetrahydro-1,6-naphthyridine (400.00 mg, 1.35 mmol, 81.56% yield, hydrochloride) as a white solid.

Step 5:

(2S)-1-(2-Chloro-4-nitroimidazol-1-yl)-3-(2-(3,5-difluorophenyl)-4-methyl-7,8-dihydro-5H-1,6-naphthyridin-6-yl)-2-methylpropan-2-ol

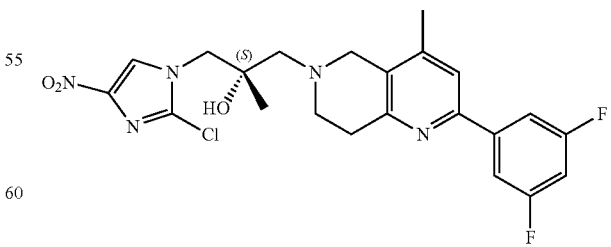

2-(3,5-Difluorophenyl)-4-methyl-5,6,7,8-tetrahydro-1,6-naphthyridine (400.00 mg, 1.35 mmol, 1.00 eq, hydrochloride) and 2-chloro-1-[[(2R)-2-methyloxiran-2-yl]methyl]-4-nitroimidazole (352.53 mg, 1.62 mmol, 1.20 eq) were mixed in tert-butanol (8.00 mL), diisopropylamine (436.19 mg, 3.38 mmol, 2.50 eq) was added in one portion at 15° C. under the nitrogen gas atmosphere. The mixture was stirred at 100° C. for 12 hours. The mixture was concentrated to dry. The residue was purified by silica gel chromatography (column height: 250 mm, diameter: 100 mm, 100 to 200 mesh silica gel, petroleum ether/ethyl acetate=30/1 to 1/2) to deliver (2S)-1-(2-chloro-4-nitroimidazol-1-yl)-3-(2-(3,5-difluorophenyl)-4-methyl-7,8-dihydro-5H-1,6-naphthyridin-6-yl)-2-methylpropan-2-ol (260.00 mg, crude) as a yellow solid. LCMS (ESI) m/z: 478 (M+1).

Step 6:

(2S)-2-((2-(3,5-Difluorophenyl)-4-methyl-7,8-dihydro-5H-1,6-naphthyridin-6-yl)methyl)-2-methyl-6-nitro-3H-imidazo[2,1-b]oxazole Compound 52

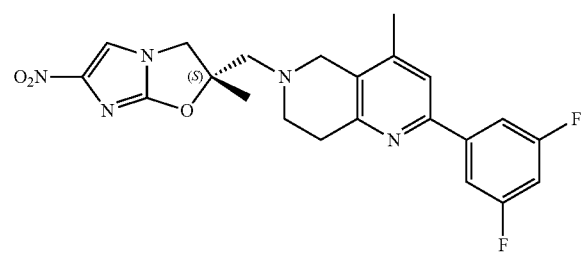

Sodium hydride (43.60 mg, 1.09 mmol, 2.00 eq) was added in one portion to a solution of (2S)-1-(2-chloro-4-nitroimidazol-1-yl)-3-(2-(3,5-difluorophenyl)-4-methyl-7,8-dihydro-5H-1,6-naphthyridin-6-yl)-2-methylpropan-2-ol (260.00 mg, 544.06 μmol, 1.00 eq) in DMF (5.00 mL) at −20° C. under the nitrogen gas atmosphere. The mixture was stirred at −20° C. for 10 minutes and then heated to 0° C. and stirred for 10 minutes, then heated to 15° C. and stirred for another 10 minutes. The mixture was added dropwise to ammonium chloride (20 mL), then the mixture was filtered and the filter cake was collected to give the crude product. The crude product was separated and purified by alkaline preparative separation chromatography (GX-D; Boston Symmetrix C18 ODS-R 150*30 mm*5 um; acetonitrile 24%-54%; water (0.225% NH₄OH); 25 mL/min) to deliver (2S)-2-((2-(3,5-difluorophenyl)-4-methyl-7,8-dihydro-5H-1,6-naphthyridin-6-yl)methyl)-2-methyl-6-nitro-3H-imidazo[2,1-b]oxazole compound 52 (60.00 mg, 135.51 μmol, 24.91% yield, 99.7% purity). ¹H NMR (400 MHz, CDCl₃): δ 7.56-7.45 (m, 3H), 7.31 (s, 1H), 6.87-6.77 (m, 1H), 4.44 (d, J=9.8 Hz, 1H), 3.97 (d, J=9.5 Hz, 1H), 3.88-3.71 (m, 2H), 3.20-2.81 (m, 6H), 2.25 (s, 3H), 1.70 (s, 3H). LCMS (ESI) m/z: 442 (M+1).

Embodiment 53

(S)-2-((2-(2-Chlorothiophen-3-yl)-7,8-dihydro-1,6-naphthyridin-6(5H)-yl)methyl)-2-methyl-6-nitro-2,3-dihydroimidazo[2,1-b]oxazole Compound 53

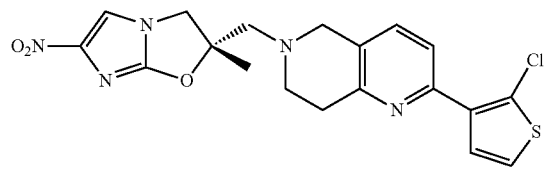

Cesium fluoride (173.71 mg, 1.14 mmol, 2.00 eq) and Pd(dppf)Cl₂ (8.37 mg, 11.44 μmol, 0.02 eq) were added to a mixed solution of (2S)-2-[(2-chloro-7,8-dihydro-5H-1,6-naphthyridin-6-yl)boxylphenethyl]-2-methyl-6-nitro-3H-imidazo[2,1-b]oxazole (200.00 mg, 571.80 μmol, 1.00 eq) and (2-chloro-3-thienyl) boronic acid (92.86 mg, 571.80 μmol, 1.00 eq) in dioxane (3.00 mL) and water (300.00 μL). The mixture was stirred at 70° C. for 12 hours. Water (50 mL) was added to quench the reaction mixture and extracted with ethyl acetate (50 mL×3). The combined organic layers were dried over sodium sulfate, filtered and concentrated under reduced pressure to give a residue. The residue was separated and purified by preparative separation chromatography (GX-F; Phenomenex Synergi C18 150*25*10 um; acetonitrile 30%-60%; ACN (0.225% fomic acid); 25 mL/min) to deliver (2S)-2-((2-(2-chlorothiophen-3-yl)-7,8-dihydro-1,6-naphthyridin-6(5H)-yl)methyl)-2-methyl-6-nitro-2,3-dihydroimidazo[2,1-b]oxazole compound 53 (26.30 mg, 59.55 μmol, 10.41% yield, 97.8% purity). ¹H NMR (400 MHz, METHANOL-d₄): δ 7.82 (s, 1H), 7.65 (d, T=6.15 Hz, 2H), 7.39 (d, J=5.90 Hz, 1H), 7.31 (d, J=5.77 Hz, 1H), 4.42 (d, T=10.54 Hz, 1H), 4.15 (d, T=10.54 Hz, 1H), 3.95 (s, 2H), 3.25-2.81 (m, 6H), 1.69 (s, 3H). LCMS (ESI) m/z: 432.2 (M+1).

Embodiment 54

(S)-2-Methyl-6-nitro-2-((2-(5-(trifluoromethyl)furan-2-yl)-7,8-dihydro-1,6-naphthyridin-6(5H)-yl)methyl)-2,3-dihydroimidazo[2,1-b]oxazole

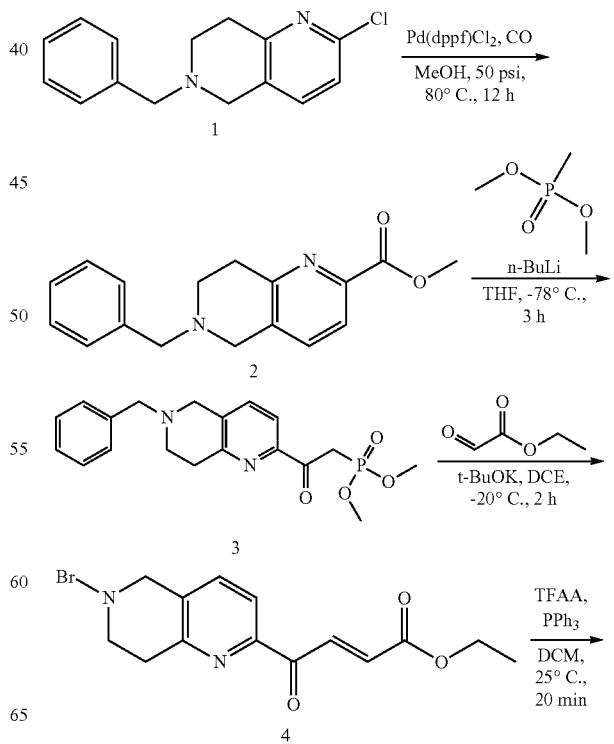

-continued

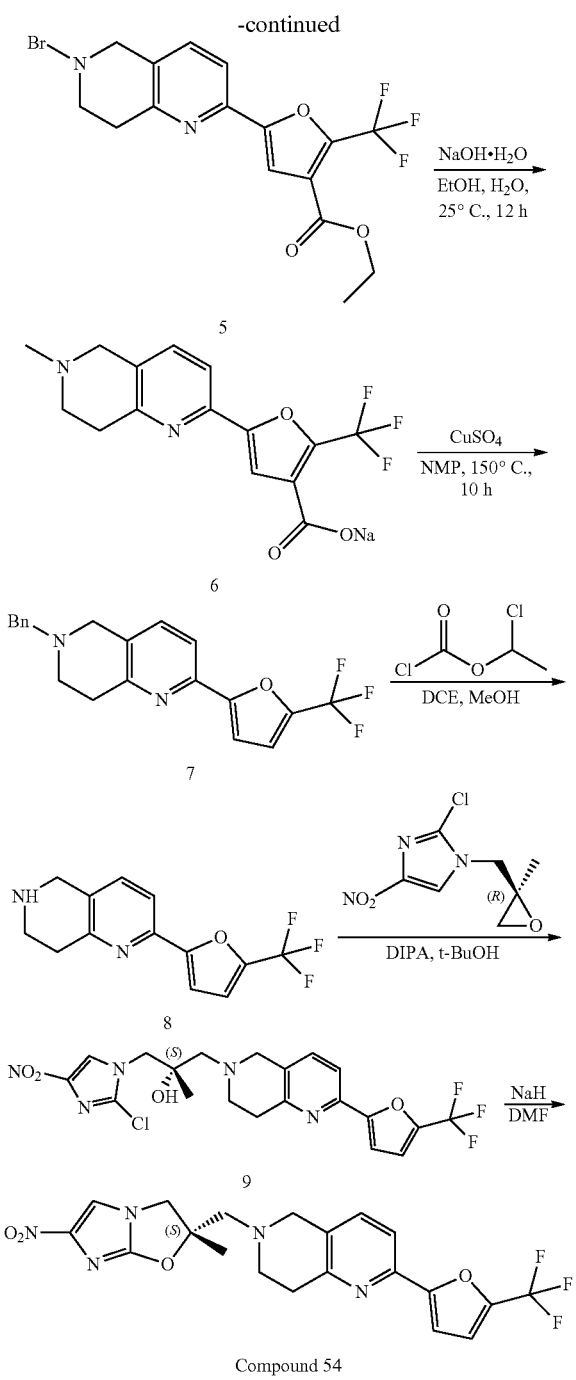

Compound 54

Step 1:

Methyl 6-benzyl-7,8-dihydro-5H-1,6-naphthyridine-2-carboxylate

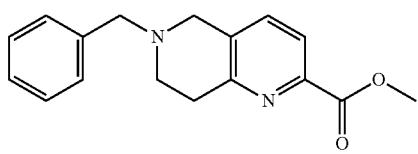 [SMILES: COC(=O)c1ccc2c(n1)CCN(Cc1ccccc1)C2]

Pd(dppf)Cl$_2$ (706.96 mg, 966.00 μmol, 0.05 eq), triethylamine (3.65 g, 36.07 mmol, 1.87 eq) were added to a solution of 6-benzyl-2-chloro-7,8-dihydro-5H-1,6-naphthyridine (5.00 g, 19.32 mmol, 1.00 eq) in methanol (50.00 mL) under the nitrogen gas atmosphere. The suspension was degassed with carbon monoxide. The mixture was stirred at 80° C. under carbon monoxide (50 psi) for 12 hours. The reaction mixture was concentrated under reduced pressure to remove the solvent. The residue was diluted, washed with sodium carbonate (100 mL) and extracted with ethyl acetate (500 mL×2). The combined organic layers were concentrated under reduced pressure to give a residue. The residue was separated by silica gel chromatography (SiO$_2$, petroleum ether/ethyl acetate=50/1 to 5:1) to deliver methyl 6-benzyl-7,8-dihydro-5H-1,6-naphthyridine-2-carboxylate (3.00 g, 10.63 mmol, 55.00% yield) as a yellow solid. LCMS (ESI) m/z: 283.2 (M+1).

Step 2:

1-(6-Benzyl-7,8-dihydro-5H-1,6-naphthyridin-2-yl)-2-dimethoxyphosphoryl-ethanone

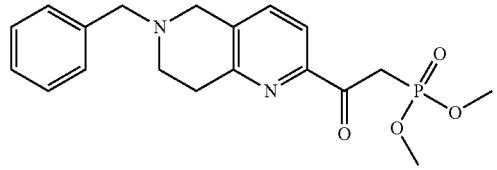 [SMILES: COP(=O)(CC(=O)c1ccc2c(n1)CCN(Cc1ccccc1)C2)OC]

N-butyllithium (2.5 M, 10.62 mL, 3.00 eq) was added dropwise to a solution of methyl 6-benzyl-7,8-dihydro-5H-1,6-naphthyridine-2-carboxylate (2.50 g, 8.85 mmol, 1.00 eq) in tetrahydrofuran (125.00 mL) at −78° C., 30 minutes after the addition, the mixture was stirred at this temperature for 30 minutes and then a solution of [methoxy(methyl)phosphoryl]oxymethane (3.51 g, 28.32 mmol, 3.20 eq) in THF (125.00 mL) was added at −78° C. The resulting mixture was stirred at −78° C. for 2 hours. The reaction was quenched by addition of ammonium chloride (30 mL) to the reaction at −78° C. and then extracted with ethyl acetate (400 mL×2). The combined organic layers were concentrated under reduced pressure to give a residue. The residue was purified by silica gel chromatography (SiO$_2$, petroleum ether/ethyl acetate=3/1 to 0:1) to deliver the compound 1-(6-benzyl-7,8-dihydro-5H-1,6-naphthyridin-2-yl)-2-dimethoxyphosphoryl-ethanone (2.35 g, 6.28 mmol, 70.93% yield) as a colorless solid.

Step 3:

(E)-Ethyl 4-(6-benzyl-7,8-dihydro-5H-1,6-naphthyridin-2-yl)-4-oxobut-2-enoate

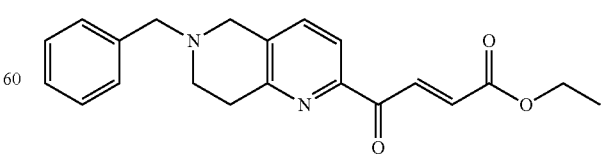

Potassium tert-butoxide (845.24 mg, 7.53 mmol, 1.20 eq) and ethyl 2-oxoacetate (2.56 g, 12.55 mmol, 2.00 eq) were added to a solution of 1-(6-benzyl-7,8-dihydro-5H-1,6- naphthyridin-2-yl)-2-dimethoxyphosphoryl-ethanone (2.35 g, 6.28 mmol, 1.00 eq) in dichloroethane (30.00 mL). The mixture was stirred at −20° C. for 2 hours. The residue was separated by silica gel chromatography (SiO₂, petroleum ether/ethyl acetate=1/0 to 20:1) to deliver the compound ethyl (E)-ethyl 4-(6-benzyl-7,8-dihydro-5H-1,6-naphthyridin-2-yl)-4-oxobut-2-enoate (1.50 g, 4.28 mmol, 68.16% yield) as a yellow solid. ¹H NMR (400 MHz, CDCl₃): δ 8.48 (d, J=15.9 Hz, 1H), 7.82 (d, J=7.9 Hz, 1H), 7.41-7.22 (m, 6H), 6.92 (d, J=15.9 Hz, 1H), 4.25-4.19 (m, 2H), 3.65 (d, J=16.9 Hz, 4H), 3.12-3.00 (m, 2H), 2.83 (t, J=6.0 Hz, 2H), 1.30-1.23 (m, 3H). LCMS (ESI) m/z: 351.1 (M+1).

Step 4:

Ethyl 5-(6-benzyl-5,6,7,8-tetrahydro-1,6-naphthyridin-2-yl)-2-(trifluoromethyl)furan-3-carboxylate

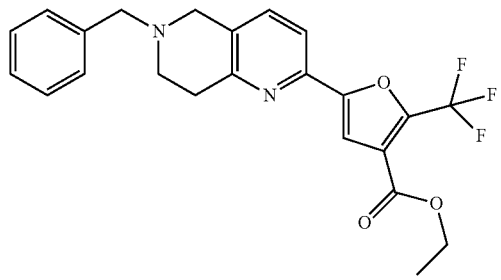 [SMILES: CCOC(=O)c1cc(-c2ccc3c(n2)CCN(Cc2ccccc2)C3)oc1C(F)(F)F]

(E)-Ethyl 4-(6-benzyl-7,8-dihydro-5H-1,6-naphthyridin-2-yl)-4-oxobut-2-enoate (1.50 g, 4.28 mmol, 1.00 eq) was added to a solution of trifluoroacetic anhydride (1.35 g, 6.42 mmol, 1.50 eq) and triphenylphosphine (1.12 g, 4.28 mmol, 1.00 eq) in dichloromethane (15.00 mL). The mixture was stirred at 25° C. for 0.5 hour. The residue was purified by column chromatography (SiO₂, petroleum ether/ethyl acetate=50/1 to 10:1) to deliver the compound ethyl 5-(6-benzyl-5,6,7,8-tetrahydro-1,6-naphthyridin-2-yl)-2-(trifluoromethyl)furan-3-carboxylate (1.30 g, 3.02 mmol, 70.57% yield) as a yellow solid.

Step 5:

Sodium 5-(6-benzyl-5,6,7,8-tetrahydro-1,6-naphthyridin-2-yl)-2-(trifluoromethyl)furan-3-carboxylate

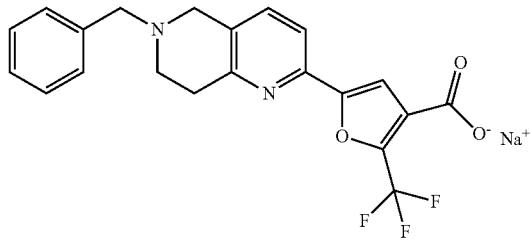 [SMILES: O=C([O-])c1cc(-c2ccc3c(n2)CCN(Cc2ccccc2)C3)oc1C(F)(F)F ; [Na+]]

Sodium hydroxide (260.80 mg, 6.52 mmol, 4.00 eq) was added to a solution of ethyl 5-(6-benzyl-5,6,7,8-tetrahydro-1,6-naphthyridin-2-yl)-2-(trifluoromethyl)furan-3-carboxylate (700.00 mg, 1.63 mmol, 1.00 eq) in ethanol (7.00 mL) and water (7.00 mL). The mixture was stirred at 25° C. for 12 hours. The reaction mixture was concentrated under reduced pressure to remove the solvent to deliver the compound sodium 5-(6-benzyl-5,6,7,8-tetrahydro-1,6-naphthyridin-2-yl)-2-(trifluoromethyl)furan-3-carboxylate (1.00 g, crude) as a yellow solid.

Step 6:

6-Benzyl-2-(5-(trifluoromethyl)furan-2-yl)-7,8-dihydro-5H-1,6-naphthyridine

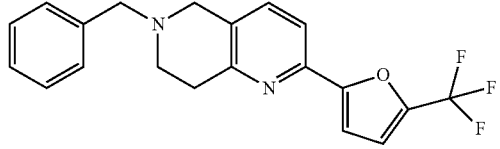 [SMILES: FC(F)(F)c1ccc(-c2ccc3c(n2)CCN(Cc2ccccc2)C3)o1]

Copper sulfate (37.67 mg, 236.00 μmol, 0.10 eq) was added to a solution of sodium 5-(6-benzyl-5,6,7,8-tetrahydro-1,6-naphthyridin-2-yl)-2-(trifluoromethyl)furan-3-carboxylate (1.00 g, 2.36 mmol, 1.00 eq) in N-methylpyrrolidone (10.00 mL). The mixture was stirred at 150° C. for 2 hours. The reaction mixture was concentrated under reduced pressure to remove the solvent. The residue was separated and purified by a preparative plate (silica, petroleum ether/ethyl acetate=2:1) to deliver the compound 6-benzyl-2-(5-(trifluoromethyl)furan-2-yl)-7,8-dihydro-5H-1,6-naphthyridine (500.00 mg, 1.40 mmol, 59.12% yield) as a yellow solid.

Step 7:

2-[5-(Trifluoromethyl)-2-furyl]-5,6,7,8-tetrahydro-1,6-naphthyridine

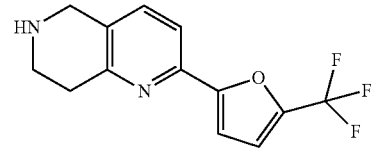 [SMILES: FC(F)(F)c1ccc(-c2ccc3c(n2)CCNC3)o1]

6-Benzyl-2-(5-(trifluoromethyl)furan-2-yl)-7,8-dihydro-5H-1,6-naphthyridine (600.00 mg, 1.67 mmol, 1.00 eq) and 1-chloroethyl carbonochloridate (358.14 mg, 2.51 mmol, 1.50 eq) were dissolved in 1,2-dichloroethane (6.00 mL). The mixture was stirred at 80° C. for 12 hours. The reaction mixture was concentrated under reduced pressure to remove the solvent and methanol (6.00 mL) was added. The mixture was stirred at 80° C. for 12 hours. The reaction mixture was concentrated under reduced pressure to remove the solvent. The pH was adjusted to about 9 by the gradually addition of a sodium carbonate solution and extracted with ethyl acetate (100 mL×2). The combined organic layers were concentrated under reduced pressure to deliver 2-[5-(trifluoromethyl)-2-furyl]-5,6,7,8-tetrahydro-1,6-naphthyridine (200.00 mg, 745.63 μmol, 44.65% yield) as a white solid. LCMS (ESI) m/z: 269.1 (M+1).

Step 8:

(2S)-1-(2-Chloro-4-nitroimidazol-1-yl)-2-methyl-3-(2-(5-(trifluoromethyl)furan-2-yl)-7,8-dihydro-5H-1,6-naphthyridin-6-yl)propan-2-ol

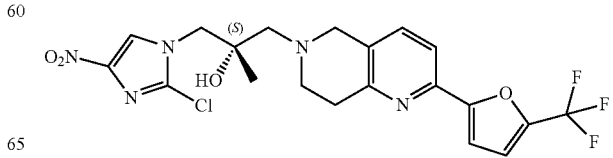

Diisopropylamine (192.73 mg, 1.49 mmol, 2.00 eq) and 2-chloro-1-[[(2R)-2-methyloxiran-2-yl]methyl]-4-nitroimidazole (178.48 mg, 820.19 µmol, 1.10 eq) were added to a solution of 2-[5-(trifluoromethyl)-2-furyl]-5,6,7,8-tetrahydro-1,6-naphthyridine (200.00 mg, 745.63 µmol, 1.00 eq) in tert-butanol (5.00 mL). The mixture was stirred at 100° C. for 12 hours. The residue was purified by silica gel chromatography (SiO₂, petroleum ether/ethyl acetate=10/1 to 1:1) to deliver (2S)-1-(2-chloro-4-nitroimidazol-1-yl)-2-methyl-3-(2-(5-(trifluoromethyl)furan-2-yl)-7,8-dihydro-5H-1,6-naphthyridin-6-yl)propan-2-ol (260.00 mg, 535.16 µmol, 71.77% yield) as a yellow solid. LCMS (ESI) m/z: 486.2 (M+1).

Step 9:

(S)-2-Methyl-6-nitro-2-((2-(5-(trifluoromethyl)furan-2-yl)-7,8-dihydro-1,6-naphthyridin-6(5H)-yl)methyl)-2,3-dihydroimidazo[2,1-b]oxazole Compound 54

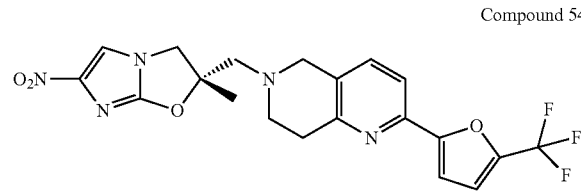 [SMILES: C[C@]1(CN2CCc3nc(-c4ccc(C(F)(F)F)o4)ccc3C2)Cn2cc([N+](=O)[O-])nc2O1]

Sodium hydrogen (32.11 mg, 1.34 mmol, 2.50 eq) was added to a solution of (2S)-1-(2-chloro-4-nitroimidazol-1-yl)-2-methyl-3-(2-(5-(trifluoromethyl)furan-2-yl)-7,8-dihydro-5H-1,6-naphthyridin-6-yl)propan-2-ol (260.00 mg, 535.16 µmol, 1.00 eq) in DMF (3.00 mL) at 0° C. for 10 minutes and the mixture was stirred at 15° C. for 50 minutes. The reaction mixture was quenched by the addition of ammonium chloride (10 mL) at 0° C. and then extracted with ethyl acetate (100 mL×2). The combined organic layers were washed with sodium chloride (20 mL*1) and concentrated under reduced pressure to give a residue. The residue was separated and purified by preparative separation chromatography (GX-I,YMC-Actus ODS-AQ 100*30 5u, acetonitrile 24%-54%; 0.1% TFA-ACN; 25 mL/min) to deliver (S)-2-methyl-6-nitro-2-((2-(5-(trifluoromethyl)furan-2-yl)-7,8-dihydro-1,6-naphthyridin-6(5H)-yl)methyl)-2,3-dihydroimidazo[2,1-b]oxazole compound 54 (48.00 mg, 105.28 µmol, 19.67% yield, 98.561% purity). ¹H NMR (400 MHz, CDCl₃): δ 7.59-7.55 (m, 1H), 7.52 (s, 1H), 7.42-7.34 (m, 1H), 7.11-7.01 (m, 1H), 6.94-6.84 (m, 1H), 4.48-4.37 (m, 1H), 4.03-3.78 (m, 3H), 3.26-2.73 (m, 6H), 1.69 (s, 3H). LCMS (ESI) m/z: 450.2 (M+1).

Embodiment 55

(S)-2-Methyl-2-((2-(4-methylthiazol-2-yl)-7,8-dihydro-1,6-naphthyridin-6(5H)-yl)methyl)-6-nitro-2,3-dihydroimidazo[2,1-b]oxazole

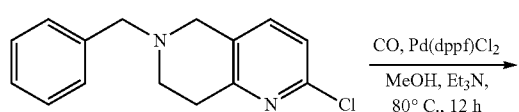

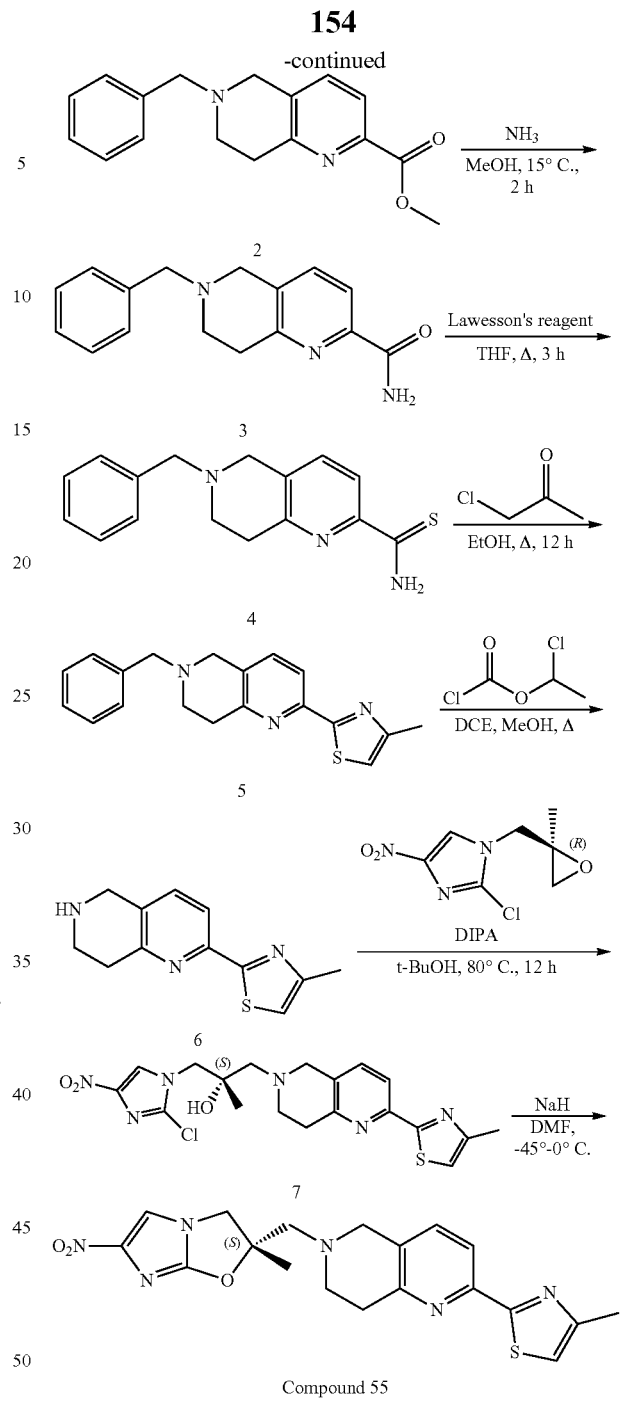

Step 1:

Methyl 6-benzyl-5,6,7,8-tetrahydro-1,6-naphthyridine-2-carboxylate

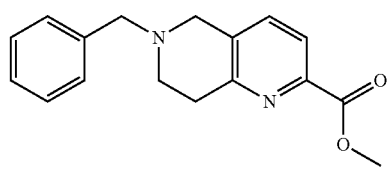 [SMILES: COC(=O)c1ccc2c(n1)CCN(Cc1ccccc1)C2]

Pd(dppf)Cl₂ (1.07 g, 1.47 mmol, 0.10 eq) was added to a solution of 6-benzyl-2-chloro-7,8-dihydro-5H-1,6-naphthyridine (3.80 g, 14.69 mmol, 1.00 eq) in triethylamine (2.00 mL) and methanol (20.00 mL) under the nitrogen gas atmosphere. The suspension was degassed under vacuum and purged with carbon monoxide. The mixture was stirred at 80° C. for 12 hours under carbon monoxide (50 Psi). The mixture was filtered and concentrated, and the residue was purified by silica gel chromatography (petroleum ether/ethyl acetate=10/1, 1/2) to deliver methyl 6-benzyl-5,6,7,8-tetrahydro-1,6-naphthyridine-2-carboxylate (3.90 g, 13.81 mmol, 94.04% yield) as a yellow solid. ¹H NMR (400 MHz, CDCl₃) δ 7.93 (d, J=7.9 Hz, 1H), 7.45 (d, J=7.9 Hz, 1H), 7.42-7.30 (m, 5H), 4.01 (s, 3H), 3.75 (s, 2H), 3.71 (s, 2H), 3.18 (t, J=6.0 Hz, 2H), 2.90 (t, J=6.0 Hz, 2H).

Step 2:

6-Benzyl-5,6,7,8-tetrahydro-1,6-naphthyridine-2-carboxamide

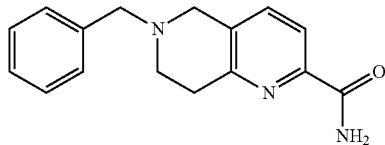 [SMILES: NC(=O)c1ccc2c(n1)CCN(Cc1ccccc1)C2]

Ammonia (4.58 g, 269.20 mmol, 20.00 eq) was passed to methanol (50.00 mL) at −50° C., after 10 minutes, methyl 6-benzyl-5,6,7,8-tetrahydro-1,6-naphthyridine-2-carboxylate (3.80 g, 13.46 mmol, 1.00 eq) was added to the solution at 15° C. The mixture was stirred at 15° C. for 120 minutes. The reaction mixture was concentrated to deliver 6-benzyl-5,6,7,8-tetrahydro-1,6-naphthyridine-2-carboxamide (3.30 g, 12.34 mmol, 91.71% yield) as a yellow solid. ¹H NMR (400 MHz, CDCl₃) δ 7.97 (d, J=7.9 Hz, 1H), 7.46 (d, J=7.9 Hz, 1H), 7.43-7.30 (m, 5H), 3.75 (s, 2H), 3.70 (s, 2H), 3.09-3.02 (m, 2H), 2.93-2.84 (m, 2H).

Step 3:

6-Benzyl-7,8-dihydro-5H-1,6-naphthyridine-2-carbothioamide

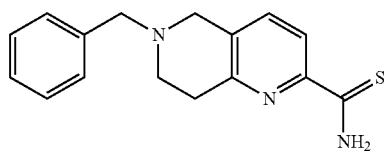 [SMILES: NC(=S)c1ccc2c(n1)CCN(Cc1ccccc1)C2]

Lawesson's reagent (3.40 g, 8.42 mmol, 1.50 eq) was added to a solution of 6-benzyl-5,6,7,8-tetrahydro-1,6-naphthyridine-2-carboxamide (1.50 g, 5.61 mmol, 1.00 eq) in tetrahydrofuran (30.00 mL) under the nitrogen gas atmosphere. The mixture was stirred at 80° C. for 4 hours. The mixture was concentrated under reduced pressure at 45° C. The residue was purified by silica gel chromatography (petroleum ether/ethyl acetate=10/1, 0/1) to deliver 6-benzyl-7,8-dihydro-5H-1,6-naphthyridine-2-carbothioamide (780.00 mg, 2.75 mmol, 49.06% yield) as a yellow solid. ¹H NMR (400 MHz, CDCl₃) δ 8.47 (d, J=8.0 Hz, 1H), 7.45 (d, J=7.8 Hz, 3H), 7.37 (d, J=7.5 Hz, 3H), 3.96 (br. s, 2H), 3.84 (d, J=7.7 Hz, 2H), 3.14 (br. s, 4H).

Step 4:

2-(6-Benzyl-7,8-dihydro-5H-1,6-naphthyridin-2-yl)-4-methyl-thiazole

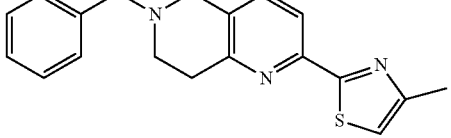

1-Chloropropan-2-one (1.48 g, 16.00 mmol, 5.82 eq) was added to a solution of 6-benzyl-7,8-dihydro-5H-1,6-naphthyridine-2-carbothioamide (780.00 mg, 2.75 mmol, 1.00 eq) in ethanol (15.00 mL) under the nitrogen gas atmosphere. The mixture was stirred at 80° C. for 12 hours. The mixture was concentrated under reduced pressure at 45° C. The residue was washed with petroleum ether: ethyl acetate=10:1 (40 mL), filtered and the filter cake was dried to deliver 2-(6-benzyl-7,8-dihydro-5H-1,6-naphthyridin-2-yl)-4-methyl-thiazole (719.00 mg, 2.24 mmol, 81.34% yield) as a brown solid. ¹H NMR (400 MHz, CDCl₃) δ 7.91 (d, J=7.9 Hz, 1H), 7.43-7.33 (m, 6H), 6.95 (s, 1H), 3.74 (s, 2H), 3.66 (s, 2H), 3.12-3.07 (m, 2H), 2.92-2.87 (m, 2H), 2.52 (s, 3H).

Step 5:

4-Methyl-2-(5,6,7,8-tetrahydro-1,6-naphthyridin-2-yl)thiazole

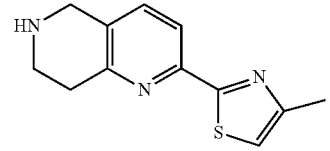 [SMILES: Cc1csc(-c2ccc3c(n2)CCNC3)n1]

1-Chloroethyl carbonochloridate (240.19 mg, 1.68 mmol, 1.50 eq) was added to a solution of 2-(6-benzyl-7,8-dihydro-5H-1,6-naphthyridin-2-yl)-4-methyl-thiazole (360.00 mg, 1.12 mmol, 1.00 eq) in dichloroethane (10.00 mL) at 0° C. under the nitrogen gas atmosphere. The mixture was stirred at 100° C. for 12 hours. The mixture was then cooled to 20° C. and concentrated under reduced pressure at 45° C. Methanol (15.00 mL) was added to the residue and stirred at 80° C. for 2 hours. The mixture was concentrated under reduced pressure at 45° C. and dichloromethane (20 mL) was added to the residue and stirred for 10 minutes, filtered and the filter cake was collected to deliver 4-methyl-2-(5,6,7,8-tetrahydro-1,6-naphthyridin-2-yl)thiazole (150.00 mg, 560.16 μmol, 50.01% yield, hydrochloric acid) as a white solid. ¹H NMR (300 MHz, DMSO-d₆) δ 7.98 (d, J=8.1 Hz, 1H), 7.81 (d, J=8.1 Hz, 1H), 7.43 (s, 1H), 4.33 (br. s., 2H), 3.47 (br. s., 2H), 3.18-3.14 (m, 2H), 2.44 (s, 3H).

Step 6:

(2S)-1-(2-Chloro-4-nitroimidazol-1-yl)-2-methyl-3-(2-(4-methylthiazol-2-yl)-7,8-dihydro-5H-1,6-naphthyridin-6-yl)propan-2-ol

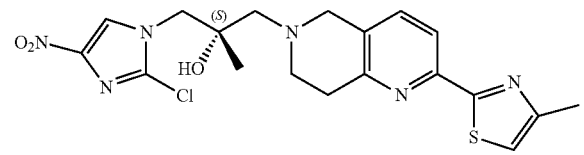

Diisopropylamine (144.79 mg, 1.12 mmol, 2.00 eq) was added to a solution of 4-methyl-2-(5,6,7,8-tetrahydro-1,6-naphthyridin-2-yl)thiazole (150.00 mg, 560.16 μmol, 1.00 eq, HCl) and 2-chloro-1-[[(2R)-2-methyloxiran-2-yl]methyl]-4-nitroimidazole (146.28 mg, 672.19 mmol, 1.20 eq) in tert-butanol (10.00 mL) under the nitrogen gas atmosphere. The mixture was stirred at 80° C. for 12 hours. The mixture was concentrated under reduced pressure at 45° C. and water (20 mL) was added to the residue and stirred for 5 minutes. The aqueous phase was extracted with ethyl acetate (30 mL×3). The combined organic phases were washed with brine (20 mL), dried over anhydrous sodium sulfate, filtered and concentrated in vacuo. The residue was separated and purified by preparative thin layer chromatography (petroleum ether/ethyl acetate=1/1) to deliver (2S)-1-(2-chloro-4-nitroimidazol-1-yl)-2-methyl-3-(2-(4-methyl-thiazol-2-yl)-7,8-dihydro-5H-1,6-naphthyridin-6-yl)propan-2-ol (73.00 mg, 162.61 μmol, 29.03% yield) as a white solid. $^1$H NMR (300 MHz, CDCl$_3$) δ 8.07 (s, 1H), 7.97 (d, J=8.1 Hz, 1H), 7.41 (d, J=8.1 Hz, 1H), 6.99 (s, 1H), 4.07 (s, 2H), 3.98-3.81 (m, 2H), 3.18-3.04 (m, 4H), 2.76-2.67 (m, 1H), 2.54 (s, 3H), 2.07 (s, 1H), 1.22 (s, 3H).

Step 7:

(S)-2-Methyl-2-((2-(4-methylthiazol-2-yl)-7,8-dihydro-1,6-naphthyridin-6(5H)-yl)methyl)-6-nitro-2,3-dihydroimidazo[2,1-b]oxazole Compound 55

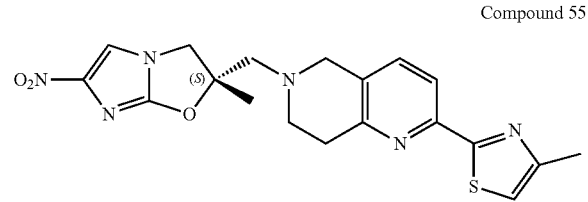

Sodium hydride (13.01 mg, 325.22 μmol, 2.00 eq) was added in one portion to a solution of (2S)-1-(2-chloro-4-nitroimidazol-1-yl)-2-methyl-3-(2-(4-methylthiazol-2-yl)-7,8-dihydro-5H-1,6-naphthyridin-6-yppropan-2-ol (73.00 mg, 162.61 μmol, 1.00 eq) in DMF (2.00 mL) at −45° C. under the nitrogen gas atmosphere. The mixture was stirred at −45 to 0° C. for 10 minutes. The residue was poured into a saturated ammonium chloride solution (30 mL) and stirred for 5 minutes. The aqueous phase was extracted with ethyl acetate (50 mL×3). The combined organic phases were washed with brine (20 mL×2), dried over anhydrous anhydrous sodium sulfate, filtered and concentrated in vacuo. The residue was separated and purified by preparative separation chromatography (GX-F; Phenomenex Synergi C18 150*25*10 um; acetonitrile 32%-62%; water (0.225% FA-ACN); 25 mL/min) to deliver (S)-2-methyl-2-((2-(4-methylthiazol-2-yl)-7,8-dihydro-1,6-naphthyridin-6(5H)-yl)methyl)-6-nitro-2,3-dihydroimidazo[2,1-b]oxazole compound 55 (27.96 mg, 65.35 μmol, 40.19% yield, 96.4% purity). $^1$H NMR (400 MHz, CDCl$_3$) δ 7.94 (d, J=8.0 Hz, 1H), 7.52 (s, 1H), 7.39 (d, J=8.0 Hz, 1H), 6.97 (s, 1H), 4.43 (d, J=9.7 Hz, 1H), 3.96 (d, J=9.5 Hz, 1H), 3.93-3.80 (m, 2H), 3.19-3.07 (m, 3H), 3.06-2.90 (m, 3H), 2.80 (d, J=14.9 Hz, 1H), 2.53 (s, 3H), 1.69 (s, 3H). LCMS (ESI) m/z: 413.1 (M+1).

Embodiment 56

(S)-2-((2-(4-Fluoro-2-methylphenyl)-7,8-dihydro-1,6-naphthyridin-6(5H)-yl)methyl)-2-methyl-6-nitro-2,3-dihydroimidazo[2,1-b]oxazole Compound 56

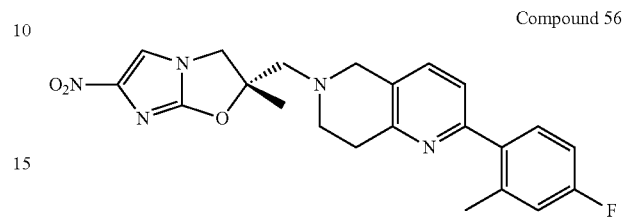

The key intermediate B (300.00 mg, 857.71 μmol, 1.00 eq) and (4-fluoro-2-methyl-phenyl) boronic acid (198.07 mg, 1.29 mmol, 1.50 eq) were dissolved in dioxane (5.00 mL) and water (500.00 μL), Pd(dppf)Cl$_2$ (31.38 mg, 42.89 μmol, 0.05 eq) and cesium fluoride (260.57 mg, 1.72 mmol, 2.00 eq) were added. The mixture was stirred at 110° C. for 10 hours. The reaction mixture was quenched by the addition of water (50 mL) and then extracted with ethyl acetate (50 mL×3). The combined organic layers were washed with saturated brine (50 mL), dried over sodium sulfate, filtered and concentrated under reduced pressure to give a residue. The residue was separated and purified by preparative separation chromatography (GX-F; Phenomenex Synergi C18 150*25*10 um; acetonitrile 28%-49%; ACN (0.225% fomic acid); 25 mL/min) to deliver (S)-2-((2-(4-fluoro-2-methylphenyl)-7,8-dihydro-1,6-naphthyridin-6(5H)-yl) methyl)-2-methyl-6-nitro-2,3-dihydroimidazo[2,1-b]oxazole compound 56 (104.70 mg, 239.60 μmol, 27.93% yield, 96.9% purity). $^1$H NMR (400 MHz, CDCl$_3$): δ 7.54 (s, 1H), 7.38 (d, J=7.91 Hz, 1H), 7.33 (dd, J=8.28, 6.02 Hz, 1H), 7.21-7.11 (m, 1H), 7.03-6.91 (m, 2H), 4.45 (d, J=9.66 Hz, 1H), 4.03-3.80 (m, 3H), 3.22-2.92 (m, 5H), 2.83 (d, J=14.81 Hz, 1H), 2.39-2.28 (s, 3H), 1.70 (s, 3H). LCMS (ESI) m/z: 424.1 (M+1).

Embodiment 57

(S)-2-((2-(4-Fluorophenyl)-5,6-dihydro-[1,2,4]triazolo[1,5-α]pyrazin-7(8H)-yl)methyl)-2-methyl-6-nitro-2,3-dihydroimidazo[2,1-b]oxazole Compound 57

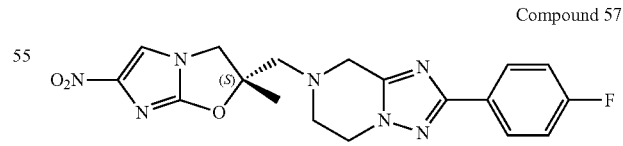

The synthesis method is as in Embodiment 50.

(S)-2-((2-(4-Fluorophenyl)-5,6-dihydro-[1,2,4]triazolo[1,5-α]pyrazin-7(8H)-yl)methyl)-2-methyl-6-nitro-2,3-dihydroimidazo[2,1-b]oxazole compound 57 (6.85 mg, 16.20 μmol, 44.13% yield, 94.46% purity). $^1$HNMR (400 MHz, METHANOL-d$_4$) δ 8.02-7.96 (m, 2H), 7.86-7.82 (m, 1H), 7.20-7.14 (m, 2H), 4.67-4.60 (m, 1H), 4.45-4.38 (m, 1H), 4.15 (s, 2H), 4.07 (s, 1H), 4.00 (s, 2H), 3.24-3.14 (m, 2H), 3.09-3.02 (m, 1H), 1.69-1.65 (m, 3H). LCMS (ESI) m/z: 400.1(M+1).

Embodiment 58

(S)-2-((2-(4-Fluoro-3-methylphenyl)-7,8-dihydro-1,6-naphthyridin-6(5H)-yl)methyl)-2-methyl-6-nitro-2,3-dihydroimidazo[2,1-b]oxazole Compound 58

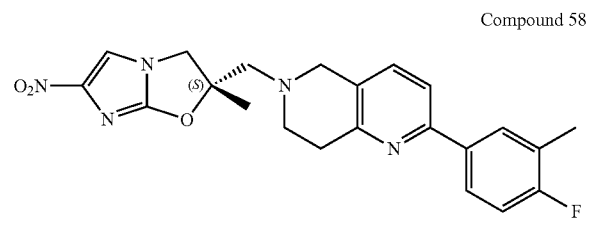

The key intermediate B (100.00 mg, 285.90 μmol, 1.00 eq) and (4-fluoro-3-methyl-phenyl) boronic acid (44.01 mg, 285.90 mmol, 1.00 eq) were dissolved in dioxane (1.00 mL) and water (100.00 μL), cesium fluoride (86.86 mg, 571.80 μmol, 2.00 eq) and Pd(dppf)Cl$_2$ (20.92 mg, 28.59 μmol, 0.10 eq) were added. The mixture was stirred at 110° C. for 10 hours. The reaction mixture was quenched by the addition of water (50 mL) and then extracted with ethyl acetate (50 mL×3). The combined organic layers were washed with saturated brine (50 mL), dried over sodium sulfate, filtered and concentrated under reduced pressure to give a residue. The residue was separated and purified by preparative separation chromatography (GX-G; Phenomenex Synergi Max-RP 250*80 10u; acetonitrile 20%-50%; ACN (0.225% fomic acid); 25 mL/min) to deliver (S)-2-((2-(4-fluoro-3-methylphenyl)-7,8-dihydro-1,6-naphthyridin-6(5H)-yl)methyl)-2-methyl-6-nitro-2,3-dihydroimidazo[2,1-b]oxazole (38.74 mg, 89.20 μmol, 31.20% yield, 97.5% purity) compound 58. $^1$H NMR (400 MHz, CDCl$_3$): δ 7.80 (d, J=7.53 Hz, 1H), 7.74-7.68 (m, 1H), 7.53 (s, 1H), 7.47-7.43 (m, 1H), 7.38-7.34 (m, 1H), 7.08 (t, J=8.97 Hz, 1H), 4.44 (d, J=9.66 Hz, 1H), 4.02-3.79 (m, 3H), 3.22-2.91 (m, 5H), 2.81 (d, J=14.81 Hz, 1H), 2.36 (s, 3H), 1.69 (s, 3H). LCMS (ESI) m/z: 424.1 (M+1).

Embodiment 59

(S)-2-((2-Cyclohexyl-7,8-dihydro-1,6-naphthyridin-6(5H)-yl)methyl)-2-methyl-6-nitro-2,3-dihydroimidazo[2,1-b]oxazole

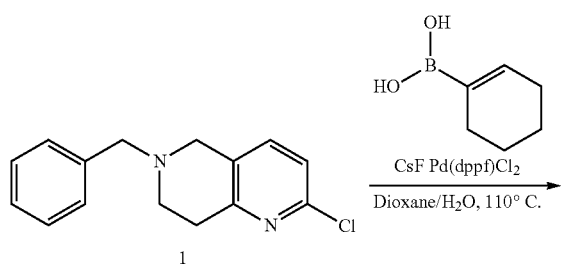

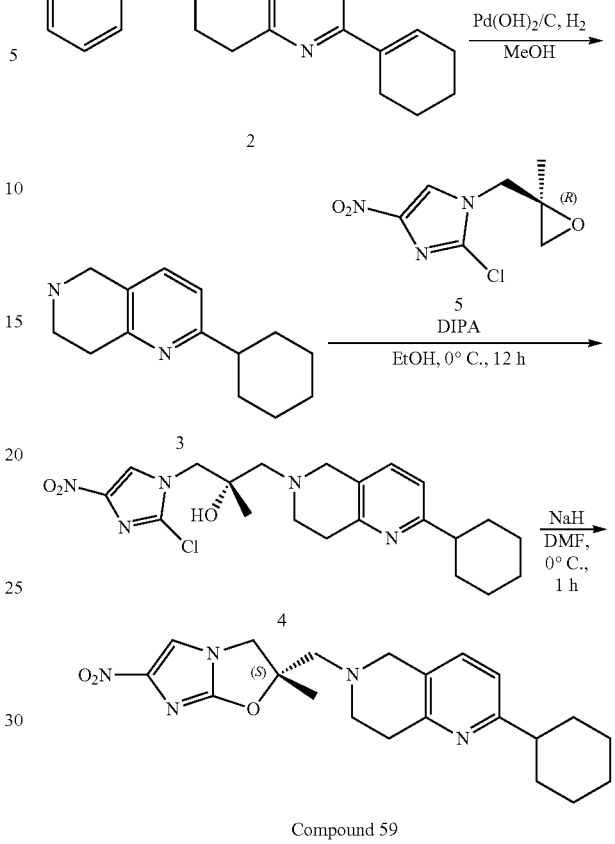

Compound 59

Step 1:

6-Benzyl-2-(cyclohexen-1-yl)-7,8-dihydro-5H-1,6-naphthyridine

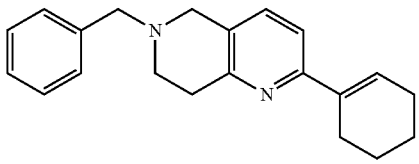 [SMILES: C1=C(c2ccc3c(n2)CCN(Cc2ccccc2)C3)CCCC1]

6-Benzyl-2-chloro-7,8-dihydro-5H-1,6-naphthyridine (200.00 mg, 772.95 μmol, 1.00 eq), cyclohexene-1-yl boronic acid (146.04 (1.65 mmol, 1.50 eq), Pd(dppf)Cl$_2$ (56.56 mg, 77.30 mmol, 0.10 eq) and cesium fluoride (234.82 mg, 1.55 mmol, 2.00 eq) were dissolved in dioxane (4.00 mL) and water (0.4 mL), and then the mixture was stirred at 110° C. for 12 hours under the nitrogen gas atmosphere. The reaction mixture was concentrated under reduced pressure, water (10 mL) was added to the residue, and extracted with ethyl acetate (20 mL). The combined organic layers were washed with brine (10 mL), dried over sodium sulfate, filtered and concentrated under reduced pressure. The residue was separated and purified by silica gel chromatography (SiO$_2$, petroleum ether/ethyl acetate=20/1 to 10:1) to deliver 6-benzyl-2-(cyclohexen-1-yl)-7,8-dihydro-5H-1,6-naphthyridine (160.00 mg, 525.57 μmol, 68.00% yield) as a yellow solid. $^1$H NMR (300 MHz, CDCl$_3$) δ 7.36-7.11 (m, 6H), 7.05-6.99 (m, 1H), 6.54 (s, 1H), 3.64 (s, 2H), 3.53 (s, 2H), 3.01-2.92 (m, 2H), 2.83-2.73 (m, 2H), 2.39 (br. s., 2H), 2.17 (d, J=6.2 Hz, 2H), 1.77-1.66 (m, 2H), 1.65-1.55 (m, 2H).

Step 2:

2-Cyclohexyl-5,6,7,8-tetrahydro-1,6-naphthyridine

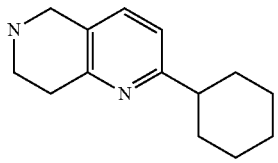 [SMILES: c1cc2c(nc1C1CCCCC1)CCNC2]

Palladium hydroxide/carbon (7.38 mg, 52.55 µmol, 0.10 eq) was added to a solution of 6-benzyl-2-(cyclohexen-1-yl)-7,8-dihydro-5H-1,6-naphthyridine (160.00 mg, 525.57 µmol, 1.00 eq) in methanol (5.00 mL) under the nitrogen gas atmosphere. The suspension was degassed and replaced with hydrogen several times. The mixture was stirred under hydrogen (30 psi) at 15° C. for 12 hours. The reaction mixture was filtered and concentrated to deliver 2-cyclohexyl-5,6,7,8-tetrahydro-1,6-naphthyridine (110.00 mg, 508.51 µmol, 96.75% yield, 100% purity) as a colorless oil.

Step 3:

(2S)-1-(2-Chloro-4-nitroimidazol-1-yl)-3-(2-cyclohexyl-7,8-dihydro-5H-1,6-naphthyridin-6-yl)-2-methylpropan-2-ol

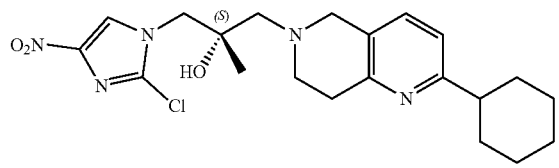

Diisopropylamine (131.44 mg, 1.02 mmol, 2.00 eq) and 2-chloro-1-[[(2R)-2-methyloxiran-2-yl]methyl]-4-nitroimidazole (132.79 mg, 610.21 µmol, 1.20 eq) were added to a solution of 2-cyclohexyl-5,6,7,8-tetrahydro-1,6-naphthyridine (110.00 mg, 508.51 µmol, 1.00 eq) in ethanol (5.00 mL). The mixture was stirred at 80° C. for 12 hours. The reaction mixture was concentrated under reduced pressure and the residue was diluted with water (20 mL) and extracted with ethyl acetate (30 mL). The combined organic layers were washed with brine (10 mL), dried over sodium sulfate, filtered and concentrated under reduced pressure. The residue was separated and purified by preparative thin layer chromatography (silica, ethyl acetate) to deliver (2S)-1-(2-chloro-4-nitroimidazol-1-yl)-3-(2-cyclohexyl-7,8-dihydro-5H-1,6-naphthyridin-6-yl)-2-methylpropan-2-ol (80.00 mg, 135.87 µmol, 26.72% yield, 73.7% purity) as a yellow solid.

Step 4:

(S)-2-((2-Cyclohexyl-7,8-dihydro-1,6-naphthyridin-6(5H)-yl)methyl)-2-methyl-6-nitro-2,3-dihydroimidazo[2,1-b]oxazole Compound 59

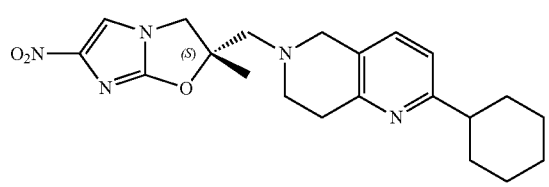

Sodium hydride (8.85 mg, 221.23 µmol, 1.20 eq) was added to a solution of (2S)-1-(2-chloro-4-nitroimidazol-1-yl)-3-(2-cyclohexyl-7,8-dihydro-5H-1,6-naphthyridin-6-yl)-2-methylpropan-2-ol (80.00 mg, 184.36 µmol, 1.00 eq) in DMF (2.00 mL) at 0° C. The mixture was stirred at 0° C. for 1 hour. The reaction mixture was slowly added to the a cooled saturated ammonium chloride solution (10 mL) and then extracted with ethyl acetate (20 mL). The combined organic layers were washed with brine (10 mL×2), dried over sodium sulfate, filtered and concentrated under reduced pressure. The residue was purified by preparative separation chromatography (Instrument: GX-D; Column: Boston Green ODS 150*30 5u; Mobile phase: 20%-50%; H$_2$O (+0.00225 FA); Rate: 25 mL/min; Monitored Wavelength: 220 nm/254 nm; Run length: 10 min/15 min; Column temperature: 30° C.) to deliver (S)-2-((2-Cyclohexyl-7,8-dihydro-1,6-naphthyridin-6(5H)-yl)methyl)-2-methyl-6-nitro-2,3-dihydroimidazo[2,1-b]oxazole compound 59 (70.00 mg, 174.71 µmol, 94.76% yield, 99.2% purity). $^1$H NMR (400 MHz, CDCl$_3$) δ 7.52 (s, 1H), 7.30 (s, 1H), 7.00 (d, J=8.0 Hz, 1H), 4.42 (d, J=9.7 Hz, 1H), 3.94 (d, J=9.7 Hz, 1H), 3.87-3.74 (m, 2H), 3.15-2.90 (m, 5H), 2.84-2.67 (m, 2H), 2.02-1.72 (m, 5H), 1.67 (s, 3H), 1.52-1.23 (m, 5H). LCMS (ESI) m/z: 398.2 (M+1).

Embodiment 60

(S)-2-((2-(4-Fluorophenyl)-7,7-dimethyl-6,7-dihydrothiazolo[5,4-c]pyridin-5(4H)-yl)methyl)-2-methyl-6-nitro-2,3-dihydroimidazo[2,1-b]oxazole

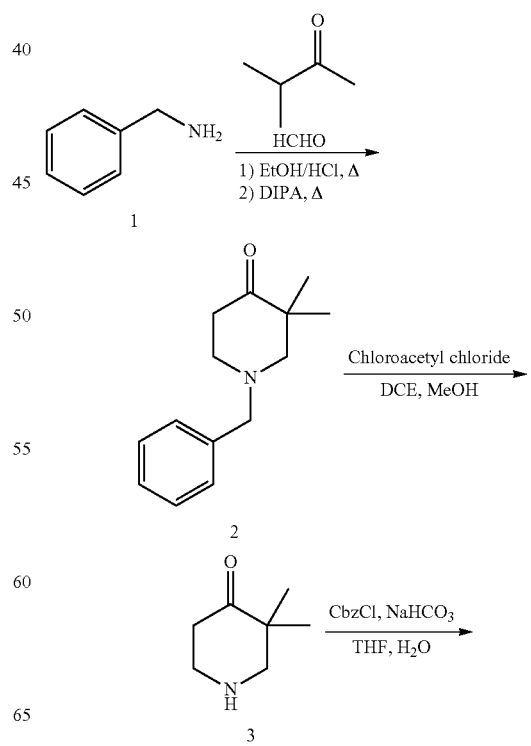

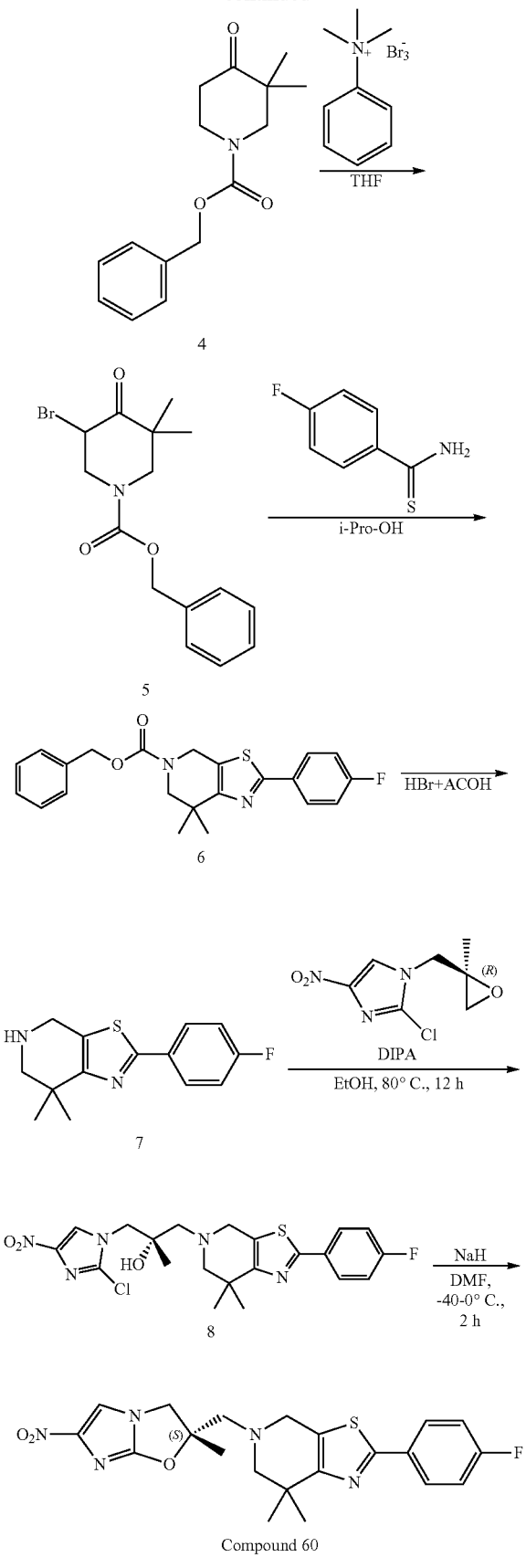

Compound 60

Step 1:
1-Benzyl-3,3-dimethylpiperidin-4-one

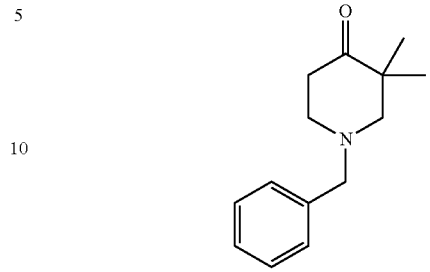

Formaldehyde (18.26 g, 225.00 mmol, 2.25 eq) was dissolved in ethanol (100.00 mL) and the benzylamine (10.72 g, 100.00 mmol, 1.00 eq) was added slowly to the solution. The mixture was stirred at 15° C. for 1 hour. The mixture was then slowly added to a refluxing solution of 3-methylbutan-2-one (8.61 g, 100.00 mmol, 1.00 eq) in ethanol (100.00 mL) and hydrochloric acid (9.20 mL). The mixture was stirred at 80° C. for 12 hours. The mixture was then cooled to 15° C. and then diisopropylamine (14.22 g, 110.00 mmol, 1.10 eq) and formaldehyde (2.44 g, 30.00 mmol, 0.30 eq) were added and the mixture was stirred at 80° C. for another 7 hours. The pH of the reaction mixture was adjusted to >10 with potassium hydroxide and then extracted with ethyl acetate (200 mL). The combined organic layers were washed with brine (100 mL), dried over sodium sulfate, filtered and concentrated under reduced pressure. The residue was purified by silica gel chromatography ($SiO_2$, petroleum ether/ethyl acetate=30/1 to 10:1) to deliver 1-benzyl-3,3-dimethylpiperidin-4-one (10.00 g, 46.02 mmol, 46.02% yield) as a colorless oil.

Step 2:

3,3-Dimethylpiperidin-4-one

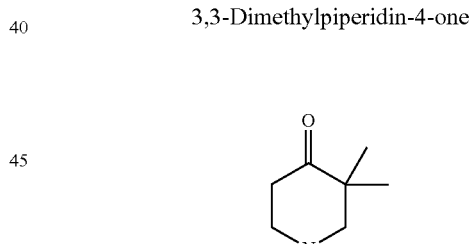

1-benzyl-3,3-dimethylpiperidin-4-one (5.00 g, 23.01 mmol, 1.00 eq) and 1-chloroethyl carbonochloridate (6.58 g, 46.02 mmol, 2.00 eq) were dissolved in dichloroethane (50.00 mL). The mixture was degassed with nitrogen for 3 times, then the mixture was stirred at 80° C. for 12 hours. The mixture was then concentrated, methanol (50.00 mL) was added and the mixture was stirred at 80° C. for an additional 4 hours. The reaction mixture was concentrated to remove MeOH and the residue was washed with dichloromethane (20 mL) and filtered. The solid was collected to deliver 3,3-dimethylpiperidin-4-one (3.00 g, 18.33 mmol, 79.67% yield, hydrochloride) as a white solid.

$^1$H NMR (400 MHz, METHANOL-$d_4$) δ 3.56 (t, J=6.7 Hz, 1H), 3.37 (s, 1H), 3.25-3.07 (m, 1H), 3.01 (s, 1H), 2.76 (t, J=6.7 Hz, 1H), 2.07-1.99 (m, 1H), 1.25 (s, 3H), 1.10 (d, J=13.2 Hz, 3H).

Step 3:

Benzyl 3,3-dimethyl-4-oxopiperidine-1-carboxylate

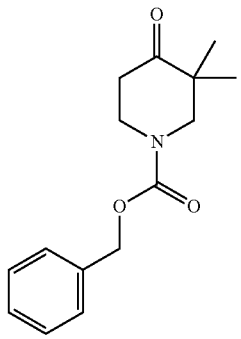 [SMILES: CC1(C)CN(C(=O)OCc2ccccc2)CCC1=O]

Sodium bicarbonate (1.28 g, 15.28 mmol, 2.50 eq) and CbzCl (1.25 g, 7.33 mmol, 1.20 eq) was added to a mixed solution of 3,3-dimethylpiperidin-4-one; hydrochloride (1.00 g, 6.11 mmol, 1.00 eq) in tetrahydrofuran (5.00 mL) and water (5.00 mL) at 0° C. The mixture was stirred at 15° C. for 12 hours. The reaction mixture was extracted with ethyl acetate (20 mL). The combined organic layers were washed with brine (10 mL×2), dried over sodium sulfate, filtered and concentrated under reduced pressure to deliver benzyl 3,3-dimethyl-4-oxopiperidine-1-carboxylate (1.60 g, 4.81 mmol, 78.66% yield, 78.5% purity) as a colorless oil. $^1$H NMR (400 MHz, CDCl$_3$) δ 7.35-7.25 (m, 6H), 5.11 (s, 2H), 3.72 (t, J=6.3 Hz, 2H), 3.42 (br. s., 2H), 2.44 (br. s., 2H), 1.02 (br. s., 6H).

Step 4:

Benzyl 5-bromo-3,3-dimethyl-4-oxopiperidine-1-carboxylate

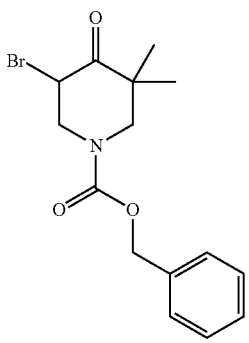 [SMILES: CC1(C)CN(C(=O)OCc2ccccc2)CC(Br)C1=O]

Phenyltrimethylamine tribromide (1.44 g, 3.83 mmol, 1.00 eq) was added to a solution of benzyl 3,3-dimethyl-4-oxopiperidine-1-carboxylate (1.10 g, 4.21 mmol, 1.10 eq) in THF (10.00 mL). The mixture was stirred at 15° C. for 1 hour. The mixture was quenched by adding water (10 mL) and then extracted with ethyl acetate (20 mL). The combined organic layers were washed with brine (10 mL), dried over sodium sulfate, filtered and concentrated under reduced pressure to deliver the crude benzyl 5-bromo-3,3-dimethyl-4-oxopiperidine-1-carboxylate (1.40 g, crude) as a yellow oil which was used directly in the next step.

Step 5:

Benzyl 2-(4-fluorophenyl)-7,7-dimethyl-4,6-dihydrothiazolo[5,4-c]pyridine-5-carboxylate

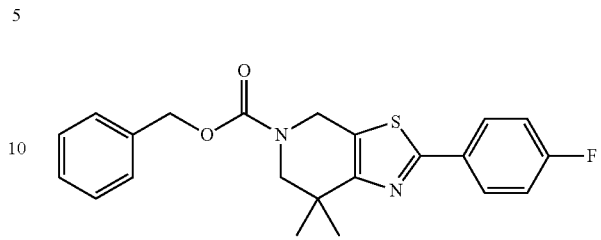

Benzyl 5-bromo-3,3-dimethyl-4-oxopiperidine-1-carboxylate (1.85 g, 5.44 mmol, 1.00 eq), 4-fluorothiobenzamide (843.89 mg, 5.44 mmol, 1.00 eq) were dissolved in isopropanol (20.00 mL), the mixture was degassed and replaced with nitrogen three times, and the mixture was allowed to react at 80° C. for 12 hours. The reaction mixture was diluted with water (20 mL) and extracted with ethyl acetate (40 mL). The combined organic layers were washed with brine 40 mL (20 mL×2), dried over sodium sulfate, filtered and concentrated under reduced pressure. The residue was purified by silica gel chromatography (SiO$_2$, petroleum ether/ethyl acetate=20/1 to 10:1) to deliver benzyl 2-(4-fluorophenyl)-7,7-dimethyl-4,6-dihydrothiazolo[5,4-c]pyridine-5-carboxylate (800.00 mg, 2.02 mmol, 37.09% yield) as a colorless oil.

Step 6:

2-(4-Fluorophenyl)-7,7-dimethyl-5,6-dihydro-4H-thiazolo[5,4-c]pyridine

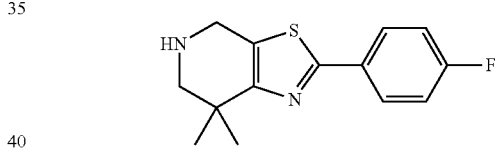

Benzyl 2-(4-fluorophenyl)-7,7-dimethyl-4,6-dihydrothiazolo[5,4-c]pyridine-5-carboxylate (500.00 mg, 1.26 mmol, 1.00 eq) was dissolved in a solution of hydrogen bromide/acetic acid (5.00 mL), and the mixture was replaced with nitrogen and then stirred at 15° C. for 2 hours. The reaction mixture was concentrated to remove part of the acetic acid and the solid was filtered to deliver 2-(4-fluorophenyl)-7,7-dimethyl-5,6-dihydro-4H-thiazolo[5,4-c]pyridine (400.00 mg, 1.17 mmol, 92.86% yield, hydrobromide) as a yellow solid. $^1$H NMR (400 MHz, CDCl$_3$) δ 7.35-7.25 (m, 6H), 5.11 (s, 2H), 3.72 (t, J=6.3 Hz, 2H), 3.42 (br. s., 2H), 2.44 (br. s., 2H), 1.02 (br. s., 6H).

Step 6:

(2S)-1-(2-Chloro-4-nitroimidazol-1-yl)-3-(2-(4-fluorophenyl)-7,7-dimethyl-4,6-dihydrothiazolo[5,4-c]pyridin-5-yl)-2-methylpropan-2-ol

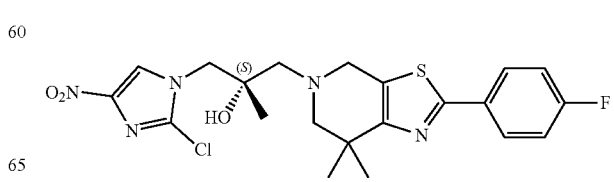

2-(4-Fluorophenyl)-7,7-dimethyl-5,6-dihydro-4H-thiazolo[5,4-c]pyridine (200.00 mg, 582.65 mmol, 1.00 eq, hydrobromide), 2-chloro-1-[[(2R)-2-methyloxiran-2-yl]methyl]-4-nitroimidazole (152.15 mg, 699.18 μmol, 1.20 eq) and diisopropylamine (225.91 mg, 1.75 mmol, 3.00 eq) were dissolved in ethanol (5.00 mL), and the mixture was replaced with nitrogen and then stirred at 80° C. for 12 hours. The reaction mixture was diluted with water (10 mL) and extracted with ethyl acetate (20 mL). The combined organic layers were washed with brine (10 mL), dried over sodium sulfate, filtered and concentrated under reduced pressure. The residue was purified by silica gel chromatography (SiO$_2$, petroleum ether/ethyl acetate=10/1 to 5/1) to deliver (2S)-1-(2-Chloro-4-nitroimidazol-1-yl)-3-(2-(4-fluorophenyl)-7,7-dimethyl-4,6-dihydrothiazolo[5,4-c]pyridin-5-yl)-2-methylpropan-2-ol (200.00 mg, 416.71 μmol, 71.52% yield) as a yellow oil. $^1$H NMR (300 MHz, CDCl$_3$) δ 8.05 (s, 1H), 7.94-7.84 (m, 2H), 7.12 (t, J=8.6 Hz, 2H), 4.09-3.78 (m, 4H), 2.90-2.57 (m, 4H), 1.47-1.35 (m, 6H), 1.31-1.26 (m, 3H).

Step 7:

(S)-2-((2-(4-Fluorophenyl)-7,7-dimethyl-6,7-dihydrothiazolo[5,4-c]pyridin-5(4H)-yl)methyl)-2-methyl-6-nitro-2,3-dihydroimidazo[2,1-b]oxazole Compound 60

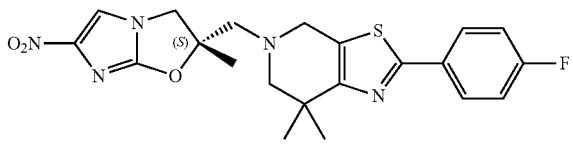

Sodium hydride (31.25 mg, 781.33 mmol, 1.50 eq) was added to a solution of (2S)-1-(2-chloro-4-nitroimidazol-1-yl)-3-(2-(4-fluorophenyl)-7,7-dimethyl-4,6-dihydrothiazolo[5,4-c]pyridin-5-yl)-2-methylpropan-2-ol (250.00 mg, 520.89 mmol, 1.00 eq) in DMF (5.00 mL) at 0° C. The mixture was stirred at 0° C. for 1 hour. The reaction mixture was added to a cooled saturated ammonium chloride solution (20 mL) and quenched, and then extracted with ethyl acetate (20 mL). The combined organic layers were washed with brine (10 mL), dried over sodium sulfate, filtered and concentrated under reduced pressure. The residue was purified by preparative separation chromatography (Instrument: GX-D; Column: Boston Green ODS 150*30 5u; Mobile phase: 58%-88%; ACN (+0.00225 FA); Rate: 25 mL/min; Monitored Wavelength: 220 nm/254 nm; Run length: 10 min/15 min; Column temperature: 30° C.) to deliver (S)-2-((2-(4-Fluorophenyl)-7,7-dimethyl-6,7-dihydrothiazolo[5,4-c]pyridin-5 (4H)-yl)methyl)-2-methyl-6-nitro-2,3-dihydroimidazo[2,1-b]oxazole compound 60 (72.40 mg, 163.25 μmol, 31.34% yield, 100% purity). $^1$H NMR (400 MHz, CDCl$_3$) δ 7.87 (dd, J=5.3, 8.8 Hz, 1H), 7.52 (s, 1H), 7.11 (t, J=8.6 Hz, 2H), 4.51 (d, J=9.7 Hz, 1H), 3.96 (d, J=9.7 Hz, 1H), 3.92-3.81 (m, 2H), 3.12 (d, J=15.1 Hz, 1H), 2.89 (d, J=11.5 Hz, 1H), 2.79 (d, J=15.1 Hz, 1H), 2.66 (d, J=11.5 Hz, 1H), 1.69 (s, 3H), 1.32 (s, 3H), 1.16 (s, 3H); LCMS (ESI) m/z: 444.2 (M+1).

Embodiment 61

(S)-2-(4-Fluorophenyl)-5-((2-methyl-6-nitro-2,3-dihydroimidazo[2,1-b]oxazol-2-yl)methyl)-4,5,6,7-tetrahydrooxazolo[5,4-c]pyridine Compound 61

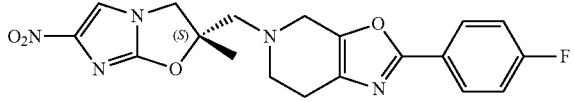

The synthesis method was as in Embodiment 41.

(S)-2-(4-Fluorophenyl)-5-((2-methyl-6-nitro-2,3-dihydroimidazo[2,1-b]oxazol-2-yl)methyl)-4,5,6,7-tetrahydrooxazolo[5,4-c]pyridine compound 61 (63.20 mg, 149.47 mmol, 8.12% yield, 94.452% purity). $^1$H NMR (400 MHz, CDCl$_3$) δ 7.94-7.86 (m, 2H), 7.46 (s, 1H), 7.06 (s, 2H), 4.35-4.29 (m, 1H), 3.91-3.85 (m, 1H), 3.77 (s, 2H), 3.09-2.97 (m, 2H), 2.93-2.84 (m, 1H), 2.75-2.67 (m, 1H), 2.56 (br. s., 2H), 1.58 (s, 3H). LCMS (ESI) m/z: 400.2 (M+1).

Embodiment 62

(S)-5-((2-Methyl-6-nitro-2,3-dihydroimidazo[2,1-b]oxazol-2-yl)methyl)-2-(3,4,5-trifluorophenyl)-4,5,6,7-tetrahydrooxazolo[5,4-c]pyridine Compound 62

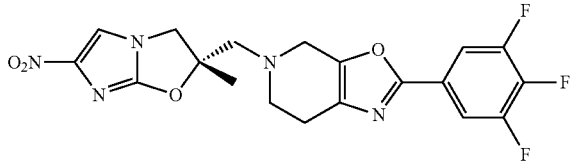

The synthesis method was as in Embodiment 41.

(S)-5-((2-Methyl-6-nitro-2,3-dihydroimidazo[2,1-b]oxazol-2-yl)methyl)-2-(3,4,5-trifluorophenyl)-4,5,6,7-tetrahydrooxazolo[5,4-c]pyridine compound 62 (222.70 mg, 484.42 μmol, 42.49% yield, 94.7% purity). $^1$H NMR (400 MHz, CDCl$_3$) δ 7.62 (t, J=7.2 Hz, 2H), 7.55 (s, 1H), 4.45-4.35 (m, 1H), 3.98 (d, J=9.8 Hz, 1H), 3.86 (s, 2H), 3.19-3.06 (m, 2H), 3.03-2.92 (m, 1H), 2.80 (d, J=14.8 Hz, 1H), 2.70-2.58 (m, 2H), 1.68 (s, 3H). LCMS (ESI) m/z: 436 (M+1).

Embodiment 63

(S)-2-Methyl-6-nitro-2-((2-(3,4,5-trifluorophenyl)-6,7-dihydrothiazolo[5,4-c]pyridin-5(4H)-yl)methyl)-2,3-dihydroimidazo[2,1-b]oxazole

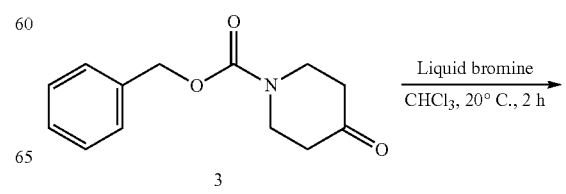

-continued

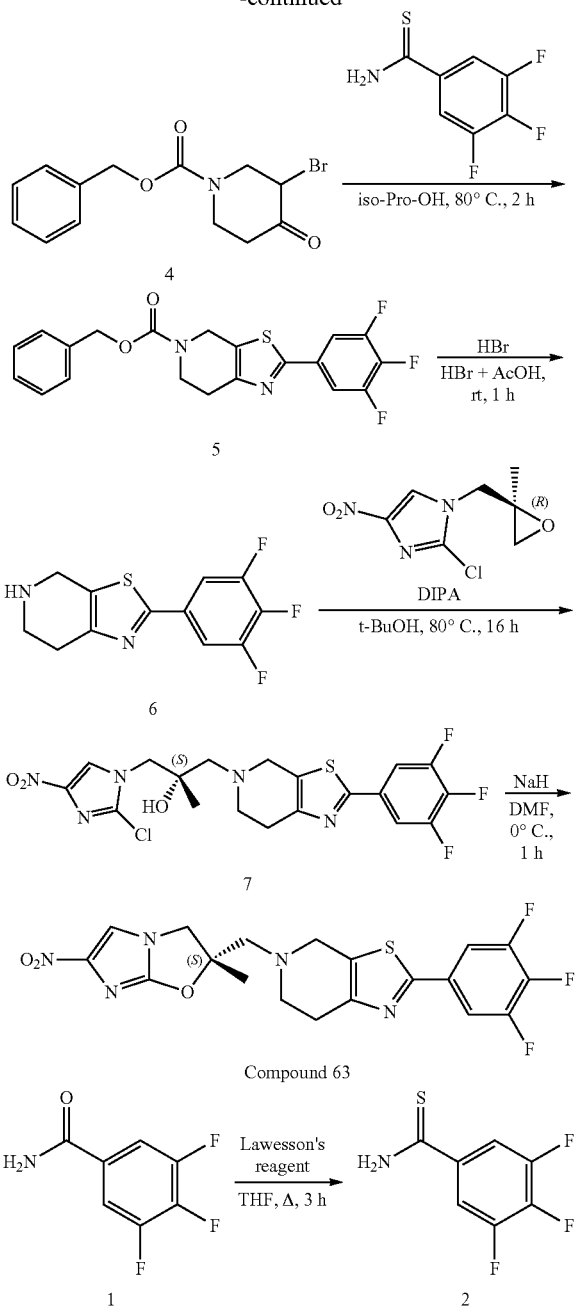

Step 1:

3,4,5-Trifluorobenzothioamide

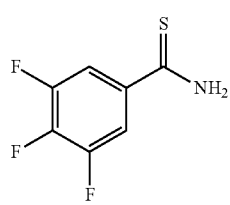 [SMILES: NC(=S)c1cc(F)c(F)c(F)c1]

Lawesson's reagent (7.37 g, 18.22 mmol, 1.10 eq) was added to a solution of 3,4,5-trifluorobenzamide (2.90 g, 16.56 mmol, 1.00 eq) in tetrahydrofuran (80.00 mL). The mixture was stirred at 70° C. for 3 hours. The reaction mixture was concentrated under reduced pressure to remove the solvent, and the residue was diluted with water (200 mL) and extracted with ethyl acetate (30 mL×3). The combined organic layers were washed with saturated brine (30 mL×2), dried over sodium sulfate, filtered and concentrated under reduced pressure. The residue was purified by silica gel chromatography (SiO$_2$, petroleum ether/ethyl acetate=5/1) to deliver 3,4,5-trifluorophenylthioamide (4.35 g, crude) as a yellow solid.

Step 2:

Benzyl 3-bromo-4-oxopiperidine-1-carboxylate

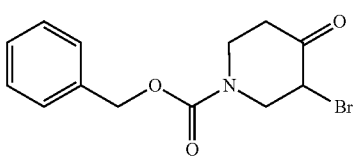 [SMILES: O=C1CCN(C(=O)OCc2ccccc2)CC1Br]

Liquid bromine (3.43 g, 21.44 mmol, 1.00 eq) was added dropwise to a solution of benzyl 4-oxopiperidine-1-carboxylate (5.00 g, 21.44 mmol, 1.00 eq) in chloroform (50.00 mL) at 0° C. under the nitrogen gas atmosphere. The mixture was stirred at 25° C. for 2 hours and the reaction mixture was added to a cooled saturated sodium sulfite solution (100 mL) and quenched, and then extracted with dichloromethane (50 mL×3). The combined organic layers were washed with saturated sodium carbonate (100 mL×2), dried over sodium sulfate, filtered and concentrated under reduced pressure to deliver the crude benzyl 3-bromo-4-oxopiperidine-1-carboxylate (7.10 g, crude) as a yellow oil which was used directly in the next step.

Step 3:

Benzyl 2-(3,4,5-trifluorophenyl)-6,7-dihydrothiazolo[5,4-c]pyridine-5(4H)-carboxylate

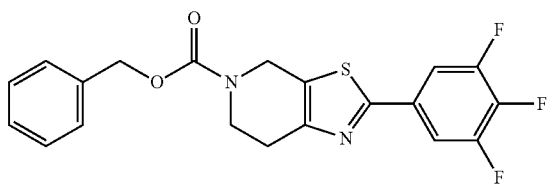 [SMILES: O=C(OCc1ccccc1)N1CCc2nc(-c3cc(F)c(F)c(F)c3)sc2C1]

3,4,5-Trifluorophenylthioamide (4.35 g, 22.74 mmol, 1.00 eq) was added to a solution of benzyl 3-bromo-4-oxopiperidine-1-carboxylate (7.10 g, 22.74 mmol, 1.00 eq) in isopropanol (50.00 mL). The mixture was stirred at 80° C. for 12 hours. The reaction mixture was concentrated to remove the solvent. The residue was purified by silica gel chromatography (SiO$_2$, petroleum ether/ethyl acetate=5/1 to 1:1, followed by dichloromethane:methanol=50:1) to deliver benzyl 2-(3,4,5-trifluorophenyl)-6,7-dihydrothiazolo[5,4-c]pyridine-5(4H)-carboxylate (1.00 g, crude) as a yellow oil. LCMS (ESI) m/z: 405 (M+1).

Step 4:

2-(3,4,5-Trifluorophenyl)-4,5,6,7-tetrahydrothiazolo[5,4-c]pyridine

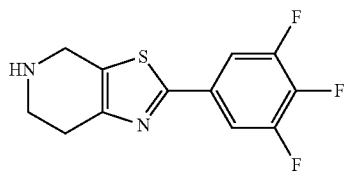 [SMILES: Fc1cc(-c2nc3c(s2)CNCC3)cc(F)c1F]

Benzyl 2-(3,4,5-trifluorophenyl)-6,7-dihydrothiazolo[5,4-c]pyridine-5(4H)-carboxylate (1.00 g, 2.47 mmol, 1.00 eq) was dissolved in a solution of hydrogen bromide/acetic acid (3.00 mL). The mixture was stirred at 25° C. for 2 hours. The reaction mixture was concentrated under reduced pressure to remove the solvent to deliver the crude 2-(3,4,5-trifluorophenyl)-4,5,6,7-tetrahydrothiazolo[5,4-c]pyridine (1.00 g, crude, hydrobromide) as a yellow solid and which was used directly in the next step. LCMS (ESI) m/z: 271 (M+1).

Step 5:

(S)-1-(2-Chloro-4-nitro-1H-imidazol-1-yl)-2-methyl-3-(2-(3,4,5-trifluorophenyl)-6,7-dihydrothiazolo[5,4-c]pyridin-5(4H)-yl)propan-2-ol

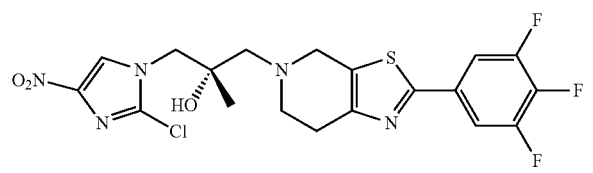 [SMILES: C[C@](O)(CN1CCc2nc(-c3cc(F)c(F)c(F)c3)sc2C1)Cn1cc([N+](=O)[O-])nc1Cl]

Diisopropylamine (386.41 mg, 2.99 mmol, 3.00 eq) was added to a solution of 2-(3,4,5-trifluorophenyl)-4,5,6,7-tetrahydrothiazolo[5,4-c]pyridine (350.00 mg, 996.61 μmol, 1.00 eq, hydrobromide) and (R)-2-chloro-1-((2-methyloxiran-2-yl)methyl)-4-nitro-1H-imidazole (260.25 mg, 1.20 mmol, 1.20 eq) in ethanol (10.00 mL). The mixture was stirred at 80° C. for 12 hours. The reaction mixture was concentrated under reduced pressure to remove the solvent, and the residue was purified by silica gel chromatography (SiO₂, petroleum ether/ethyl acetate=5/1 to 1:1) to deliver (S)-1-(2-chloro-4-nitro-1H-imidazol-1-yl)-2-methyl-3-(2-(3,4,5-trifluorophenyl)-6,7-dihydrothiazolo[5,4-c]pyridin-5(4H)-yl)propan-2-ol (200.00 mg, 409.94 μmol, 41.13% yield) as a yellow solid. LCMS (ESI) m/z: 488/490 (M+1/M+3).

Step 6:

(S)-2-Methyl-6-nitro-2-((2-(3,4,5-trifluorophenyl)-6,7-dihydrothiazolo[5,4-c]pyridin-5(4H)-yl)methyl)-2,3-dihydroimidazo[2,1-b]oxazole Compound 63

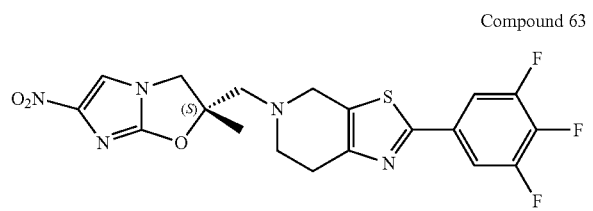

Sodium hydride (9.84 mg, 245.96 μmol, 1.20 eq) was added to a solution of (S)-1-(2-chloro-4-nitro-1H-imidazol-1-yl)-2-methyl-3-(2-(3,4,5-trifluorophenyl)-6,7-dihydrothiazolo[5,4-c]pyridin-5(4H)-yl)propan-2-ol (100.00 mg, 204.97 μmol, 1.00 eq) in DMF (2.00 mL) at 0° C. The mixture was stirred at 0° C. for 30 min, quenched with a saturated ammonium chloride solution (50 mL) and extracted with dichloromethane (10 mL×3). The combined organic layers were washed with saturated brine (10 mL×2), dried over sodium sulfate, filtered and concentrated under reduced pressure. The residue was purified by preparative separation chromatography (GX-F; Phenomenex Synergi C18 150*30 mm*4 um; acetonitrile 50%-80%; water (0.225% formic acid); Rate: 25 mL/min) to deliver (S)-2-Methyl-6-nitro-2-((2-(3,4,5-trifluorophenyl)-6,7-dihydrothiazolo[5,4-c]pyridin-5 (4H)-yl)methyl)-2,3-dihydroimidazo[2,1-b]oxazole compound 63 (23.00 mg, 50.67 μmol, 24.72% yield, 99.448% purity). ¹H NMR (400 MHz, CDCl₃) δ 7.60-7.48 (m, 3H), 4.41 (d, J=8.0 Hz, 2H), 4.03-3.91 (m, 3H), 3.22-3.10 (m, 2H), 3.09-2.99 (m, 1H), 2.91-2.83 (m, 2H), 2.79 (d, J=16.0 Hz, 2H), 1.68 (s, 3H). LCMS (ESI) m/z: 452(M+1).

Embodiment 64

(S)-2-(4-Fluorophenyl)-5-((2-methyl-6-nitro-2,3-dihydroimidazo[2,1-b]oxazol-2-yl)methyl)-4,5,6,7-tetrahydrofuro[3,2-c]pyridine

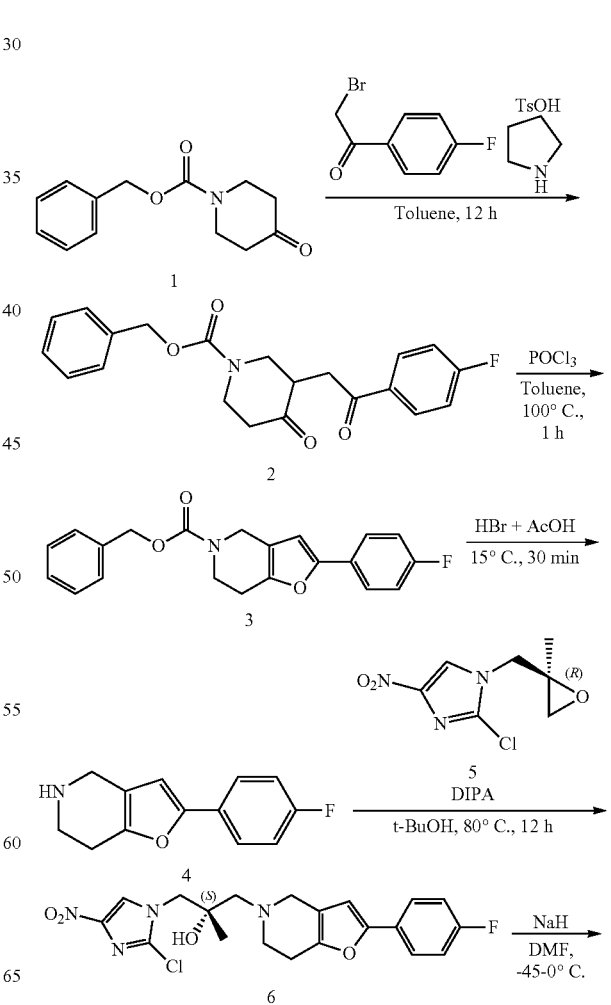

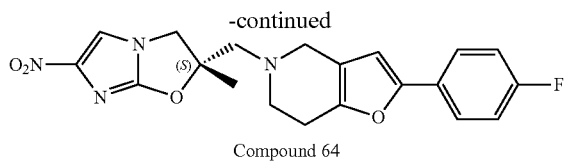

Compound 64

Step 1:

Benzyl 3-(2-(4-fluorophenyl)-2-oxoethyl)-4-oxopiperidine-1-carboxylate

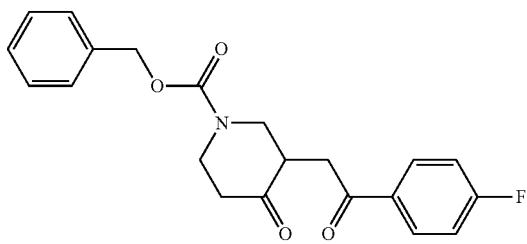 [SMILES: O=C(CC1CN(C(=O)OCc2ccccc2)CCC1=O)c1ccc(F)cc1]

Benzyl 4-oxopiperidine-1-carboxylate (5.00 g, 21.44 mmol, 1.00 eq) and pyrrolidine (6.10 g, 85.76 mmol, 4.00 eq), TsOH.H$_2$O (407.83 mg, 2.14 mmol, 0.10 eq) were dissolved in toluene (20.00 mL). The mixture was heated to 130° C. and stirred while separating water with a water separator. After 12 hours, about 0.5 mL of water was separated and the mixture was concentrated at 50° C. The crude product benzyl 4-pyrrolidin-1-yl-3,6-dihydro-2H-pyridine-1-carboxylate (7.00 g, crude) was a brown oil. 2-Bromo-1-(4-fluorophenyl) ethanone (1.14 g, 5.24 mmol, 1.00 eq) was added in one portion to a solution of the crude product (1.50 g, 5.24 mmol, 1.00 eq) in toluene (15.00 mL) at 10° C. under the nitrogen gas atmosphere. The mixture was stirred at 10° C. for 12 hours, concentrated, and the residue was purified by silica gel chromatography (petroleum ether/ethyl acetate=10/1, 2/1) to deliver benzyl 3-(2-(4-fluorophenyl)-2-oxoethyl)-4-oxopiperidine-1-carboxylate (550.00 mg, 1.49 mmol, 28.41% yield) as a yellow oil.

Step 2:

Benzyl 2-(4-fluorophenyl)-6,7-dihydrofuro[3,2-c]pyridine-5(4H)-carboxylate

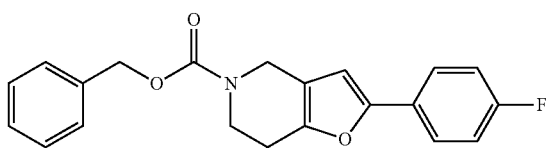 [SMILES: O=C(OCc1ccccc1)N1CCc2oc(-c3ccc(F)cc3)cc2C1]

Phosphorus oxychloride (1.81 g, 11.80 mmol, 10.93 eq) was added in one portion to a solution of benzyl 3-(2-(4-fluorophenyl)-2-oxoethyl)-4-oxopiperidine-1-carboxylate (400.00 mg, 1.08 mmol, 1.00 eq) in toluene (6.00 mL) at 15° C. under the nitrogen gas atmosphere. The mixture was stirred at 100° C. for 1 hour. The mixture was poured into water (30 mL) and stirred for 5 minutes. The aqueous phase was extracted with ethyl acetate (50 mL×3). The combined organic phases were washed with brine (30 mL), dried over anhydrous sodium sulfate, filtered and concentrated in vacuo. The residue was purified by silica gel chromatography (petroleum ether/ethyl acetate=1/0, 10/1) to deliver benzyl 2-(4-fluorophenyl)-6,7-dihydrofuro[3,2-c]pyridine-5(4H)-carboxylate (200.00 mg, 569.20 μmot, 52.70% yield) as a yellow oil.

Step 3:

2-(4-Fluorophenyl)-4,5,6,7-tetrahydrofuro[3,2-c]pyridine

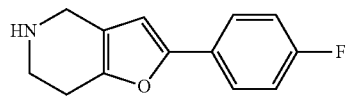

Benzyl 2-(4-fluorophenyl)-6,7-dihydrofuro[3,2-c]pyridine-5(4H)-carboxylate (233.00 mg, 663.12 μmol, 1.00 eq) was dissolved in a solution of hydrogen bromide in acetic acid (5 mL, 92.08 mmol, 138.86 eq). The mixture was concentrated at 45° C. to deliver 2-(4-fluorophenyl)-4,5,6,7-tetrahydrofuro[3,2-c]pyridine (200.00 mg, crude, hydrobromide) solid. LCMS (ESI) m/z: 218.1 (M+1).

Step 4:

(2S)-1-(2-Chloro-4-nitroimidazol-1-yl)-3-(2-(4-fluorophenyl)-6,7-dihydro-4H-furo[3,2-c]pyridin-5-yl)-2-methylpropan-2-ol

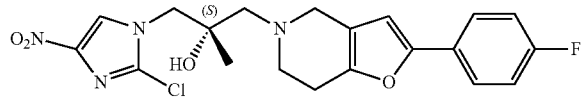

Diisopropylamine (171.40 mg, 1.33 mmol, 2.00 eq) was added in one portion to a solution of 2-(4-fluorophenyl)-4,5,6,7-tetrahydrofuro[3,2-c]pyridine (197.71 mg, 663.12 μmol, 1.00 eq, hydrobromide) and 2-chloro-1-[[(2R)-2-methyloxiran-2-yl]methyl]-4-nitroimidazole (158.73 mg, 729.43 μmol, 1.10 eq) in tert-butyl alcohol (10.00 mL) under the nitrogen gas atmosphere. The mixture was stirred at 80° C. for 12 hours and the mixture was concentrated at 45° C. The residue was purified by silica gel chromatography (petroleum ether/ethyl acetate=1/0, 2/1) to deliver (2S)-1-(2-chloro-4-nitroimidazol-1-yl)-3-(2-(4-fluorophenyl)-6,7-dihydro-4H-furo[3,2-c]pyridin-5-yl)-2-methylpropan-2-ol (190.00 mg, 436.93 μmol, 65.89% yield) as a yellow solid. $^1$H NMR (400 MHz, CDCl$_3$) δ 8.08 (s, 1H), 7.64-7.57 (m, 2H), 7.12-7.04 (m, 2H), 6.39 (s, 1H), 4.07-4.02 (m, 2H), 3.65 (d, J=14.9 Hz, 2H), 3.12-2.95 (m, 2H), 2.85-2.78 (m, 2H), 2.70 (d, J=14.1 Hz, 1H), 2.54 (d, J=14.2 Hz, 1H), 1.20 (s, 3H).

Step 5:

(S)-2-(4-Fluorophenyl)-5-((2-methyl-6-nitro-2,3-dihydroimidazo[2,1-b]oxazol-2-yl)methyl)-4,5,6,7-tetrahydrofuro[3,2-c]pyridine

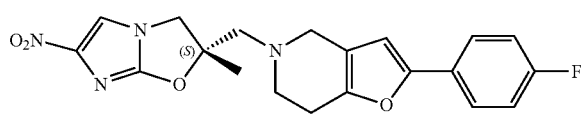

Compound 64

Sodium hydride (34.95 mg, 873.86 µmol, 2.00 eq) was added in one portion to a solution of (2S)-1-(2-chloro-4-nitroimidazol-1-yl)-3-(2-(4-fluorophenyl)-6,7-dihydro-4H-furo[3,2-c]pyridin-5-yl)-2-methylpropan-2-ol (190.00 mg, 436.93 µmol, 1.00 eq) in DMF (5.00 mL) at −45° C. under the nitrogen gas atmosphere. The mixture was stirred at −45 to 0° C. for 10 minutes and the mixture was poured into a saturated ammonium chloride solution (30 mL) and stirred for 5 minutes. And extracted with ethyl acetate (50 mL×3). The combined organic phases were washed with brine (30 mL), dried over anhydrous sodium sulfate, filtered and concentrated in vacuo. The residue was purified by preparative separation chromatography (GX-D; Boston Green ODS 150*30 5u; acetonitrile 40%-70%; water (0.225% fomic acid); 25 mL/min) to deliver (S)-2-(4-fluorophenyl)-5-((2-methyl-6-nitro-2,3-dihydroimidazo[2,1-b]oxazol-2-yl)methyl)-4,5,6,7-tetrahydrofuro[3,2-c]pyridine compound 64 (33.40 mg, 82.41 µmol, 18.86% yield, 98.3% purity). $^1$H NMR (400 MHz, CDCl$_3$) δ 7.58 (dd, J=5.3, 8.8 Hz, 2H), 7.54 (s, 1H), 7.06 (t, J=8.7 Hz, 2H), 6.36 (s, 1H), 4.42 (d, J=9.5 Hz, 1H), 3.94 (d, J=9.5 Hz, 1H), 3.63 (s, 2H), 3.19-3.06 (m, 2H), 2.98-2.88 (m, 1H), 2.74 (d, J=14.9 Hz, 1H), 2.71-2.56 (m, 2H), 1.67 (s, 3H). LCMS (ESI) m/z: 399.1 (M+1).

Embodiment 65

(S)-2-(3,4-Difluorophenyl)-5-((2-methyl-6-nitro-2,3-dihydroimidazo[2,1-b]oxazol-2-yl)methyl)-4,5,6,7-tetrahydrooxazolo[4,5-c]pyridine

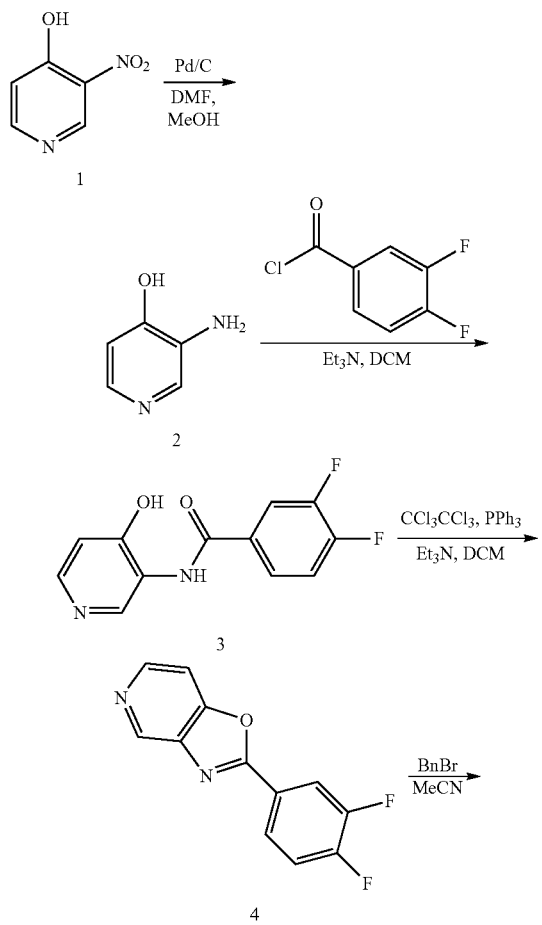

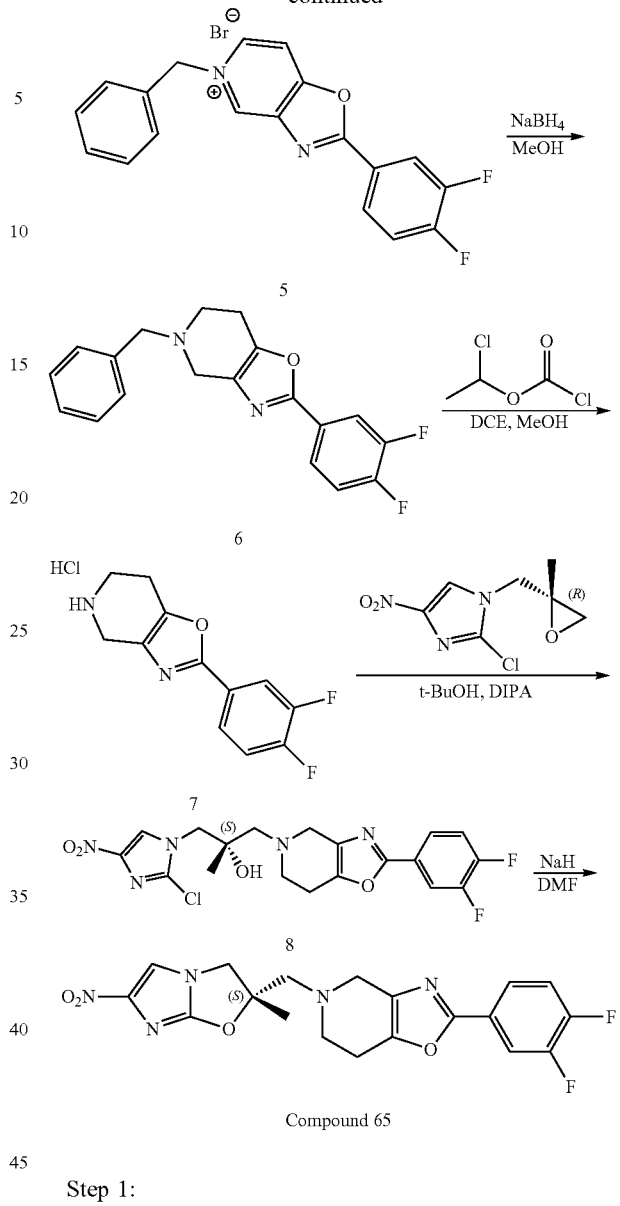

Step 1:

3-Aminopyridin-4-ol

Palladium on carbon (3.00 g, 214.13 mmol, 1.00 eq) was added in one portion to a mixed solution of 3-nitropyridin-4-ol (30.00 g, 214.13 mmol, 1.00 eq) in methanol (500.00 mL) and DMF (10.00 mL) at 15° C. under the nitrogen gas atmosphere. The mixture was stirred at 15° C. under hydrogen (25-40 psi) for 4 hours, filtered and the filtrate was concentrated to dry. Hydrochloride/Methanol (4N, 100 mL) was added to the residue and the mixture was filtered and the cake was washed with dichloromethane (200 mL), filtered and the filter cake was collected to deliver 3-aminopyridin-4-ol (31.00 g, 211.50 mmol, 98.77% yield, hydrochloric acid) as an off-white solid. $^1$H NMR (400 MHz, DMSO-d$_6$) δ 14.44 (br, s, 1H), 7.96-7.84 (m, 2H), 7.27 (d, J=6.3 Hz, 1H).

Step 2:

3,4-Difluoro-N-(4-hydroxy-3-pyridyl)benzamide

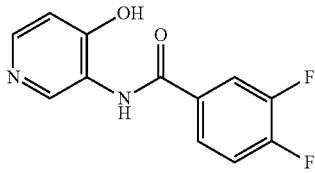 [SMILES: O=C(Nc1cnccc1O)c1ccc(F)c(F)c1]

Triethylamine (41.42 g, 409.36 mmol, 56.74 mL, 4.00 eq) was added in one portion to a solution of 3-aminopyridin-4-ol (15.00 g, 102.34 mmol, 1.00 eq, hydrochloride) in dichloromethane (200.00 mL) at 0° C. Then, 3,4-difluorobenzoyl chloride (25.30 g, 143.28 mmol, 17.94 mL, 1.40 eq) was added and the resulting mixture was stirred at 15° C. for 12 hours. The mixture was filtered and the filter cake was washed with dichloromethane (50 mL) to deliver 3,4-difluoro-N-(4-hydroxy-3-pyridyl)benzamide (30.00 g, crude) as a yellow solid. $^1$H NMR (400 MHz, DMSO-d$_6$) δ 11.91 (br, s, 1H), 9.39 (s, 1H), 8.69 (br, s, 1H), 7.97 (ddd, J=2.1, 7.8, 11.2 Hz, 1H), 7.84-7.77 (m, 1H), 7.73 (d, J=5.1 Hz, 1H), 7.62 (td, J=8.4, 10.3 Hz, 1H), 6.31 (d, J=7.0 Hz, 1H). LCMS (ESI) m/z: 251 (M+1).

Step 3:

2-(3,4-Difluorophenyl)oxazolo[4,5-c]pyridine

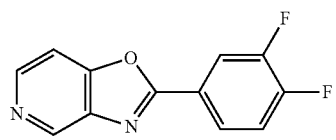 [SMILES: Fc1ccc(-c2nc3cnccc3o2)cc1F]

Hexachloroethane (35.48 g, 149.88 mmol, 16.98 mL, 2.50 eq), triphenylphosphine (47.17 g, 179.86 mmol, 3.00 eq) and triethylamine (48.53 g, 479.62 mmol, 66.48 mL, 8.00 eq) were dissolved in dichloromethane (200.00 mL), the mixture was stirred at 15° C. for 0.5 hour and then 3,4-difluoro-N-(4-hydroxy-3-pyridyl)benzamide (15.00 g, 59.95 mmol, 1.00 eq) was added in portions. The resulting mixture was then stirred at 15° C. for 12 hours. The reaction mixture was added dropwise to 1N hydrochloric acid at 0° C. and the aqueous layer was extracted with dichloromethane (100 mL×3). The pH of the aqueous layer was then adjusted to 8 with a saturated aqueous sodium bicarbonate solution and the aqueous layer was extracted with dichloromethane (100 mL×3). The combined organic phases were washed with brine (100 mL), dried over anhydrous sodium sulfate, filtered and concentrated in vacuo to deliver 2-(3,4-difluorophenyl)oxazolo[4,5-c]pyridine (4.50 g, 19.38 mmol, 32.33% yield) as a yellow solid. $^1$H NMR (400 MHz, CDCl$_3$) δ 9.13 (d, J=0.8 Hz, 1H), 8.67-8.58 (m, 1H), 8.16-8.02 (m, 2H), 7.62-7.53 (m, 1H), 7.38 (td, J=8.4, 9.3 Hz, 1H). LCMS (ESI) m/z: 233 (M+1).

Step 4:

5-Benzyl-2-(3,4-difluorophenyl)oxazolo[4,5-c]pyridin-5-ium bromide

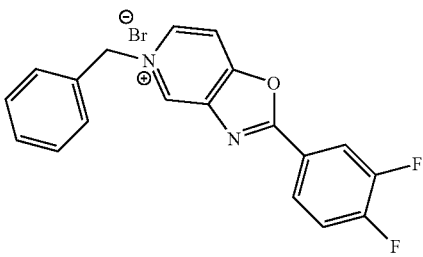 [SMILES: Fc1ccc(-c2nc3c[n+](Cc4ccccc4)ccc3o2)cc1F ; [Br-]]

Benzyl bromide was added (16.57 g, 96.90 mmol, 11.51 mL, 5.00 eq) 2-(3,4-difluorophenyl)oxazolo[4,5-c]pyridine (4.50 g, 19.38 mmol, 1.00 eq) in acetonitrile (80.00 mL) at 0° C. under the nitrogen gas atmosphere. The mixture was stirred at 15° C. for 12 hours. The mixture was filtered and the filter cake was collected to deliver 5-benzyl-2-(3,4-difluorophenyl)oxazolo[4,5-c]pyridin-5-ium bromide (6.00 g, 14.88 mmol, 76.78% yield) as a white solid. $^1$H NMR (400 MHz, METHANOL-d$_4$) δ 9.78 (s, 1H), 9.12 (d, J=7.0 Hz, 1H), 8.46 (d, J=6.8 Hz, 1H), 8.37-8.21 (m, 2H), 7.69-7.55 (m, 3H), 7.54-7.42 (m, 3H), 6.04-5.95 (m, 2H). LCMS (ESI) m/z: 323 (M+1).

Step 5:

5-Benzyl-2-(3,4-difluorophenyl)-6,7-dihydro-4H-oxazolo[4,5-c]pyridine

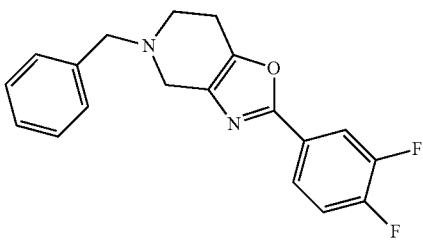 [SMILES: Fc1ccc(-c2nc3c(o2)CCN(Cc2ccccc2)C3)cc1F]

Sodium borohydride (4.69 g, 124.00 mmol, 10.00 eq) was added to a solution of 5-benzyl-2-(3,4-difluorophenyl)oxazolo[4,5-c]pyridin-5-ium bromide (5.00 g, 12.40 mmol, 1.00 eq) in methanol (80.00 mL) at 0° C. under the nitrogen gas atmosphere. The mixture was stirred at 15° C. for 12 hours. Water (200 mL) was added to the mixture, and then extracted with ethyl acetate (200 mL×4). The combined organic phases were washed with saturated brine (100 mL), dried over anhydrous sodium sulfate, filtered and concentrated in vacuo. The residue was purified by silica gel chromatography (column height: 250 mm, diameter: 100 mm, 100 to 200 mesh silica gel, petroleum ether/ethyl acetate=20/1 to 5/1) to deliver 5-benzyl-2-(3,4-difluorophenyl)-6,7-dihydro-4H-oxazolo[4,5-c]pyridine (3.80 g, crude) as a yellow oil. $^1$H NMR (400 MHz, CDCl$_3$) δ 7.81 (ddd, J=2.1, 7.6, 11.0 Hz, 1H), 7.77-7.72 (m, 1H), 7.43-7.30 (m, 5H), 7.28-7.19 (m, 2H), 3.82-3.76 (m, 2H), 3.60-3.53 (m, 2H), 2.95-2.88 (m, 2H), 2.88-2.79 (m, 2H).

Step 6:

2-(3,4-Difluorophenyl)-4,5,6,7-tetrahydrooxazolo[4,5-c]pyridine hydrochloride

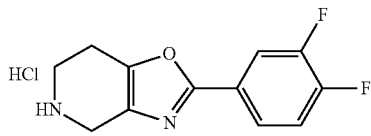

1-Chloroethyl carbonochloridate (4.99 g, 34.92 mmol, 3.00 eq) was added in one portion to a solution of 5-benzyl-2-(3,4-difluorophenyl)-6,7-dihydro-4H-oxazolo[4,5-c]pyridine (3.80 g, 11.64 mmol, 1.00 eq) in dichloroethane (60.00 mL) at 0° C. under the nitrogen gas atmosphere. The mixture was stirred at 100° C. for 12 hours. The mixture was concentrated to remove the solvent, methanol (80 mL) was added to the residue, and the mixture was stirred at 80° C. for 1 hour. The mixture was then concentrated to dryness and the residue was added with ethyl acetate (50 mL). The mixture was filtered and the cake was collected to give 2-(3,4-difluorophenyl)-4,5,6,7-tetrahydrooxazolo[4,5-c]pyridine hydrochloride (3.80 g, crude, hydrochloride) as a yellow solid. $^1$H NMR (400 MHz, DMSO-$d_6$) δ 9.85 (br, s, 2H), 8.01-7.93 (m, 1H), 7.87-7.79 (m, 1H), 7.69-7.59 (m, 1H), 4.20 (br, s, 2H), 3.52-3.49 (m, 2H), 3.12-3.03 (m, 2H).

Step 7:

(2S)-1-(2-Chloro-4-nitroimidazol-1-yl)-3-(2-(3,4-difluorophenyl)-6,7-dihydro-4H-oxazolo[4,5-c]pyridin-5-yl)-2-methylpropan-2-ol

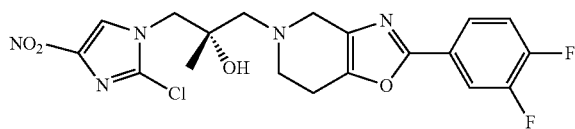 [SMILES: C[C@](O)(CN1CCc2oc(-c3ccc(F)c(F)c3)nc2C1)Cn1cc([N+](=O)[O-])nc1Cl]

Diisopropylamine (2.37 g, 18.34 mmol, 3.20 mL, 2.50 eq) was added in one portion to a solution of 2-(3,4-difluorophenyl)-4,5,6,7-tetrahydrooxazolo[4,5-c]pyridine (2.00 g, 7.33 mmol, 1.00 eq, hydrochloride) and 2-chloro-1-[[(2R)-2-methyloxiran-2-yl]methyl]-4-nitroimidazole (1.60 g, 7.33 mmol, 1.00 eq) in tert-butanol (30.00 mL) at 15° C. under the nitrogen gas atmosphere. The mixture was stirred at 100° C. for 12 hours. The mixture was concentrated to dryness and the residue was purified by silica gel chromatography (column height: 250 mm, diameter: 100 mm, 100 to 200 mesh silica gel, petroleum ether/ethyl acetate=20/1 to 1/1) to deliver (2S)-1-(2-chloro-4-nitroimidazol-1-yl)-3-(2-(3,4-difluorophenyl)-6,7-dihydro-4H-oxazolo[4,5-c]pyridin-5-yl)-2-methylpropan-2-ol (1.00 g, 2.20 mmol, 30.06% yield) as a yellow solid. LCMS (ESI) m/z: 454 (M+1).

Step 8:

(S)-2-(3,4-Difluorophenyl)-5-((2-methyl-6-nitro-2,3-dihydroimidazo[2,1-b]oxazol-2-yl)methyl)-4,5,6,7-tetrahydrooxazolo[4,5-c]pyridine Compound 65

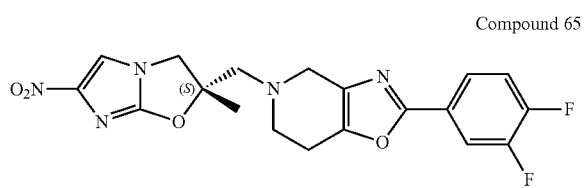

Sodium hydride (176.00 mg, 4.40 mmol, 60% purity, 2.00 eq) was added in one portion to a solution of (2S)-1-(2-chloro-4-nitroimidazol-1-yl)-3-(2-(3,4-difluorophenyl)-6,7-dihydro-4H-oxazolo[4,5-c]pyridin-5-yl)-2-methylpropan-2-ol (1.00 g, 2.20 mmol, 1.00 eq) in DMF (10.00 mL) at −5° C. under the nitrogen gas atmosphere. The mixture was stirred at −5° C. for 0.5 hour. The mixture was added dropwise to a solution of ammonium chloride (100 mL), filtered and the filter cake was collected to give the crude product which was purified by silica gel chromatography (column height: 250 mm, diameter: 100 mm, 100 to 200 mesh silica gel, petroleum ether/ethyl acetate=20/1 to 1/1) to deliver (S)-2-(3,4-difluorophenyl)-5-((2-methyl-6-nitro-2,3-dihydroimidazo[2,1-b]oxazol-2-yl)methyl)-4,5,6,7-tetrahydrooxazolo[4,5-c]pyridine (386.40 mg, 907.28 μmol, 41.24% yield, 98.0% purity). $^1$H NMR (400 MHz, CDCl$_3$) δ 7.80 (ddd, J=2.0, 7.6, 10.9 Hz, 1H), 7.74 (ddd, J=1.7, 4.0, 8.6 Hz, 1H), 7.55-7.51 (m, 1H), 7.24 (td, J=8.3, 9.8 Hz, 1H), 4.37 (d, J=9.7 Hz, 1H), 3.96 (d, J=9.7 Hz, 1H), 3.77-3.65 (m, 2H), 3.23 (td, J=4.9, 12.1 Hz, 1H), 3.16 (d, J=15.1 Hz, 1H), 2.94 (ddd, J=4.6, 7.9, 12.3 Hz, 1H), 2.78 (d, J=15.1 Hz, 1H), 2.75-2.66 (m, 1H), 2.66-2.55 (m, 1H), 1.68 (s, 3H). LCMS (ESI) m/z: 418 (M+1).

Embodiment 66

(S)-2-(4-Fluorophenyl)-5-((2-methyl-6-nitro-2,3-dihydroimidazo[2,1-b]oxazol-2-yl)methyl)-4,5,6,7-tetrahydrooxazolo[4,5-c]pyridine Compound 66

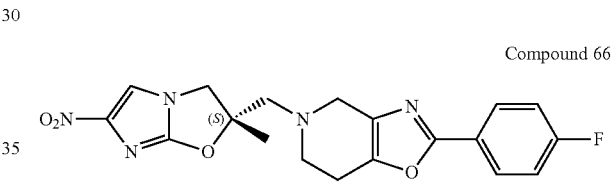

The synthesis method was as in Embodiment 65.

(S)-2-(4-Fluorophenyl)-5-((2-methyl-6-nitro-2,3-dihydroimidazo[2,1-b]oxazol-2-yl)methyl)-4,5,6,7-tetrahydrooxazolo[4,5-c]pyridine compound 66 (16.60 mg, 39.04 μmol, 21.27% yield, 93.931% purity). $^1$H NMR (400 MHz, CDCl$_3$) δ 7.94-7.84 (m, 2H), 7.45 (s, 1H), 7.09 (s, 2H), 4.32-4.22 (m, 1H), 3.96-3.70 (m, 3H), 3.31-3.17 (m, 2H), 3.04-2.70 (m, 4H), 1.63 (s, 3H). LCMS (ESI) m/z: 400.2 (M+1).

Embodiment 67

(S)-2-((2-(4-Fluorophenyl)-6,7-dihydrothiazolo[4,5-c]pyridin-5(4H)-yl)methyl)-2-methyl-6-nitro-2,3-dihydroimidazo[2,1-b]oxazole

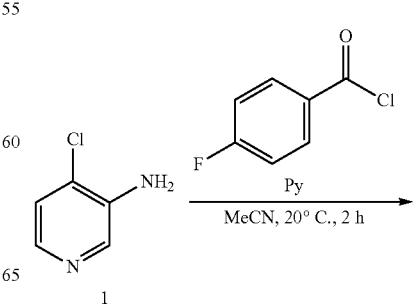

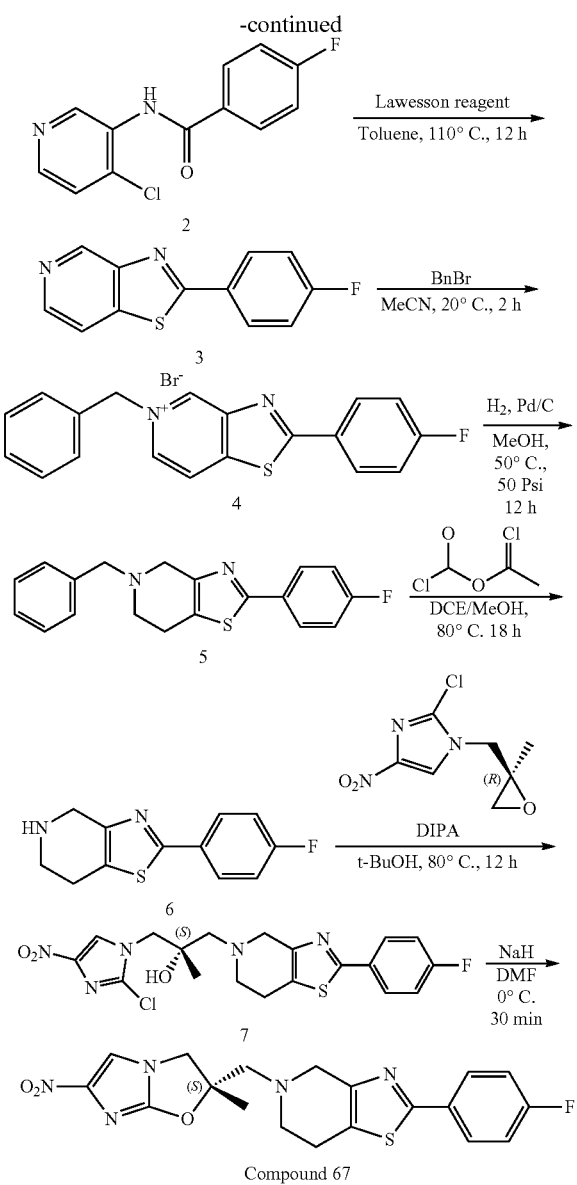

(200 mL×3). The combined organic layers were dried over sodium sulfate, filtered and concentrated under reduced pressure to deliver N-(4-chloro-3-pyridinyl)-4-fluorobenzamide (3.20 g, 12.77 mmol, 82.07% yield) as a white solid. $^1$H NMR (300 MHz, CDCl$_3$) δ 9.65 (s, 1H), 8.28 (d, J=5.27 Hz, 1H), 8.12 (br. s., 1H), 7.93-7.83 (m, 2H), 7.33 (d, J=5.09 Hz, 1H), 7.22-7.11 (m, 3H).

Step 2:

2-(4-Fluorophenyl)thiazolo[4,5-c]pyridine

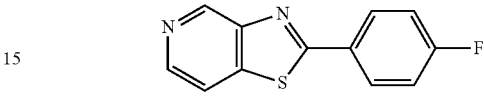

Lawesson's reagent (3.62 g, 8.94 mmol, 0.70 eq) was added to a solution of N-(4-chloro-3-pyridinyl)-4-fluorobenzamide (3.20 g, 12.77 mmol, 1.00 eq) in toluene (50.00 mL). The mixture was stirred at 110° C. for 12 hours. The reaction mixture was concentrated, a saturated sodium bicarbonate solution (100 mL) was added to the residue, and then extracted with dichloromethane (150 mL×3). The combined organic layers were dried over sodium sulfate, filtered and concentrated under reduced pressure. The residue was purified by silica gel chromatography (column height: 300 mm, diameter: 50 mm, 100 to 200 mesh silica gel, petroleum ether/ethyl acetate=5/1, 3/1, 1/1) to deliver 2-(4-fluorophenyl)thiazolo[4,5-c]pyridine (1.50 g, 6.51 mmol, 51.01% yield) as a white solid. $^1$H NMR (400 MHz, CDCl$_3$) δ 9.28 (s, 1H), 8.46 (d, J=5.52 Hz, 1H), 8.09-8.00 (m, 2H), 7.79 (d, J=5.40 Hz, 1H), 7.21-7.09 (m, 2H).

Step 3:

5-Benzyl-2-(4-fluorophenyl)thiazolo[4,5-c]pyridin-5-ium bromide

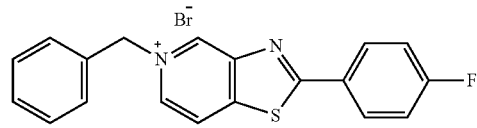 [SMILES: [Br-] ; Fc1ccc(-c2nc3c[n+](Cc4ccccc4)ccc3s2)cc1]

2-(4-Fluorophenyl)thiazolo[4,5-c]pyridine (700.00 mg, 3.04 mmol, 1.00 eq) and benzyl bromide (519.94 mg, 3.04 mmol, 1.00 eq) were dissolved in acetonitrile (5.00 mL). The mixture was replaced with nitrogen and then stirred at 20° C. for 2 hours. The mixture was filtered and the filter cake was washed with dichloromethane (20 mL). The filter cake was collected to deliver 5-benzyl-2-(4-fluorophenypthiazolo[4,5-c]pyridin-5-ium bromide (1.20 g, 2.99 mmol, 98.36% yield) as a white solid.

Step 4:

5-Benzyl-2-(4-fluorophenyl)-4,5,6,7-tetrahydrothiazolo[4,5-c]pyridine

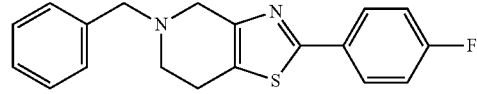 [SMILES: Fc1ccc(-c2nc3c(s2)CCN(Cc2ccccc2)C3)cc1]

Step 1:

N-(4-Chloro-3-pyridinyl)-4-fluorobenzamide

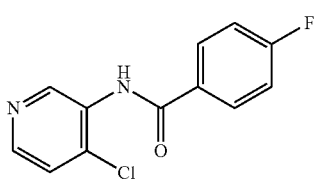

Pyridine (2.46 g, 31.12 mmol, 2.00 eq) and 4-fluorobenzoyl chloride (2.71 g, 17.12 mmol, 1.10 eq) were added to a solution of 4-chloropyridin-3-amine (2.00 g, 15.56 mmol, 1.00 eq) in acetonitrile (20.00 mL). The mixture was stirred at 20° C. for 2 hours. The reaction mixture was concentrated under reduced pressure. Then water (100 mL) was added and then the mixture was extracted with dichloromethane Palladium hydroxide/carbon (157.28 mg, 1.12 mmol, 0.50 eq) was added to a solution of 5-benzyl-2-(4-fluorophenypthiazolo[4,5-c]pyridin-5-ium bromide (900.00 mg, 2.24 mmol, 1.00 eq) in methanol (200.00 mL) under the nitrogen gas atmosphere. The suspension was degassed and replaced with hydrogen three times. The mixture was stirred in hydrogen (50 psi) at 50° C. for 12 hours. The reaction was filtered. The filtrate was concentrated under reduced pressure to deliver 5-benzyl-2-(4-fluorophenyl)-4,5,6,7-tetrahydrothiazolo[4,5-c]pyridine (580.00 mg, 1.79 mmol, 79.91% yield) as a white solid. $^1$H NMR (400 MHz, METHANOL-$d_4$) δ 8.01-7.91 (m, 2H), 7.68-7.51 (m, 5H), 7.23 (t, J=8.72 Hz, 2H), 4.59 (s, 2H), 4.49-4.37 (m, 2H), 3.74 (br. s., 2H), 3.38-3.33 (m, 2H).

Step 5:

2-(4-Fluorophenyl)-4,5,6,7-tetrahydro[4,5-c]pyridine

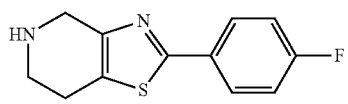

1-Chloroethyl carbonochloridate (396.74 mg, 2.78 mmol, 1.50 eq) was added to a solution of 5-benzyl-2-(4-fluorophenyl)-4,5,6,7-tetrahydrothiazolo[4,5-c]pyridine (600.00 mg, 1.85 mmol, 1.00 eq) in dichloroethane (5.00 mL). The mixture was stirred at 80° C. for 16 hours. The dichloroethane was removed by concentration and methanol (5.00 mL) was added, and the mixture was stirred at 60° C. for 2 hours. The mixture was filtered and the cake was dried to deliver 2-(4-fluorophenyl)-4,5,6,7-tetrahydro[4,5-c]pyridine (280.00 mg, 1.20 mmol, 64.60% yield) as a white solid. LCMS (ESI) m/z: 235 (M+1).

Step 6:

(2S)-1-(2-Chloro-4-nitroimidazol-1-yl)-3-(2-(4-fluorophenyl)-6,7-dihydro-4H-thiazolo[4,5-c]pyridin-5-yl)-2-methylpropan-2-ol

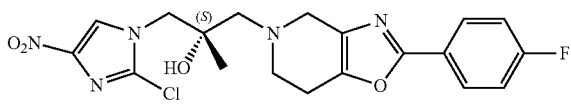

Diisopropylamine (220.65 mg, 1.71 mmol, 2.00 eq) was added to a solution of 2-(4-fluorophenyl)-4,5,6,7-tetrahydro[4,5-c]pyridine (200.00 mg, 853.64 µmol, 1.00 eq) and 2-chloro-1-[[(2R)-2-methyloxiran-2-yl]methylethyl]-4-nitroimidazole (222.91 mg, 1.02 mmol, 1.20 eq) in tert-butanol (2.00 mL). The mixture was stirred at 80° C. for 12 hours. Water (50 mL) was added to the reaction mixture, and then extracted with ethyl acetate (50 mL×3). The combined organic layers were dried over sodium sulfate, filtered and concentrated under reduced pressure. The residue was purified by silica gel chromatography (column height: 300 mm, diameter: 50 mm, 100 to 200 mesh silica gel, petroleum ether/ethyl acetate=5/1, 3/1) to deliver (2S)-1-(2-chloro-4-nitroimidazol-1-yl)-3-(2-(4-fluorophenyl)-6,7-dihydro-4H-thiazolo[4,5-c]pyridin-5-yl)-2-methylpropan-2-ol (230.00 mg, 508.96 µmol, 59.62% yield) as a yellow solid.

Step 7:

(S)-2-((2-(4-Fluorophenyl)-6,7-dihydrothiazolo[4,5-c]pyridin-5(4H)-yl)methyl)-2-methyl-6-nitro-2,3-dihydroimidazo[2,1-b]oxazole

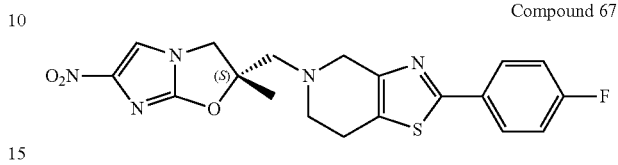

Compound 67

Sodium hydride (40.72 mg, 1.02 mmol, 2.00 eq) was added to a solution of (2S)-1-(2-chloro-4-nitroimidazol-1-yl)-3-(2-(4-fluorophenyl)-6,7-dihydro-4H-thiazolo[4,5-c]pyridin-5-yl)-2-methylpropan-2-ol (230.00 mg, 508.96 µmol, 1.00 eq) in DMF (3.00 mL). The mixture was stirred at −45° C. for 30 minutes, and then stirred at 0° C. for 30 minutes. The reaction mixture was added to a saturated ammonium chloride solution (50 mL) and then extracted with ethyl acetate (50 mL×3). The combined organic layers were dried over sodium sulfate, filtered and concentrated under reduced pressure to give a residue. The residue was purified by preparative chromatography (GX-I; Phenomenex Gemini 150*25 mm*10 um; acetonitrile 36%-66%; ACN (0.225% fomic acid); 25 mL/min) to deliver (S)-2-((2-(4-fluorophenyl)-6,7-dihydrothiazolo[4,5-c]pyridin-5(4H)-yl)methyl)-2-methyl-6-nitro-2,3-dihydroimidazo[2,1-b]oxazole compound 67 (84.60 mg, 200.99 µmol, 39.49% yield, 98.7% purity). $^1$H NMR (400 MHz, CDCl$_3$-d) δ 7.83-7.72 (m, 2H), 7.44 (s, 1H), 7.09-6.98 (m, 2H), 4.31 (d, J=9.66 Hz, 1H), 3.92-3.72 (m, 3H), 3.16-3.01 (m, 2H), 2.84-2.52 (m, 4H), 1.60 (s, 3H). LCMS (ESI) m/z: 416 (M+1).

Embodiment 68

(S)-2-((2-(3,4-Difluorophenyl)-6,7-dihydrothiazolo[4,5-e]pyridin-5(4H)-yl)methyl)-2-methyl-6-nitro-2,3-dihydroimidazo[2,1-b]oxazole

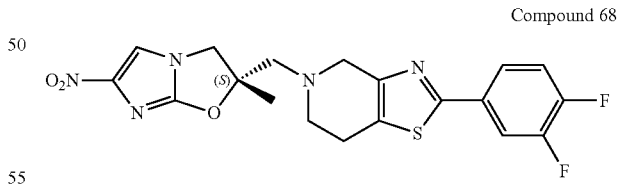

Compound 68

The synthesis method was as in Embodiment 67.

(S)-2-((2-(3,4-Difluorophenyl)-6,7-dihydrothiazolo[4,5-e]pyridin-5 (4H)-yl)methyl)-2-methyl-6-nitro-2,3-dihydroimidazo[2,1-b]oxazole compound 68 (75.10 mg, 171.19 µmol, 32.18% yield, 98.8% purity). $^1$H NMR (400 MHz, CDCl$_3$) δ 7.73 (ddd, J=2.2, 7.6, 11.0 Hz, 1H), 7.62-7.56 (m, 1H), 7.53 (s, 1H), 7.26-7.17 (m, 1H), 4.39 (d, J=9.5 Hz, 1H), 3.99-3.82 (m, 3H), 3.28-3.11 (m, 2H), 2.92-2.74 (m, 3H), 2.73-2.61 (m, 1H), 1.69 (s, 3H). LCMS (ESI) m/z: 434.2 (M+1).

Embodiment 69

(S)-2-((2-(4-Fluorophenyl)-4H-pyrrolo[3,4-d]thiazol-5(6H)-yl)methyl)-2-methyl-6-nitro-2,3-dihydroimidazo[2,1-b]oxazole

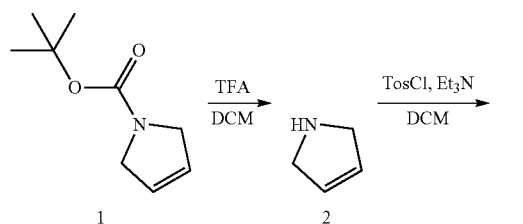

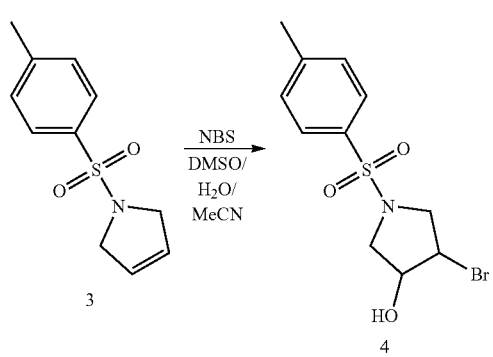

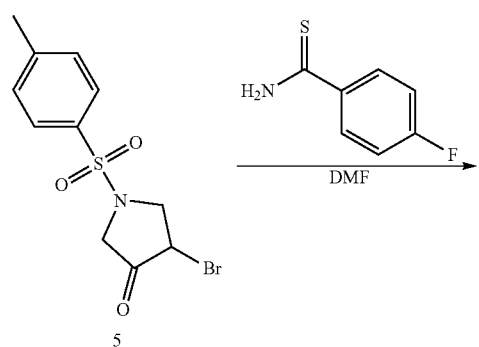

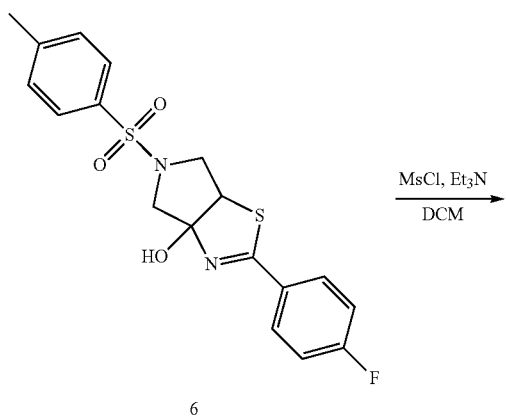

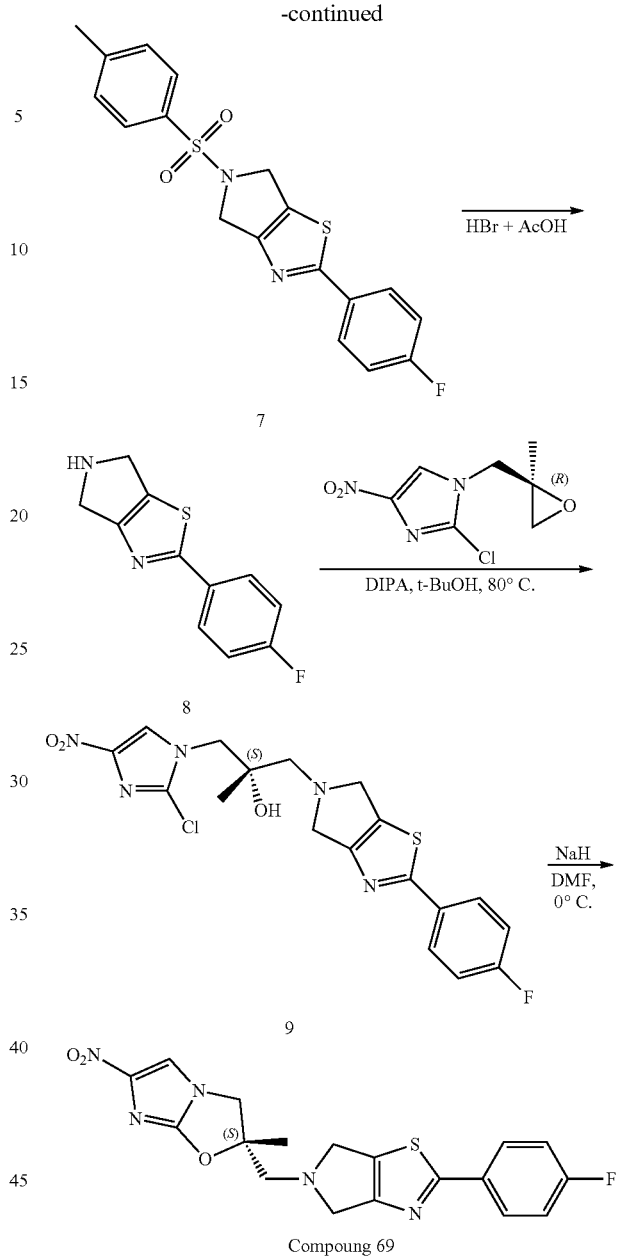

Step 1:

2,5-Dihydro-1H-pyrrole

Trifluoroacetic acid (9.18 g, 80.51 mmol, 6.81 eq) was added to a solution of tert-Butyl 2,5-dihydropyrrole-1-carboxylate (2.00 g, 11.82 mmol, 1.00 eq) in dichloromethane (6.00 mL), the mixture was stirred at 20° C. for 1 hour. The mixture was concentrated under reduced pressure to give the crude product as a dark brown oil which was used directly in the next step.

Step 2:

1-Tosyl-2,5-dihydro-1H-pyrrole

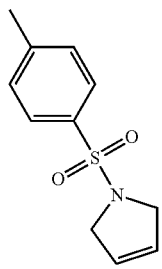

TosCl (2.70 g, 14.15 mmol, 1.20 eq) and triethylamine (3.58 g, 35.37 mmol, 3.00 eq) were added to a solution of 2,5-dihydro-1H-pyrrole (2.16 g, 11.79 mmol, 1.00 eq, TFA) in dichloromethane (10.00 mL). The mixture was stirred at 20° C. for 16 hours. The reaction mixture was washed with 1 M dilute hydrochloric acid (30 mL), saturated NaHCO$_3$ solution (30 mL) and brine (30 mL). The organic layer was dried over anhydrous sodium sulfate, filtered and concentrated under reduced pressure to deliver 1-(p-toluenesulfonyl)-2,5-dihydropyrrole (1.50 g, 6.72 mmol, 56.98% yield) as a brown solid.

Step 3:

4-Bromo-1-tosylpyrrolidin-3-ol

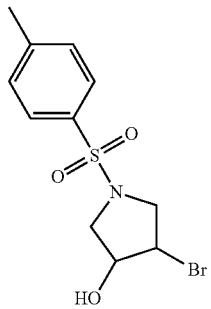 [SMILES: Cc1ccc(S(=O)(=O)N2CC(O)C(Br)C2)cc1]

NBS (1.79 g, 10.08 mmol, 1.50 eq) was added portionwise to a solution of 1-(p-toluenesulfonyl)-2,5-dihydropyrrole (1.50 g, 6.72 mmol, 1.00 eq) in DMSO (10.00 mL) and acetonitrile (5.00 mL) at 0° C. The mixture was then stirred at 15° C. for 16 hours. Water (50 mL) was added to the reaction mixture and extracted with ethyl acetate (30 mL×2). The combined organic layers were washed with brine (30 mL), dried over anhydrous sodium sulfate, filtered and concentrated under reduced pressure. The residue was purified by silica gel chromatography (SiO$_2$, petroleum ether/ethyl acetate=10:1 to 3:1) to deliver 4-bromo-1-(p-toluenesulfonyl)pyrrolidin-3-ol (1.58 g, 4.93 mmol, 73.43% yield) as a white solid.

Step 4:

4-Bromo-1-tosylpyrrolidin-3-one

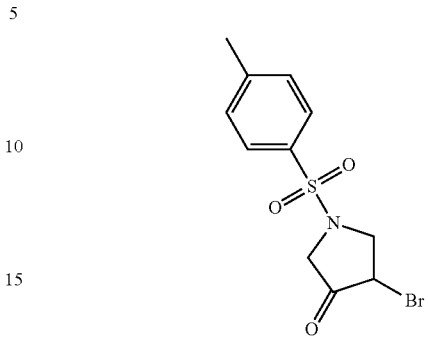

Dess-Martin periodinane (4.19 g, 9.87 mmol, 2.00 eq) was added to a solution of 4-bromo-1-(p-toluenesulfonyl) pyrrolidin-3-ol (1.58 g, 4.93 mmol, 1.00 eq) in dichloromethane (15.00 mL). Then the mixture was replaced with nitrogen and stirred at 10 to 15° C. for 12 hours. The reaction mixture was washed with aqueous sodium bicarbonate solution (50 mL×2) and extracted with ethyl acetate (30 mL×2). The combined organic layers were dried over anhydrous sodium sulfate, filtered and concentrated under reduced pressure. The residue was purified by silica gel chromatography (silica, petroleum ether/ethyl acetate=10:1 to 1:1) to deliver 4-bromo-1-(p-toluenesulfonyl)pyrrolidin-3-one (980.00 mg, 3.08 mmol, 62.47% yield) as a yellow solid. $^1$H NMR (300 MHz, CDCl$_3$) δ 7.69-7.61 (d, J=8.1 Hz, 2H), 7.35-7.28 (d, J=7.8 Hz, 2H), 4.32-4.25 (t, J=6.3 Hz, 1H), 4.00-3.91 (m, 1H), 3.61 (s, 2H), 3.55-3.47 (m, 1H), 2.39 (s, 3H).

Step 5:

2-(4-Fluorophenyl)-5-tosyl-4,5,6,6a-tetrahydro-3aH-pyrrolo[3,4-d]thiazol-3a-ol

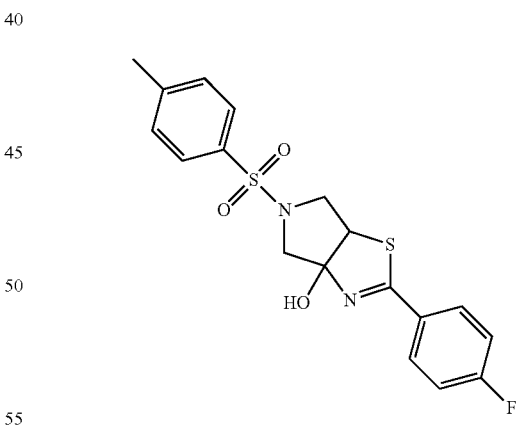

4-Fluorothiobenzamide (430.00 mg, 2.77 mmol, 1.00 eq) was added to a solution of 4-bromo-1-(p-toluenesulfonyl) pyrrolidin-3-one (880.00 mg, 2.77 mmol, 1.00 eq) in DMF (12.00 mL). The mixture was stirred at 60° C. for 16 hours. The reaction mixture was concentrated under reduced pressure and the residue was diluted with ethyl acetate (10 mL), filtered, the filter cake was collected and the filtered liquid was purified by silica gel chromatography (SiO$_2$, petroleum ether ethyl acetate=10:1, 3:1) to deliver 2-(4-fluorophenyl)-5-tosyl-4,5,6,6a-tetrahydro-3aH-pyrrolo[3,4-d]thiazol-3a-ol (900.00 mg, 2.49 mmol) as an off-white solid.

Step 6:

2-(4-Fluorophenyl)-5-tosyl-5,6-dihydro-4H-pyrrolo[3,4-d]thiazole

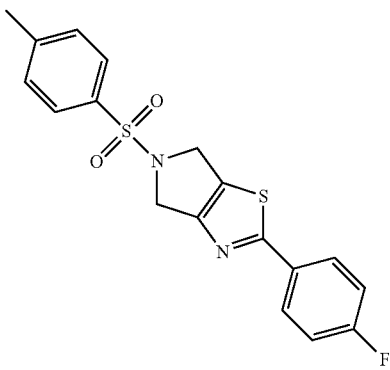 [SMILES: Cc1ccc(S(=O)(=O)N2Cc3nc(-c4ccc(F)cc4)sc3C2)cc1]

2-(4-Fluorophenyl)-5-tosyl-4,5,6,6a-tetrahydro-3aH-pyrrolo[3,4-d]thiazol-3a-ol (900.00 mg, 2.29 mmol, 1.00 eq), methanesulfonyl chloride (444.00 mg, 3.88 mmol, 1.69 eq) and triethylamine (730.00 mg, 7.21 mmol, 3.15 eq) were dissolved in dichloromethane (20.00 mL), the mixture was degassed and the mixture was stirred at 20° C. for 16 hours under the nitrogen gas atmosphere. Water (50 mL) was added and extracted with dichloromethane (30 mL×2). The combined organic layers were dried over anhydrous sodium sulfate, filtered and concentrated under reduced pressure. The residue was purified by silica gel chromatography (SiO$_2$, petroleum ether/ethyl acetate=20:1 to 1:1) to deliver 2-(4-fluorophenyl)-5-tosyl-5,6-dihydro-4H-pyrrolo[3,4-d]thiazole (600.00 mg, 1.11 mmol, 48.28% yield, 69% purity) as a light yellow solid.

Step 7:

2-(4-Fluorophenyl)-5,6-dihydro-4H-pyrrolo[3,4-d]thiazole

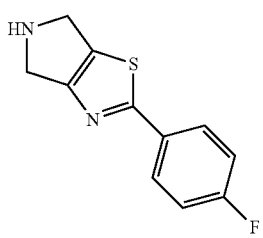 [SMILES: Fc1ccc(-c2nc3c(s2)CNC3)cc1]

A solution of acetic acid in acetic acid (81.72 mg, 1.01 mmol, 1.00 eq) was added to a mixed solution of 2-(4-fluorophenyl)-5-tosyl-5,6-dihydro-4H-pyrrolo[3,4-d]thiazole (550.00 mg, 1.01 mmol, 1.00 eq) in water (3.00 mL) and AcOH (15.00 mL). The mixture was stirred at 20° C. for 1 hour. The reaction mixture was concentrated under reduced pressure, then diluted with water (50 mL) and extracted with ethyl acetate (50 mL). The aqueous layer was basified with NaOH to adjust the pH to 11 and then extracted with ethyl acetate (40 mL×2), dried over anhydrous sodium sulfate, filtered and concentrated under reduced pressure to deliver 2-(4-fluorophenyl)-5,6-dihydro-4H-pyrrolo[3,4-d]thiazole (145.00 mg, 658.28 μmol, 65.18% yield) as a pale yellow solid.

Step 8:

(S)-1-(2-Chloro-4-nitro-1H-imidazol-1-yl)-3-(2-(4-fluorophenyl)-4H-pyrrolo[3,4-d]thiazol-5(6H)-yl)-2-methylpropan-2-ol

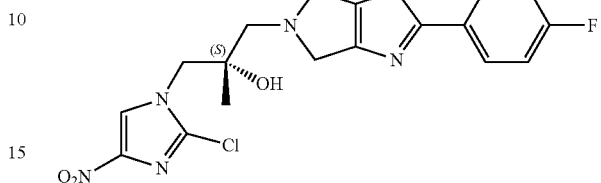

2-Chloro-1-[[(2R)-2-methyloxiran-2-yl]methyl]-4-nitroimidazole (158.00 mg, 726.07 μmol, 1.00 eq) and diisopropylamine (481.00 mg, 3.72 mmol, 5.12 eq) were added to a solution of 2-(4-fluorophenyl)-5,6-dihydro-4H-pyrrolo[3,4-d]thiazole (160.00 mg, 726.38 μmol, 1.00 eq) in tert-butanol. The mixture was stirred at 80° C. for 16 hours. Water (50 mL) was added and extracted with ethyl acetate (30 mL×2). The combined organic layers were dried over anhydrous sodium sulfate, filtered and concentrated under reduced pressure, the residue was purified by preparative thin layer chromatography (silica, dichloromethane:methanol=20:1) to deliver (S)-1-(2-chloro-4-nitro-1H-imidazol-1-yl)-3-(2-(4-fluorophenyl)-4H-pyrrolo[3,4-d]thiazol-5 (6H)-yl)-2-methylpropan-2-ol (150.00 mg, 342.56 μmol, 47.16% yield) as a pale yellow solid.

Step 9:

(S)-2-((2-(4-Fluorophenyl)-4H-pyrrolo[3,4-d]thiazol-5(6H)-yl)methyl)-2-methyl-6-nitro-2,3-dihydroimidazo[2,1-b]oxazole Compound 69

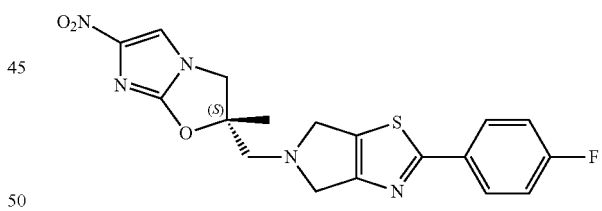

Sodium hydride (30.00 mg, 750.00 mmol, 2.19 eq) was added to a solution of (S)-1-(2-chloro-4-nitro-1H-imidazol-1-yl)-3-(2-(4-fluorophenyl)-4H-pyrrolo[3,4-d]thiazol-5 (6H)-yl)-2-methylpropan-2-ol (150.00 mg, 342.56 μmol, 1.00 eq) in DMF (5.00 mL) at 0° C. under the nitrogen gas atmosphere. The mixture was stirred at 0° C. for 1 hour. The reaction mixture was poured into a saturated ammonium chloride solution (40 mL) at 0° C. and then extracted with ethyl acetate (30 mL×2). The combined organic layers were dried over anhydrous sodium sulfate, filtered, and concentrated under reduced pressure. The residue was purified with ethyl acetate to deliver (S)-2-((2-(4-fluorophenyl)-4H-pyrrolo[3,4-d]thiazol-5 (6H)-yl)methyl)-2-methyl-6-nitro-2,3-dihydroimidazo[2,1-b]oxazole (17.71 mg, 40.90 mmol, 11.94% yield, 92.71% purity). $^1$H NMR (400 MHz, CDCl$_3$) δ 7.91-7.84 (m, 2H), 7.57 (s, 1H), 7.17-7.09 (t, J=8.4 Hz, 2H), 4.53-4.48 (d, J=9.6 Hz, 1H), 4.20 (d, J=3.3 Hz, 3H), 4.13-4.07 (m, 1H), 4.03-3.97 (m, J=9.6 Hz, 1H), 3.42 (d, J=14.8 Hz, 1H), 3.12 (d, J=14.8 Hz, 1H), 1.64-1.60 (m, 3H). LCMS (ESI) m/z: 402.10 (M+1).

Embodiment 70

(S)-2-((2-(3-Fluorophenyl)-4H-pyrrolo[3,4-d]thiazol-5(6H)-yl)methyl)-2-methyl-6-nitro-2,3-dihydroimidazo[2,1-b]oxazole Compound 70

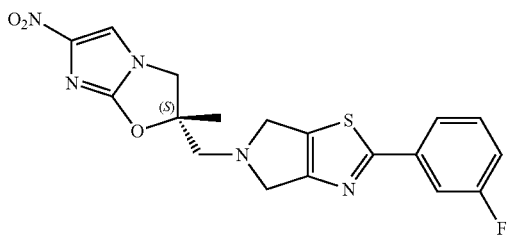

The synthesis method was as in Embodiment 69.

(S)-2-((2-(3-Fluorophenyl)-4H-pyrrolo[3,4-d]thiazol-5 (6H)-yl)methyl)-2-methyl-6-nitro-2,3-dihydroimidazo[2,1-b]oxazole compound 70 (67.10 mg, 165.99 mmol, 48.46% yield, 99.3% purity). ¹H NMR (400 MHz, CDCl₃) δ 7.67-7.58 (m, 2H), 7.55 (s, 1H), 7.39 (dt, J=5.8, 8.0 Hz, 1H), 7.11 (dt, J=1.8, 8.3 Hz, 1H), 4.49 (d, J=9.7 Hz, 1H), 4.26-4.17 (m, 3H), 4.14-4.06 (m, 1H), 3.98 (d, J=9.7 Hz, 1H), 3.40 (d, J=14.8 Hz, 1H), 3.11 (d, J=14.7 Hz, 1H), 1.70 (s, 3H). LCMS (ESI) m/z: 402.2 (M+1).

Embodiment 71

(S)-2-((2-(3,4-Difluorophenyl)-4H-pyrrolo[3,4-d]thiazol-5(6H)-yl)methyl)-2-methyl-6-nitro-2,3-dihydroimidazo[2,1-b]oxazole Compound 71

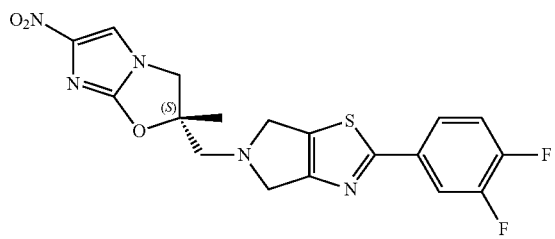

The synthesis method was as in Embodiment 69.

(S)-2-((2-(3,4-Difluorophenyl)-4H-pyrrolo[3,4-d]thiazol-5 (6H)-yl)methyl)-2-methyl-6-nitro-2,3-dihydroimidazo[2,1-b]oxazole compound 71 (49.80 mg, 115.42 μmol, 21.05% yield, 97.2% purity). ¹H NMR (400 MHz, CDCl₃) δ 7.75 (ddd, J=2.2, 7.5, 11.0 Hz, 1H), 7.65-7.58 (m, 1H), 7.56 (s, 1H), 7.25-7.19 (m, 1H), 4.49 (d, J=9.7 Hz, 1H), 4.27-4.18 (m, 3H), 4.13-4.07 (m, 1H), 4.00 (d, J=9.7 Hz, 1H), 3.42 (d, J=14.8 Hz, 1H), 3.12 (d, J=14.7 Hz, 1H), 1.72 (s, 3H). LCMS (ESI) m/z: 420.2 (M+1).

Embodiment 72

(S)-2-methyl-6-nitro-2-((2-(4-(trifluoromethyl)phenyl)-4H-pyrrolo[3,4-d]thiazol-5(6H)-yl)methyl)-2,3-dihydroimidazo[2,1-b]oxazole Compound 72

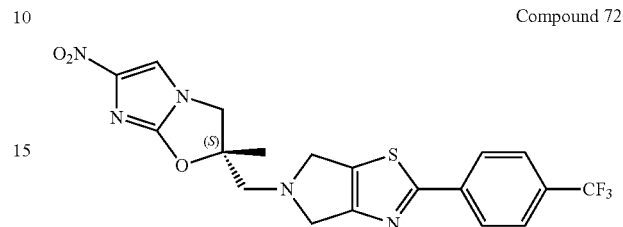

The synthesis method was as in Embodiment 69.

(S)-2-methyl-6-nitro-2-((2-(4-(trifluoromethyl)phenyl)-4H-pyrrolo[3,4-d]thiazol-5 (6H)-yl)methyl)-2,3-dihydroimidazo[2,1-b]oxazole compound 72 (24.30 mg, 52.53 μmol, 17.68% yield, 97.59% purity). ¹H NMR (400 MHz, CDCl₃) δ 8.01 (d, J=8.0 Hz, 2H), 7.70 (d, J=8.3 Hz, 2H), 7.57 (s, 1H), 4.50 (d, J=9.7 Hz, 1H), 4.29-4.20 (m, 3H), 4.16-4.09 (m, 1H), 4.00 (d, J=9.7 Hz, 1H), 3.43 (d, J=14.8 Hz, 1H), 3.13 (d, J=14.7 Hz, 1H), 1.72 (s, 3H). LCMS (ESI) m/z: 452.2 (M+1).

Embodiment 73

(S)-2-Methyl-6-nitro-2-((2-(4-(trifluoromethoxy) phenyl)-4H-pyrrolo[3,4-d]thiazol-5(6H)-yl)methyl)-2,3-dihydroimidazo[2,1-b]oxazole Compound 73

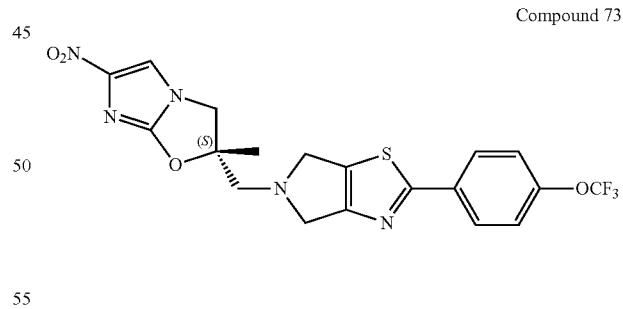

The synthesis method was as in Embodiment 69.

(S)-2-Methyl-6-nitro-2-((2-(4-(trifluoromethoxy)phenyl)-4H-pyrrolo[3,4-d]thiazol-5 (6H)-yl)methyl)-2,3-dihydroimidazo[2,1-b]oxazole compound 73 (46.00 mg, 97.82 μmol, 16.43% yield, 99.4% purity). ¹H NMR (400 MHz, CHLOROFORM-d)=7.96-7.89 (m, 1H), 7.56 (s, 1H), 7.31-7.29 (m, 2H), 4.54-4.46 (m, 1H), 4.29-4.17 (m, 3H), 4.16-4.07 (m, 1H), 4.00 (d, J=9.7 Hz, 1H), 3.42 (d, J=14.7 Hz, 1H), 3.12 (d, J=14.7 Hz, 1H), 1.72 (s, 3H). LCMS (ESI) m/z: 468.1 (M+1).

Embodiment 74

(S)-2-((2-(2-Fluorophenyl)-4H-pyrrolo[3,4-d]thiazol-5(6H)-yl)methyl)-2-methyl-6-nitro-2,3-dihydroimidazo[2,1-b]oxazole

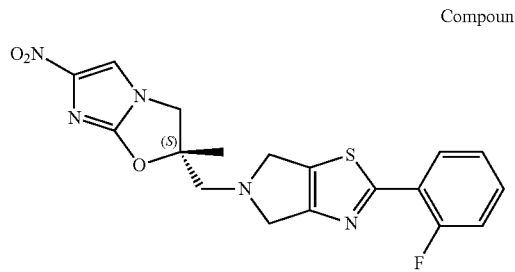

Compound 74

The synthesis method was as in Embodiment 69.

(S)-2-((2-(2-Fluorophenyl)-4H-pyrrolo[3,4-d]thiazol-5(6H)-yl)methyl)-2-methyl-6-nitro-2,3-dihydroimidazo[2,1-b]oxazole compound 74 (45.45 mg, 110.14 μmol, 34.45% yield, 97.271% purity). $^1$H NMR (400 MHz, CDCl$_3$) δ 8.23-8.16 (m, 1H), 7.56 (s, 1H), 7.44-7.36 (m, 1H), 7.28-7.17 (m, 2H), 4.51 (d, J=8.0 Hz, 1H), 4.29-4.22 (m, 3H), 4.17-4.10 (m, 1H), 4.00 (d, J=12.0 Hz, 1H), 3.43(d, J=16.0 Hz, 1H), 3.13 (d, J=16.0 Hz, 1H), 1.72 (s, 3H). LCMS (ESI) m/z: 402(M+1).

Embodiment 75

(S)-2-((2-(4-Fluorophenyl)-5H-pyrrolo[3,4-d]thiazol-5-yl)methyl)-2-methyl-6-nitro-2,3-dihydroimidazo[2,1-b]oxazole

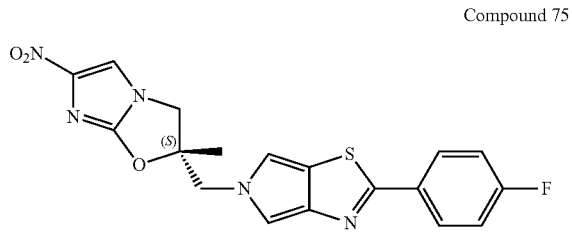

Compound 75

A solution of (2S)-2-[[2-(4-fluorophenyl)-4,6-dihydropyrrolo[3,4-d]thiazol-5-yl]methyl]-2-methyl-6-nitro-3H-imidazo[2,1-b]oxazole (100.00 mg, 249.12 μmol, 1.00 eq) in ethyl acetate (30.00 mL) was stirred in air at 80° C. for 20 hours. The reaction mixture was concentrated under reduced pressure and the residue was purified by preparative thin layer chromatography (silica, dichloromethane:methanol=15:1). And then the resulting product was washed with methanol (5 mL) to deliver (S)-2-((2-(4-fluorophenyl)-5H-pyrrolo[3,4-d]thiazol-5-yl)methyl)-2-methyl-6-nitro-2,3-dihydroimidazo[2,1-b]oxazole compound 75 (12.30 mg, 30.40 μmol, 12.20% yield, 98.7% purity). $^1$H NMR (400 MHz, DMSO-d$_6$) δ 8.04 (s, 1H), 8.01-7.93 (m, 2H), 7.41-7.31 (m, 3H), 7.04 (d, J=1.8 Hz, 1H), 4.69-4.54 (m, 2H), 4.29-4.16 (m, 2H), 1.56 (s, 3H). LCMS (ESI) m/z: 400.2 (M+1).

Embodiment 76

(S)-2-((2-(4-Chlorophenyl)-4H-pyrrolo[3,4-d]thiazol-5(6H)-yl)methyl)-2-methyl-6-nitro-2,3-dihydroimidazo[2,1-b]oxazole

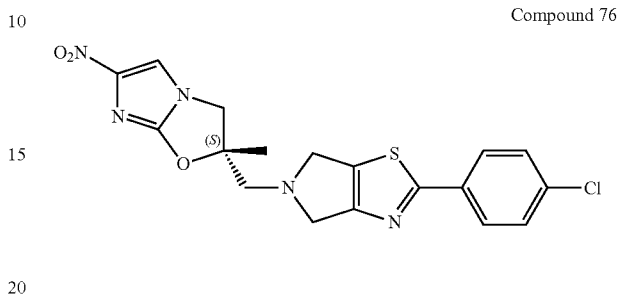

Compound 76

The synthesis method was as in Embodiment 69.

(S)-2-((2-(4-Chlorophenyl)-4H-pyrrolo[3,4-d]thiazol-5(6H)-yl)methyl)-2-methyl-6-nitro-2,3-dihydroimidazo[2,1-b]oxazole compound 76 (114.50 mg, 267.79 μmol, 60.83% yield, 97.729% purity). $^1$HNMR (400 MHz, CDCl$_3$) δ 7.83 (d, J=8.5 Hz, 2H), 7.56 (s, 1H), 7.41 (d, J=8.5 Hz, 2H), 4.50 (d, J=9.5 Hz, 1H), 4.29-4.16 (m, 3H), 4.14-4.05 (m, 1H), 4.00 (d, J=9.8 Hz, 1H), 3.42 (d, J=14.8 Hz, 1H), 3.11 (d, J=14.8 Hz, 1H), 1.71 (s, 3H). LCMS (ESI) m/z: 418.2 (M+1).

Embodiment 77

(S)-2-((2-(2-chloro-4-fluorophenyl)-4H-pyrrolo[3,4-d]thiazol-5(6H)-yl)methyl)-2-methyl-6-nitro-2,3-dihydroimidazo[2,1-b]oxazole

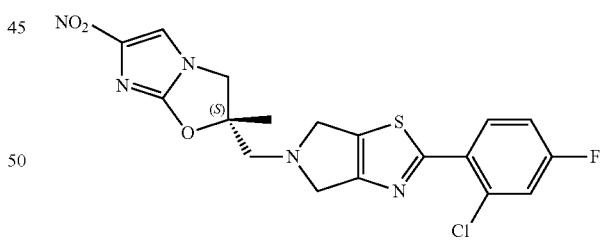

Compound 77

The synthesis method was as in Embodiment 69.

(S)-2-((2-(2-chloro-4-fluorophenyl)-4H-pyrrolo[3,4-d]thiazol-5 (6H)-yl)methyl)-2-methyl-6-nitro-2,3-dihydroimidazo[2,1-b]oxazole compound 77 (38.00 mg, 85.78 μmol, 27.01% yield, 98.384% purity). $^1$H NMR (400 MHz, CDCl$_3$) δ 8.13-8.06 (m, 1H), 7.56 (s, 1H), 7.27-7.23 (m, 1H), 7.13-7.07 (m, 1H), 4.50 (d, J=8.0 Hz, 1H), 4.30-4.20 (m, 3H), 4.18-4.09 (m, 1H), 4.00 (d, J=12.0 Hz, 1H), 3.42 (d, J=12.0 Hz, 1H), 3.13 (d, J=12.0 Hz, 1H), 1.72 (s, 3H). LCMS (ESI) m/z: 436/438(M+1/M+3).

Embodiment 78

(S)-2-((2-(2,4-Difluorophenyl)-4H-pyrrolo[3,4-d]
thiazol-5(6H)-yl)methyl)-2-methyl-6-nitro-2,3-dihy-
droimidazo[2,1-b]oxazole

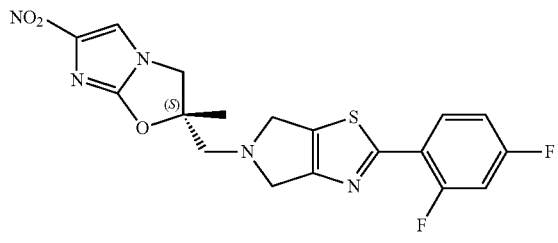

Compound 78

The synthesis method was as in Embodiment 69.

(S)-2-((2-(2,4-Difluorophenyl)-4H-pyrrolo[3,4-d]thiazol-5 (6H)-yl)methyl)-2-methyl-6-nitro-2,3-dihydroimidazo[2,1-b]oxazole compound 78 (117.40 mg, 271.83 µmol, 82.61% yield, 97.107% purity). $^1$H NMR (400 MHz, CDCl$_3$) δ 8.23-8.14 (m, 1H), 7.56 (s, 1H), 7.03-6.92 (m, 2H), 4.50 (d, J=8.0 Hz, 1H), 4.28-4.21 (m, 3H), 4.16-4.08 (m, 1H), 4.00 (d, J=12.0 Hz, 1H), 3.42 (d, J=12.0 Hz, 1H), 3.12 (d, J=12.0 Hz, 1H), 1.72 (s, 3H). LCMS (ESI) m/z: 420(M+1).

Embodiment 79

(S)-2-((2-(4-Fluoro-2-methylphenyl)-4H-pyrrolo[3,4-d]thiazol-5(6H)-yl)methyl)-2-methyl-6-nitro-2,3-dihydroimidazo[2,1-b]oxazole

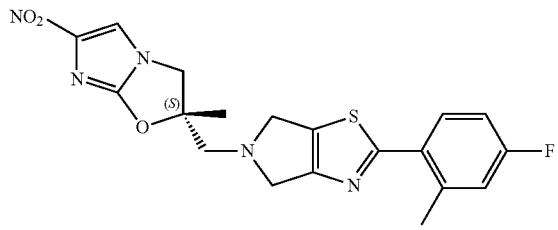

Compound 79

The synthesis method was as in Embodiment 69.

(S)-2-((2-(4-Fluoro-2-methylphenyl)-4H-pyrrolo[3,4-d]thiazol-5 (6H)-yl)methyl)-2-methyl-6-nitro-2,3-dihydroimidazo[2,1-b]oxazole compound 79 (332.10 mg, 786.28 µmol, 39.12% yield, 98.36% purity). $^1$HNMR (400 MHz, CDCl$_3$) δ 7.65-7.54 (m, 2H), 7.05-6.92 (m, 2H), 4.56-4.46 (m, 1H), 4.31-4.17 (m, 3H), 4.15-4.09 (m, 1H), 4.03-3.97 (m, 1H), 3.47-3.35 (m, 1H), 3.20-3.06 (m, 1H), 2.56 (s, 3H), 1.72 (s, 3H). LCMS (ESI) m/z: 416.1 (M+1).

Embodiment 80

(S)-2-((2-(4-Fluoro-2-methoxyphenyl)-4H-pyrrolo
[3,4-d]thiazol-5(6H)-yl)methyl)-2-methyl-6-nitro-2,
3-dihydroimidazo[2,1-b]oxazole

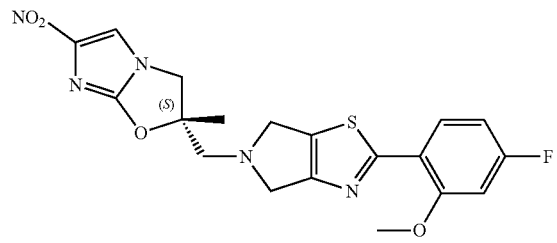

Compound 80

The synthesis method was as in Embodiment 69.

(S)-2-((2-(4-Fluoro-2-methoxyphenyl)-4H-pyrrolo[3,4-d]thiazol-5 (6H)-yl)methyl)-2-methyl-6-nitro-2,3-dihydroimidazo[2,1-b]oxazole compound 80 (47.90 mg, 105.87 µmol, 38.11% yield, 95.36% purity). $^1$H NMR (400 MHz, CHLOROFORM-d) δ=8.21-8.12 (m, 1H), 7.47 (s, 1H), 6.73-6.61 (m, 2H), 4.43 (d, J=9.7 Hz, 1H), 4.19-4.08 (m, 3H), 4.06-3.97 (m, 1H), 3.93 (s, 3H), 3.89 (d, J=9.7 Hz, 1H), 3.32 (d, J=14.7 Hz, 1H), 3.02 (d, J=14.8 Hz, 1H), 1.62 (s, 3H). LCMS (ESI) m/z: 432.1 (M+1).

Embodiment 81

(S)-2-((2-(3,5-difluoropyridin-2-yl)-4H-pyrrolo[3,4-d]thiazol-5(6H)-yl)methyl)-2-methyl-6-nitro-2,3-dihydroimidazo[2,1-b]oxazole

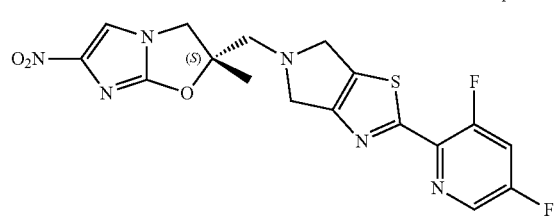

Compound 81

The synthesis method was as in Embodiment 69.

(S)-2-((2-(3,5-difluoropyridin-2-yl)-4H-pyrrolo[3,4-d]thiazol-5 (6H)-yl)methyl)-2-methyl-6-nitro-2,3-dihydroimidazo[2,1-b]oxazole compound 81 (24.50 mg, 55.89 µmol, 36.48% yield, 95.9% purity). $^1$H NMR (400 MHz, CDCl$_3$) δ 8.30 (d, J=2.1 Hz, 1H), 7.47 (s, 1H), 7.32-7.25 (m, 1H), 4.42 (d, J=9.7 Hz, 1H), 4.25-4.13 (m, 3H), 4.10-4.03 (m, 1H), 3.90 (d, J=9.8 Hz, 1H), 3.34 (d, J=14.7 Hz, 1H), 3.05 (d, J=14.7 Hz, 1H), 1.63 (s, 3H). LCMS (ESI) m/z: 421.1 (M+1).

Embodiment 82

(S)-2-((2-(5-Fluoropyridin-2-yl)-4H-pyrrolo[3,4-d]
thiazol-5(6H)-yl)methyl)-2-methyl-6-nitro-2,3-dihydroimidazo[2,1-b]oxazole

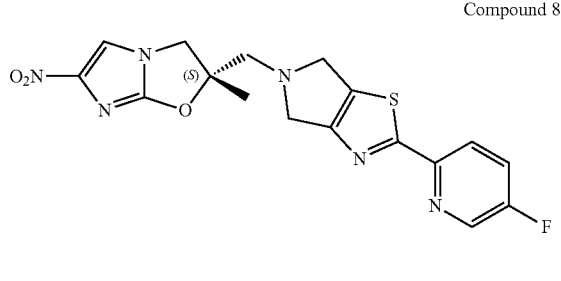

Compound 82

The synthesis method was as in Embodiment 69.

(S)-2-((2-(5-Fluoropyridin-2-yl)-4H-pyrrolo[3,4-d]thiazol-5 (6H)-yl)methyl)-2-methyl-6-nitro-2,3-dihydroimidazo[2,1-b]oxazole compound 82 (970.60 mg, 2.37 mmol, 63.61% yield, 98.1% purity). $^1$H NMR (400 MHz, CDCl$_3$) δ 8.45 (d, J=2.8 Hz, 1H), 8.11 (dd, J=4.5, 8.7 Hz, 1H), 7.56 (s, 1H), 7.51 (dt, J=2.8, 8.4 Hz, 1H), 4.51 (d, J=9.5 Hz, 1H), 4.27-4.18 (m, 3H), 4.14-4.07 (m, 1H), 3.99 (d, J=9.7 Hz, 1H), 3.42 (d, J=14.7 Hz, 1H), 3.12 (d, J=14.8 Hz, 1H), 1.72 (s, 3H). LCMS (ESI) m/z: 403 (M+1).

Embodiment 83

(S)-2-Methyl-6-nitro-2-((2-(2,4,5-trifluorophenyl)-4H-pyrrolo[3,4-d]thiazol-5(6H)-yl)methyl)-2,3-dihydroimidazo[2,1-b]oxazole

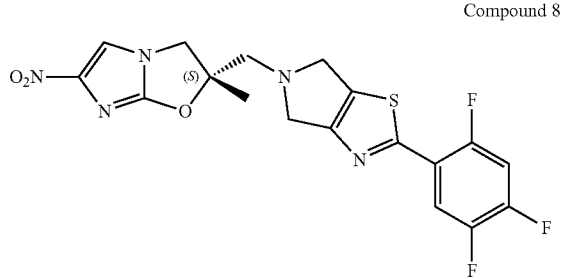

Compound 83

The synthesis method was as in Embodiment 69.

(S)-2-Methyl-6-nitro-2-((2-(2,4,5-trifluorophenyl)-4H-pyrrolo[3,4-d]thiazol-5 (6H)-yl)methyl)-2,3-dihydroimidazo[2,1-b]oxazole compound 83 (50.80 mg, 114.98 μmol, 14.54% yield, 99% purity). $^1$H NMR (400 MHz, CDCl$_3$) δ 8.06 (ddd, J=6.8, 8.8, 10.9 Hz, 1H), 7.61-7.49 (m, 1H), 7.12-7.01 (m, 1H), 4.50 (d, J=9.7 Hz, 1H), 4.29-4.18 (m, 3H), 4.16-4.07 (m, 1H), 4.01 (d, J=9.7 Hz, 1H), 3.42 (d, J=14.7 Hz, 1H), 3.13 (d, J=14.8 Hz, 1H), 1.72 (s, 3H). LCMS (ESI) m/z: 438.0 (M+1).

Embodiment 84

(S)-2-((2-(3,5-Difluorophenyl)-4H-pyrrolo[3,4-d]
thiazol-5(6H)-yl)methyl)-2-methyl-6-nitro-2,3-dihydroimidazo[2,1-b]oxazole

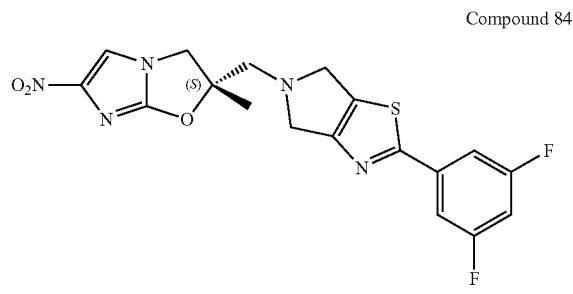

Compound 84

The synthesis method was as in Embodiment 69.

(S)-2-((2-(3,5-Difluorophenyl)-4H-pyrrolo[3,4-d]thiazol-5(6H)-yl)methyl)-2-methyl-6-nitro-2,3-dihydroimidazo[2,1-b]oxazole compound 84 (48.70 mg, 115.57 mmol, 27.67% yield, 99.53% purity). $^1$H NMR (400 MHz, CDCl$_3$) δ 7.56 (s, 1H), 7.47-7.39 (m, 2H), 6.87 (tt, J=2.3, 8.7 Hz, 1H), 4.49 (d, J=9.5 Hz, 1H), 4.28-4.19 (m, 3H), 4.15-4.08 (m, 1H), 4.00 (d, J=9.7 Hz, 1H), 3.42 (d, J=14.8 Hz, 1H), 3.12 (d, J=14.7 Hz, 1H), 1.72 (s, 3H). LCMS (ESI) m/z: 420.1 (M+1)

Embodiment 85

(S)—N-(4-Fluorophenyl)-N-methyl-5-((2-methyl-6-nitro-2,3-dihydroimidazo[2,1-b]oxazol-2-yl)methyl)-5,6-dihydro-4H-pyrrolo[3,4-d]thiazol-2-amine

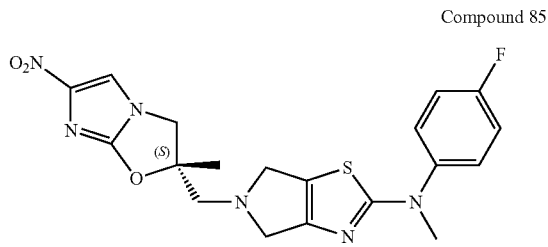

Compound 85

The synthesis method was as in Embodiment 69.

(S)—N-(4-Fluorophenyl)-N-methyl-5-((2-methyl-6-nitro-2,3-dihydroimidazo[2,1-b]oxazol-2-yl)methyl)-5,6-dihydro-4H-pyrrolo[3,4-d]thiazol-2-amine compound 85 (27.10 mg, 62.20 μmol, 14.52% yield, 98.8% purity). $^1$H NMR (400 MHz, CDCl$_3$) δ 7.54 (s, 1H), 7.36-7.30 (m, 2H), 7.17-7.08 (m, 2H), 4.48 (d, J=9.7 Hz, 1H), 4.09-3.87 (m, 5H), 3.46 (s, 3H), 3.35 (d, J=14.7 Hz, 1H), 3.04 (d, J=14.8 Hz, 1H), 1.67 (s, 3H). LCMS (ESI) m/z: 431 (M+1).

Embodiment 86

(S)-2-((2-(4,4-Difluoropiperidin-1-yl)-4H-pyrrolo[3,4-d]thiazol-5(6H)-yl)methyl)-2-methyl-6-nitro-2,3-dihydroimidazo[2,1-b]oxazole Compound 86

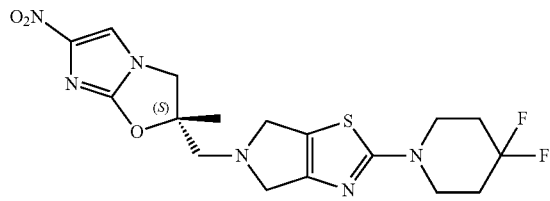

The synthesis method was as in Embodiment 69.
(S)-2-((2-(4,4-Difluoropiperidin-1-yl)-4H-pyrrolo[3,4-d]thiazol-5 (6H)-yl)methyl)-2-methyl-6-nitro-2,3-dihydroimidazo[2,1-b]oxazole compound 86 (9.30 mg, 20.98 μmol, 13.31% yield, 96.2% purity). $^1$H NMR (400 MHz, CDCl$_3$) δ 7.54 (s, 1H), 4.48 (d, J=9.7 Hz, 1H), 4.08-4.00 (m, 3H), 3.98-3.85 (m, 2H), 3.66-3.58 (m, 4H), 3.35 (d, J=14.7 Hz, 1H), 3.04 (d, J=14.8 Hz, 1H), 2.15-2.02 (m, 4H), 1.68 (s, 3H). LCMS (ESI) m/z: 427.0 (M+1).

Embodiment 87

(S)-2-((2-(4-Fluorophenyl)-5H-pyrrolo[3,4-d]pyrimidin-6(7H)-yl)methyl)-2-methyl-6-nitro-2,3-dihydroimidazo[2,1-b]oxazole Compound 87

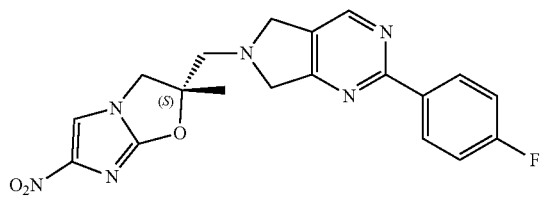

The synthesis method was as in Embodiment 44.
(S)-2-((2-(4-Fluorophenyl)-5H-pyrrolo[3,4-d]pyrimidin-6 (7H)-yl)methyl)-2-methyl-6-nitro-2,3-dihydroimidazo[2,1-b]oxazole compound 87 (14.60 mg, 35.57 μmol, 13.21% yield, 96.567% purity). $^1$H NMR (400 MHz, CDCl$_3$) δ 8.58 (s, 1H), 8.47-8.36 (m, 2H), 7.55 (s, 1H), 7.19-7.11 (m, 2H), 4.46 (d, J=8.0 Hz, 1H), 4.28-4.11 (m, 4H), 4.00 (d, J=8.0 Hz, 1H), 3.33 (d, J=12.0 Hz, 1H), 3.11 (d, J=12.0 Hz, 1H), 1.73 (s, 3H). LCMS (ESI) m/z: 397(M+1).

Embodiment 88

(S)-2-((2-(4-Fluorophenyl)-5H-pyrrolo[3,4-b]pyridin-6(7H)-yl)methyl)-2-methyl-6-nitro-2,3-dihydroimidazo[2,1-b]oxazole

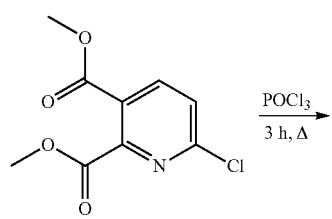

POCl$_3$
3 h, Δ

1

-continued

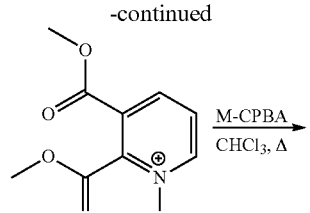

M-CPBA
CHCl$_3$, Δ

2

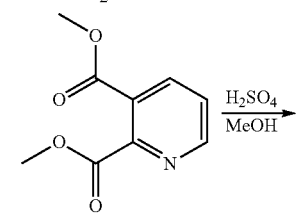

H$_2$SO$_4$
MeOH

3

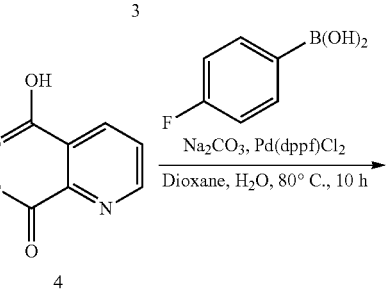

Na$_2$CO$_3$, Pd(dppf)Cl$_2$
Dioxane, H$_2$O, 80° C., 10 h

4

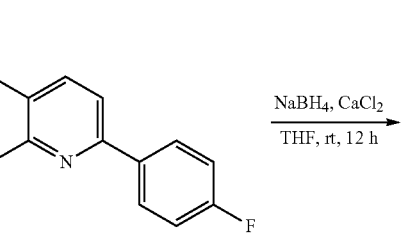

NaBH$_4$, CaCl$_2$
THF, rt, 12 h

5

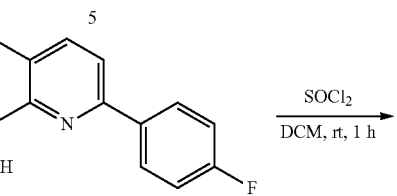

SOCl$_2$
DCM, rt, 1 h

6

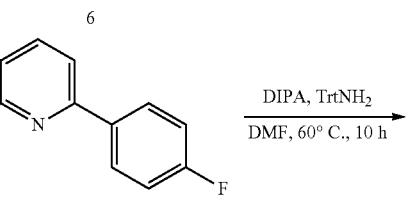

DIPA, TrtNH$_2$
DMF, 60° C., 10 h

7

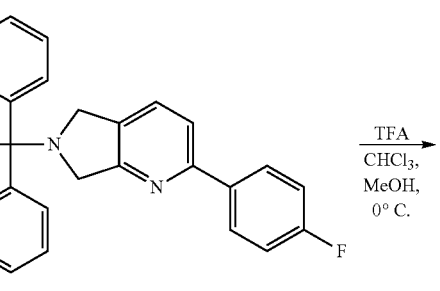

TFA
CHCl$_3$,
MeOH,
0° C.

8

-continued

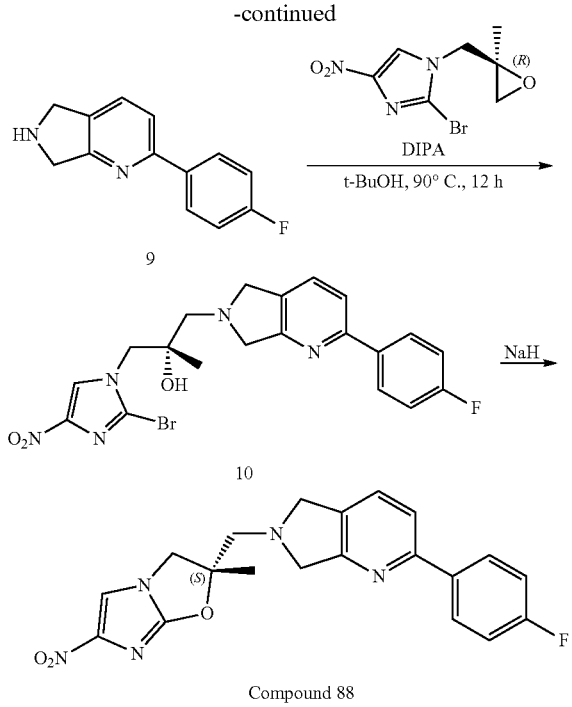

Compound 88

Step 1:

Dimethyl pyridine-2,3-dicarboxylate

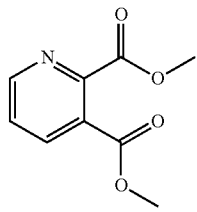

Concentrated sulfuric acid (17.61 g, 179.51 mmol, 9.57 mL, 1.50 eq) was added to a solution of pyridine-2,3-dicarboxylic acid (20.00 g, 119.67 mmol, 1.00 eq) in methanol (150.00 mL). The mixture was stirred at 60° C. for 10 hours. A sodium carbonate solution was added to adjust the pH to about 9 and the mixture was extracted with ethyl acetate (200 mL×2). The combined organic layers were concentrated under reduced pressure and the residue was chromatographed on silica gel (SiO₂, petroleum ether/ethyl acetate=20/1 to 3:1) to deliver dimethyl pyridine-2,3-dicarboxylate (20.00 g, 102.47 mmol, 85.63% yield) as a white solid.

Step 2:

Dimethyl pyridine-1-oxide-1-onium-2,3-dicarboxylate

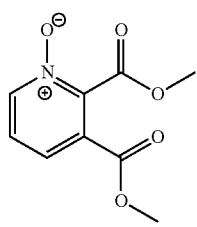

m-CPBA (28.74 g, 133.21 mmol, 80% purity, 1.30 eq) was added to a solution of dimethyl pyridine-2,3-dicarboxylate (20.00 g, 102.47 mmol, 1.00 eq) in chloroform (160.00 mL). The mixture was stirred at 60° C. for 4 hours. An aqueous solution of sodium bicarbonate (200 mL) was added to the reaction mixture and the mixture was extracted with dichloromethane (500 mL×4). The combined organic layers were concentrated under reduced pressure, washed with ethyl acetate (50 mL) and the filter cake was collected by filtration to deliver dimethyl pyridine-1-oxide-1-onium-2,3-dicarboxylate (17.50 g, crude) as a white solid which is used directly in the next step.

Step 3:

Dimethyl 6-chloropyridine-2,3-dicarboxylate

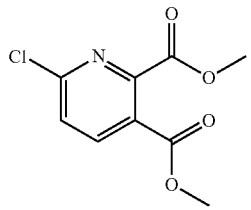

Phosphorus oxychloride (50.83 g, 331.50 mmol, 30.81 mL, 5.00 eq) was added to a solution of dimethyl pyridine-1-oxide-1-onium-2,3-dicarboxylate (14.00 g, 66.30 mmol, 1.00 eq) in dioxane (140.00 mL). The mixture was stirred at 100° C. for 2 hours. The reaction mixture was poured into water (100 mL), the pH was adjusted to about 9 with a sodium carbonate solution and extracted with ethyl acetate (500 mL×2). The combined organic layers were concentrated under reduced pressure and the residue was purified by silica gel chromatography (SiO₂, petroleum ether/ethyl acetate=40/1 to 10:1) to deliver dimethyl 6-chloropyridine-2,3-dicarboxylate (9.50 g, 41.37 mmol, 62.40% yield) as a yellow oil.

Step 4:

Dimethyl 6-(4-fluorophenyl)pyridine-2,3-dicarboxylate

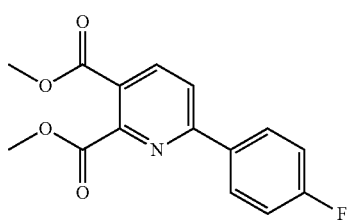 [SMILES: COC(=O)c1ccc(-c2ccc(F)cc2)nc1C(=O)OC]

Dimethyl 6-chloropyridine-2,3-dicarboxylate (5.00 g, 21.78 mmol, 1.00 eq), (4-fluorophenyl) boronic acid (3.96 g, 28.31 mmol, 1.30 eq), Pd(dppf)Cl₂ (796.65 mg, 1.09 mmol, 0.05 eq), sodium carbonate (4.62 g, 43.56 mmol, 2.00 eq) were dissolved in dioxane (30.00 mL) and H₂O (400.00 μL), the solution was degassed and replaced with nitrogen, and the mixture was stirred at 80° C. for 10 hours The reaction mixture was concentrated under reduced pressure to remove the solvent, and the residue was separated by silica gel chromatography (SiO2, petroleum ether/ethyl acetate=30/1 to 10:1) to deliver dimethyl 6-(4-fluorophenyl)pyridine-2,3-dicarboxylate (5.00 g, 17.29 mmol, 79.36% yield) as a white solid. LCMS (ESI) m/z: 290.2 (M+1).

Step 5:

[6-(4-Fluorophenyl)-2-(hydroxymethyl)-3-pyridyl]methanol

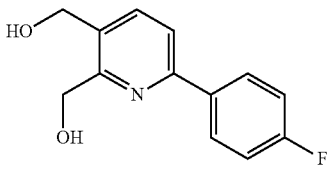 [SMILES: OCc1ccc(-c2ccc(F)cc2)nc1CO]

Calcium chloride (2.30 g, 20.75 mmol, 1.20 eq) and sodium borohydride (6.54 g, 172.90 mmol, 10.00 eq) were added to a solution of dimethyl 6-(4-fluorophenyl)pyridine-2,3-dicarboxylate (5.00 g, 17.29 mmol, 1.00 eq) in methanol (100.00 mL). The mixture was stirred at 15° C. for 3 hours. The reaction mixture was extracted with ethyl acetate (1 L×2). The combined organic layers were concentrated under reduced pressure and the residue was separated and purified by silica gel chromatography (SiO$_2$, petroleum ether/ethyl acetate=20/1 to 3:1) to deliver [6-(4-fluorophenyl)-2-(hydroxymethyl)-3-pyridyl]methanol (3.50 g, 15.01 mmol, 86.79% yield) as a white solid.

Step 6:

2,3-Bis(chloromethyl)-6-(4-fluorophenyl)pyridine

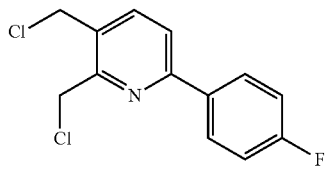 [SMILES: Fc1ccc(-c2ccc(CCl)c(CCl)n2)cc1]

Thionyl chloride (19.68 g, 165.42 mmol, 12.00 mL, 25.73 eq) was added to a solution of [6-(4-fluorophenyl)-2-(hydroxymethyl)-3-pyridyl]methanol (1.50 g, 6.43 mmol, 1.00 eq) in dichloromethane (20.00 mL). The mixture was stirred at 0° C. for 0.5 hour. The reaction mixture was concentrated under reduced pressure to remove the solvent to deliver 2,3-bis(chloromethyl)-6-(4-fluorophenyl)pyridine (2.00 g, crude) as a yellow oil. LCMS (ESI) m/z: 270.1 (M+1).

Step 7:

2-(4-Fluorophenyl)-6-trityl-5,7-dihydropyrrolo[3,4-b]pyridine

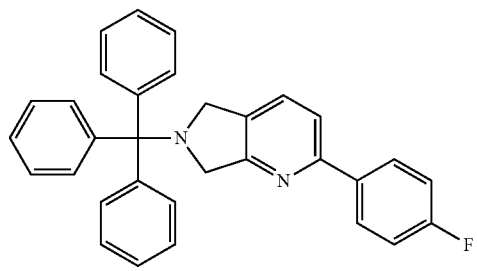 [SMILES: Fc1ccc(-c2ccc3c(n2)CN(C(c2ccccc2)(c2ccccc2)c2ccccc2)C3)cc1]

Diisopropylamine (2.87 g, 22.20 mmol, 3.88 mL, 3.00 eq) and tritylamine (2.88 g, 11.10 mmol, 1.50 eq) were added to a solution of 2,3-bis(chloromethyl)-6-(4-fluorophenyl)pyridine (2.00 g, 7.40 mmol, 1.00 eq) in DMF (60.00 mL). The mixture was stirred at 80° C. for 20 hours. The reaction mixture was concentrated under reduced pressure to remove the solvent. The residue was extracted with ethyl acetate (200 mL×2). The combined organic layers were concentrated under reduced pressure and the residue was purified by silica gel chromatography (SiO$_2$, petroleum ether/ethyl acetate=1/0 to 50:1) to deliver 2-(4-fluorophenyl)-6-trityl-5,7-dihydropyrrolo[3,4-b]pyridine (1.50 g, crude) as a white solid. $^1$H NMR (400 MHz, CDCl$_3$) δ 7.80 (dd, J=5.4, 8.8 Hz, 2H), 7.53 (d, J=7.5 Hz, 6H), 7.33 (s, 2H), 7.26-7.18 (m, 8H), 7.11 (d, J=7.3 Hz, 4H), 7.03 (s, 2H), 4.04-3.90 (m, 4H).

Step 8:

2-(4-Fluorophenyl)-6,7-dihydro-5H-pyrrolo[3,4-b]pyridine; 2,2,2-trifluoroacetic acid

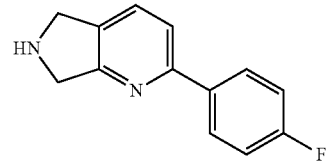 [SMILES: Fc1ccc(-c2ccc3c(n2)CNC3)cc1]

Trifluoroacetic acid (10.78 g, 94.54 mmol, 7.00 mL, 28.74 eq) was added to a solution of 2-(4-fluorophenyl)-6-trityl-5,7-dihydropyrrolo[3,4-b]pyridine (1.50 g, 3.29 mmol, 1.00 eq) in methanol (7.00 mL) and chloroform (7.00 mL). The mixture was stirred at 0° C. for 0.5 hour and the reaction mixture was washed with water (150 mL×2). The combined aqueous phases were concentrated under reduced pressure to deliver 2-(4-fluorophenyl)-6,7-dihydro-5H-pyrrolo[3,4-b]pyridine; 2,2,2-trifluoroacetic acid (1.00 g, crude) as a yellow solid. LCMS (ESI) m/z: 215.2 (M+1).

Step 9:

(2S)-1-(2-bromo-4-nitroimidazol-1-yl)-3-(2-(4-fluorophenyl)-5,7-dihydropyrrolo[3,4-b]pyridin-6-yl)-2-methylpropan-2-ol

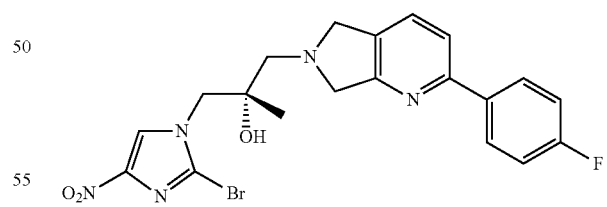

Diisopropylamine (1.18 g, 9.14 mmol, 1.60 mL, 3.00 eq) and 2-bromo-1-[[(2R)-2-methyloxiran-2-yl]methyl]-4-nitroimidazole (1.20 g, 4.58 mmol, 1.50 eq) were added to a solution of 2-(4-fluorophenyl)-6,7-dihydro-5H-pyrrolo[3,4-b]pyridine; 2,2,2-trifluoroacetic acid (1.00 g, 3.05 mmol, 1.00 eq) in tert-butanol (50.00 mL). The mixture was stirred at 40° C. for 10 hours. The reaction mixture was concentrated under reduced pressure to remove the solvent, and the residue was purified by column silica gel chromatography (SiO$_2$, petroleum ether/ethyl acetate=10/1 to 3:1) to deliver (2S)-1-(2-bromo-4-nitroimidazol-1-yl)-3-(2-(4-fluorophenyl)-5,7-dihydropyrrolo[3,4-b]pyridin-6-yl)-2-methylpropan-2-ol (700.00 mg, crude) as a brown oil. LCMS (ESI) m/z: 476.0 (M+1).

Step 10:

(S)-2-((2-(4-Fluorophenyl)-5H-pyrrolo[3,4-b]pyridin-6(7H)-yl)methyl)-2-methyl-6-nitro-2,3-dihydroimidazo[2,1-b]oxazole Compound 88

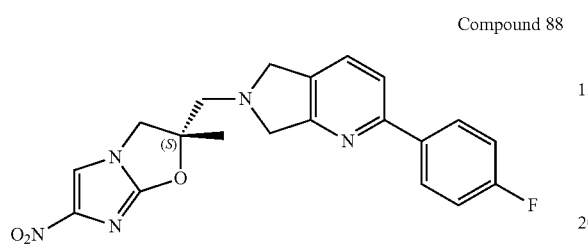

Sodium hydride (70.54 mg, 2.94 mmol, 2.00 eq) was added to a solution of (2S)-1-(2-bromo-4-nitroimidazol-1-yl)-3-(2-(4-fluorophenyl)-5,7-dihydropyrrolo[3,4-b]pyridin-6-yl)-2-methylpropan-2-ol (700.00 mg, 1.47 mmol, 1.00 eq) in DMF (4.00 mL). The mixture was stirred at 0° C. for 10 minutes. The reaction mixture was added to a saturated aqueous ammonium chloride solution (200 mL) at 0° C. The filter cake was filtered and dried. The filter cake was purified by preparative thin layer chromatography (silica, DCM:methanol=15:1) to deliver (S)-2-((2-(4-fluorophenyl)-5H-pyrrolo[3,4-b]pyridin-6(7H)-yl)methyl)-2-methyl-6-nitro-2,3-dihydroimidazo[2,1-b]oxazole compound 88 (243.60 mg, 600.70 μmol, 40.86% yield, 97.5% purity). $^1$H NMR (400 MHz, CDCl$_3$) δ 7.97-7.89 (m, 2H), 7.55 (s, 3H), 7.21-7.11 (m, 2H), 4.58-4.46 (m, 1H), 4.34-4.08 (m, 4H), 4.04-3.93 (m, 1H), 3.41-3.25 (m, 1H), 3.15-3.04 (m, 1H), 1.73 (s, 3H). LCMS (ESI) m/z: 396.2 (M+1).

Embodiment 89

(S)-2-(4-Fluorophenyl)-5-((2-methyl-6-nitro-2,3-dihydroimidazo[2,1-b]oxazol-2-yl)methyl)-5,6-dihydro-4H-pyrrolo[3,4-d]oxazole

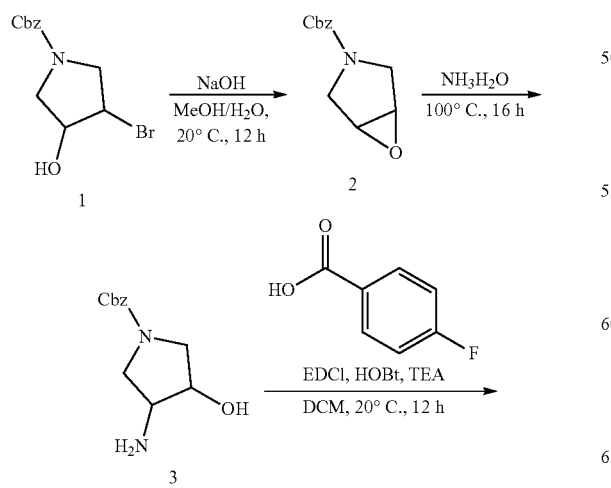

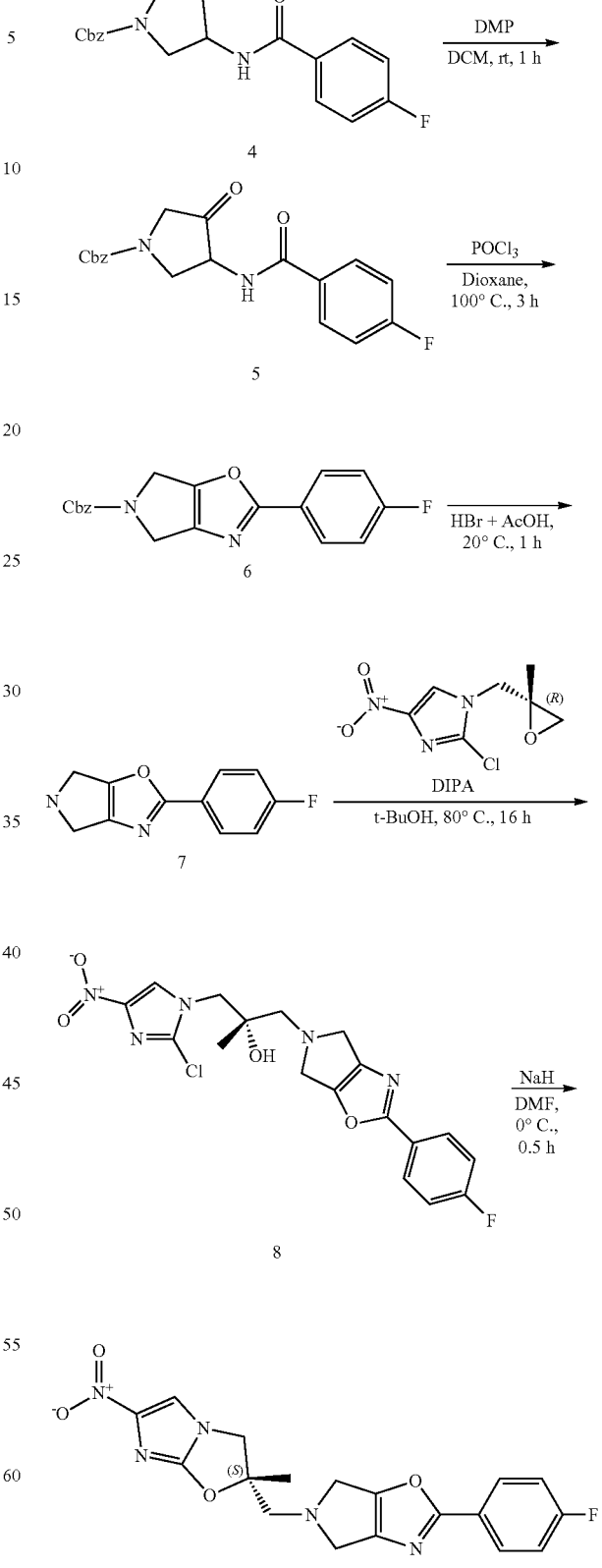

Compound 89

Step 1:

Benzyl 6-oxa-3-azabicyclo[3.1.0]hexane-3-carboxylate

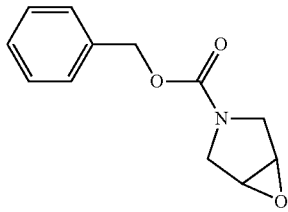 [SMILES: O=C(OCc1ccccc1)N1CC2OC2C1]

Sodium hydroxide (1.50 g, 37.49 mmol, 1.50 eq) was added to a mixed solution of benzyl 3-bromo-4-hydroxy-pyrrolidine-1-carboxylate (7.50 g, 24.99 mmol, 1.00 eq) in methanol (50.00 mL) and water (50.00 mL). The mixture was stirred at 20° C. for 12 hours. Water (200 mL) was added to the mixture, and then extracted with ethyl acetate (200 mL×3). The combined organic layers were dried over sodium sulfate, filtered and concentrated under reduced pressure to deliver benzyl 6-oxa-3-azabicyclo[3.1.0]hexane-3-carboxylate (350.00 mg, 1.60 mmol, 95.81% Yield) as a slightly yellow oil. $^1$H NMR (300 MHz, CDCl$_3$) δ 7.36-7.31 (m, 5H), 5.14-5.12 (m, 2H), 3.88 (t, J=12.90 Hz, 1H), 3.68-3.63 (m, 2H), 3.43-3.37 (m, 3H).

Step 2:

Benzyl 3-amino-4-hydroxypyrrolidine-1-carboxylate

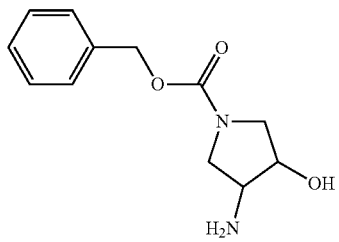 [SMILES: NC1CN(C(=O)OCc2ccccc2)CC1O]

Benzyl 6-oxa-3-azabicyclo[3.1.0]hexane-3-carboxylate (5.40 g, 24.63 mmol, 1.00 eq) and ammonia (43.17 g, 1.23 mol, 47.43 mL, 50.00 eq) were mixed, the mixture was then stirred at 100° C. for 16 hours. The mixture was concentrated under reduced pressure to deliver benzyl 3-amino-4-hydroxy-pyrrolidine-1-carboxylate (5.00 g, 21.16 mmol, 85.92% yield) as a slightly yellow oil.

Step 3:

Benzyl 3-(4-fluorobenzamido)-4-hydroxypyrrolidine-1-carboxylate

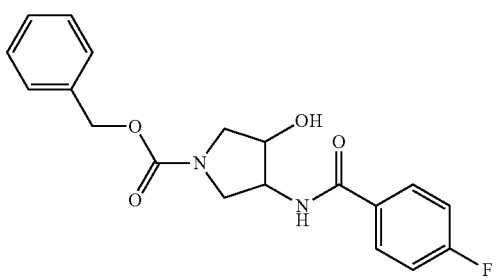 [SMILES: O=C(NC1CN(C(=O)OCc2ccccc2)CC1O)c1ccc(F)cc1]

HOBt (2.57 g, 19.05 mmol, 1.00 eq), EDCI (7.30 g, 38.10 mmol, 2.00 eq) and triethylamine (5.78 g, 57.15 mmol, 7.92 mL, 3.00 eq) were added to a solution of benzyl 3-amino-4-hydroxy-pyrrolidine-1-carboxylate (4.50 g, 19.05 mmol, 1.00 eq) and 4-fluorobenzoic acid (2.67 g, 19.05 mmol, 1.00 eq) in dichloromethane (50.00 mL). The mixture was stirred at 20° C. for 12 hours. Water (200 mL) was added to the reaction mixture and extracted with dichloromethane (150 mL×3). The combined organic layers were washed with saturated brine, dried over sodium sulfate, filtered and concentrated under reduced pressure. The residue was purified by silica gel chromatography (column height: 300 mm, diameter: 50 mm, 100 to 200 mesh silica gel, petroleum ether/ethyl acetate=5/1, 2/1, 0/1) to deliver benzyl 3-(4-fluorobenzamido)-4-hydroxypyrrolidine-1-carboxylate (2.78 g, 7.76 mmol, 40.73% yield) and benzyl 3-[(4-fluorobenzoyl)amino]-4-(4-fluorobenzoyDoxy-pyrrolidine-1-carboxylate (2.20 g, 4.58 mmol, 24.04% yield) as a light yellow solid. $^1$H NMR (400 MHz, DMSO-d$_6$) δ 8.52 (d, J=6.40 Hz, 1H), 7.92 (dd, J=6.90, 5.77 Hz, 2H), 7.38-7.36 (m, 5H), 7.30 (d, J=8.78 Hz, 2H), 5.08-5.06 (m, 2H), 4.23-4.11 (m, 2H), 3.65-3.57 (m, 2H), 3.29-3.16 (m, 2H).

Step 4:

Benzyl 3-(4-fluorobenzamido)-4-oxopyrrolidine-1-carboxylate

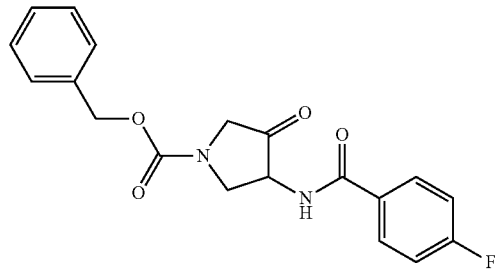 [SMILES: O=C(NC1CN(C(=O)OCc2ccccc2)CC1=O)c1ccc(F)cc1]

Dess-Martin periodinane (9.94 g, 23.44 mmol, 7.26 mL, 2.00 eq) was added to a solution of 3-(4-fluorobenzamido)-4-hydroxypyrrolidine-1-carboxylate (4.20 g, 11.72 mmol, 1.00 eq) in DCM (3.00 mL) at 0° C. The mixture was stirred at 20° C. for 2 hours. Sodium sulfite solution (100 mL) and sodium bicarbonate solution (100 mL) were added to the reaction mixture, the resulting mixture was extracted with dichloromethane (200 mL×3), and the combined organic layers were washed with saturated brine (200 mL*1), dried over sodium sulfate, filtered and concentrated under reduced pressure to deliver benzyl 3-(4-fluorobenzamido)-4-oxopyrrolidine-1-carboxylate (4.00 g, 11.22 mmol, 95.78% yield) as a slightly yellow oil. $^1$H NMR (400 MHz, DMSO) δ 9.15 (d, J=6.52 Hz, 1H), 7.92 (dd, J=8.47, 5.58 Hz, 2H), 7.41-7.33 (m, 7H), 5.15 (s, 2H), 4.51 (d, J=8.91 Hz, 1H), 4.09-3.77 (m, 3H), 3.40 (s, 1H).

Step 5:

Benzyl 2-(4-fluorophenyl)-4,6-dihydropyrrolo[3,4-d]oxazole-5-carboxylate

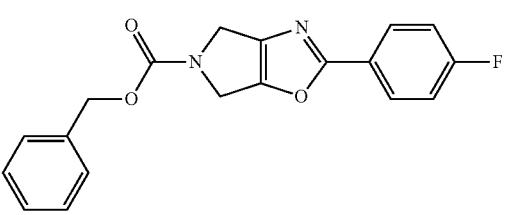 [SMILES: O=C(OCc1ccccc1)N1Cc2nc(-c3ccc(F)cc3)oc2C1]

Phosphorus oxychloride (9.62 g, 62.74 mmol, 5.83 mL, 5.59 eq) was added to a solution of benzyl 3-(4-fluorobenzamido)-4-oxopyrrolidine-1-carboxylate (4.00 g, 11.22 mmol, 1.00 eq) in dioxane (5.00 mL). The mixture was stirred at 100° C. for 4 hours. After the mixture was cooled, the mixture was slowly added to H₂O (200 mL), filtered and the filter cake was washed with dichloromethane (50 mL) and the filter cake was collected to deliver benzyl 2-(4-fluorophenyl)-4,6-dihydropyrrolo[3,4-d]oxazole-5-carboxylate (1.50 g, 4.43 mmol, 39.48% yield) as a brown solid. ¹H NMR (400 MHz, DMSO-$d_6$) δ 8.03 (dd, J=7.40, 5.40 Hz, 2H), 7.44-7.36 (m, 7H), 5.18 (s, 2H), 4.68-4.60 (m, 2H), 4.50-4.41 (m, 2H).

Step 6:

2-(4-Fluorophenyl)-5,6-dihydro-4H-pyrrolo[3,4-d]oxazole

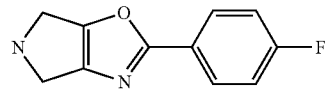

Benzyl 2-(4-fluorophenyl)-4,6-dihydropyrrolo[3,4-d]oxazole-5-carboxylate (1.50 g, 4.43 mmol, 1.00 eq) was dissolved in a solution of hydrogen bromide in acetic acid (7.17 g, 88.60 mmol, 4.81 mL, 20.00 eq), and stirred at 20° C. under nitrogen for 1 hour. The mixture was concentrated under reduced pressure, dichloromethane (20 mL) and ethyl acetate (20 mL) were added, filtered and the filter cake was dried in vacuo to deliver 2-(4-fluorophenyl)-5,6-dihydro-4H-pyrrolo[3,4-d]oxazole (1.00 g, 3.51 mmol, 79.17% yield, hydrobromide) as a black solid. ¹H NMR (300 MHz, DMSO) δ 8.07-7.89 (m, 2H), 7.48-7.27 (m, 2H), 4.58-4.23 (m, 4H).

Step 7:

(2S)-1-(2-Chloro-4-nitroimidazol-1-yl)-3-(2-(4-fluorophenyl)-4,6-dihydropyrrolo[3,4-d]oxazol-5-yl)-2-methylpropan-2-ol

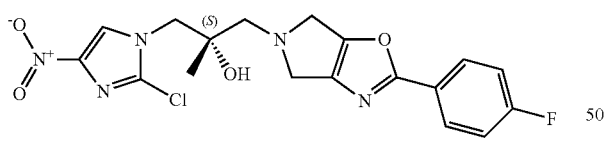

Diisopropylamine (906.60 mg, 7.01 mmol, 1.23 mL, 2.00 eq) was added to a solution of 2-(4-fluorophenyl)-5,6-dihydro-4H-pyrrolo[3,4-d]oxazole (1.00 g, 3.51 mmol, 1.00 eq, hydrobromide) and 2-chloro-1-[[(2R)-2-methyloxiran-2-yl]methyl]-4-nitroimidazole (916.57 mg, 4.21 mmol, 1.20 eq) in tert-butanol (20.00 mL). The mixture was stirred at 80° C. for 12 hours. Water (50 mL) was added to the reaction mixture, and then extracted with ethyl acetate (100 mL×3). The combined organic layers were dried over sodium sulfate, filtered and concentrated under reduced pressure to give a residue. The residue was purified by silica gel chromatography (column height: 300 mm, diameter: 50 mm, 100 to 200 mesh silica gel, petroleum ether/ethyl acetate=5/1, 3/1, 1/1) to deliver (2S)-1-(2-chloro-4-nitroimidazol-1-yl)-3-(2-(4-fluorophenyl)-4,6-dihydropyrrolo[3,4-d]oxazol-5-y 1)-2-methylpropan-2-ol (700.00 mg, 1.66 mmol, 47.28% yield) as a yellow solid. LCMS (ESI) m/z: 422.1 (M+1).

Step 8:

(S)-2-(4-Fluorophenyl)-5-((2-methyl-6-nitro-2,3-dihydroimidazo[2,1-b]oxazol-2-yl)methyl)-5,6-dihydro-4H-pyrrolo[3,4-d]oxazole Compound 89

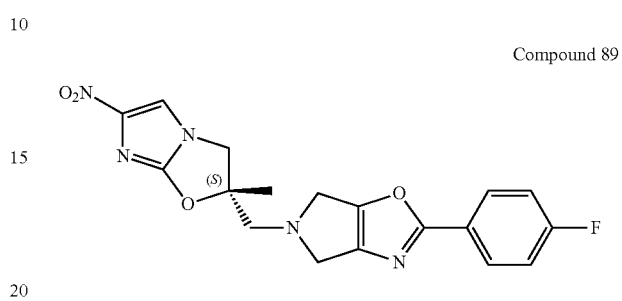

Sodium hydride (132.76 mg, 3.32 mmol, 60% purity, 2.00 eq) was added to a solution of (2S)-1-(2-chloro-4-nitroimidazol-1-yl)-3-(2-(4-fluorophenyl)-4,6-dihydropyrrolo[3,4-d]oxazol-5-yl)-2-methylpropan-2-ol (700.00 mg, 1.66 mmol, 1.00 eq) in DMF (5.00 mL) at −45° C. The mixture was stirred at −45° C. for 30 minutes and then stirred at 0° C. for 30 minutes. The reaction mixture was added to a saturated ammonium chloride solution (150 mL), and the mixture was filtered and the filter cake was purified by preparative separation chromatography (GX-A; Phenomenex Gemini 150*25 mm*10 um; acetonitrile 40%-70%; water (0.05% ammonia hydroxide v/v); 25 mL/min) to deliver (S)-2-(4-fluorophenyl)-5-((2-methyl-6-nitro-2,3-dihydroimidazo[2,1-b]oxazol-2-yl)methyl)-5,6-dihydro-4H-pyrrolo[3,4-d]oxazole compound 89 (46.00 mg, 117.70 μmol, 7.09% yield, 98.6% purity). ¹H NMR (400 MHz, CDCl₃) δ 7.98 (dd, J=8.85, 5.33 Hz, 2H), 7.56 (s, 1H), 7.15 (t, J=8.66 Hz, 2H), 4.46 (d, J=9.66 Hz, 1H), 4.11-3.89 (m, 5H), 3.42 (d, J=14.93 Hz, 1H), 3.10 (d, J=14.81 Hz, 1H), 1.70 (s, 3H). LCMS (ESI) m/z: 386.1 (M+1).

Embodiment 90

(S)-2-(3,4-Difluorophenyl)-5-((2-methyl-6-nitro-2,3-dihydroimidazo[2,1-b]oxazol-2-yl)methyl)-5,6-dihydro-4H-pyrrolo[3,4-d]oxazole Compound 90

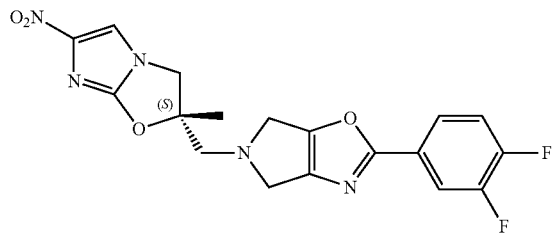

The synthesis method was as in Embodiment 89.

(S)-2-(3,4-Difluorophenyl)-5-((2-methyl-6-nitro-2,3-dihydroimidazo[2,1-b]oxazol-2-yl)methyl)-5,6-dihydro-4H-pyrrolo[3,4-d]oxazole compound 90 (24.80 mg, 59.27 μmol, 35.88% yield, 96.4% purity). ¹H NMR (400 MHz, CDCl₃) δ 7.84-7.77 (m, 1H), 7.77-7.71 (m, 1H), 7.56 (s, 1H), 7.27-7.21 (m, 1H), 4.45 (d, J=9.66 Hz, 1H), 4.10-3.89 (m, 5H), 3.42 (d, J=14.93 Hz, 1H), 3.10 (d, J=14.93 Hz, 1H), 1.70 (s, 3H).

Embodiment 91

(S)-2-(2,4-Difluorophenyl)-5-((2-methyl-6-nitro-2,3-dihydroimidazo[2,1-b]oxazol-2-yl)methyl)-5,6-dihydro-4H-pyrrolo[3,4-d]oxazole Compound 91

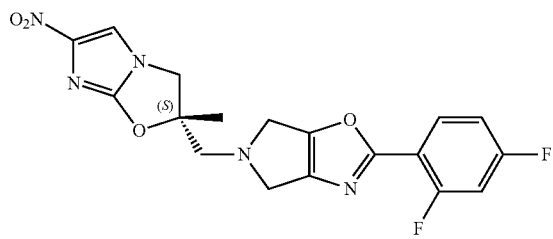

The synthesis method was as in Embodiment 89.

(S)-2-(2,4-Difluorophenyl)-5-((2-methyl-6-nitro-2,3-dihydroimidazo[2,1-b]oxazol-2-yl)methyl)-5,6-dihydro-4H-pyrrolo[3,4-d]oxazole compound 91 (31.30 mg, 75.82 μmol, 24.48% yield, 97.7% purity). $^1$HNMR (400 MHz, CDCl$_3$) δ 8.03-7.91 (m, 1H), 7.56 (s, 1H), 6.98 (d, J=8.2 Hz, 2H), 4.49-4.42 (m, 1H), 4.16-3.89 (m, 5H), 3.48-3.37 (m, 1H), 3.17-3.03 (m, 1H), 1.70 (s, 3H). LCMS (ESI) m/z: 404.1 (M+1).

Embodiment 92

(S)-2-(3,5-Difluoropyridin-2-yl)-5-((2-methyl-6-nitro-2,3-dihydroimidazo[2,1-b]oxazol-2-yl)methyl)-5,6-dihydro-4H-pyrrolo[3,4-d]oxazole Compound 92

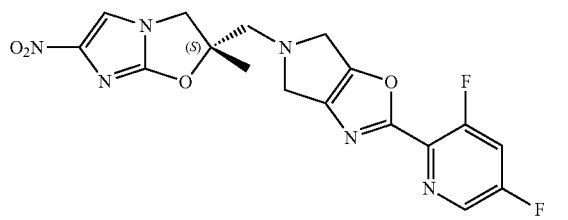

The synthesis method was as in Embodiment 89.

(S)-2-(3,5-Difluoropyridin-2-yl)-5-((2-methyl-6-nitro-2,3-dihydroimidazo[2,1-b]oxazol-2-yl)methyl)-5,6-dihydro-4H-pyrrolo[3,4-d]oxazole compound 92 (125.10 mg, 305.38 μmol, 51.10% yield, 98.7% purity). $^1$H NMR (400 MHz, CDCl$_3$) δ 8.48 (d, J=2.1 Hz, 1H), 7.56 (s, 1H), 7.41 (ddd, J=2.3, 7.8, 10.0 Hz, 1H), 4.43 (d, J=9.7 Hz, 1H), 4.20-4.06 (m, 3H), 4.05-3.92 (m, 2H), 3.43 (d, J=14.8 Hz, 1H), 3.13 (d, J=14.8 Hz, 1H), 1.71 (s, 3H). LCMS (ESI) m/z: 405.0 (M+1).

Embodiment 93

(S)-2-(5-Fluoropyridin-2-yl)-5-((2-methyl-6-nitro-2,3-dihydroimidazo[2,1-b]oxazol-2-yl)methyl)-5,6-dihydro-4H-pyrrolo[3,4-d]oxazole Compound 93

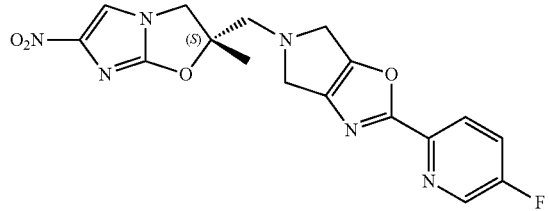

The synthesis method was as in Embodiment 89.

(S)-2-(5-Fluoropyridin-2-yl)-5-((2-methyl-6-nitro-2,3-dihydroimidazo[2,1-b]oxazol-2-yl)methyl)-5,6-dihydro-4H-pyrrolo[3,4-d]oxazole compound 93 (175.46 mg, 445.96 μmol, 52.09% yield, 98.194% purity). $^1$H NMR (400 MHz, CDCl$_3$) δ 8.56 (d, J=0.4 Hz, 1H), 8.13-8.07 (m, 1H), 7.57-7.51 (m, 2H), 4.43 (d, J=12.0 Hz, 1H), 4.19-4.02 (m, 3H), 4.01-3.92 (m, 2H), 3.42 (d, J=16.0 Hz, 1H), 3.11 (d, J=16.0 Hz, 1H), 1.70 (s, 3H). LCMS (ESI) m/z: 387(M+1).

Embodiment 94

(S)-5-((2-Methyl-6-nitro-2,3-dihydroimidazo[2,1-b]oxazol-2-yl)methyl)-2-(2,4,5-trifluorophenyl)-5,6-dihydro-4H-pyrrolo[3,4-d]oxazole Compound 94

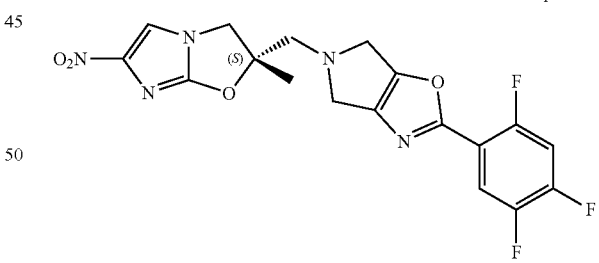

The synthesis method was as in Embodiment 89.

(S)-5-((2-Methyl-6-nitro-2,3-dihydroimidazo[2,1-b]oxazol-2-yl)methyl)-2-(2,4,5-trifluorophenyl)-5,6-dihydro-4H-pyrrolo[3,4-d]oxazole compound 94 (491.75 mg, 1.14 mmol, 57.13% yield, 97.416% purity). $^1$H NMR (400 MHz, CDCl$_3$) δ 7.89-7.74 (m, 1H), 7.57 (s, 1H), 7.15-7.02 (m, 1H), 4.50-4.39 (m, 1H), 4.14-3.90 (m, 5H), 3.48-3.38 (m, 1H), 3.16-3.07 (m, 1H), 1.71 (s, 3H). LCMS (ESI) m/z: 422(M+1).

Embodiment 95

(S)-2-(3,5-Difluorophenyl)-5-((2-methyl-6-nitro-2,3-dihydroimidazo[2,1-b]oxazol-2-yl)methyl)-5,6-dihydro-4H-pyrrolo[3,4-d]oxazole

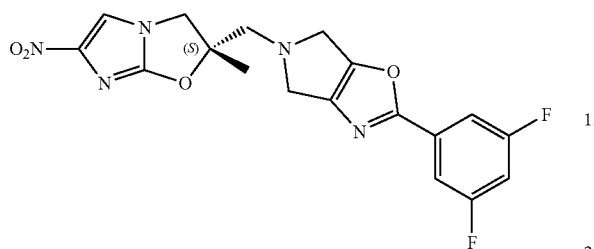

Compound 95

The synthesis method was as in Embodiment 89.

(S)-2-(3,5-Difluorophenyl)-5-((2-methyl-6-nitro-2,3-dihydroimidazo[2,1-b]oxazol-2-yl)methyl)-5,6-dihydro-4H-pyrrolo[3,4-d]oxazole compound 95 (21.60 mg, 53.29 μmol, 10.32% yield, 99.5% purity). $^1$H NMR (400 MHz, CDCl$_3$) δ 7.56 (s, 1H), 7.54-7.48 (m, 2H), 6.95-6.83 (m, 1H), 4.43 (s, 1H), 4.15-3.88 (m, 5H), 3.41 (s, 1H), 3.10 (d, J=14.8 Hz, 1H), 1.71 (s, 3H). LCMS (ESI) m/z: 404.2 (M+1).

Embodiment 96

(S)-2-((2-(4-Fluorophenyl)-8,9-dihydro-5H-pyrido[3,2-c]azepin-6(7H)-yl)methyl)-2-methyl-6-nitro-2,3-dihydroimidazo[2,1-b]oxazole

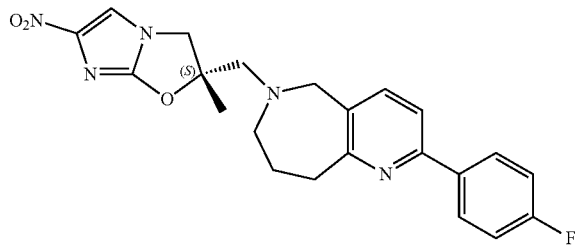

Compound 96

The synthesis method was as in Embodiment 7.

(S)-2-((2-(4-Fluorophenyl)-8,9-dihydro-5H-pyrido[3,2-c]azepin-6(7H)-yl)methyl)-2-methyl-6-nitro-2,3-dihydroimidazo[2,1-b]oxazole compound 96 (85.50 mg, 196.26 μmol, 36.10% yield, 97.2% purity). $^1$H NMR (400 MHz, CDCl$_3$) δ 8.08-7.93 (m, 2H), 7.54-7.40 (m, 3H), 7.16 (t, J=8.7 Hz, 2H), 4.36 (d, J=9.5 Hz, 1H), 4.03-3.84 (m, 3H), 3.31-3.15 (m, 4H), 2.96 (d, J=15.3 Hz, 1H), 2.54 (d, J=15.3 Hz, 1H), 1.80 (br, s, 2H), 1.59 (s, 3H). LCMS (ESI) m/z: 424 (M+1).

Embodiment 97

(S)-2-((2-(4-Fluorophenyl)-8,9-dihydro-5H-pyrido[2,3-d]azepin-7(6H)-yl)methyl)-2-methyl-6-nitro-2,3-dihydroimidazo[2,1-b]oxazole

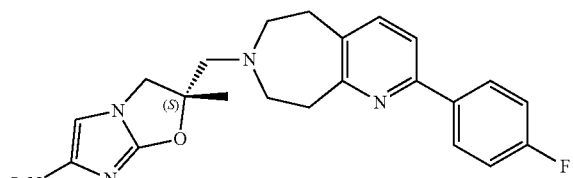

Compound 97

The synthesis method was as in Embodiment 7.

(S)-2-((2-(4-Fluorophenyl)-8,9-dihydro-5H-pyrido[2,3-d]azepin-7 (6H)-yl)methyl)-2-methyl-6-nitro-2,3-dihydroimidazo[2,1-b]oxazole compound 97 (23.80 mg, 50.02 μmol, 9.20% yield, 89% purity). $^1$H NMR (400 MHz, CDCl$_3$) δ 8.11-7.89 (m, 2H), 7.56-7.46 (m, 1H), 7.45-7.34 (m, 2H), 7.15 (t, J=8.7 Hz, 2H), 4.36 (d, J=9.5 Hz, 1H), 4.00-3.89 (m, 1H), 3.19-2.62 (m, 10H), 1.72-1.57 (m, 3H). LCMS (ESI) m/z: 424 (M+1).

Embodiment 98

(2S)-2-((2-(4-Fluorophenyl)-6,7,8,9-tetrahydro-5H-5,8-epiminocyclohepta[b]pyridin-10-yl)methyl)-2-methyl-6-nitro-2,3-dihydroimidazo[2,1-b]oxazole

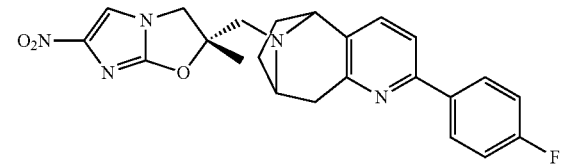

Compound 98A
Compound 98B

The synthesis method was as in Embodiment 7.

(2S)-2-((2-(4-Fluorophenyl)-6,7,8,9-tetrahydro-5H-5,8-epiminocyclohepta[b]pyridin-10-yl)methyl)-2-methyl-6-nitro-2,3-dihydroimidazo[2,1-b]oxazole compound 98A (30.26 mg, 69.49 mmol, 32.79% yield, 100% purity). $^1$H NMR (400 MHz, CDCl$_3$) δ 7.94-7.87 (m, 2H), 7.45 (s, 1H), 7.42-7.38 (m, 1H), 7.36-7.31 (m, 1H), 7.19-7.10 (m, 2H), 4.39 (d, J=9.7 Hz, 1H), 4.06 (d, J=6.0 Hz, 1H), 3.93 (d, J=9.7 Hz, 1H), 3.63 (t, J=6.1 Hz, 1H), 3.39 (dd, J=4.8, 17.9 Hz, 1H), 3.08 (d, J=14.7 Hz, 1H), 2.75-2.64 (m, 2H), 2.29-2.08 (m, 2H), 1.83-1.78 (m, 1H), 1.73-1.63 (m, 4H). LCMS (ESI) m/z: 436.3 (M+1).

(2S)-2-((2-(4-Fluorophenyl)-6,7,8,9-tetrahydro-5H-5,8-epiminocyclohepta[b]pyridin-10-yl)methyl)-2-methyl-6-nitro-2,3-dihydroimidazo[2,1-b]oxazole compound 98B (41.29 mg, 94.82 mmol, 44.75% yield, 100% purity). $^1$H NMR (400 MHz, CDCl$_3$) δ 7.97-7.90 (m, 2H), 7.55 (s, 1H), 7.50-7.45 (m, 1H), 7.42-7.37 (m, 1H), 7.19-7.11 (m, 2H), 4.50 (d, J=9.4 Hz, 1H), 4.03 (d, J=6.0 Hz, 1H), 3.94 (d, J=9.4 Hz, 1H), 3.71-3.62 (m, 1H), 3.22 (d, J=14.6 Hz, 1H), 2.99 (d, J=14.8 Hz, 1H), 2.80 (d, J=14.8 Hz, 1H), 2.67 (d, J=17.8

Hz, 1H), 2.15 (d, J=11.7 Hz, 1H), 2.05-1.93 (m, 1H), 1.76 (d, J=12.3 Hz, 2H), 1.60 (s, 3H). LCMS (ESI) m/z: 436.3 (M+1).

Embodiment 99

(2S)-2-((2-(4-Fluorophenyl)-5,6,7,8-tetrahydro-4H-5,8-epiminocyclohepta[d]thiazol-9-yl)methyl)-2-methyl-6-nitro-2,3-dihydroimidazo[2,1-b]oxazole

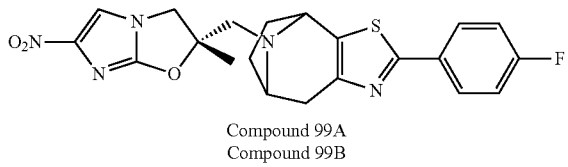 [SMILES: C[C@]1(CN2C3CCC2c2sc(-c4ccc(F)cc4)nc2C3)Cn2cc([N+](=O)[O-])nc2O1]

Compound 99A
Compound 99B

The synthesis method was as in Embodiment 69.

(2S)-2-((2-(4-Fluorophenyl)-5,6,7,8-tetrahydro-4H-5,8-epiminocyclohepta[d]thiazol-9-yl)methyl)-2-methyl-6-nitro-2,3-dihydroimidazo[2,1-b]oxazole compound 99A (3.70 mg, 8.26 µmol, 2.47% yield, 98.594% purity). $^1$H NMR (400 MHz, CDCl$_3$) δ 7.91-7.84 (m, 2H), 7.53 (s, 1H), 7.16-7.09 (m, 2H), 4.35 (d, J=8.0 Hz, 1H), 4.25 (d, J=4.0 Hz, 1H), 3.95 (d, J=8.0 Hz, 1H), 3.69-3.63 (m, 1H), 3.38-3.27 (m, 1H), 3.04 (d, J=16.0 Hz, 1H), 2.80 (d, J=16.0 Hz, 1H), 2.56 (d, J=16.0 Hz, 1H), 2.19-2.10 (m, 2H), 1.99-1.91 (m, 1H), 1.67 (s, 3H), 1.69-1.61 (m, 1H). LCMS (ESI) m/z: 442(M+1).

(2S)-2-((2-(4-Fluorophenyl)-5,6,7,8-tetrahydro-4H-5,8-epiminocyclohepta[d]thiazol-9-yl)methyl)-2-methyl-6-nitro-2,3-dihydroimidazo[2,1-b]oxazole compound 99B (3.70 mg, 8.33 µmol, 2.49% yield, 99.431% purity). $^1$H NMR (400 MHz, CDCl$_3$) δ 7.94-7.85 (m, 2H), 7.56 (s, 1H), 7.17-7.09 (m, 2H), 4.45 (d, J=12.0 Hz, 1H), 4.31-4.26 (m, 1H), 3.95 (d, J=8.0 Hz, 1H), 3.68-3.60 (m, 1H), 3.23-3.14 (m, 1H), 3.07 (d, J=16.0 Hz, 1H), 2.78 (d, J=12.0 Hz, 1H), 2.61-2.53 (m, 1H), 2.21-2.09 (m, 1H), 1.96-1.86 (m, 2H), 1.61 (s, 3H), 1.57-1.53 (m, 1H). LCMS (ESI) m/z: 442(M+1).

Embodiment 100

(S)-2-((2-(4-Fluorophenyl)-7,8-dihydro-4H-thiazolo[4,5-d]azepin-6(5H)-yl)methyl)-2-methyl-6-nitro-2,3-dihydroimidazo[2,1-b]oxazole

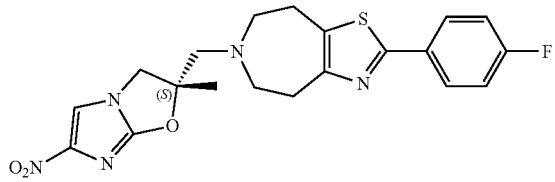

Compound 100

The synthesis method was as in Embodiment 69.

(S)-2-((2-(4-Fluorophenyl)-7,8-dihydro-4H-thiazolo[4,5-d]azepin-6(5H)-yl)methyl)-2-methyl-6-nitro-2,3-dihydroimidazo[2,1-b]oxazole compound 100 (35.30 mg, 77.62 µmol, 10.33% yield, 94.431% purity). $^1$H NMR (400 MHz, CDCl$_3$) δ 7.87-7.78 (m, 2H), 7.56 (s, 1H), 7.13-7.07 (m, 2H), 4.40 (d, J=8.0 Hz, 2H), 3.97 (d, J=8.0 Hz, 2H), 3.24 (d, J=16.0 Hz, 2H), 3.17-3.09 (m, 1H), 3.07-2.86 (m, 6H), 2.82 (d, J=16.0 Hz, 2H), 2.76-2.66 (m, 1H), 1.67 (s, 3H). LCMS (ESI) m/z: 430(M+1).

Part of the Pharmacology.

Part I: The in vitro efficacy of anti-Mycobacterium tuberculosis compounds was tested using H37Rv strain.

On the day of the test, the compound was dissolved in pure DMSO (Sigma 276855-2L) to a concentration of 10 mg/mL which was used as the mother liquor of the compound. 30 µL of DMSO was added to wells of column 2 to 11 s of the v-bottom 96-well plates (Axygen-wipp02280). 30 µL of the mother liquor of the compound was added to the well of column 2, after mixing, 30 µL was taken from the well of column 2 and added to the well of column 3, and then pipetted and mixed. The operation was taken to column 10. Column 11 was free of medicine and contained only 30 µL of DMSO. This was the "motherplate" of the compound. From column 2 to 11, the corresponding concentration of the compound was 5, 2.5, 1.25, 0.625, 0.3125, 0.156, 0.078, 0.039, 0.02, 0 mg/mL. For compounds with good efficacy, the test concentration was appropriately reduced. A flat bottom 96-well plate (Greiner 655090) was used as a "daughterplate". 98 µL of 7H9 (Sigma M0178) medium was added to the wells of all daughterplates. 2 µL of compound was extracted from the motherboard and added to the corresponding daughter plate. Line A and H, column 1 and 12 of the daughterplate contained only 7H9 medium.

The H37Rv strain in the glycerol cryovial was inoculated into 7H9 medium containing 0.05% Tween 80 and cultured for 4 weeks at 37° C. in a shaker with 200 rpm. The bacterial liquid was washed twice with 7H9 medium containing 0.05% Tween 80 and resuspended in the same medium. The absorbance of the bacteria liquid was adjusted to OD550=0.4-0.5 using the same medium. The bacteria liquid was sub-packed in microcentrifuge tubes and stored at −80° C. Storage time was no more than 1 month. On the day of the test, the packaged bacteria liquid would be frozen. The bacteria liquid was diluted 20 times and then diluted 50 times with 7H9 medium, and a total of 1000 times dilution. The bacteria liquid would be used to inoculate on the daughterplate. 100 µL of bacterial liquid was inoculated in each well of the daughterboard, 100 µL 7H9 medium was added to column 12 and without bacteria liquid.

The test daughterplate was placed in an incubator at 37° C. and the humidity was maintained at >80%. A week later, 12.5 µL of 7H9 medium containing 20% Tween 80 and 20 µL of Alamar Blue (Invitrogen DAL1100) were added to the well of a column 1 containing bacteria and the well of a column 12 without bacteria every day, and then continue to incubate for 24 hours and observed. When the added Alamar Blue was reduced to pink in 24 hours by the bacteria liquid in the well of column 1, the 7H9 medium containing 20% Tween 80 and Alamar Blue were added to all wells on the test plate and the fluorescence values were measured after incubation for 24 hours at 37° C.

The minimum inhibitory concentration (MIC) is defined as: the minimum drug concentration of Alamar blue discoloration could be completely inhibited by naked eye observation or the minimum drug concentration of more than 90% reduction of Alamar blue could be generated by fluorescence measurement. The results of some of the compounds were shown in Table 1.

Part II: Methods for testing the efficacy of Mycobacterium tuberculosis compounds in vitro using Mycobacterium bovis BCG strain TMC1019 (ATCC35737).

On the day of the test, the compound was dissolved in pure DMSO (Sigma 276855-2L) to a concentration of 12.8 mg/mL which was used as the mother liquor of the compound. 30 μL of DMSO was added to wells of column 1 to 12 s of the v-bottom 96-well plates (Axygen-wipp02280). 30 μL of the mother liquor of the compound was added to the well of column 1. 30 μL was taken from the well of column 1 and added to the well of column 2, and then pipetted and mixed. The operation was use to dilute the gradient twice to column 11. Column 12 was free of compound and contained only 30 μL of DMSO. All wells in line A and H contained only 30 μL of DMSO. This was the "motherplate" of the compound. From column 1 to 12, the corresponding concentrations of the compound were 6.4, 3.2, 1.6, 0.8, 0.4, 0.2, 0.1, 0.05, 0.025, 0.0125, 0.00625 and 0 mg/mL. For compounds with good efficacy, the test concentration was appropriately reduced. A flat bottom 96-well plate (Greiner 655090) was used as a "daughterplate". 2 μL of compound was extracted from the motherboard and added to the corresponding daughter plate. Line A and H, column 12 of the daughterplate contained only 7H9 medium.

The BCG strain in the glycerol cryovial was inoculated into 7H9 medium containing 0.05% Tween 80 and cultured for 4 weeks at 37° C. in a shaker with 200 rpm. The bacterial liquid was washed twice with 7H9 medium containing 0.05% Tween 80 and resuspended in the same medium. The absorbance of the bacteria liquid was adjusted to OD550=0.4-0.5 using the same medium. The bacteria liquid was sub-packed in microcentrifuge tubes and stored at −80° C. Storage time was no more than 1 month. On the day of the test, the packaged bacteria liquid would be frozen. The bacteria liquid was diluted 20 times and then diluted 50 times with 7H9 medium, and a total of 1000 times dilution. The bacteria liquid would be used to for inoculation. 100 μL of bacterial liquid was inoculated in each well of the daughterboard except line A, 100 μL 7H9 medium was added to line A and without bacteria liquid. The final concentrations of the test compound were 64, 32, 16, 8, 4, 1, 0.5, 0.25, 0.125, 0.0625 and 0 μg/mL. The test daughterplate was incubated in an incubator at 37° C. and the humidity was maintained at >80%.

A week later, 12.5 μL of 7H9 medium containing 20% Tween 80 and 20 μL of Alamar Blue (Invitrogen DAL1100) were added to the well of a line A without bacteria and the well of line H containing bacteria every day, and then continue to incubate for 24 hours and observed. When the added Alamar Blue was reduced to pink in 24 hours by the bacteria liquid in the well of line H, the Alamar Blue was added to all wells on the test plate and the minimum inhibitory concentrations (MIC) were observed after incubation for 24 hours at 37° C.

The minimum inhibitory concentration (MIC) is defined as: the minimum drug concentration of Alamar blue discoloration could be completely inhibited by naked eye observation or the minimum drug concentration of more than 90% reduction of Alamar blue could be generated by fluorescence measurement. The results of some of the compounds were shown in Table 1.

TABLE 1

In vitro Activity of Some of the Molecules of the Present Invention Against Mycobacterium Bovis BCG Strain and Mycobacterium Tuberculosis H37Rv Strain

| Compound Number | Embodiment Number | M. bovis ATCC35737 (ug/mL) | M. tuberculosis H37Rv MABA (MIC) (ug/mL) | M. tuberculosis H37R LORA (MIC) (ug/mL) | Vero Cell (IC$_{50}$) (ug/mL) |
|---|---|---|---|---|---|
| 1B | 1 | +++ | +++ | ++ | + |
| 5 | 5 | +++ | +++ | ++ | + |
| 6 | 6 | +++ | +++ | ++ | + |
| 7 | 7 | +++ | +++ | ++ | + |
| 10 | 10 | +++ | +++ | | + |
| 11 | 11 | ++ | | | |
| 12 | 12 | +++ | +++ | ++ | + |
| 13 | 13 | +++ | +++ | ++ | + |
| 14 | 14 | +++ | +++ | ++ | + |
| 15 | 15 | +++ | | | |
| 16 | 16 | +++ | | | |
| 17 | 17 | +++ | | | |
| 18 | 18 | +++ | | | |
| 19 | 19 | +++ | | | |
| 20 | 20 | +++ | +++ | ++ | + |
| 21 | 21 | +++ | | | |
| 22 | 22 | +++ | | | |
| 23 | 23 | +++ | | | |
| 25 | 25 | +++ | +++ | ++ | + |
| 26 | 26 | +++ | | | |
| 28 | 28 | +++ | | | |
| 33 | 33 | +++ | | | |
| 48 | 48 | +++ | | | |
| 53 | 53 | +++ | | | |
| 59 | 59 | +++ | | | |
| 61 | 61 | +++ | +++ | ++ | + |
| 64 | 64 | +++ | | | |
| 67 | 67 | +++ | +++ | | + |
| 69 | 69 | +++ | +++ | ++ | + |
| 70 | 70 | +++ | +++ | | + |
| 71 | 71 | +++ | +++ | | + |
| 73 | 73 | ++ | | | |
| 75 | 75 | ++ | | | |
| 77 | 77 | +++ | +++ | | + |
| 78 | 78 | +++ | +++ | | + |

TABLE 1-continued

In vitro Activity of Some of the Molecules of the Present Invention Against
Mycobacterium Bovis BCG Strain and Mycobacterium Tuberculosis H37Rv Strain

| Compound Number | Embodiment Number | M. bovis ATCC35737 (ug/mL) | M. tuberculosis H37Rv MABA (MIC) (ug/mL) | M. tuberculosis H37R LORA (MIC) (ug/mL) | Vero Cell ($IC_{50}$) (ug/mL) |
|---|---|---|---|---|---|
| 83 | 83 | +++ | | | |
| 85 | 85 | +++ | +++ | | + |
| 89 | 89 | +++ | +++ | | + |
| 90 | 90 | +++ | | | |
| 94 | 94 | +++ | | | |
| 96 | 96 | +++ | +++ | ++ | + |

+++: <1;
++: 1~32;
+: >32

The results showed that the compounds involved in the present invention had good inhibitory activity against both Mycobacterium bovis BCG strain and Mycobacterium tuberculosis H37Rv strain, and the minimum inhibitory concentration of all the molecules was <1 ug/mL, and the compounds of the present invention were free of cytotoxicity.

Part III: Kinetic solubility and MDR1-MDCK cell bi-directional permeability assessment experiments. The testing results were shown in Table 2.

1. Kinetic solubility test: The quantitative compound sample was weighed and dissolved in pure DMSO, the final concentration was 10 mM. The test compound and the control compound (10 mM DMSO mother liquor, 10 uL per well) were added to a 96-well plate containing 490 uL of buffer per well. After vortexing for 2 minutes, the plates were incubated on the shaker at room temperature (22±2° C.) for 24 hours. The 200 uL sample was then transferred to a MultiScreen filter plate (polycarbonate film), filtered through a millipore vacuum manifold, and the filtrate was collected. The concentration of the compound in the filtrate was determined by HPLC-UV. Three different concentrations of UV standard solution and solubility test samples were injected successively. Each sample was injected 2 times, and the concentration was taken into the standard curve, and the average value was calculated.

2. MDR1-MDCK cell bi-directional permeability evaluation experiment: MDR1-MDCK cells that permanently express human P-glycoprotein (P-glycoprotein) were planted on 96-well Insert cell plates and cultured for 4 to 7 days to form aggregated monolayer cells. The assessment of unidirectional (A→B) permeability of the fenoterol (low permeability marker) and propranolol (high permeability marker) and the bi-directional permeability of Digoxin (a P-glycoprotein substrate) were used to verify the quality of monolayer cells. The three control compounds do two complex wells.

The standard conditions for the transport experiments of the test compound were as follows:

Test concentration: 2 μM (DMSO≤1%);

Repetition: n=3;

Direction: bidirectional transport consisting of two directions: A→B and B→A;

Incubation time: single time point, 2.5 hours;

Transport buffer: HB SS, pH 7.4;

Incubation conditions: 37° C., 5% $CO_2$, 95% relative humidity.

After the incubation, the sample solutions taken from the donor wells and the receive wells were immediately mixed with a cold acetonitrile solution containing the internal standard. And the amount of accumulation of intracellular compounds was measured by lysing the cells with a cold acetonitrile solution containing the internal standard. The concentrations of the test compound in all samples (including the initial administration solution, the supernatant of donor wells, the receiver solution, the cell lysate) were analyzed by the LC/MS/MS method. The concentration of the test compound was expressed by the ratio of its peak area to the internal standard peak area. The kinetic solubility (Kinetic Solubility, KS) of the candidate compounds and the permeability data in the MDR1-MDCK monolayer cells were listed in Table 2.

TABLE 2

Kinetic Solubility and MDR1-MDCK Cells Bi-Directional Permeability Results of some of the molecules of the present invention

| Compound Number | Kinetic Solubility pH 2.0 (uM) | MDR1-MDCK Monolayer Cell Bi-directional Permeability Parameters A to B ($\times 10^{-6}$ cm/s) | B to A ($\times 10^{-6}$ cm/s) | Efflux Ratio |
|---|---|---|---|---|
| OPC-67683 | 10.5 | 0.09 | 0.17 | 1.9 |
| 1B | 129.53 | 16.82 | 22.67 | 1.35 |
| 7 | 143.49 | 17.69 | 19.29 | 1.09 |
| 69 | 39.30 | 20.92 | 15.85 | 0.76 |
| 89 | 100.39 | 25.93 | 18.46 | 0.71 |

Obviously, the above four candidate compounds were superior to OPC-67683 in the kinetic solubility. Good solubility is beneficial to the study of the absorption and preparations of drugs in vivo. It is not difficult to see that the preferred molecules are highly permeable molecules through the permeation parameters. Compared to the reference compound (OPC-67683), the advantages are obvious. Good permeability could further promote the absorption of drugs and achieve good anti-Mycobacterium tuberculosis effect.

Part IV: Pharmacokinetics In Vivo

The pharmacokinetic characteristics of rodents after intravenous and oral administration of the compound were tested in a standard protocol. Specifically, the candidate compounds of the experiment were injected intravenously and administered orally for 7 to 10 weeks old CD-1 male mice. The oral preparation was a 0.5% suspension of methylcellulose, and the intravenous preparation was a clear solution of ethanol/DMSO/polyethylene glycol 400/pure water (10:10:50:30). Plasma and lung samples were collected and analyzed by the LC-MS/MS method and the pharmacokinetic parameters were calculated. The pharmacokinetic parameters of the candidate compound 7 were shown in Table 3.

TABLE 3

Pharmacokinetic Parameters in vivo

| Compound Number | Cmax (nM) PO | Pulmonary Drug Concentration (nM/Kg) PO 1 (h) |
|---|---|---|
| OPC-67683 | 4740 | 1677 |
| 7 | 6723 | 16147 |

It was clear that the pharmacokinetic parameters of the newly discovered compound 7 were superior to the reference compound (OPC-67683) and it is noteworthy that the drug concentration in lung of compound 7 was much higher than that of the reference compound (OPC-67683) 1 hour after administration, reaching more than 9 times the reference compound. For patients with pulmonary infection in Mycobacterium tuberculosis, the higher the amount of drug exposure means the better efficacy, which is very important.

Through the activity test of H37Rv strain, we found that the molecules involved in the present invention all have good anti-Mycobacterium tuberculosis in vitro. From the structure we can see that all molecules have alkaline nitrogen atoms and are capable of salifing, which are beneficial to improve the solubility of molecules, thus it is easier to carry out the research of the preparation, the experimental data of the solubility also confirms our hypothesis. Permeability tests show that most of the molecules we have found are highly permeable molecules that are conducive to the distribution and absorption in the body and are expected to achieve better efficacy. The pharmacokinetic data in vivo further validates, compound 7 with excellent solubility and high permeability showed excellent lung exposure. In view of the data collected, we have no reason to doubt that these molecules will exhibit better efficacy than the reference compound (OPC-67683), thus benefiting the majority of patients.

What is claimed is:

1. A compound having a structure of formula (I), a pharmaceutically acceptable salt thereof or an optical isomer thereof,

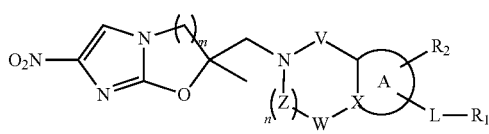

(I)

wherein,
ring A is a 5- to 6-membered heteroaryl;
X is N, C(R) or C;
R is H, a halogen, OH, CN, NO$_2$, or selected from the group consisting of an amino, a C$_{1-6}$ alkylamino, a N,N-di(C$_{1-6}$ alkyl)amino, a C$_{1-6}$ alkyl, a C$_{1-6}$ heteroalkyl, a C$_{2-6}$ alkenyl, a C$_{2-6}$ alkynyl, a C$_{3-7}$ cycloalkyl, a C$_{3-7}$ heterocycloalkyl, a 5- to 7-membered aryl, and a 5- to 7-membered heteroaryl, each of which is optionally substituted by any substituent;
each of V and W is independently selected from the group consisting of a methylene, —CH$_2$CH$_2$—, C(=O), —S(=O)— and —S(=O)$_2$—, wherein, the methylene and the —CH$_2$CH$_2$— are optionally substituted by 1 or 2 R(s);
Z is a methylene which is optionally substituted by 1 or 2 R(s);
L is a single bond, —O—, —S—, N(R), C(R)(R), —C(=O)—, —C(=S)—, —S(=O)—, or —S(=O)$_2$—;
each of R$_1$ and R$_2$ is independently selected from H, a halogen, OH, CN, NO$_2$, or each of R$_1$ and R$_2$ is independently selected from the group consisting of an amino, a C$_{1-6}$ alkyl, a C$_{1-6}$ heteroalkyl, a C$_{2-6}$ alkenyl, a C$_{2-6}$ alkynyl, a C$_{3-7}$ cycloalkyl, a C$_{3-7}$ cycloalkyl-C$_{1-6}$ alkyl, a C$_{3-7}$ heterocycloalkyl, a 5- to 7-membered aryl or heteroaryl, each of which is optionally substituted by any substituent independently selected from the group consisting of H, F, Cl, Br, I, OH, ON, NH$_2$, a C$_{1-4}$ alkyl and a C$_{1-4}$ heteroalkyl, wherein the C$_{1-4}$ alkyl and the C$_{1-4}$ heteroalkyl are optionally further substituted by 0 to 3 substituents selected from a halogen, OH, and NH$_2$;
optionally, the substituent R on Z and the substituent R on V are attached to the same atom or atomic group to form a 5- to 7-membered ring;
optionally, the moiety

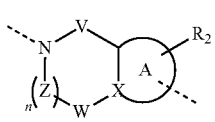

may be replaced with

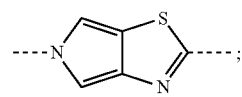

R$_2$ may also be absent;
m is 1, 2 or 3;
n is 0, 1, 2 or 3;
the "hetero" represents a heteroatom or a hetero-atomic group, which is selected from the group consisting of —C(=O)NH—, —NH—, —C(=NH)—, —S(=O)$_2$NH—, —S(=O)NH—, —O—, —S—, N, =O, =S, —C(=O)O—, —C(=O)—, —C(=S)—, —S(=O)—, —S(=O)$_2$—, and —NHC(=O)NH—;
the number of the heteroatom or the hetero-atomic group is independently selected from 0, 1, 2 or 3.

2. The compound, the pharmaceutically acceptable salt thereof or the optical isomer thereof according to claim 1, wherein, the R is independently selected from the group consisting of H, F, Cl, Br, I, OH, CN, NH$_2$, a C$_{1-4}$ alkyl and a C$_{1-4}$ heteroalkyl, wherein the C$_{1-4}$ alkyl or the C$_{1-4}$ heteroalkyl are optionally further substituted by 0 to 3 substituents selected from a halogen, OH, and NH$_2$;
or, each of the substituents is selected from the group consisting of F, Cl, Br, I, CN, —CF$_3$, —OCF$_3$, —CH$_2$CF$_3$, OCH$_3$, and (CH$_3$)$_3$COC(=O)—.

3. The compound, the pharmaceutically acceptable salt thereof or the optical isomer thereof according to claim 1, wherein, each of R$_1$ and R$_2$ is independently selected from the group consisting of H, halogen, CN, or selected from the group consisting of

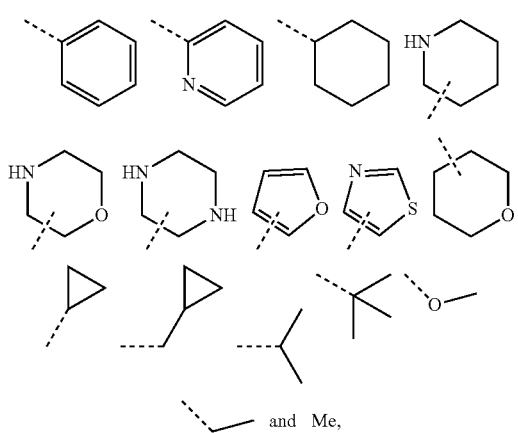

each of which is optionally substituted by any substituent independently selected from the group consisting of H, F, Cl, Br, I, OH, CN, $NH_2$, a $C_{1-4}$ alkyl and a $C_{1-4}$ heteroalkyl, wherein the $C_{1-4}$ alkyl or the $C_{1-4}$ heteroalkyl are optionally further substituted by 0 to 3 substituents selected from a halogen, OH and $NH_2$;

or, each of $R_1$ and $R_2$ is independently selected from the group consisting of H, halogen, CN, or selected from the group consisting of

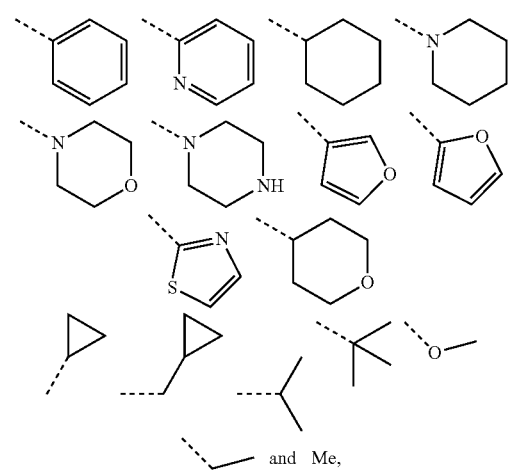

each of which is optionally substituted, by any substituent independently selected from the group consisting of H, F, Cl, Br, I, OH, CN, $NH_2$, a $C_{1-4}$ alkyl and a $C_{1-4}$ heteroalkyl, wherein the $C_{1-4}$ alkyl or the $C_{1-4}$ heteroalkyl are optionally further substituted by 0 to 3 substituents selected from a halogen, OH and $NH_2$;

or, each of $R_1$ and $R_2$ is independently selected from the group consisting of

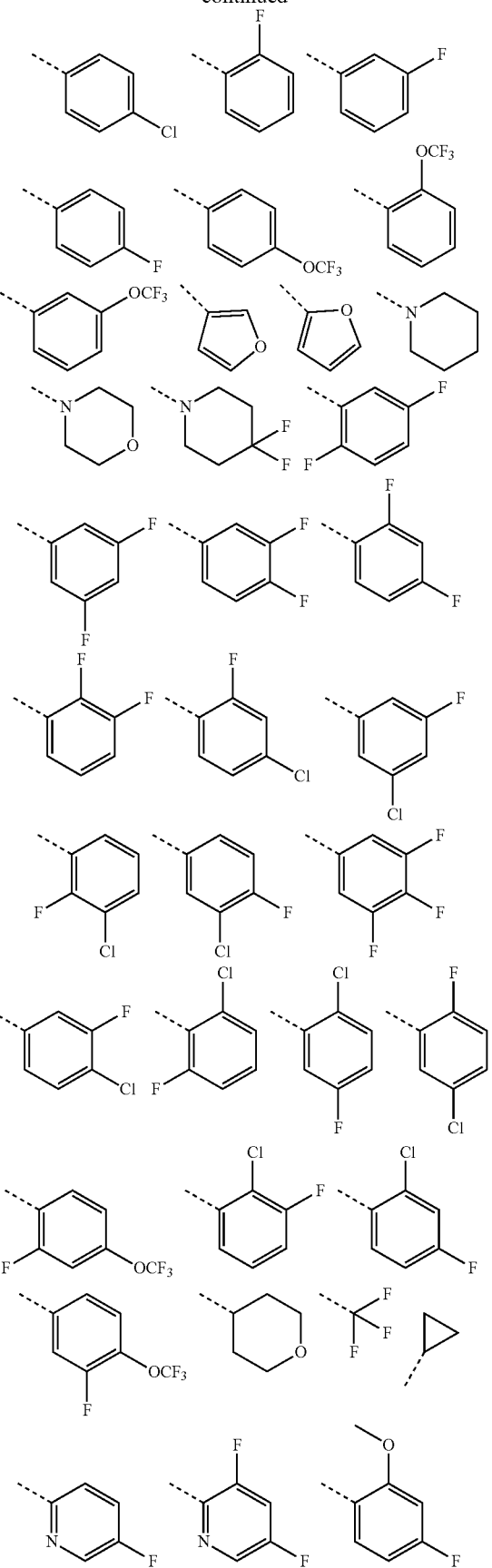

-continued

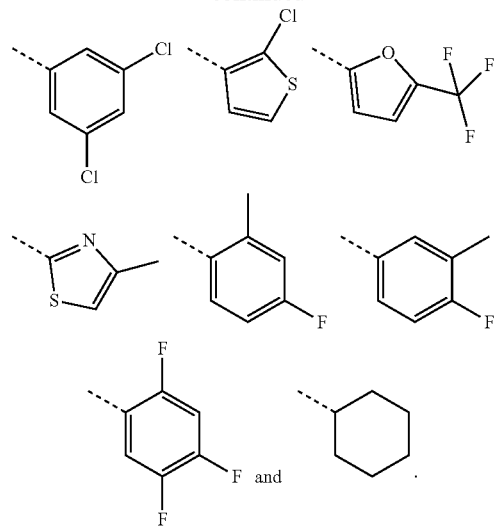

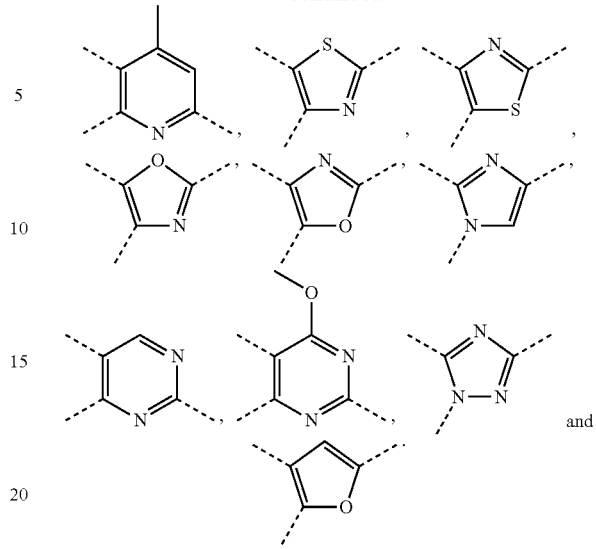

4. The compound, the pharmaceutically acceptable salt thereof or the optical isomer thereof according to claim 1, wherein, the R is selected from the group consisting of H, Cl, Br, I, OH, CN, NH$_2$, Me and Et.

5. The compound, the pharmaceutically acceptable salt thereof or the optical isomer thereof according to claim 1, wherein, the ring A is selected from the group consisting of a pyridyl, a thiazolyl, an oxazolyl, an imidazolyl and a pyrimidinyl;

or, the ring A is selected from the group consisting of

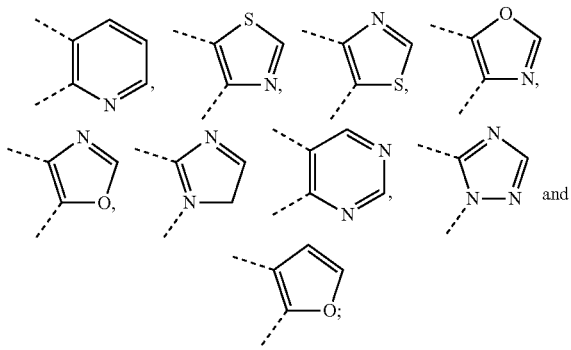

or, the moiety

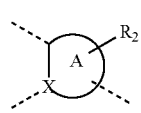

is selected from the group consisting of

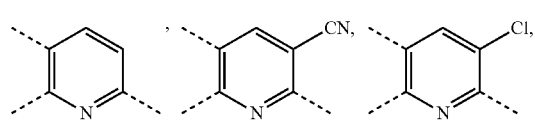

6. The compound, the pharmaceutically acceptable salt thereof or the optical isomer thereof according to claim 1, wherein, the moiety

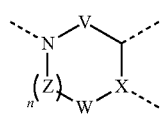

is selected from the group consisting of

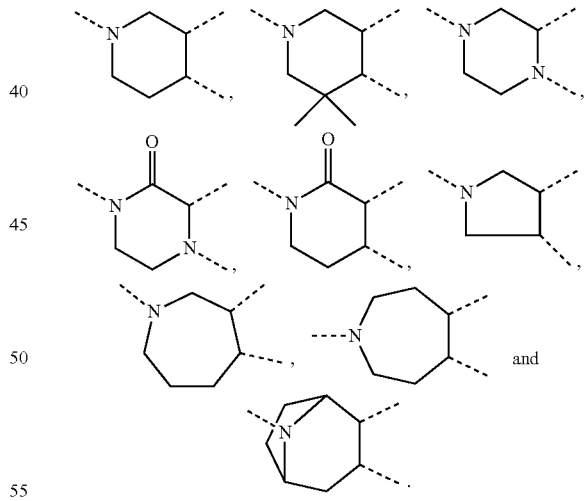

7. The compound, the pharmaceutically acceptable salt thereof or the optical isomer thereof according to claim 1, wherein, the moiety

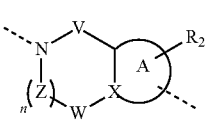

is selected from the group consisting of
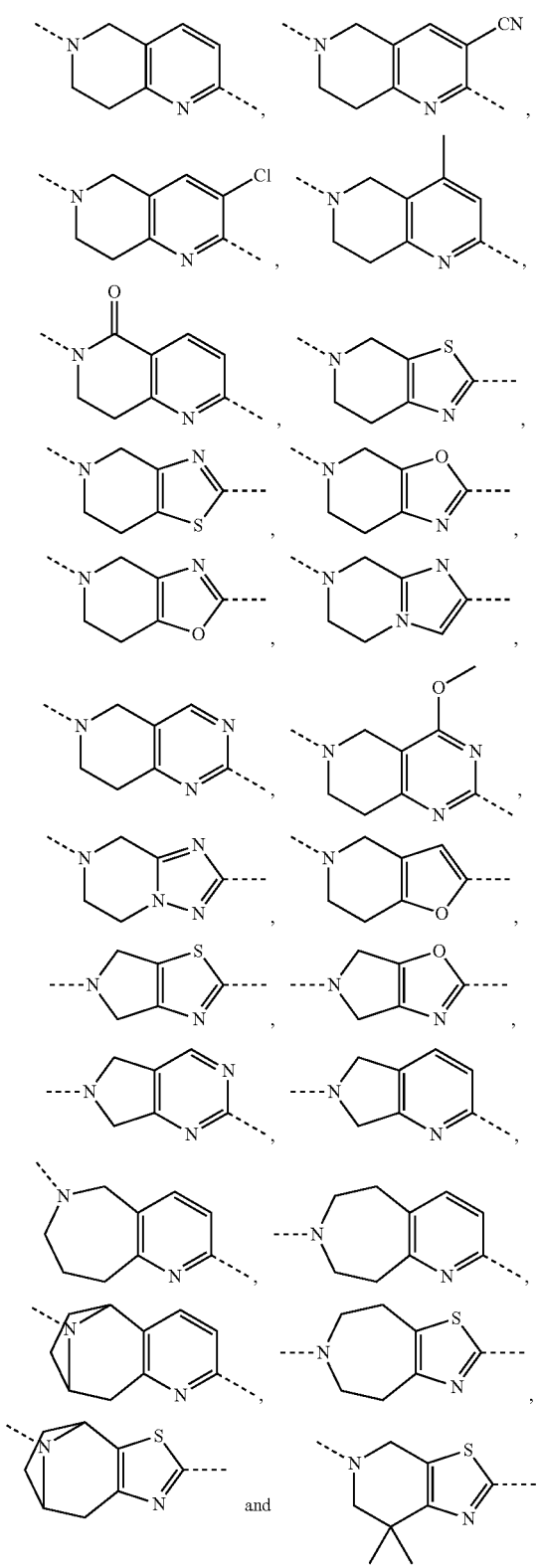
and
8. The compound, the pharmaceutically acceptable salt thereof or the optical isomer thereof according to claim 1, which is selected from the group consisting of
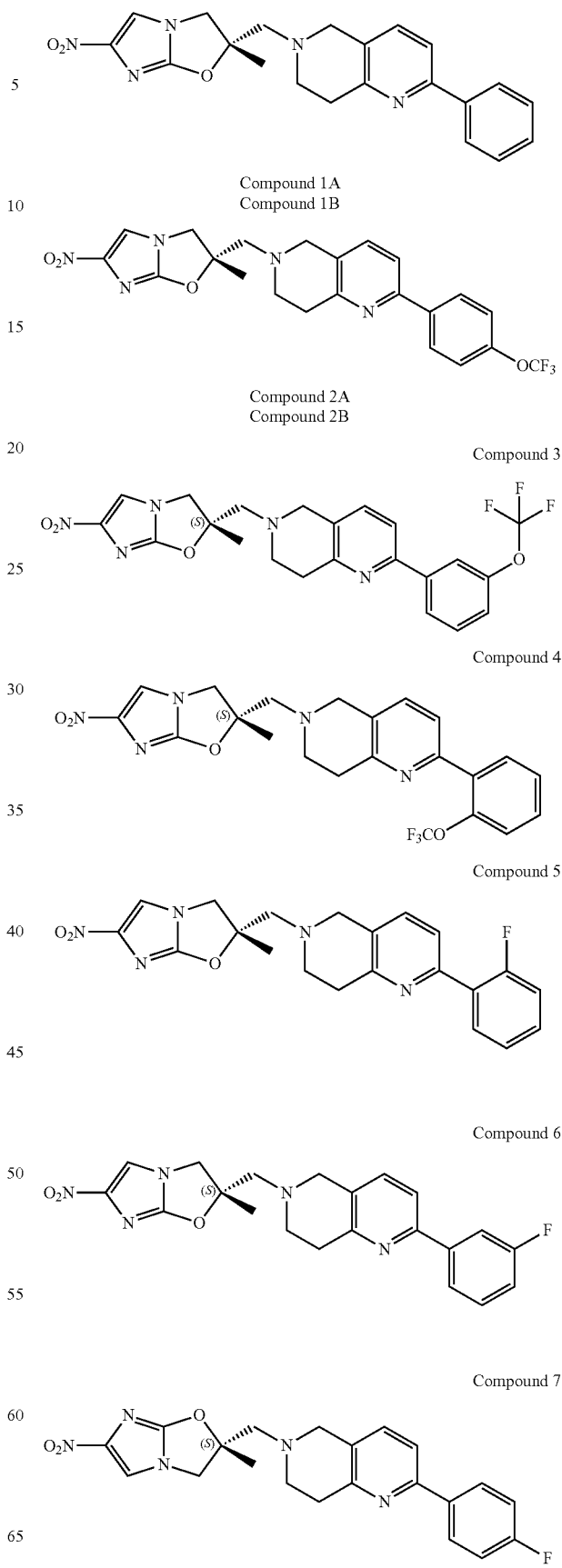
Compound 1A
Compound 1B
Compound 2A
Compound 2B
Compound 3
Compound 4
Compound 5
Compound 6
Compound 7

-continued

Compound 8

Compound 9

Compound 10

Compound 11

Compound 12

Compound 13

Compound 14

Compound 15

-continued

Compound 16

Compound 17

Compound 18

Compound 19

Compound 20

Compound 21

Compound 22

Compound 23
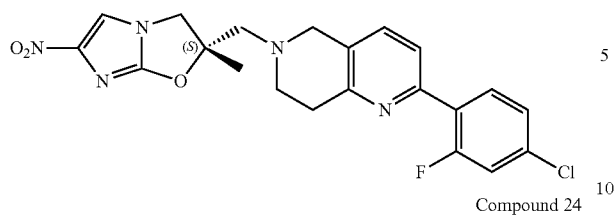
Compound 31
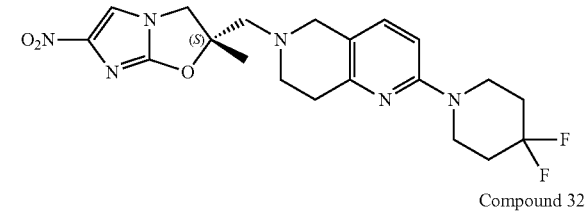
Compound 24
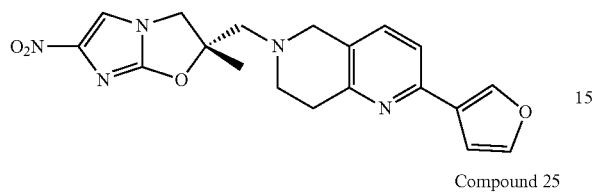
Compound 25
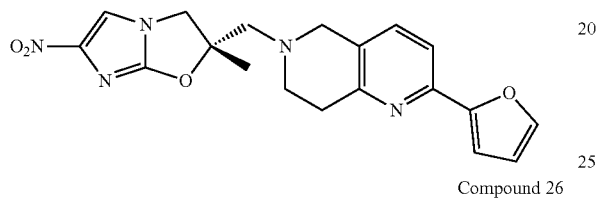
Compound 32
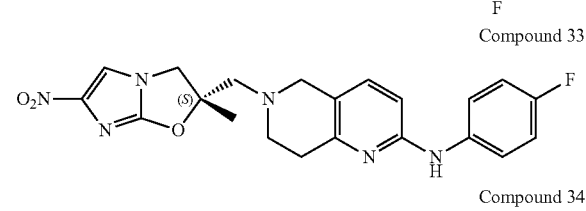
Compound 26
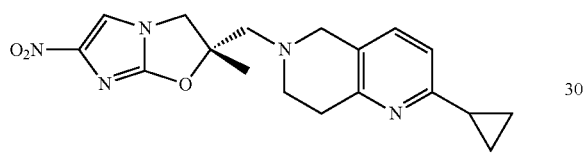
Compound 33
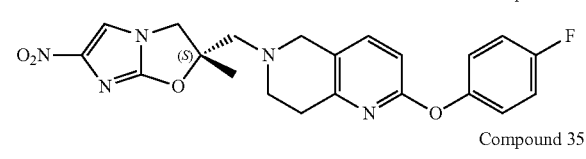
Compound 27
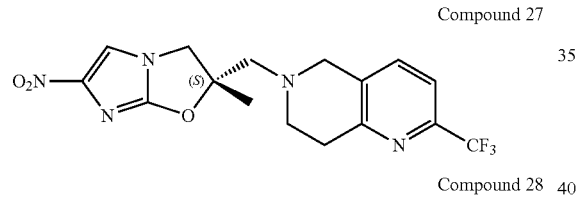
Compound 34
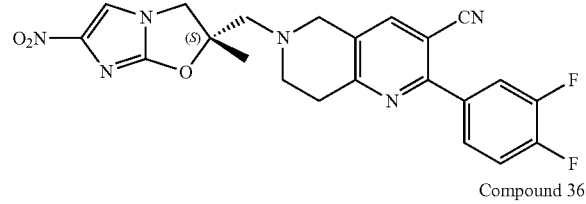
Compound 28
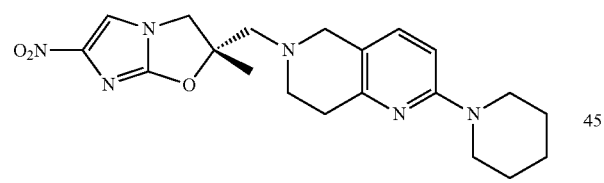
Compound 35
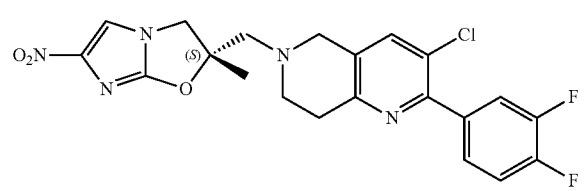
Compound 29
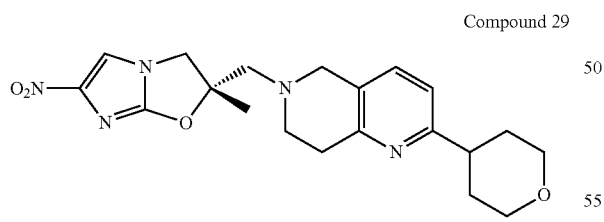
Compound 36
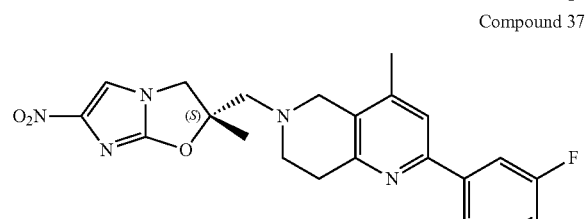
Compound 30
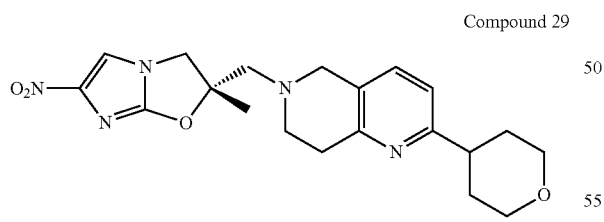
Compound 37
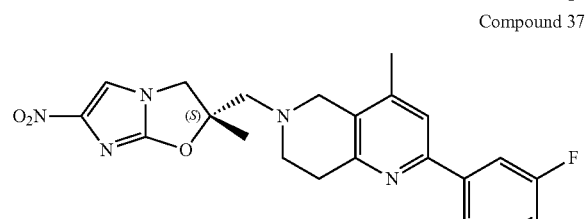
Compound 38

Compound 39
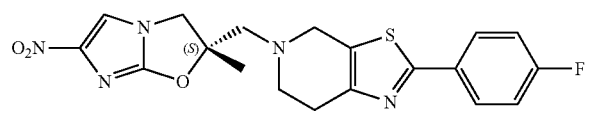
Compound 40
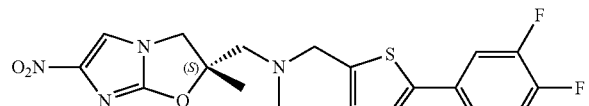
Compound 41
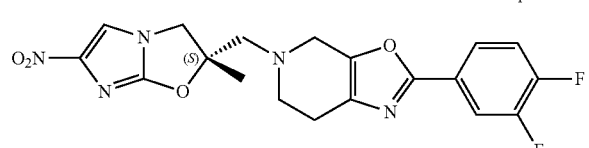
Compound 42
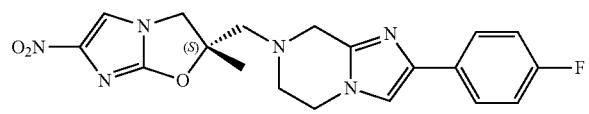
Compound 43
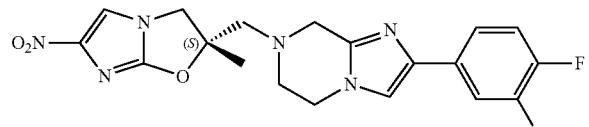
Compound 44
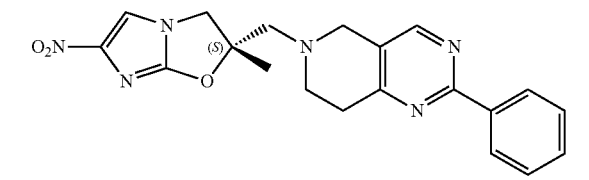
Compound 45
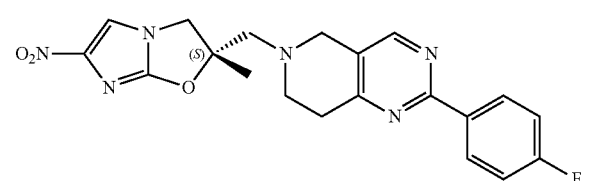
Compound 46
Compound 47
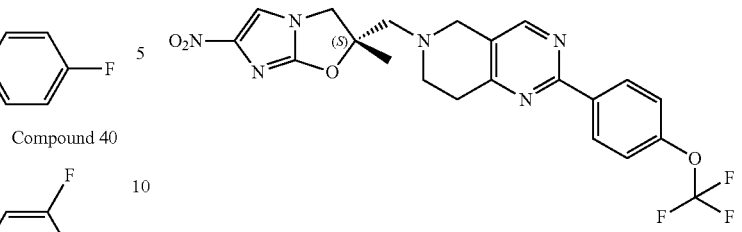
Compound 48
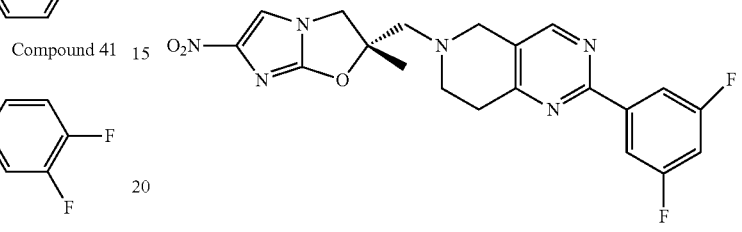
Compound 49
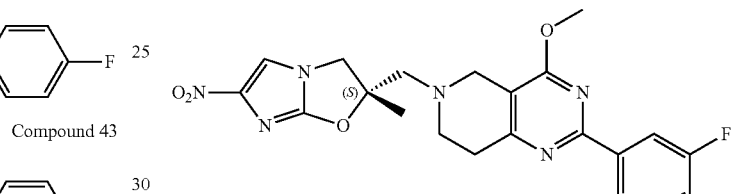
Compound 50
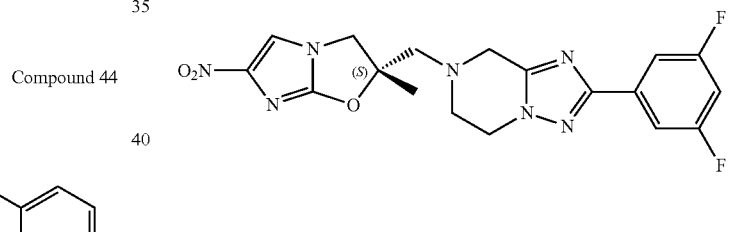
Compound 51
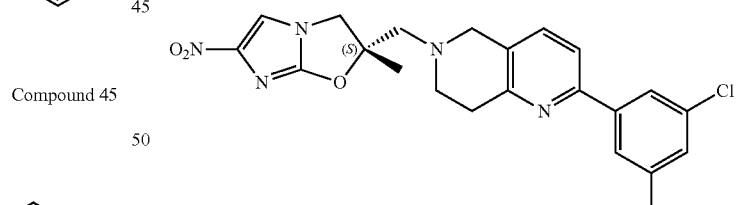
Compound 52
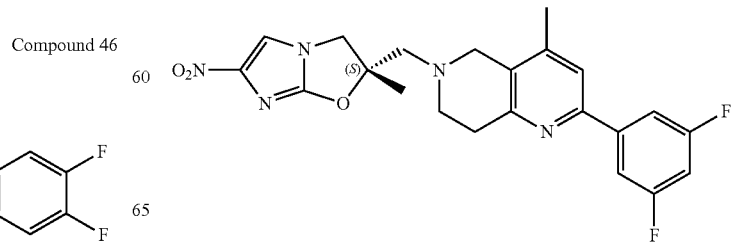

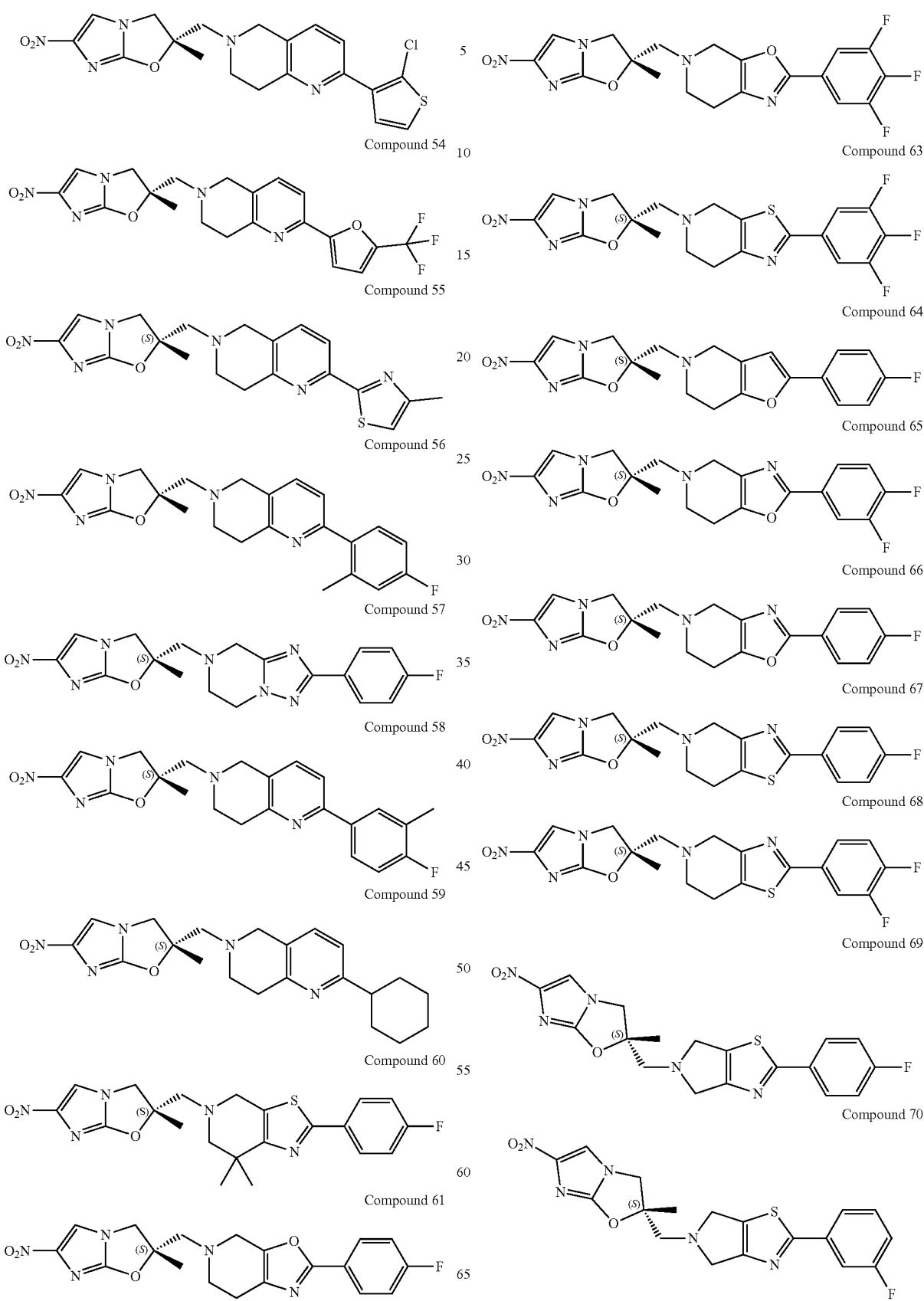

Compound 71
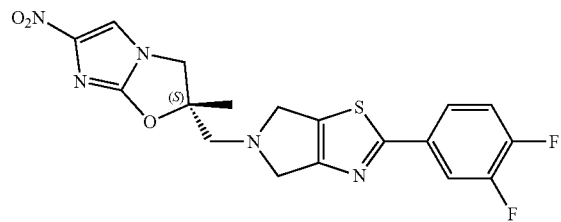
Compound 72
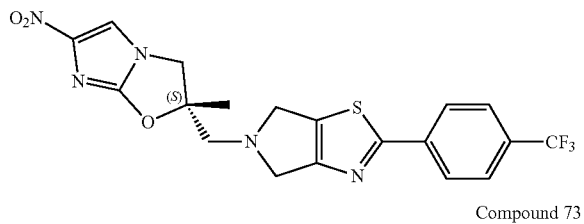
Compound 73
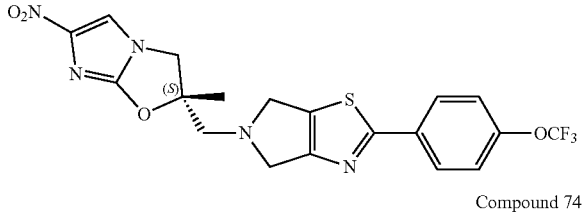
Compound 74
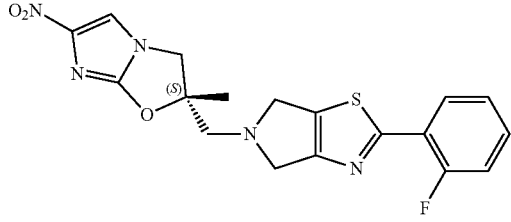
Compound 75
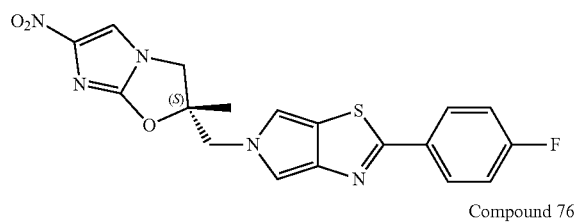
Compound 76
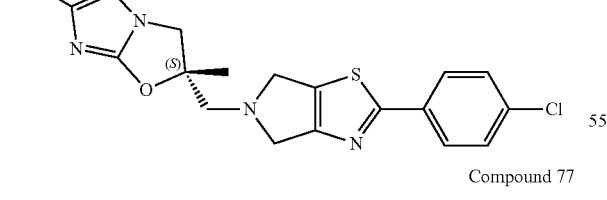
Compound 77
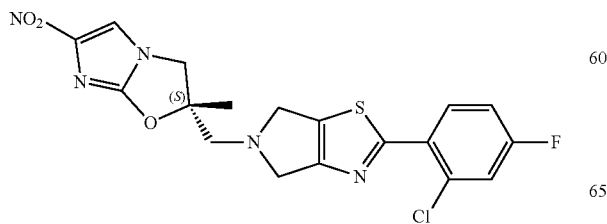
Compound 78
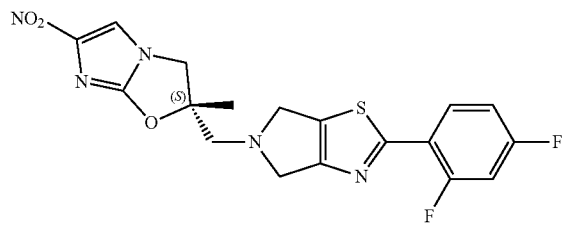
Compound 79
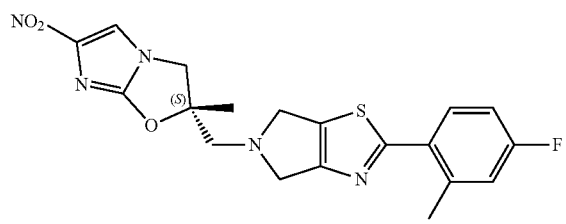
Compound 80
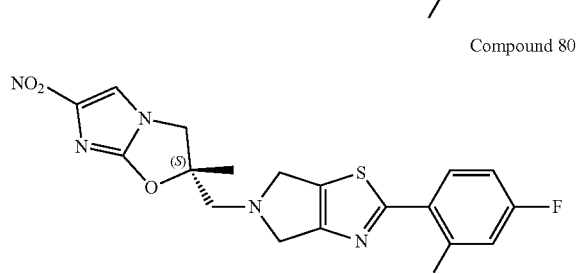
Compound 81
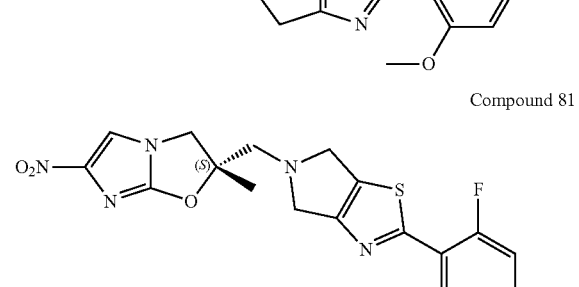
Compound 82
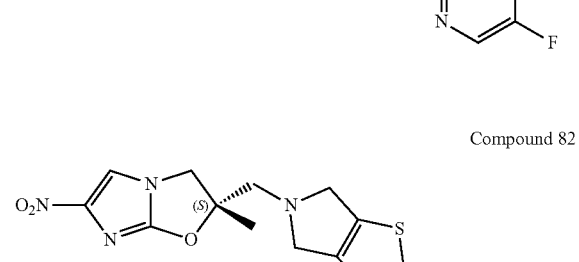
Compound 83
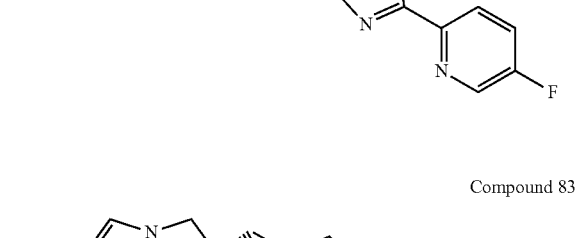
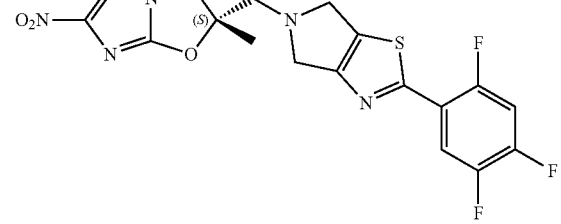

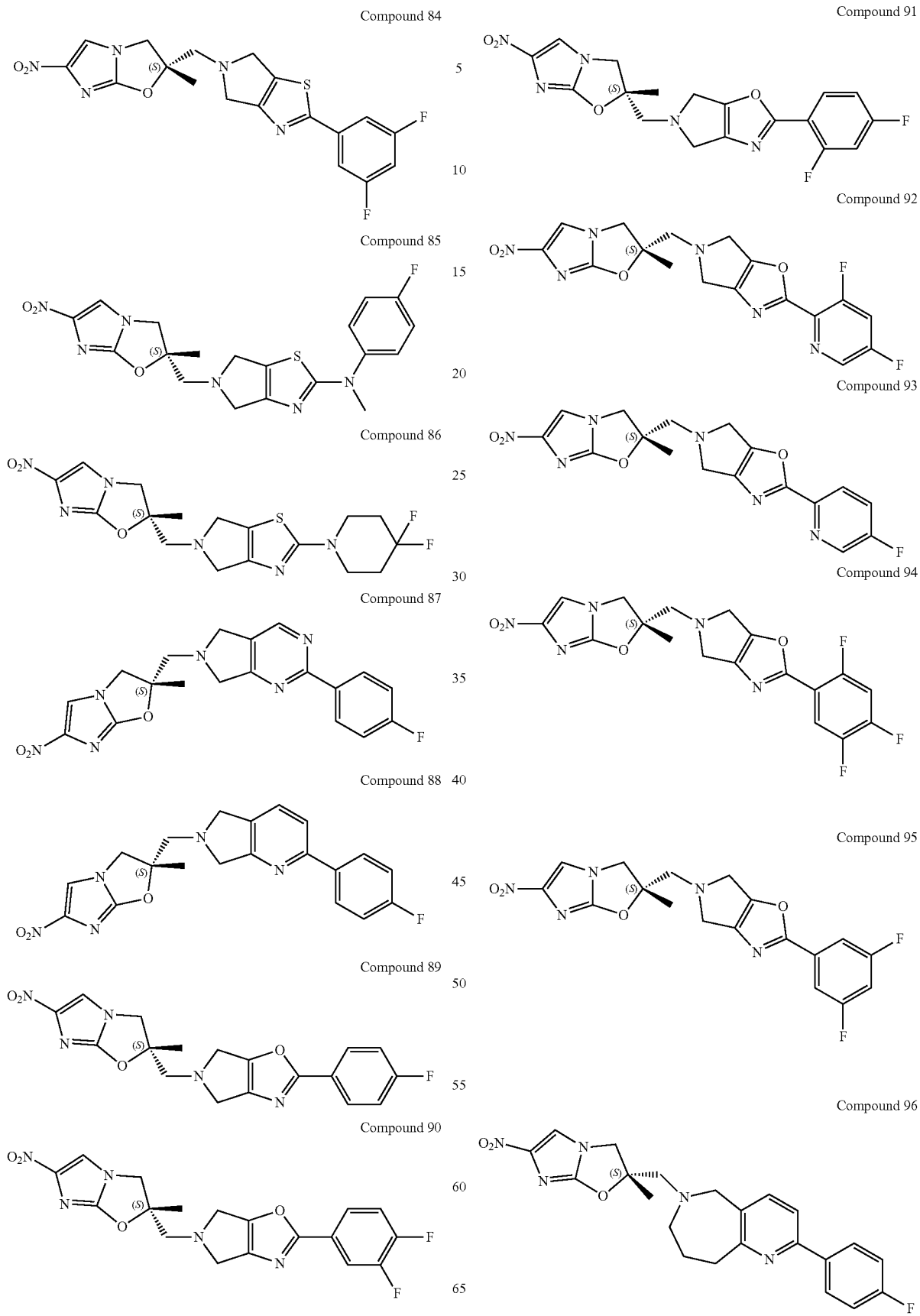

Compound 97

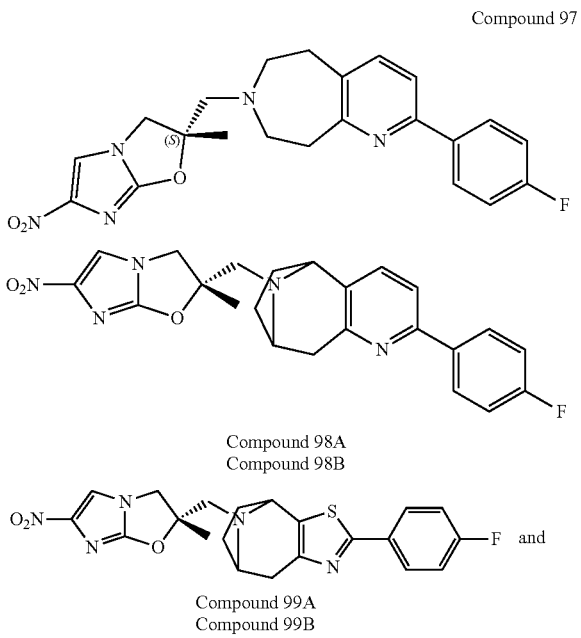

Compound 98A
Compound 98B

Compound 99A
Compound 99B

Compound 100

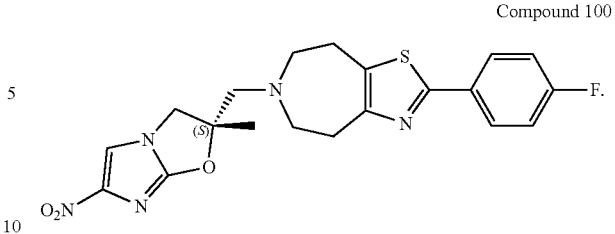

9. A pharmaceutical composition comprising an effective amount of the compound of formula (I), the pharmaceutically acceptable salt thereof, the optical isomer thereof according to claim 1, or a pharmaceutically acceptable carrier.

10. A method for treating or preventing Mycobacterium tuberculosis or other microbial infections in a subject in need thereof, comprising: administrating the compound of formula (I), the pharmaceutically acceptable salt thereof, the optical isomer thereof according to claim 1 to the subject.

11. A method for treating or preventing Mycobacterium tuberculosis or other microbial infections in a subject in need thereof, comprising: administrating the composition according to claim 9 to the subject.

* * * * *